United States Patent
Mitchum et al.

(10) Patent No.: US 10,246,722 B2
(45) Date of Patent: Apr. 2, 2019

(54) CROP RESISTANCE TO NEMATODES

(75) Inventors: Melissa G. Mitchum, Columbia, MO (US); Amy Replogle, Columbia, MO (US); Jianying Wang, Columbia, MO (US); Xiaohong Wang, Ithaca, NY (US); Shiyan Chen, Ithaca, NY (US); Ping Lang, Ithaca, NY (US)

(73) Assignees: The Curators of the University of Missouri, Columbia, MO (US); Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 744 days.

(21) Appl. No.: 14/232,041

(22) PCT Filed: Jul. 13, 2012

(86) PCT No.: PCT/US2012/046631
§ 371 (c)(1),
(2), (4) Date: Apr. 4, 2014

(87) PCT Pub. No.: WO2013/010064
PCT Pub. Date: Jan. 17, 2013

(65) Prior Publication Data
US 2014/0298537 A1    Oct. 2, 2014

Related U.S. Application Data

(60) Provisional application No. 61/507,478, filed on Jul. 13, 2011.

(51) Int. Cl.
C12N 15/82    (2006.01)

(52) U.S. Cl.
CPC ..... *C12N 15/8285* (2013.01); *C12N 15/8218* (2013.01); *C12N 15/8239* (2013.01); *Y02A 40/164* (2018.01)

(58) Field of Classification Search
None
See application file for complete search history.

(56) References Cited

U.S. PATENT DOCUMENTS

| | | | | |
|---|---|---|---|---|
| 8,569,578 | B1 * | 10/2013 | Wang | C12N 15/113 800/279 |
| 2002/0092041 | A1 | 7/2002 | Ronald et al. | |
| 2003/0005491 | A1 | 1/2003 | Hauge et al. | |
| 2004/0067506 | A1 | 4/2004 | Scheres et al. | |
| 2006/0080749 | A1 | 4/2006 | Hussey et al. | |
| 2006/0162019 | A1 * | 7/2006 | Palva | C12N 9/1205 800/279 |
| 2009/0012029 | A1 | 1/2009 | Hussey et al. | |
| 2009/0019601 | A1 | 1/2009 | Kovalic | |
| 2009/0077687 | A1 | 3/2009 | Hussey et al. | |
| 2009/0241218 | A1 | 9/2009 | Frankard et al. | |
| 2010/0186129 | A1 | 7/2010 | Hussey et al. | |
| 2010/0192257 | A1 | 7/2010 | Jones et al. | |
| 2010/0281572 | A1 | 11/2010 | Hussey et al. | |
| 2012/0192315 | A1 * | 7/2012 | Lightfoot | C07K 14/415 800/298 |
| 2013/0326736 | A1 | 12/2013 | Mitchum et al. | |
| 2013/0333061 | A1 * | 12/2013 | Wu | C07K 14/415 800/260 |
| 2014/0298537 | A1 | 10/2014 | Mitchum et al. | |

OTHER PUBLICATIONS

Kim et al (*Arabidopsis* WRKY38 and WRKY62 Transcription Factors Interact with Histone Deacetylase 19 in Basal Defense. The Plant Cell, vol. 20: 2357-2371, Sep. 2008).*
Guo et al (CLAVATA2 forms a distinct CLE-binding receptor complex regulating *Arabidopsis* stem cell specification. Plant J. 63(6): 889-900, Sep. 2010).*
Kinoshita et al (RPK2 is an essential receptor-like kinase that transmits the CLV3 signal in *Arabidopsis*. Development 137, 3911-3920, 2010).*
Mitchum et al (Diverse and conserved roles of CLE peptides. Current Opinion in Plant Biology 2008, 11:75-81).*
Urwin et al., "Enhanced Transgenic Plant Resistance to Nematodes by Dual Proteinase Inhibitor Constructs", Planta, 1998, pp. 472-479, vol. 204.
Bakhetia et al., "QPCR Analysis and RNAi Define Pharyngeal Gland Cell-Expressed Genes of Heterodera Glycines Required for Initial Interactions with the Host", Molecular Plant-Microbe Interactions, Mar. 2007, pp. 306-312, vol. 20 No. 3.
Bleckmann et al., "Stem Cell Signaling in *Arabidopsis* Requires CRN to Localize CLV2 to the Plasma Membrane", Plant Physiology, Jan. 2010, pp. 166-176, vol. 152 No. 1.
Davis et al., "Getting to the Roots of Parasitism by Nematodes", Trends in Parasitology, Mar. 2004, pp. 134-141, vol. 20 No. 3.
Davis et al., "Nematodes. Sophisticated Parasites of Legumes", Plant Physiology, Apr. 2005, pp. 1182-1188, vol. 137.
Davis et al., "Parasitism Proteins in Nematode-Plant Interactions", Current Opinion in Plant Biology, Aug. 2008, pp. 360-366, vol. 11 Issue 4.
Deyoung et al., "The CLAVATA1-Related BAM1, BAM2 and BAM3 Receptor Kinase-Like Proteins are Required for Meristem Function in *Arabidopsis*", The Plant Journal: For Cell and Molecular Biology, Jan. 2006, pp. 1-16, vol. 45 No. 1.

(Continued)

*Primary Examiner* — Medina A Ibrahim
*Assistant Examiner* — Wayne Zhong
(74) *Attorney, Agent, or Firm* — Thompson Coburn LLP; J. Wendy Davis

(57) ABSTRACT

Methods of inhibiting plant parasitic nematodes, methods of obtaining transgenic plants useful for inhibiting such nematodes, and transgenic plants that are resistant to plant parasitic nematodes through inhibition of plant nematode CLAVATA3/ESR (CLE) peptide receptor genes are provided. Methods for expressing genes at plant parasitic nematode feeding sites with plant nematode CLE peptide receptor gene promoters are also provided, along with nematode CLE peptide receptor gene promoters that are useful for expressing genes in nematode feeding sites as well as transgenic plants and nematode resistant transgenic plants comprising the promoters.

9 Claims, 22 Drawing Sheets

Figure 5:
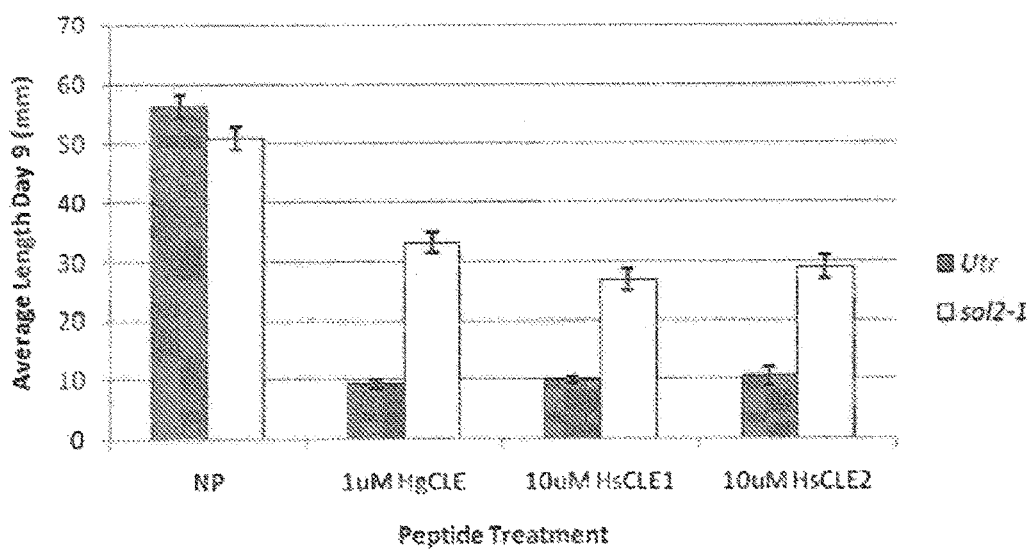

Specification includes a Sequence Listing.

(56) References Cited

OTHER PUBLICATIONS

Durbak et al., "CLAVATA signaling pathway receptors of *Arabidopsis* Regulate Cell Proliferation in Fruit Organ Formation as Well as in Meristems", Genetics, Jun. 24, 2011.
EMBL Accession No. AK244255, Glycine max cDNA, Nov. 19, 2008, downloaded from the Internet Sep. 21, 2012 <http://www.ebi.ac.uk/Tools/dbfetch?db=embl&id=AK244255&f . . . >, p. 1-2.
Gao et al., "The Parasitome of the Phytonematode Heterodera Glycines", Molecular Plant-Microbe Interactions, Aug. 2003, pp. 720-726, vol. 16 No. 8.
Hirakawa et al., "Non-Cell-Autonomous Control of Vascular Stem Cell Fate by a CLE Peptide/Receptor System", Proceedings of the National Academy of Sciences, Sep. 2008, pp. 15208-15213, vol. 105, No. 39.
Hussey, "Go Where the Science Leads You", Annual Review of Phytopathology, 2010, pp. 1-19, vol. 48.
Ithal et al., "Developmental Transcript Profiling of Cyst Nematode Feeding Cells in Soybean Roots", Molecular Plant-Microbe Interactions, May 2007, pp. 510-525, vol. 20 No. 5.
Jeong et al., "The *Arabidopsis* CLAVATA2 Gene Encodes a Receptor-Like Protein Required for the Stability of the CLAVATA1 Receptor-Like Kinase", The Plant Cell, Oct. 1999, pp. 1925-1934, vol. 11 No. 10.
Liu et al., "Soybean Cyst Nematode Resistance in Soybean is Independent of the Rhg4 Locus LRR-RLK Gene", Functional Integrated Genomics, 2011, pp. 539-549, vol. 11.
Liu, "Dissertation entitled: Molecular Characterization of Soybean Resistance to Soybean Cyst Nematode", Ph.D Dissertation, Dec. 2009, p. 5.
Lu et al., "Structural and Functional Diversity of CLAVATA3/ESR (CLE)-Like Genes from the Potato Cyst Nematode Globodera Rostochiensis", Molecular Plant-Microbe Interactions, Sep. 2009, pp. 1128-1142, vol. 22 No. 9.
Mitchum et al., "Diverse and Conserved Roles of CLE Peptides", Current Opinion in Plant Biology, Feb. 2008, pp. 75-81, vol. 11 Issue 1.
Mitchum et al., "The Promoter of the *Arabidopsis thaliana* Cel1 Endo-1, 4-Beta Glucanase Gene is Differentially Expressed in Plant Feeding Cells Induced by Root-Knot and Cyst Nematodes", Molecular Plant Pathology, May 1, 2004, pp. 175-181, vol. 5 No. 3.
Muller et al., "The Receptor Kinase of CORYNE of *Arabidopsis* Transmits the Stem Cell-Limiting Signal CLAVATA3 Independently of CLAVATA1", The Plant Cell, Apr. 2008, pp. 934-946, vol. 20 No. 4.
Patel et al., "Similarity and Functional Analyses of Expressed Parasitism Genes in Heterodera Schachtii and Heterodera Glycines", Journal of Nematology, Dec. 2008, pp. 299-310, vol. 40 No. 4.
Replogle et al., "Abstract Perception of CLE Peptides in *Arabidopsis* During Cyst Nematode Pathogenesis", 2009 APS Annual Meeting, Aug. 1-5, 2009, Portland, Oregon.
Shiu et al., "Plant Receptor-Like Kinase Gene Family: Diversity, Function, and Signaling", Science's STKE: Signal Transduction Knowledge Environment, Dec. 18, 2001, pp. re22, vol. 2001 Issue 113.
Shpak et al., "Dominant-Negative Receptor Uncovers Redundancy in the *Arabidopsis* ERECTA Leucine-Rich Repeat Receptor-Like Kinase Signaling Pathway that Regulates Organ Shape", The Plant Cell, May 2003, pp. 1095-1110, vol. 15 No. 5.
Wang et al., "A Parasitism Gene from a Plant-Parasitic Nematode with Function Similar to CLAVATA3/ESR (CLE) of *Arabidopsis thaliana*", Molecular Plant Pathology, Mar. 2005, pp. 187-191, vol. 6 No. 2.
Wang et al., "CLE Peptide Signaling During Plant Development", Protoplasma, 2009, pp. 33-43, vol. 240.
Wang et al., "Dual Roles for the Variable Domain in Protein Trafficking and Host-Specific Recognition of Heterodera Glycines CLE Effector Proteins", The New Phytologist, Sep. 2010, pp. 1003-1017, vol. 187 No. 4.
Wang et al., "Identification of Potential Host Plant Mimics of CLAVATA3/ESR (CLE)-Like Peptides from the Plant-Parasitic Nematode Heterodera Schachtii", Molecular Plant Pathology, Feb. 2011, pp. 177-186, vol. 12 No. 2.
Wang et al., "Signal Peptide-Selection of cDNA Cloned Directly from the Esophageal Gland Cells of the Soybean Cyst Nematode Heterodera Glycines", Molecular Plant Microbe Interactions, Apr. 2001, pp. 536-544, vol. 14 No. 4.
Wang et al., "The Tobacco Cel7 Gene Promoter is Auxin-Responsive and Locally Induced in Nematode Feeding Sites of Heterologous Plants", Molecular Plant Pathology, Jul. 2007, pp. 423-436, vol. 8 No. 4.
Whitford et al., "Plant CLE Peptides From Two Distinct Functional Classes Synergistically Induce Division of Vascular Cells", Proceeding of the National Academy of Science of the United States of America, Nov. 25, 2008, pp. 18625-18630, vol. 105 No. 47.
Zhu et al., "Analysis of Interactions Among the CLAVATA3 Receptors Reveals a Direct Interaction Between CLAVATA2 and CORYNE in *Arabidopsis*", The Plant Journal: For Cell and Molecular Biology, pp. 223-233, vol. 61 No. 2.
Friedberg, "Automated Protein Function Prediction—the Genomic Challenge", Briefings in Bioinformatics, Jan. 25, 2006, pp. 225-242, vol. 7, No. 3.
Guo et al., "Protein Tolerance to Random Acid Change", Proceedings of the National Acadamey of the Sciences, Jun. 22, 2004, pp. 9205-9210, vol. 101, No. 25.
Hill et al., "Functional Analysis of Conserved Histidines in ADP-Glucose Pyrophosphorylase from *Escherichia coli*", Biochemical and Biophysical Research Communications, 1998, pp. 573-577, vol. 244, Article No. RC988301.
Chen et al., "In Planta Processing and Glycosylation of a Nematode CLAVATA3/Endosperm Surrounding Region-Like Effector and Its Interaction with a Host CLAVATA2-Like Receptor to Promote Parasitism", Plant Physiology, Jan. 2015, pp. 262-272, vol. 167.
Guo et al., "Enhanced Resistance to Soybean Cyst Nematode Heterodera Glycines in Transgenic Soybean by Silencing Putative CLE Receptors", Plant Biotechnology Journal, 2015, pp. 1-10.
Senthil-Kumar et al., "Caveat of RNAi in Plants: The Off-Target Effect", RNAi and Plant Gene Function Analysis, 2011, pp. 13-25, vol. 744.
Replogle et al., "Synergistic Interaction of CLAVATA1, CLAVATA2, and Receptor-Like Protein Kinase 2 in Cyst Nematode Parasitism of *Arabidopsis*", Molecular Plant-Microbe Interactions Journal, 2013, pp. 87-96, vol. 26, No. 1.
Kayes et al., "CLAVATA2, a Regulator of Meristem and Organ Development in *Arabidopsis*", Development, 1998, pp. 3843-3851, vol. 125.
Replogle et al., "Nematode CLE Signaling in *Arabidopsis* Requires CLAVATA2 and CORYNE", The Plant Journal, 2011, pp. 430-440, vol. 65.

\* cited by examiner

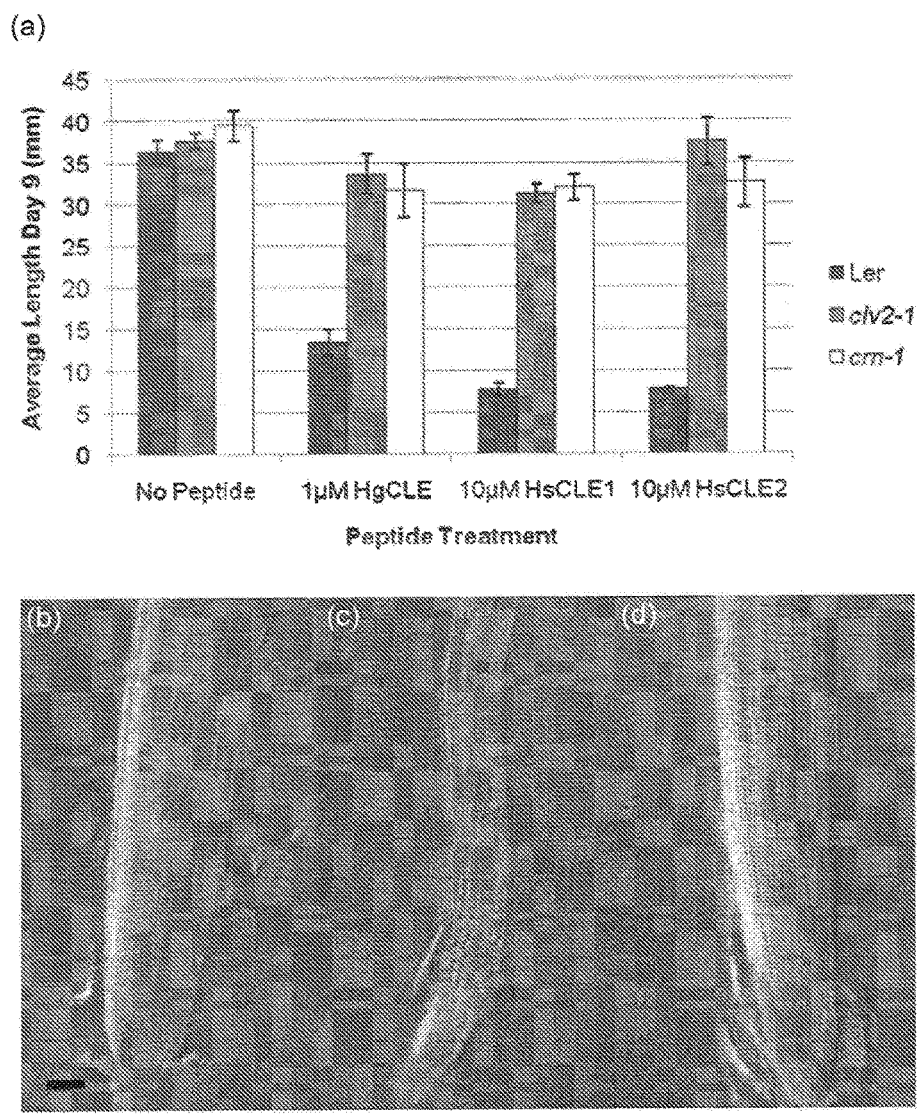

Figure 1. Effect of cyst nematode CLE peptides on receptor mutants. (a) Average root length wild-type (L*er*), *clv2-1*, and *crn-1* seedlings grown for 9 days on media with or without the synthetic nematode dodecapeptide CLE motif. Data represent the mean ± SE, n = 10. (b)-(d) Representative roots tips of seedlings grown on media with or without synthetic CLE peptides for 10 days and visualized with differential interference microscopy. (b) No peptide, (c) Sensitive to peptide, and (d) Resistant to peptide. (Scale bar, 50 μm).

FIGURE 1

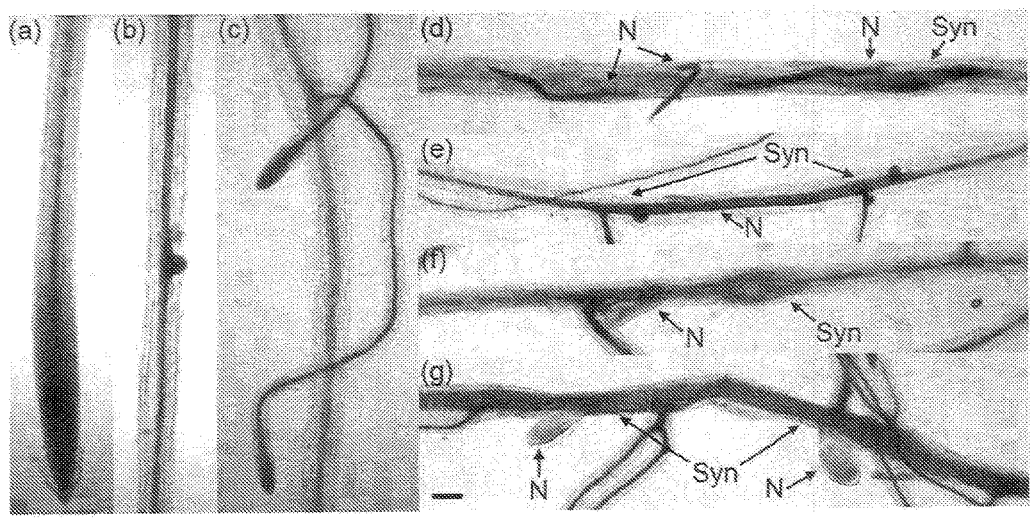
Figure 2. *CRN* expression during nematode infection. (a)-(c) *CRN:GUS* expression in uninfected Arabidopsis root tips (a), middle of the root (b), and older part of the root towards the hypocotyl (c). (d)-(g) *CRN:GUS* expression in response to *H. schachtii*; early parasitic J2 (d), late parasitic J2 (e), J3 parasitic (f), J4 parasitic (g). Abbreviations: nematode, N; Syn, Syncytium. (Scale bar, 50 μm).

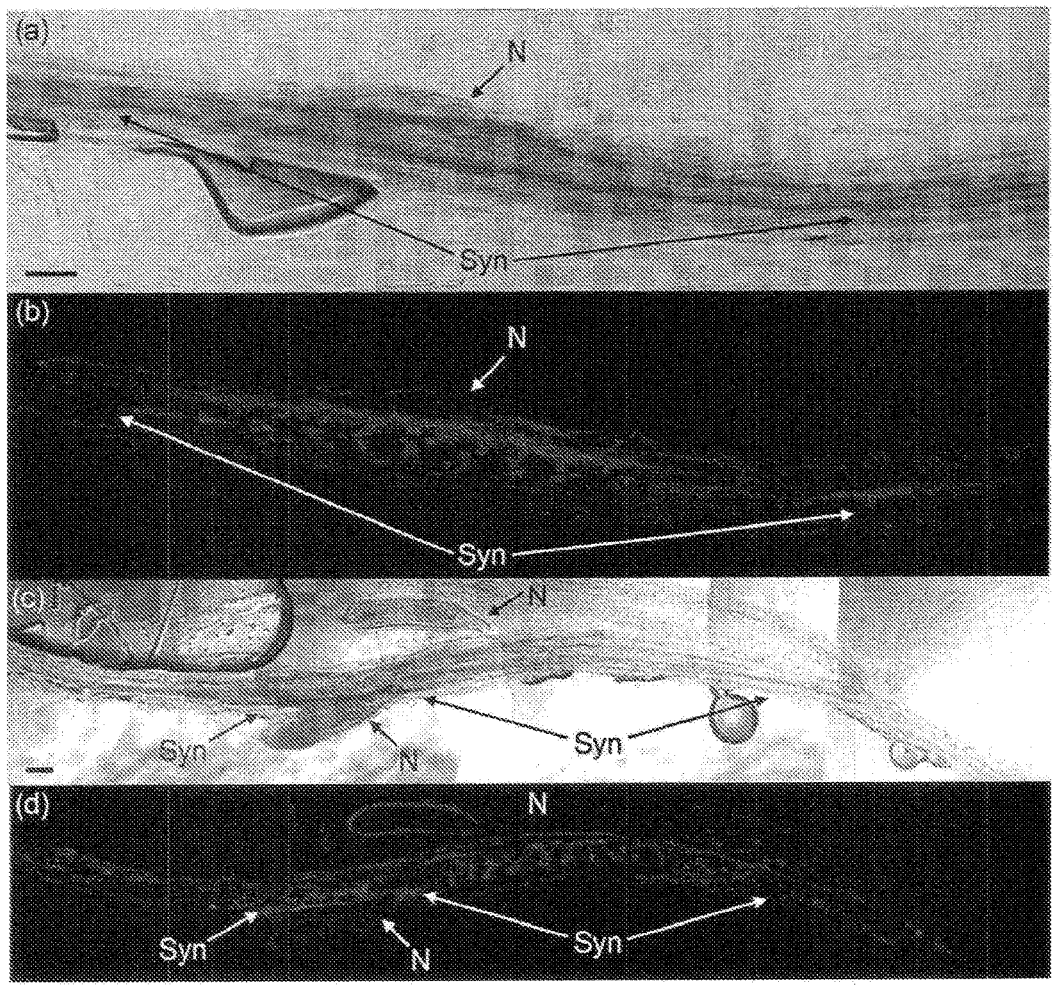
Figure 3. Confocal images of *CLV2* expression of *CLV2:H2B-mCherry* during nematode infection. (a) J2 parasitic with DIC. (b) J2 parasitic with mCherry fluorescence. (c) J3 parasitic with DIC. (d) J3 parasitic with mCherry fluorescence. Abbreviations: nematode, N; Syn, Syncytium. (Scale bars, 50 μm).

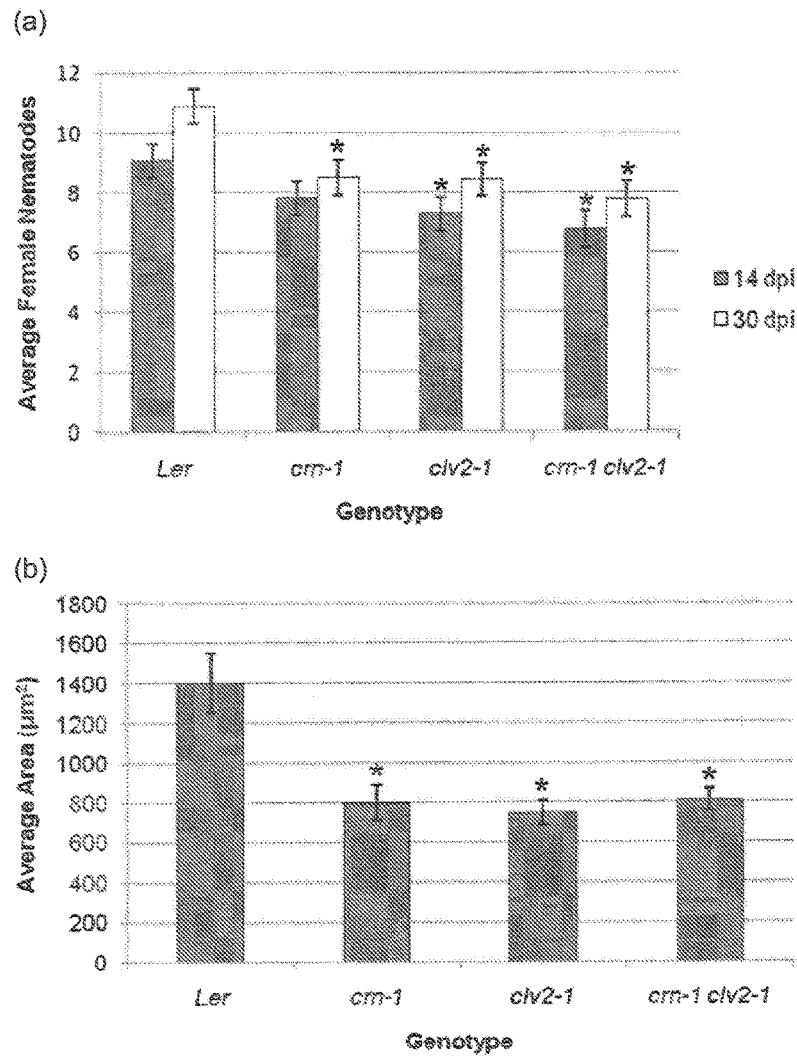

Figure 4. Effect of *clv2-1* and *cm-1* mutant alleles on *H. schachtii* infection. (a) J4 females were counted at 14dpi and adult females were counted at 30 dpi. Data represent mean ± SE, n = 35 for L*er*, 32 for *cm-1*, 34 for *clv2-1*, and 29 for *cm-1 clv2-1*. Data representative of three independent experiments. (b) Seedlings were grown on vertical square plates for 10 days and inoculated with 10 ppJ2s/root. At 14 dpi, syncytia that fed only one nematode and appeared translucent were microscopically examined and their area was determined. Data represent mean ± SE, n = 11 for L*er* and *cm-1*, 14 for *clv2-1*, and 12 for *cm-1 clv2-1*. Asterisks indicate statistically significant differences compared to L*er* by Student's *t* test ($P < 0.05$).

FIGURE 4

Fig. S1. Average root length wild-type (Utr) and *sol2-1* seedlings grown for 9 days on media with or without the synthetic nematode dodecapeptide CLE motif. Data represent the mean ± SE, n = 10.

Figure S2. Confocal image of nematode autofluorescence in a wild-type root. (a and b) Feeding site induced by a parasitic J2. (a) DIC image. (b) mCherry fluorescence. (Scale bar 50um).

(a)

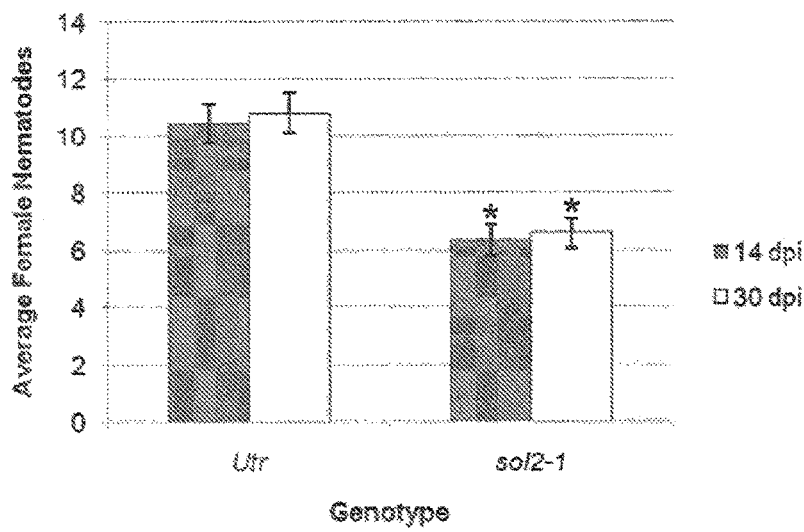

(b)

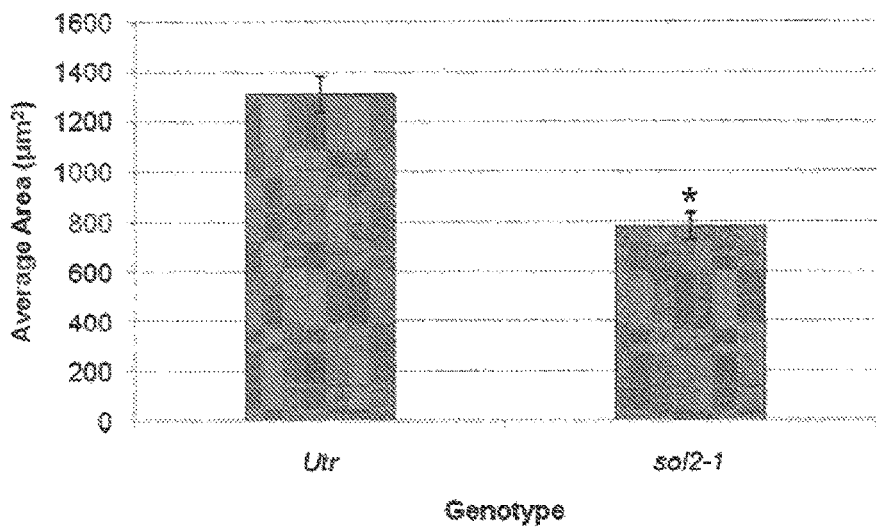

Fig. S3. Effect of *sol2-1* mutant allele on *H. schachtii* infection (a). J4 females were counted at 14dpi and adult females were counted at 30 dpi. Data represent mean ± SE, n = 36. Asterisks indicate statistically significant differences compared to Ler by Student's $t$ test (P < 0.0001). Effect of *sol2-1* mutant allele on size of syncytia (b). Seedlings were grown on vertical square plates for 10 days and inoculated with 10 ppJ2s/root. At 14 dpi, syncytia that fed only one nematode and appeared translucent were microscopically examined and their area was determined. Data represent mean ± SE, n = 11 for Utr and n = 9 for *sol2-1*. Asterisks indicate statistically significant differences compared to Ler by Student's $t$ test (P < 0.05).

FIGURE 7

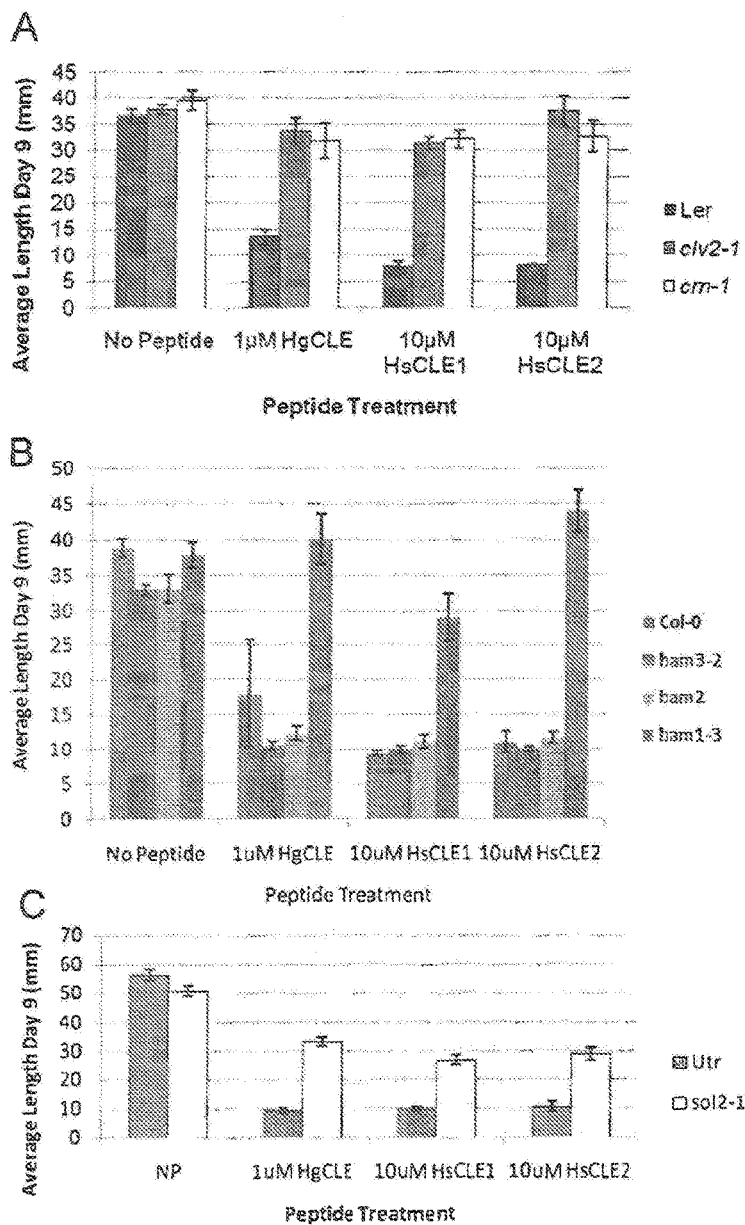

Fig.8 . Effect of *Heterodera glycines* (HgCLE) and *Heterodera schachtii* (HsCLE) nematode CLE peptides on receptor mutants. Seedlings were grown for 9 days on media with or without the synthetic nematode dodecapeptide CLE motif. Data represent the mean ± SE, n = 10.(A) Average root length of wild-type (Ler), *clv2-1*, and *crn-1*. (B) Average root length of wild-type (Col-0,) *bam3-2*, *bam2*, and *bam1-3*. (C) Average root length of wild-type (Utr) and *sol2-1*.

FIGURE 8

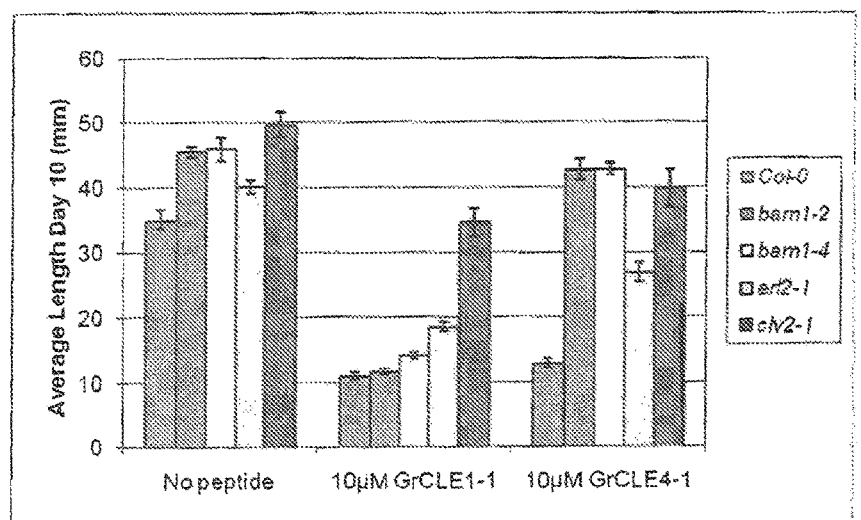
Fig.9 . Effect of *Globodera rostochiensis* (GrCLE) nematode CLE peptides on receptor mutants. Seedlings were grown for 9 days on media with or without the synthetic nematode dodecapeptide CLE motif. Data represent the mean ± SE, n = 10. Average Fig 10 Effect of mutant alleles on *H. schachtii* infection. J4 females were counted at 14dpi and adult females were counted at 30 dpi. Asterisks indicate statistically significant differences compared to wild-type by Student's *t* test (P < 0.05). Data represent mean ± SE. Similar results were obtained from two additional biological replicates.

Figure 11:
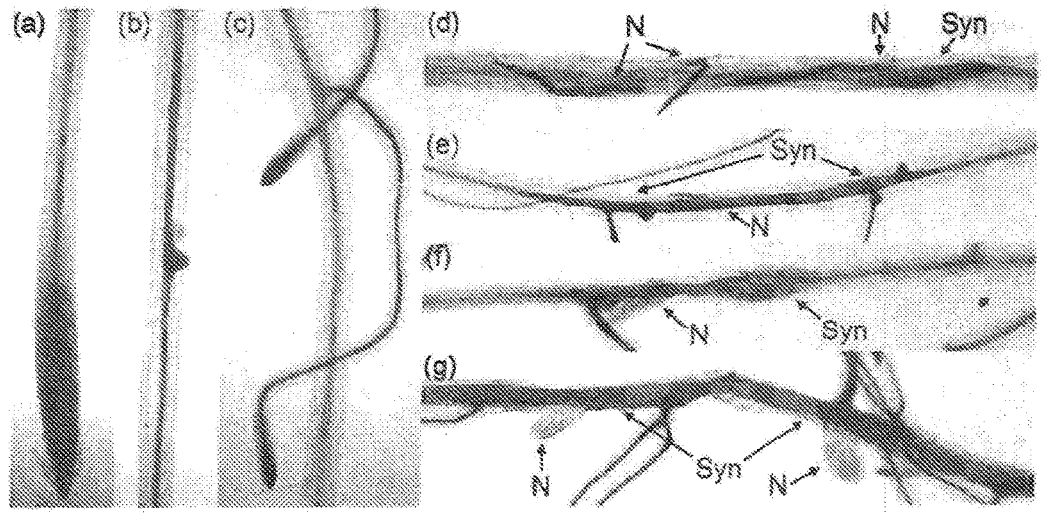

Fig.11 *CRN::GUS* expression during nematode infection. (A-C) *CRN::GUS* expression in uninfected Arabidopsis root tips (A), middle of the root (B), and older part of the root towards the hypocotyl (C). (D-G) *CRN::GUS* expression in nematode-infected roots; (D) early J2p, (E) late J2p, (F) J3 and (G) J4 females.

Figure 12:
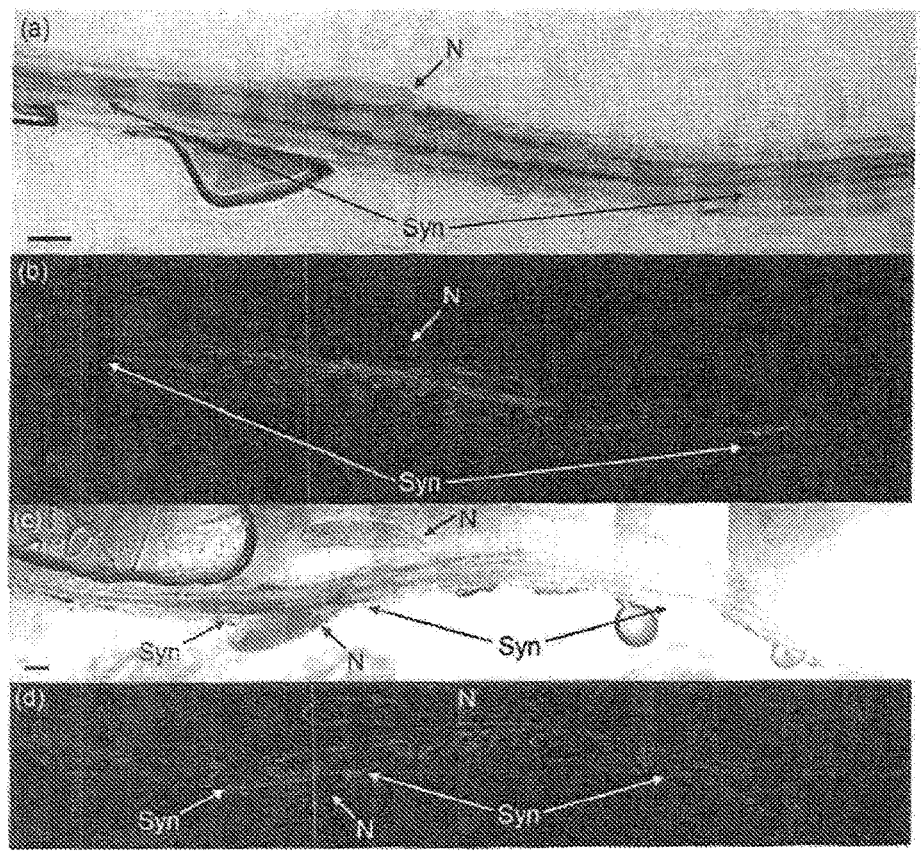

Fig.12 CLV2 expression during nematode infection. (A-D) Confocal section of a nematode induced feeding site 4 dpi (A-B) and 8dpi (A-B) expressing CLV2:H2B-mCherry which is shown in red.

Figure 13:
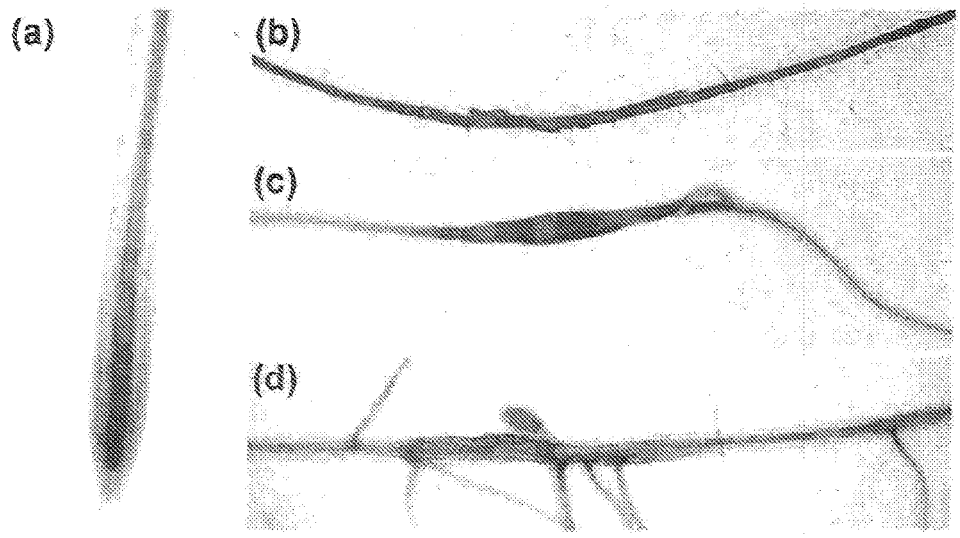

Fig13 *BAM1:GUS* expression in Arabidopsis in response to nematode infection. (A) Uninfected root tip. (B-D) GUS expression in nematode infected roots; (B) Early parasitic J2, (C) Parasitic J3, and (D) Parasitic J4.

Figure 14:
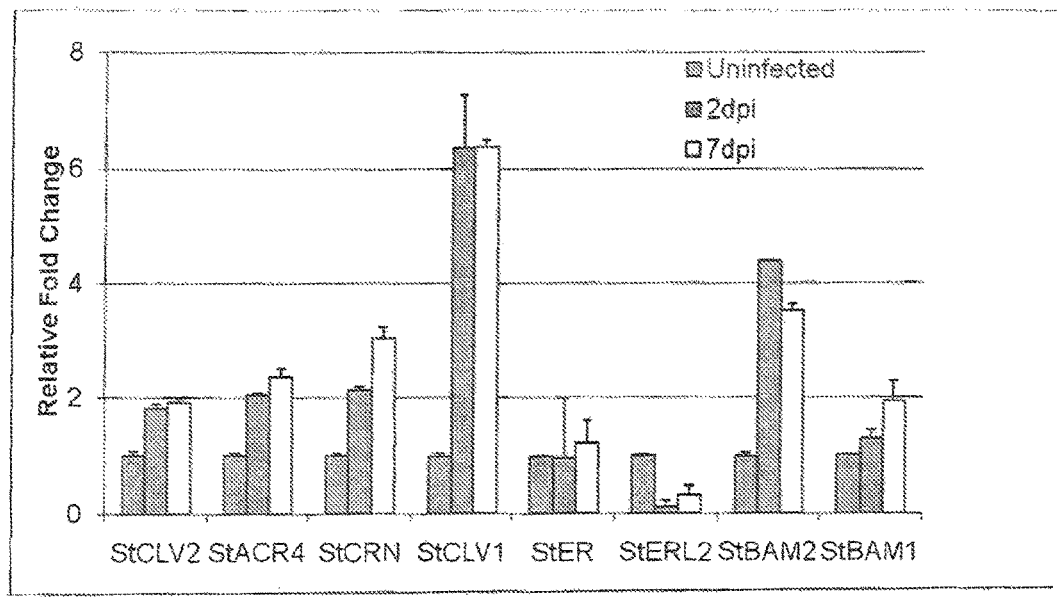

Fig 14 qRT-PCR analysis showing differential expression of candidate potato receptor genes in G. rostochiensis-infected potato roots.

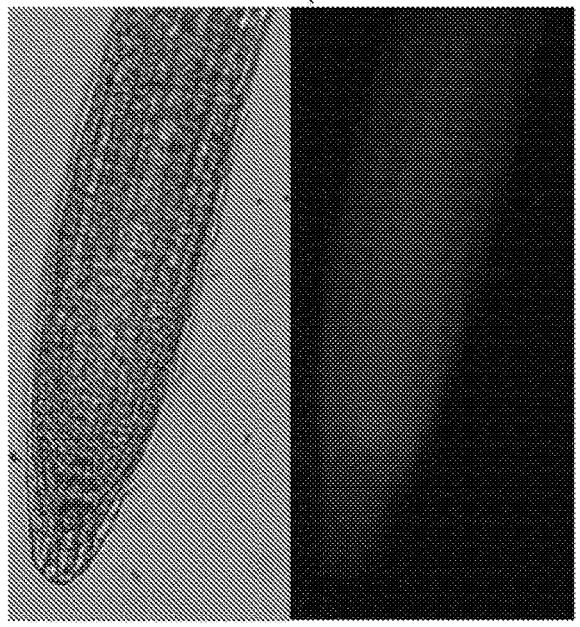
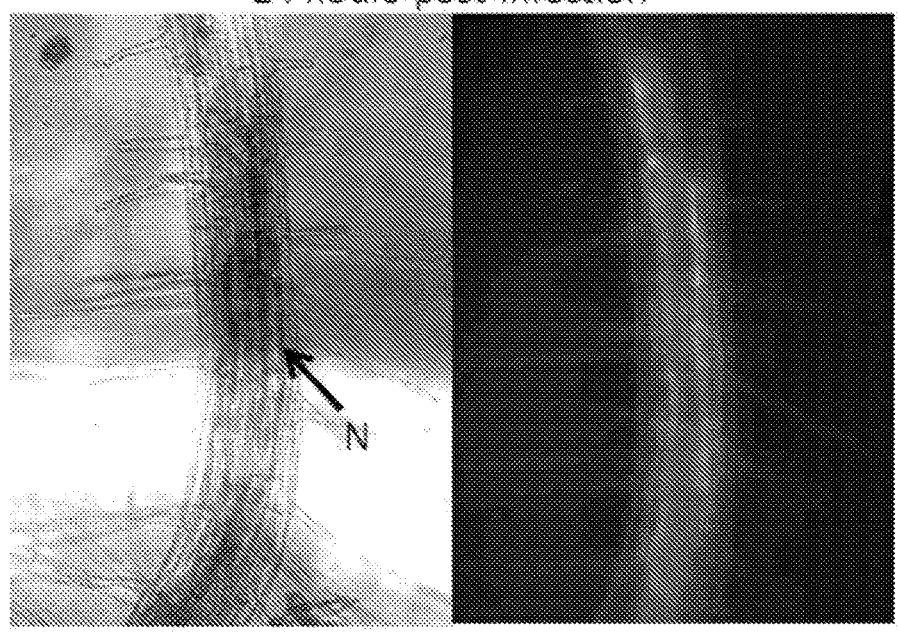
pRPK2::RPK2-GFP Arabidopsis
FIGURE 18

CROP RESISTANCE TO NEMATODES

CROSS REFERENCE TO RELATED APPLICATIONS

This application is the U.S. National Stage of International Patent Application PCT/US2012/046631, filed Jul. 13, 2012 and incorporated herein by reference in its entirety, which claims the benefit of U.S. Provisional Application Ser. No. 61/507,478 filed Jul. 13, 2011, which is incorporated herein by reference in its entirety.

STATEMENT REGARDING GOVERNMENTAL SUPPORT

This invention was made with Government support under Grant Numbers 2007-35607-17790, 2008-34113-19420, 2009-35302-0534, all awarded by the USDA-NR1, and USDA Special Grant (grant no. 2008-34113-19420). The government has certain rights to this invention.

INCORPORATION OF SEQUENCE LISTING

A computer readable form of the Sequence Listing is provided herein, contained in the file named "UMC002.txt," which is 339,716 bytes (as measured in MS-DOS), and is herein incorporated by reference in its entirety. This Sequence Listing consists of SEQ ID NOs: 1-75.

BACKGROUND

Obligate biotrophs are pathogens that establish intimate parasitic relationships with the host that they infect. Often times these relationships involve some kind of modification or reprogramming of the host cell(s) to accommodate the pathogen's subsequent growth and development. Plant-parasitic nematodes are obligate biotrophs that mainly attack the roots of plants and cause over $100 billion in crop damage annually (Sasser and Freckman, 1987). The most economically important plant-parasitic nematodes include the cyst forming nematodes of *Heterodera* and *Globodera* spp. These sedentary endoparasitic nematodes form intimate parasitic relationships with their hosts by penetrating the root as motile juveniles and migrating intracellularly until they reach the root vasculature where they select a single cell to initiate a feeding site. The initial syncytial cell undergoes developmental changes to re-differentiate into a syncytium to support subsequent nematode growth and development in later sedentary stages (Davis et al., 2004). The syncytium forms when neighboring cells fuse as a result of partial cell wall degradation (Endo, 1964), creating a permanent feeding cell that shares characteristics with plant cell types including meristematic cells, endosperm cells, transfer cells, and developing xylem (Mitchum et al., 2008). It has been proposed that the development and maintenance of the syncytium is dependent on the secretory effector proteins originating in the esophageal gland cells and delivered into the host root through the stylet of plant-parasitic nematodes (Davis et al., 2008). Recently, the cyst nematode secreted CLAVATA3/ESR(CLE)-like effector proteins have been shown to act as ligand mimics of plant CLE peptides, and are required for successful nematode infection (Wang et al., 2005; Patel et al., 2008; Lu et al., 2009; Wang et al., 2010a; Wang et al., 2010b).

Plant CLEs are small peptide ligands involved in regulating a population of specialized cells, called stem cells, which allow postembryonic organogenesis to occur (Simon and Stahl 2006). These stem cell pools can be found in the shoot apical meristem (SAM), the root apical meristem (RAM), and the vascular cambium. Whether or not these stems cells remain in an undifferentiated state or differentiate into new plant tissues is tightly controlled by CLE signaling pathways. In *Arabidopsis*, the population of stem cells which resides in the organizing center (OC) of the SAM is maintained by the expression of the transcription factor WUSCHEL (WUS) (Laux et al., 1996). Differentiation of those stems cells is promoted when the ligand-receptor pair of CLAVATA3 (CLV3), a small extracellular peptide ligand in the CLE family (Fletcher et al., 1999; Rojo et al., 2002), binds to CLV1 (Ogawa et al., 2008), a leucine-rich-repeat receptor like kinase (LRR-RLK) and downregulates WUS. Previous models have suggested that CLV1 forms a receptor complex with the LRR-receptor like protein (RLP) CLV2 (Clark et al., 1993; Kayes and Clark, 1998; Jeong et al., 1999; Trotochaud et al., 1999). More recently, it has been suggested that CLV1 acts in parallel or together with the heterodimer receptor complex of CLV2 and CORYNE (CRN) (Miwa et al., 2008; Muller, 2008; Bleckmann et al., 2010; Zhu et al., 2010). In comparison to the SAM, much less is known about the regulation of the stem cells in the RAM. The quiescent center (QC) is the equivalent to the OC in the SAM. However, there are significant differences between the OC and the QC. In contrast to the OC, the cells surrounding the QC are maintained as stem cells. In addition, stem cells are differentiated in both proximal and distal directions. This indicates that there is a signaling ligand involved in cell-cell communication to maintain the cells surrounding the QC as stem cells, and a signal to promote differentiation (Sarkar et al., 2007; Stahl et al., 2009). Previous reports have identified that the WUS-related homeobox 5 (WOX5) transcription factor is expressed in the QC of the RAM and is required to maintain the distal stem cell pool (Sarkar et al., 2007). Recently it has been shown that CLE40, the closest homolog to CLV3, is expressed in the columella cells and regulates expression of WOX5 (Stahl et al., 2009). The WOX5/CLE40 signaling pathway appears to only control the distal stem cell pool, indicating that other CLE signaling pathways may exist to control the proximal stem cell pool. Consistent with these observations, a number of *Arabidopsis* CLEs are expressed in roots (Sharma et al., 2003), and when some of these CLEs are overexpressed they have been shown to cause premature termination of the primary root meristem (Fiers et al., 2004; Strabala et al., 2006; Meng et al., 2010). In addition, the short root phenotype has been shown to be dependent on CLV2 and CRN perception (Casamitjana-Martinez et al., 2003; Fiers et al., 2005; Miwa et al., 2008; Meng et al., 2010). Taken together this indicates that a CLV-like and CLE-controlled signaling pathway can act in the root.

CLE-like genes from nematodes have been reported in the soybean cyst nematode (SCN, *Heterodera glycines*) (Wang et al., 2005; Wang et al., 2010a), the beet cyst nematode (BCN, *H. schachtii*) (Patel et al., 2008; Wang et al., 2010b), and the potato cyst nematode (PCN, *G. rostochiensis*) (Lu et al., 2009). BCN CLEs have been detected in the dorsal gland ampulla indicating they are likely secreted from the stylet into host cells (Patel et al., 2008). More recently, SCN CLEs have been shown to be secreted directly to the syncytial cytoplasm where the variable domain is thought to redirect the nematode CLE peptides to the apoplast (Wang et al., 2010a). These findings suggest that when delivered to the apoplast, nematode CLEs would be available to interact with extracellular receptors to function as ligand mimics of plant CLE signaling pathways. Overexpression studies have shown that nematode CLEs can trigger plant CLE signaling pathways (Wang et al., 2005; Lu et al., 2009; Wang et al., 2010a; Wang et al., 2010b), but the identity of the receptors and downstream signaling pathways that are activated to initiate developmental cascades required for the re-differentiation of root cells to form syncytia, are currently unknown.

US Patent Applications 20090077687 and 20090012029, identified nematode parasitism (effector) genes and described potential mechanisms to disrupt their expression and the function of their products to inhibit nematode parasitism of plants.

SUMMARY OF INVENTION

This invention provides for methods of inhibiting plant parasitic nematodes, methods of obtaining transgenic plants useful for inhibiting such nematodes, methods for expressing genes at plant parasitic nematode feeding sites, and transgenic plants that are resistant to plant parasitic nematodes. Also provided are RPK2 promoters that are useful for expressing genes in nematode feeding sites as well as transgenic plants and nematode resistant transgenic plants comprising the same. It is anticipated that the RPK2 promoters provided herewith can in certain embodiments be operably linked to genes that provide for inhibition of plant parasitic nematodes when introduced into transgenic plants and for plants that display such inhibition. Such genes that provide for inhibition of plant parasitic nematodes that can be used with the promoters provided herewith include, but are not limited to, genes disclosed in US Patent Application 20090012029, which is specifically incorporated herein by reference in its entirety.

In certain embodiments of the invention, a plant RPK2 gene is inhibited to reduce nematode infections in the plant. In certain embodiments of the invention, a plant CLV1, CLV2, and a plant RPK2 gene are all inhibited in parallel to reduce nematode infections in the plant. In any of the aforementioned embodiments, inhibition of the plant RPK2 gene may be limited to inhibition in roots or limited to the site of nematode infection by use of root-specific and/or nematode inducible promoters. In certain embodiments, the plant can be a soybean, potato, or tomato plant.

Also provided are promoters including, but not limited to a RPK2 promoter, that are useful for expressing genes in nematode feeding sites as well as transgenic plants and nematode resistant transgenic plants comprising the same. In certain embodiments, RPK2 promoters provided herewith can be operably linked to genes that provide for inhibition of plant parasitic nematodes when introduced into transgenic plants and for plants that display such inhibition. Such genes that provide for inhibition of plant parasitic nematodes that can be used with the promoters provided herewith include, but are not limited to, genes disclosed in US Patent Application 20090012029, which is specifically incorporated herein by reference in its entirety.

Method for inhibiting plant parasitic nematode damage to a plant comprising growing a plant comprising a mutation or a transgenes that provide for inhibition of a plant RECEPTOR-LIKE PROTEIN KINASE 2 (RPK2)-like gene in the presence of plant parasitic nematodes are thus provided. In certain embodiments of the methods, the plant further comprises one or more mutations or one or more transgenes that provide for inhibition of: i) at least one endogenous plant gene selected from the group consisting of a CLV 1-like gene, a CLAVATA2-like (CLV2-like) gene, a BAM 1-like gene, a BAM2-like gene, a CRN-like gene, a ACR4-like gene, an ER-like gene, and an ERL2-like gene; or, ii) for inhibition of a CLV1-like and a CLV2-like gene. In certain embodiments of any of the aforementioned methods, the methods can further comprise the step of harvesting a product of the plant. In certain embodiments of any of the aforementioned methods, the product is a leaf, stem, flower, seed, root, or tuber. In certain embodiments of any of the aforementioned methods, the yield and/or quality of the product is increased relative to a control plant that is grown in presence of plant parasitic nematodes and that lacks the mutations or the transgenes that provide for inhibition of the RPK2-like gene. In certain embodiments of any of the aforementioned methods, the transgene comprises: i) an siRNA directed against the plant gene; ii) an artificial microRNA targeting the plant gene; iii) a dominant negative form of the plant gene; iv) an antisense or sense form of the plant gene; or v) a genomic insertion that disrupts the plant gene. In certain embodiments of any of the aforementioned methods, the plant is a soybean, potato, or tomato plant.

Methods for obtaining a transgenic plant that exhibits resistance to a plant parasitic nematode comprising the steps of: a) introducing one or more transgenes that provide for; i) inhibition of an endogenous plant RPK2-like gene; ii) inhibition of a plant RPK2-like gene and for inhibition of at least one endogenous plant gene selected from the group consisting of a CLV1-like gene, a CLV2-like gene, a BAM1-like gene, a BAM2-like gene, a CRN-like gene, a ACR4-like gene, an ER-like gene, and an ERL2-like gene; or, iii) inhibition of a plant RPK2-like gene and for inhibition of a CLV1-like and a CLV2-like gene, into a plant cell; and b) selecting a transgenic plant obtained from the plant cell, wherein the selected transgenic plant comprises the transgene and exhibits resistance to a plant nematode are also provided.

Methods for obtaining a transgenic plant expressing a gene product at a plant parasitic nematode feeding site, comprising the steps of: a) introducing a transgene wherein a RPK2 promoter is operably linked to a gene encoding the gene product into a plant cell; and, b) selecting a transgenic plant obtained from the plant cell, wherein the selected transgenic plant comprises the transgene and exhibits expression of the gene product at the nematode feeding site are also provided. In certain embodiments of the aforementioned methods, the gene product is inhibitory to the plant parasitic nematode. In certain embodiments of the aforementioned methods, the inhibitory gene product is a siRNA or an amiRNA directed against a plant parasitic nematode gene.

In certain embodiments of any of the aforementioned methods, the plant nematode is a cyst nematode. In certain embodiments of the aforementioned methods, the cyst nematode is a *Heterodera* or *Globodera* spp. In certain embodiments of the aforementioned methods, the *Heterodera* spp. is *H. avenae, H. bifenestra, H. cajani. H carotae, H. ciceri, H. cruciferae, H. cynodontis, H. cyperi, H. davert, H. elachista, H. fii, H. galeopsidis, H. goettingiana, H. graminis, H. hordecalis, H. humuli, H. iri, H. latipons, H. lespedeza, H. leucilyma, H. longicaudata, H. mani, H. maydis, H. medicaginis, H. oryzae, H. oryzicola, H. sacchari, H. salixophila, H. schachtii, H. sorghii, H. trifoii, H. urticae, H. vigna,* or *H. zeae.* In certain embodiments of the aforementioned methods, the *Globodera* spp. is *G. achilleae, G. artemisiae, G. hypolysi, G. leptonepia, G. mali, G. pallida, G. rostochiensis, G. tabacum,* or *G. zeylandica.*

In certain embodiments of any of the aforementioned methods, the plant is a monocot or dicot plant, or is selected from the group consisting of a tobacco, cereal, sugar beet, cotton, fruit, fiber, oilseed, potato, rice, corn, soybean, vegetable, and wheat plant. In certain embodiments of any of the aforementioned methods, the RPK2-like gene, CLV1-like gene, the CLV2-like gene, BAM1-like gene, a BAM2-like gene, a CRN-like gene, a ACR4-like gene, an ER-like gene, or an ERL2-like gene is an ortholog of a corresponding *Arabidopsis*, Soybean, Tomato, or Potato RPK2, CLV1, CLV2, BAM1, BAM2, CRN, ACR4, ER, or ERL2 gene. In certain embodiments of the aforementioned methods, the endogenous plant RPK2-like gene, CLV1-like gene, CLV2-like gene, BAM1-like gene, BAM2-like gene, CRN-like gene, ACR4-like gene, ER-like gene, and ERL2-like gene is a potato StRPK2, StCLV1, StCLV2, StBAM1, StBAM2, StCRN, StACR4, StER, or StERL2 gene and the plant is a potato plant. In In certain embodiments of the aforementioned method, the plant parasitic nematode is *G. rostochiensis* or *G. pallida*.

In certain embodiments of any of the aforementioned methods, the endogenous plant RPK2-like gene, CLV1-like gene, a CLV2-like gene, a BAM1-like gene, a BAM2-like gene, a CRN-like gene, a ACR4-like gene, an ER-like gene, and/or ERL2-like gene is a soybean gene and the plant is a soybean plant. In certain embodiments of the aforementioned methods, plant parasitic nematode is *Heterodera glycines* or *H. schachtii*.

In certain embodiments of any of the aforementioned methods, the endogenous plant RPK2-like gene, CLV1-like gene, a CLV2-like gene, a BAM1-like gene, a BAM2-like gene, a CRN-like gene, a ACR4-like gene, an ER-like gene, and/or ERL2-like gene is a tomato gene and the plant is a tomato plant. In certain embodiments of the aforementioned methods, plant parasitic nematode is a *Heterodera* spp. or *Globodera* spp.

Also provided herein are plant parasitic nematode resistant transgenic plant comprising i) a transgene that provides for inhibition of a plant RPK2-like gene; or, ii) one or more transgenes that provide for inhibition of a plant RPK2-like gene and for at least one endogenous plant gene selected from the group consisting of a CLV1-like gene, a CLV2-like gene, a BAM1-like gene, a BAM2-like gene, a CRN-like gene, a ACR4-like gene, an ER-like gene, and an ERL2-like gene; or iii) inhibition of a plant RPK2-like gene and for inhibition of a CLV1-like and a CLV2-like gene. In certain embodiments, the transgene(s) comprises: i) an siRNA directed against the plant genes; ii) an artificial microRNA targeting the plant genes; iii) a dominant negative form of the plant genes; iv) an antisense or sense form of the plant genes; v) a genomic insertion that disrupts the plant genes; or any combination thereof. In certain embodiments, the plant RPK2-like, CLV1-like gene, CLV2-like gene, BAM1-like gene, a BAM2-like gene, CRN-like gene, ACR4-like gene, ER-like gene, and ERL2-like genes are soybean genes and the plant is a soybean plant. In certain embodiments, the plant RPK2-like gene is a potato StRPK2 gene, wherein the endogenous plant gene encoding a receptor for a nematode CLE is a potato StCLV1, StCLV2, StBAM1, StBAM2, StCRN, StACR4, StER, or StERL2 gene, and wherein the plant is a potato plant. In certain embodiments, the plant RPK2-like gene is a tomato SlRPK2 gene, wherein the endogenous plant gene encoding a receptor for a nematode CLE is a tomato SlCLV1, SlCLV2, SlBAM1, SlBAM2, SlCRN, SlACR4, SlER, or SlERL2 gene and the plant is a tomato plant. Also provided herein are the use of any of the aforementioned transgenic plants to control nematode infections of plants, obtain a plant product, and/or to obtain a processed plant product. Such processed plant products include, but are not limited to, a ground meal, a feed, a cake, and the like. In certain embodiments, such processed product would comprise a detectable amount of a transgene used to inhibit the PNCLEPRG. In certain embodiments, the plant product or processed plant product is a non-regenerable plant product or a non-regenerable processed plant product.

Also provided herein are plant parasitic nematode resistant transgenic plants comprising a transgene wherein a RPK2 promoter is operably linked to a gene encoding a gene product that is inhibitory to a plant parasitic nematode. In certain embodiments, the gene product is a siRNA or an amiRNA directed against a plant parasitic nematode gene. In certain embodiments, the RPK2 promoter comprises a promoter selected from the group consisting of an *Arabidopsis* RPK2 promoter, a soybean RPK2 promoter of SEQ ID NO:17 or SEQ ID NO:20, a potato RPK2 promoter of SEQ ID NO:24, a potato RPK2 promoter of SEQ ID NO:60, a tomato RPK2 promoter of SEQ ID NO:25, a variant thereof that has at least 70% sequence identity to the promoter, and a variant thereof comprising at least about 500 nucleotides of the nucleic acid sequence located 5' to the start codon or mRNA 5' cap site of the endogenous gene associated with the promoter. Also provided herein are the use of any of the aforementioned transgenic plants to control nematode infections of plants, obtain a plant product, and/or to obtain a processed plant product. Such processed plant products include, but are not limited to, a ground meal, a feed, a cake, and the like. In certain embodiments, such processed product would comprise a detectable amount of a transgene wherein a RPK2 promoter is operably linked to a gene encoding a gene product that is inhibitory to a plant parasitic nematode. In certain embodiments, the plant product or processed plant product is a non-regenerable plant product or a non-regenerable processed plant product.

Also provided herein is a recombinant DNA construct comprising a RPK2 promoter that is operably linked to a heterologous gene, wherein the RPK2 promoter comprises a promoter selected from the group consisting of a soybean RPK2 promoter of SEQ ID NO:17, a soybean RPK2 promoter of SEQ ID NO:20, a potato RPK2 promoter of SEQ ID NO:24, a potato RPK2 promoter of SEQ ID NO:60, a tomato RPK2 promoter of SEQ ID NO:25, a variant thereof that has at least 70%, 85%, 90%, 95%, or 99% sequence identity to the promoter, and a variant thereof comprising at least about 500 nucleotides of the nucleic acid sequence located 5' to the start codon or mRNA 5' cap site of the endogenous gene associated with the promoter. In certain embodiments, the RPK2 promoter is operably linked to a gene encoding a gene product that is inhibitory to a plant parasitic nematode.

DESCRIPTIONS OF THE DRAWINGS

FIG. 1. Effect of cyst nematode CLE peptides on receptor mutants.

(a) Average root length wild-type (Ler), clv2-1, and crn-1 seedlings grown for 9 days on media with or without the synthetic nematode dodecapeptide CLE motif. Data represent the mean±SE, n=10. (b)-(d) Representative roots tips of seedlings grown on media with or without synthetic CLE peptides for 10 days and visualized with differential interference microscopy. (b) No peptide, (c) Sensitive to peptide, and (d) Resistant to peptide. (Scale bar, 50 µm).

FIG. 2. CRN: GUS expression during nematode infection. (a)-(c) GUS expression in uninfected *Arabidopsis* root tips (a), middle of the root (b), and older part of the root towards the hypocotyl (c). (d)-(g) CRN: GUS expression in response to *H. schachtii*; early parasitic J2 (d), late parasitic J2 (e), J3 parasitic (f), J4 parasitic (g). Abbreviations: nematode, N; Syn, Syncytium. (Scale bar, 50 μm).

FIG. 3. Confocal images of CLV2:H2B-mCherry expression during nematode infection. (a) J2 parasitic with DIC. (b) J2 parasitic with mCherry fluorescence. (c) J3 parasitic with DIC. (d) J3 parasitic with mCherry fluorescence. Abbreviations: nematode, N; Syn, Syncytium. (Scale bars, 50 μm).

FIG. 4. Effect of clv2-1 and crn-1 mutant alleles on *H. schachtii* infection.

(a) J4 females were counted at 14 dpi and adult females were counted at 30 dpi. Data represent mean±SE, n=35 for Ler, 32 for crn-1, 34 for clv2-1, and 29 for crn-1 clv2-1. Data are representative of three independent experiments.

(b) Seedlings were grown on vertical square plates for 10 days and inoculated with 10 J2s/root. At 14 dpi, syncytia that fed only one nematode and appeared translucent were microscopically examined and their area was determined. Data represent mean±SE, n=11 for Ler and crn-1, 14 for clv2-1, and 12 for crn-1 clv2-1.

Asterisks indicate statistically significant differences compared to Ler by Student's t test (P<0.05)

FIG. 5. Response of wild-type (Utr) and sol2-1 seedlings to the synthetic 12-aa nematode CLE peptide. Average root length (Utr) and sol2-1 seedlings grown for 9 days on media with or without the synthetic nematode dodecapeptide CLE motif. Data represent the mean±SE, n=10.

Figure 6:
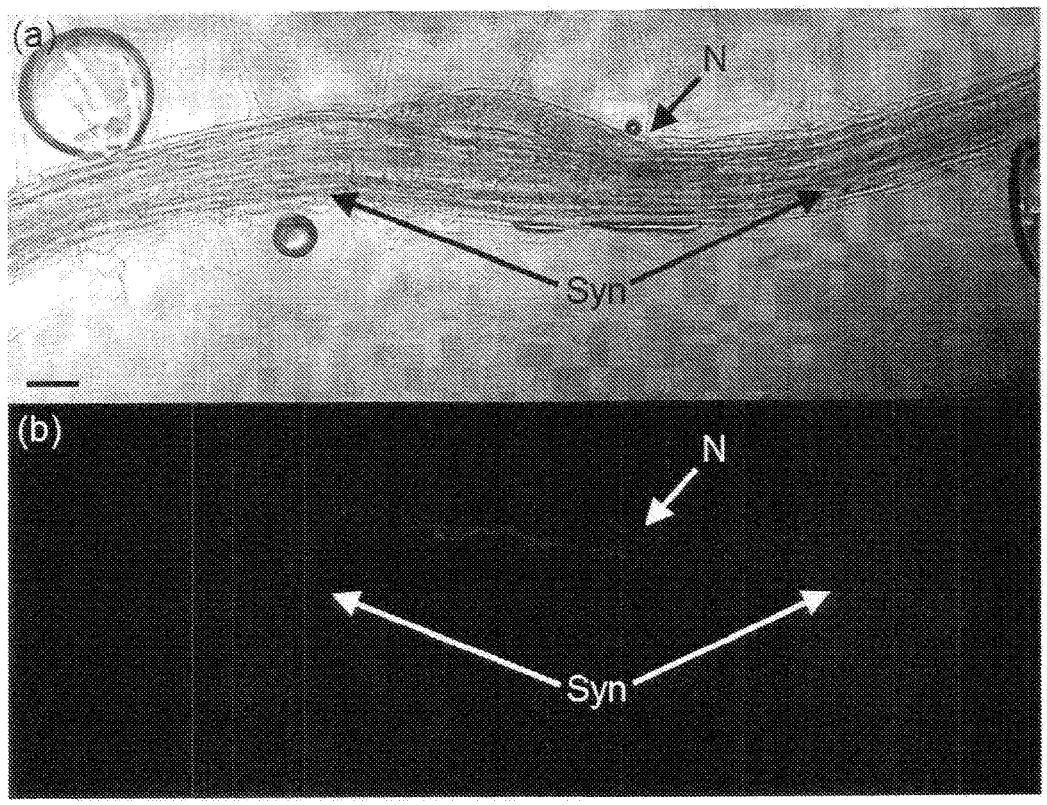

FIG. 6. Confocal images of nematode autofluorescence in wild-type roots. (a and b) Feeding site induced by a parasitic J2. (a) DIC image. (b) mCherry fluorescence. (Scale bar 50 μm).

FIG. 7. Effect of sol2-1 mutant allele on *Heterodera schachtii* infection. (a). J4 females were counted at 14 dpi and adult females were counted at 30 dpi. Data represent mean±SE, n=36, Asterisks indicate statistically significant differences compared to Ler by Student's t test (P<0.0001). Effect of sol2-1 mutant allele on size of syncytia (b). Seedlings were grown on vertical_square plates for 10 days and inoculated with 10 ppJ2s/root. At 14 dpi, syncytia that fed only one nematode and appeared translucent were microscopically examined and their area was determined. Data represent mean±SE, n=11 for Utr and n=9 for sol2-1. Asterisks indicate statistically significant differences compared to Ler by Student's t test (P<0.05).

FIG. 8. Effect of *Heterodera glycines* (HgCle) and *Heterodera schachtii* (HsCLE) nematode CLE peptides on receptor mutants. Seedlings were grown for 9 days on media with or without the synthetic nematode dodecapeptide CLE motif Data represent the mean±SE, n=10. (A) Average root length of wild-type (Ler), clv2-1, and cm-1. (B) Average root length of wild-type (Col-0) bam3-2, bam2, and bam1-3. (C) Average root length of wild-type (Utr) and so/201.

FIG. 9. Effect of *Globodera rostochiensis* (GrCLE) nematode CLE peptides on receptor mutants. Seedlings were grown for 9 days on media with or without the synthetic nematode dodecapeptide CLE motif. Data represent the mean±SE, n=10. Average root length of wild-type (Col-0), bam1-2, bam1-4, erl2-1, and clv2-1.

Figure 10:
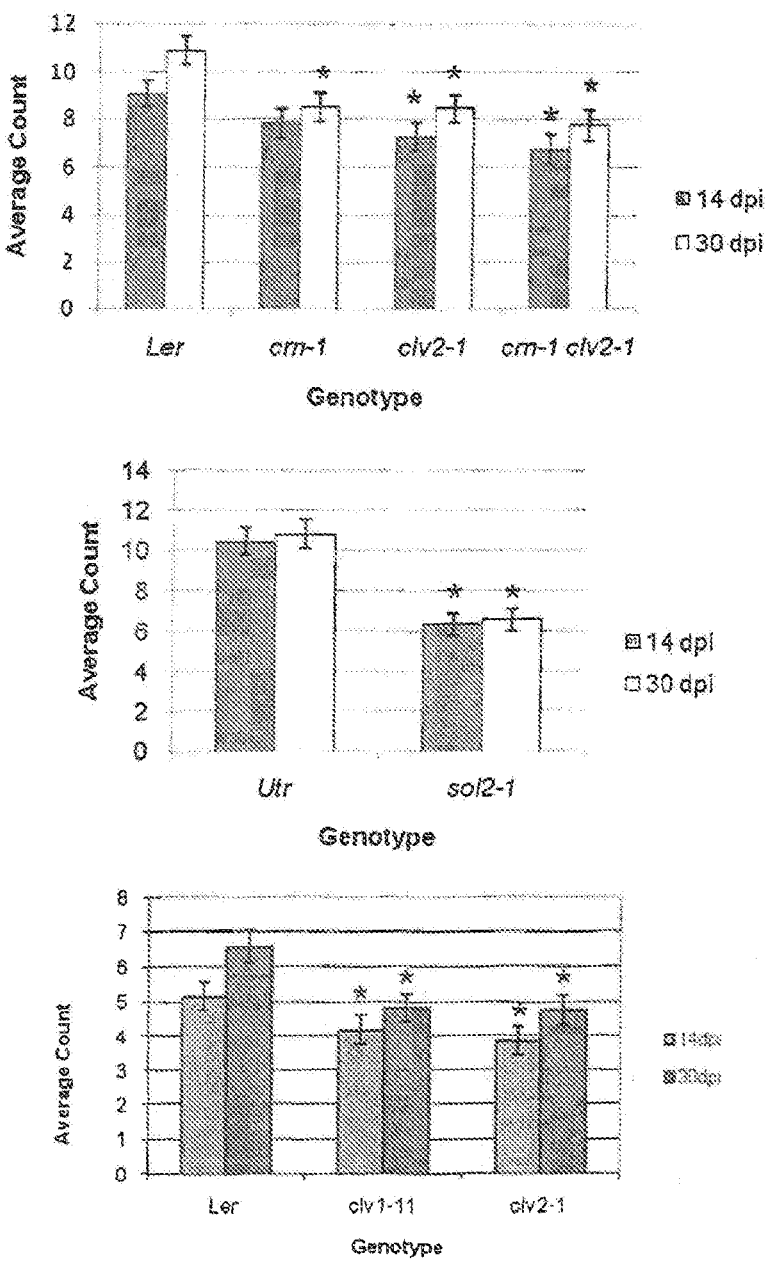

FIG. 10. Effect of receptor mutant alleles on *H. schachtii* infection. J4 females were counted at 14 dpi and adult females were counted at 30 dpi. Asterisks indicate statistically significant differences compared to wild-type by student's t test (P<0.05). Data represent mean±SE. Similar results were obtained from two additional biological replicates.

FIG. 11. CRN:GUS expression during nematode infection. (A-C) CRN::GUS expression in uninfected *Arabidopsis* root tips (A), middle of the root (B), and older part of the root towards the hypocotyl (C). (D-G) CRN::GUS expression in nematode-infected roots; (D) early J2p, (E) late J2p, (F) J3 and (G) J4 females.

FIG. 12. CLV2:GUS expression during nematode infection. (A-D) Confocal section of a nematode induced feeding site 4 dpi (A-B) and 8 dpi (A-B) expressing CLV2:H2B-mCherry which is shown in red.

FIG. 13. BAM1:GUS expression in *Arabidopsis* in response to nematode infection. (A) Uninfected root tip. (B-D) GUS expression in nematode infected roots; (B) Early parasitic J2, (C) Parasitic J3, and (D) Parasitic J4.

FIG. 14. Differential expression of candidate potato CLE receptor genes in *G. rostochiensis*-infected potato roots.

Figure 15:
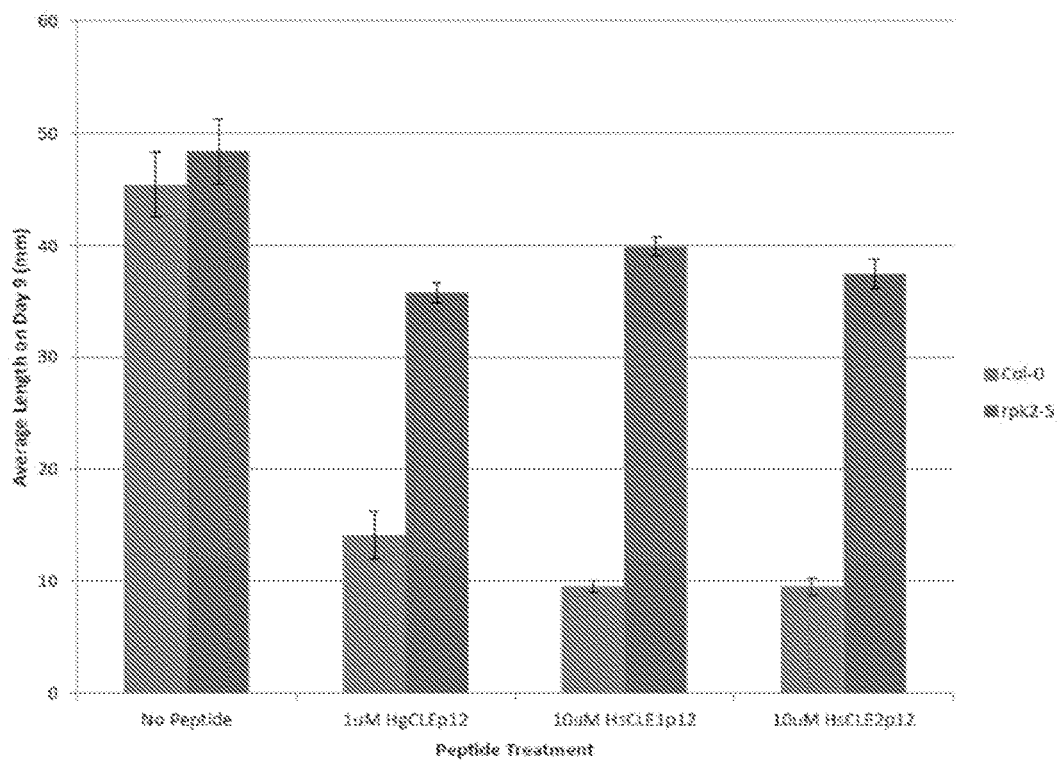

FIG. 15. Effect of nematode CLE peptides on rpk2-5 receptor mutants.

Figure 16:
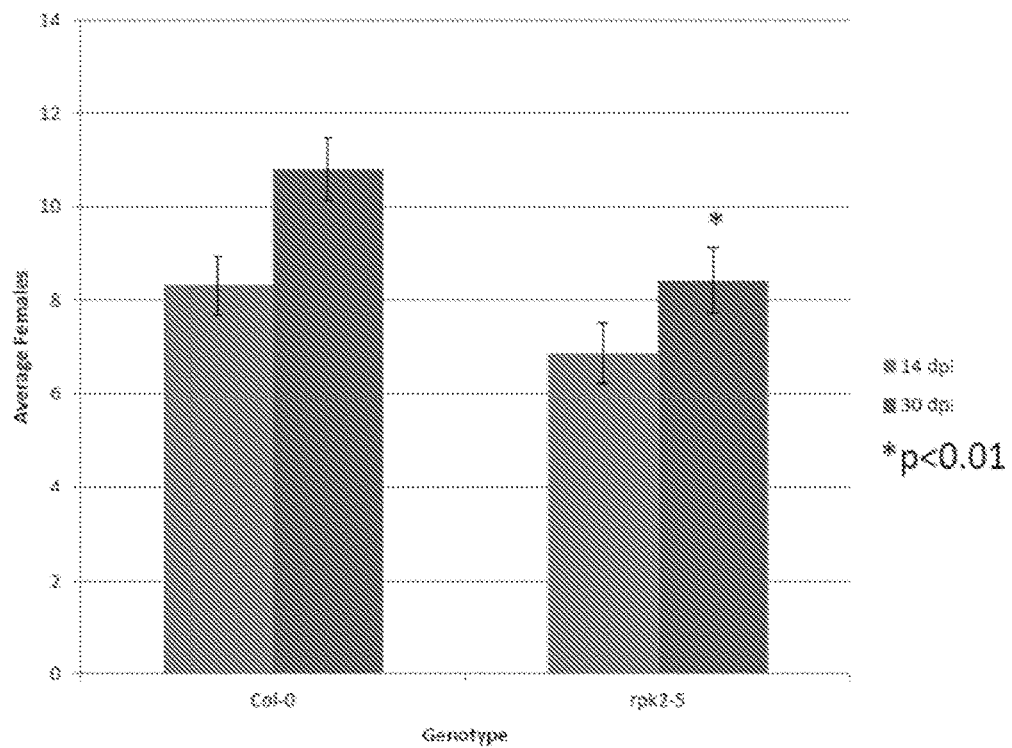

FIG. 16. Effect of rpk2-5 mutant alleles on *H. schachtii* infection in *Arabidopsis*.

Figure 17:
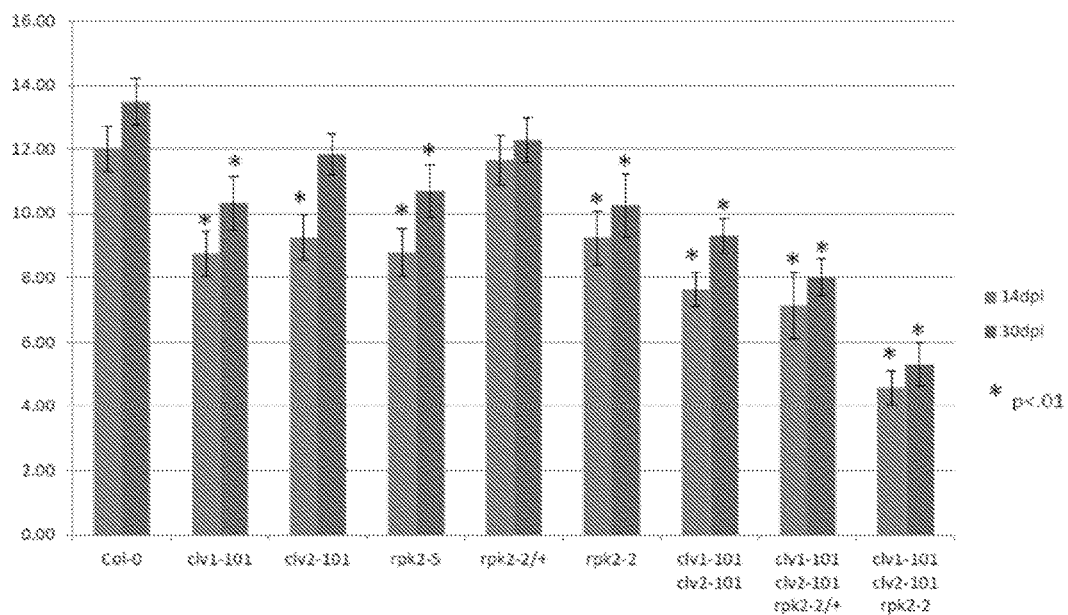

FIG. 17. Effect of clv1-101, clv2-101, rpk2-2, rpk2-5 mutant alleles and combinations thereof on *H. schachtii* infection in *Arabidopsis*.

FIG. 18. FIG. 18 shows the upregulation of a pRPK2 promoter fusion to a GFP gene in transgenic *Arabidopsis* infected with *H. schachtii* relative to mock infected control plants.

Figure 19:
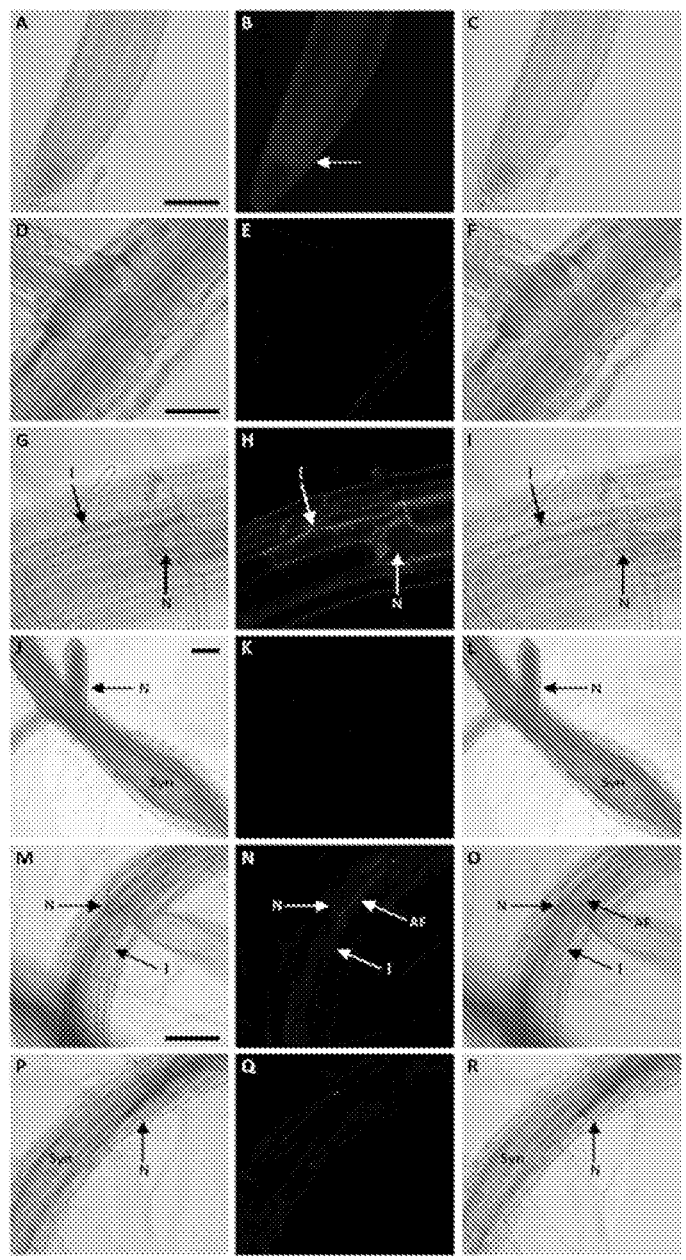

FIG. 19. Confocal images of pRPK2::RPK2:GFP expression during nematode infection. Abbreviations: nematode, N; initial syncytial cell, I; syncytium, Syn; autofluorescence, AF. (A) to (C) pRPK2::RPK2:GFP in an uninfected root tip showing protein accumulation in the RAM surrounding the QC (arrow) Scale bar, 50 μm. (D) to (F) pRPK2::RPK2:GFP in an uninfected root section representative of where nematodes initiate feeding showing no GFP autofluorescence. Scale bar, 25 μm. (G) to (I) pRPK2::RPK2:GFP in response to nematode infection 24-48 hpi showing some autofluorescence around the nematode head, and induction of RPK2 protein accumulation in the initial syncytial cell. See scale bar in (D). (J) to (L)$_p$RPK2::RPK2:GFP in response to J3 parasitic stage nematode 8 dpi showing no protein accumulation of RPK2 in the syncytium. Scale bar, 50 μm. (M) to (O) GFP autofluorescence in a wild-type root in response to nematode infection 24-48 hpi showing some autofluorescence around the head and/or migration path of the nematode. Scale bar, 50 μm. (P) to (R) GFP autofluorescence in a wild-type root in an established syncytium showing little to no autofluorescence. See scale bar in (M)

Figure 20:
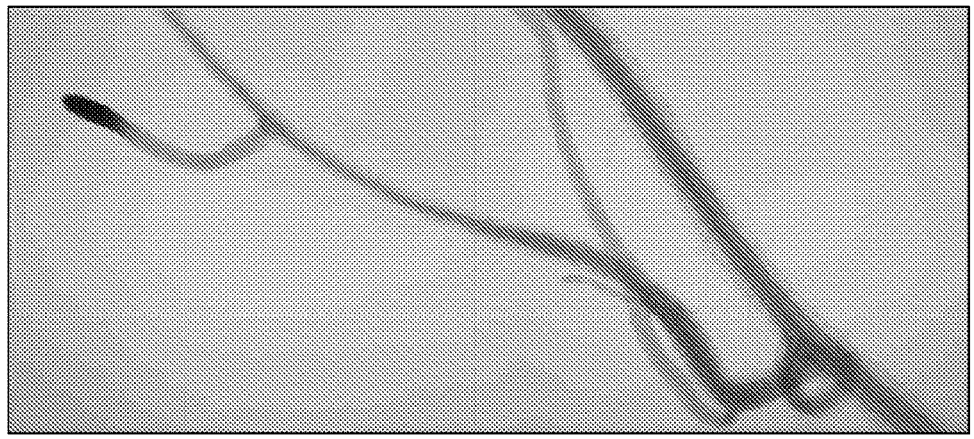

FIG. 20. FIG. 20 shows RPK2: GUS expression during nematode infection. In *Arabidopsis* roots RPK2 is normally restricted to root tips (rectangle). Upon nematode infection (arrow), RPK2 expression was observed in established feeding sites. Scale bar, 100 μm.

Figure 21:
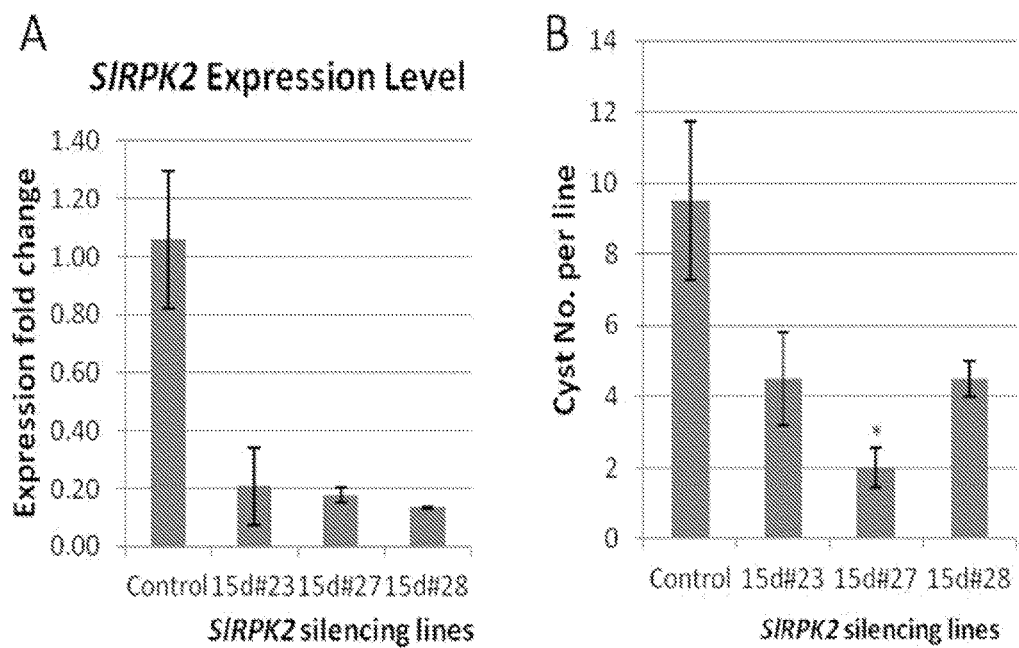

FIG. 21. Transgenic tomato lines with reduced SlRPK2 expression showed decreased susceptibility to *Globodera rostochiensis* infection. SlRPK2 expression was reduced in transgenic lines of 15d#23, 15d#27, and 15d#28 compared to the vector control line (A). Less numbers of nematode cysts were recovered from the three SlRPK2 knock-down lines compared to the vector control line, indicating that SlRPK2 is important for *G. rostochiensis* parasitism.

Figure 22:
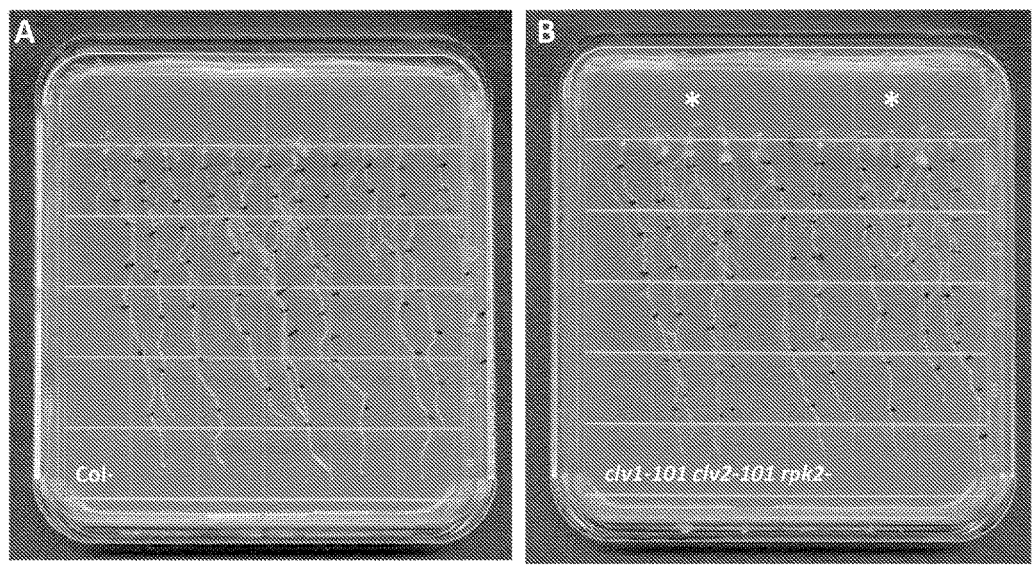

FIG. 22. Seedlings of wild-type Col-0 and clv1-101 clv2-101 rpk2-2/+ grown vertically for 10 days on modified Knop's media. Asterisks denote clv1-101 clv2-101 rpk2-2 triple mutants confirmed by genotyping. No gross root morphological or growth phenotypes were observed in the double and triple mutants.

DETAILED DESCRIPTION OF THE INVENTION

We describe the use of synthetic CLE peptides, nematode CLE overexpression lines, promoter-reporter lines, and nematode infection assays of receptor mutants to investigate a role for RPK2 in nematode CLE signaling. Our results indicate that the RPK2 signaling pathway is required for successful nematode infection and syncytium development.

Plant-parasitic cyst nematodes secrete CLAVATA3 (CLV3)/ESR(CLE)-like effector proteins. These proteins have been shown to act as ligand mimics of plant CLE peptides and are required for successful nematode infection; however, the receptors for nematode CLE-like peptides have not been identified. Here we demonstrate that RPK2, members of the receptor kinase family, are required for nematode CLE signaling. Exogenous peptide assays and overexpression of nematode CLEs in *Arabidopsis* showed that RPK2 are required for nematode CLE perception. In addition, promoter-reporter assays showed that both receptors are expressed in nematode-induced syncytia. Lastly, infection assays with receptor mutants revealed a decrease in both nematode infection and syncytia size. Taken together, our results indicate that nematode CLE perception by RPK2 is not only required for successful nematode infection, but is also involved in the formation or maintenance of nematode-induced syncytia. It is also demonstrated that the inhibitory effects of inhibiting the CLV1 and CLV2 genes are enhanced when the RPK2 gene is inhibited in parallel with the CLV1 and CLV2 genes.

Plant Nematode CLE Receptor Genes that can be Used to Obtain Nematode Resistant Plants and Methods of Use A variety of plant nematode CLE peptide receptor genes (hereinafter referred to as "PNCLEPRG") that provide for inhibition of plant parasitic nematode infections are provided herewith, along with associated methods of use, and plants comprising transgenes or mutations wherein expression of the PNCLEPRG are inhibited. Reduced expression of the PNCLEPRG in plants inhibits infection of the plants by nematodes. Such reductions in nematode infection result in improved plant yield and plant product quality.

Reductions in expression of the endogenous PNCLEPRG can be effected by any method that at least provides for reductions in the amount or activity of the PNCLEPRG at the site of nematode infection in the plant. Such sites of infection are commonly the plant roots, but can also comprise other plant parts such as tubers.

In certain embodiments, inhibition of PNCLEPRG expression in a plant can be effected by transgenes. Such transgenes include, but are not limited to, transgenes that: i) produce an siRNA directed against the PNCLEPRG; ii) produce an artificial microRNA targeting the PNCLEPRG; iii) produce a dominant negative form of the protein product of the PNCLEPRG; iv) produce an antisense or sense form of the PNCLEPRG; or v) comprise a genomic insertion that disrupts the endogenous PNCLEPRG. Exemplary vector systems that can provide for production of siRNA in plants include, but are not limited to, vectors disclosed by Dafny-Yelin, et al. (Plant Physiol., 2007, Vol. 145: 1272-1281), Wesley et al. 2001, Plant J. 27: 581-590, and Miki and Shimamoto, (2004) Plant Physiol. 138: 1903-1913. Vectors for producing an siRNA are also described in U.S. Pat. No. 6,635,805, incorporated herein by reference in its entirety. Exemplary vector systems that can provide for production of artificial miRNA in plants include, but are not limited to, vectors disclosed by Warthmann et al. (2008) PLoS ONE 3(3): e1829. doi:10.1371/journal.pone.0001829; and Alvarez et al. (2006) Plant Cell 18: 1134-1151. Vectors for effecting efficient inhibition of endogenous plant genes by expression of hairpin RNAs are also disclosed in U.S. Patent Application Nos. 20050164394, 20050160490, and 20040231016, each of which is incorporated herein by reference in their entirety. Exemplary dominant negative mutations that can provide for inhibition endogenous PNCLEPRG include, but are not limited to, mutations modeled after dominant negative mutations in other Leucine Rich Repeat-Receptor Like Kinase (LRR-RLK) proteins. In one embodiment, the dominant negative mutation can comprise a deletion or other loss-of-function mutation in the kinase domain. Such mutations have been disclosed for plant LRR-RLK proteins (Shpak et al., Plant Cell, Vol. 15, 1095-1110, 2003). Methods of identifying transgene insertions into specific genomic loci have also been disclosed. T-DNA of *Agrobacterium* is also an insertional mutagen that can be used as an agent to reduce expression of an endogenous PNCLEPRG. T-DNA mutagenesis has been described in *Arabidopsis* (Krysan et al., Plant Cell, 1999, 1: 2283-2290) and rice (Jeon et al., Plant J. June 2000; 22(6):561-70). Transposons such as those in the Ac/Ds (Activator-Disassociation) family and the Enhancer-inhibitor system can also be used to effect mutagenesis of an endogenous PNCLEPRG. Transposon mutagenesis schemes have been described (Speulman et al. Plant Cell, Vol. 11, 1853-1866, October 1999; Das, L., and Martienssen, R, 1995, Plant Cell 7:287-294).

Plants wherein expression of the endogenous PNCLEPRG is inhibited by a mutation and the use of such plants is also provided. Methods of identifying plants comprising mutations in PNCLEPRG include, but are not limited to, "TILLING" (Targeting Induced Local Lesions in Genomes). The TILLING technique comprises the induction of mutations across the genome followed by the identification and isolation of plants with mutations in desired genes (McCallum, *Plant Physiology*, 2000, Vol. 123, pp. 439-44).

PNCLEPRG target genes useful in the methods and plants of this invention include, but are not limited to, the RPK2, ACR4, CLV1, CLV2, CRN, BAM1, BAM2, ER, and ERL2 genes of *Arabidopsis* and the orthologous RPK2, ACR4, CLV1, CLV2, CRN, BAM1, BAM2, ER, and ERL2 genes of crop and ornamental plants subject to nematode infestation. Such orthologous genes are referred to herein as "RPK2-like, CR4-like, CLV1-like, CLV2-like, CRN-like, BAM1-like, BAM2-like, ER-like, and ERL2-like" genes. As used herein, the terms "orthologous" and "-like" (when appended to a gene) thus refer to genes that at least have a similar role in plant nematode CLE peptide signal transduction in their respective plant species of origin. In certain embodiments, the PNCLEPRG target genes are obtained from a plant that is a monocot or dicot plant, or that is a crop plant such as a tobacco, cereal, sugar beet, cotton, fruit, fiber, oilseed, potato, rice, corn, soybean, vegetable, and wheat plant. Exemplary vegetable plants include, but are not limited to, carrot, pepper, cucurbit, and tomato plants.

In certain embodiments, the PNCLEPRG target genes are derived from the plant that will be used (i.e. protected from nematode infection). However, a PNCLEPRG of a given plant species can be used in a distinct plant species when it has sufficient homology to the orthologous PNCLEPRG of a distinct plant species. In this context, "sufficient homology" is that amount of homology necessary to provide for transgene-mediated inhibition of the orthologous gene. For certain transgene-mediated gene inhibition methods, a PNCLEPRG sequence of about is 23 nucleotides or longer with least 80%, 85%, 90%, 95%, 98%, 99% or 100% identity to the target orthologous sequence can be used. In certain embodiments, a hairpin RNA may comprise a 5' sequence of roughly 19-24 nucleotides of sense strand target gene sequence with 100% identity followed by a spacer nucleotide of about 8-10 nucleotides followed by a sequence of roughly 19-24 nucleotides of antisense sequence that is capable of base pairing with the preceding sense strand sequence. In certain embodiments, a 19-24 base region of a PNCLEPRG that exhibits 100% identity over 19-24 nucleotides to an orthologous PNCLEPRG can also be used to inhibit that orthologous gene.

In certain embodiments, an *Arabidopsis* PNCLEPRG can be used to obtain nematode resistant plants, where the plants are *Arabidopsis* or other plants that comprise orthologous PNCLEPRGs that can be inhibited by the *Arabidopsis* PNCLEPRG. *Arabidopsis* PNCLEPRG include, but are not limited to, the RPK2, ACR4, CLV1, CLV2, CRN, BAM1, BAM2, ER, and ERL2 genes can in certain embodiments be used to control plant parasitic nematode infections of cruciferous plants that include, but are not limited to, arugula, cauliflower, cabbage, cress, bok choy, broccoli, radish, canola, turnip, watercress, and the like.

In certain embodiments, a potato PNCLEPRG can be used to obtain nematode resistant plants, where the plants are potato plants or other plants that comprise orthologous PNCLEPRGs that can be inhibited by the potato PNCLEPRG. Potato PNCLEPRG provided herein include, but are not limited to, StRPK2 (SEQ ID NO: 23), StCRN (SEQ ID NO:6), StBAM1 (SEQ ID NO:7), StBAM2 (SEQ ID NO:8), StER (SEQ ID NO:9), StCLV1 (SEQ ID NO:10), StCLV2 (SEQ ID NO:11), StACR4 (SEQ ID NO:12), and StERL2 (SEQ ID NO:13 and SEQ ID NO:63). Also provided herewith are related sequences with at least 70%, 80%, 85%, 90%, 95%, 97%, 98%, or 99% identity to StRPK2 (SEQ ID NO: 23), StCRN (SEQ ID NO:6), StBAM1 (SEQ ID NO:7), StBAM2 (SEQ ID NO:8), StER (SEQ ID NO:9), StCLV1 (SEQ ID NO:10), StCLV2 (SEQ ID NO:11), StACR4 (SEQ ID NO:12), and StERL2 (SEQ ID NO:13 and SEQ ID NO:63) as well as methods of using such sequences to control plant nematodes.

In certain embodiments, the use of such potato PNCLEPRGs and related sequences to control plant nematode, and particularly, plant cyst nematode infections, in solanaceous plants including, but not limited to, eggplant, tobacco, potato, and tomato is provided. In certain embodiments, the use of such potato PNCLEPRGs and related sequences to control *Globedera* sp. infections of potato plants is provided. In any of the aforementioned embodiments, inhibition of the plant PNCLEPRG can be limited to inhibition in roots or limited to inhibition at the site of nematode infection by use of root-specific and/or nematode inducible promoters, respectively.

In certain embodiments, a soybean PNCLEPRG can be used to obtain nematode resistant plants, where the plants are soybean plants or other plants that comprise orthologous PNCLEPRGs that can be inhibited by the soybean PNCLEPRG. Soybean PNCLEPRG provided herein include, but are not limited to, soybean RPK2 (SEQ ID NOs: 17, 18, 20, and 21), CRN (SEQ ID NOs: 48 and 51), BAM1 (SEQ ID NOs: 27 and 30), BAM2 (SEQ ID NOs: 33 and 36), CLV1 (SEQ ID NOs: 42 and 45), and CLV2 (SEQ ID NOs: 39 and 54) orthologs. Also provided herewith are related sequences with at least 70%, 80%, 85%, 90%, 95%, 97%, 98%, or 99% identity to the soybean RPK2 (SEQ ID NOs: 17, 18, 20, and 21), CRN (SEQ ID NOs: 48 and 51), BAM1 (SEQ ID NOs:27 and 30), BAM2 (SEQ ID NOs: 33 and 36), CLV1 (SEQ ID NOs:42 and 45), and CLV2 (SEQ ID NOs:39 and 54) orthologs as well as methods of using such sequences to control plant nematodes. In certain embodiments, the use of such soybean PNCLEPRGs and related sequences to control plant nematodes, and particularly, plant cyst nematode infections, in leguminous plants including, but not limited to, alfalfa, clover, peas, beans, lentils, lupins, mesquite, carob, soybean, and peanuts, is provided. In certain embodiments, the use of such soybean PNCLEPRGs and related sequences to control *Heterodera glycine* infections of soybean plants is provided. In any of the aforementioned embodiments, inhibition of the plant PNCLEPRG can be limited to inhibition in roots or limited to inhibition at the site of nematode infection by use of root-specific and/or nematode inducible promoters, respectively.

In certain embodiments, a tomato PNCLEPRG can be used to obtain nematode resistant plants, where the plants are tomato plants or other plants that comprise orthologous PNCLEPRGs that can be inhibited by the tomato PNCLEPRG. Tomato PNCLEPRG provided herein include, but are not limited to, slRPK2 (SEQ ID NO: 61). A useful portion of the slRPK2 gene that can be targeted with amiRNA or other techniques to provide for nematode resistance comprises the sequence of SEQ ID NO:62.

In certain embodiments of the invention, combinations of two or more a plant PNCLEPRG are inhibited in a plant to provide resistance to plant parasitic nematode infections. Plants wherein combinations of two or more PNCLEPRG selected from the group of RPK2, CRN, BAM1, BAM2, ER, CLV1, CLV2, ACR4, and ERL2 genes or orthologs thereof are inhibited can be used to provide resistance to plant parasitic nematode infections. Plants wherein combinations of an RPK2 gene and at least one PNCLEPRG selected from the group of CRN, BAM1, BAM2, ER, CLV1, CLV2, ACR4, and ERL2 genes or orthologs thereof are inhibited can be used to provide resistance to plant parasitic nematode infections are also provided. In certain embodiments, a plant RPK2-like, a plant CLV 1-like, and a plant CLV2-like gene are all inhibited in the same plant to reduce nematode infections in the plant. In certain embodiments of the invention, a plant RPK2-like and a plant CLV1-like or CLV2-like gene are both inhibited in the same plant to reduce nematode infections in the plant. In certain embodiments, combinations of two or more of a soybean RPK2 (SEQ ID NOs: 17, 18, 20, and 21), CRN (SEQ ID NOs: 48 and 51), BAM1 (SEQ ID NOs: 27 and 30), BAM2 (SEQ ID NOs: 33 and 36), CLV1 (SEQ ID NOs: 42 and 45), and CLV2 (SEQ ID NOs: 39 and 54) ortholog or a related sequence are inhibited in a soybean or other plant to provide resistance to plant parasitic nematode infections. In certain embodiments, combinations of a potato StRPK2 (SEQ ID NO: 23) gene and at least one of a potato StCRN (SEQ ID NO:6), StBAM1 (SEQ ID NO:7), StBAM2 (SEQ ID NO:8), StER (SEQ ID NO:9), StCLV1 (SEQ ID NO:10), StCLV2 (SEQ ID NO:11), StACR4 (SEQ ID NO:12), and/or StERL2 (SEQ ID NO:13 and SEQ ID NO: 63) gene are inhibited in a potato or other plant to provide resistance to plant parasitic nematode infections. In certain embodiments, combinations of a tomato S1RPK2 gene (SEQ ID NO:61) and at least one of a tomato S1CLV1 (SEQ ID NO:67), SlCLV2 (SEQ ID NO:64, 65, or 66), S1BAM1 (SEQ ID NO:68), S1BAM2 (SEQ ID NO:69), S1BAM3 (SEQ ID NO:70), S1CRN (SEQ ID NO:72 or 73), SlACR4 (SEQ ID NO:75), S1ER (SEQ ID NO:73), or S1ERL2 (SEQ ID NO:74) gene are inhibited in a tomato or other plant to provide resistance to plant parasitic nematode infections. In any of the aforementioned embodiments, inhibition of the plant PNCLEPRG can be limited to inhibition in roots or limited to inhibition at the site of nematode infection by use of root-specific and/or nematode inducible promoters, respectively.

In addition to nematode resistant plants, the instant invention also provides for parts of those plants and plant cells. Plant parts provided herein include, but are not limited to, seeds, tubers, roots, leaves, stalks, lint, and the like. Also provided herein are processed products of the nematode resistant plants. Such processed plant products include, but are not limited to, a ground meal, a feed, a cake, and the like. In certain embodiments, such processed product would comprise a detectable amount of a transgene used to inhibit the PNCLEPRG.

Promoters from Plant Nematode CLE Receptor Genes and Methods of Use

Promoters from PNCLEPRG and recombinant DNA constructs providing such promoters that are useful for expressing genes of interest in plant cells where the nematodes feed are provided. Such promoters are particularly useful for expressing nucleic acid and/or protein sequences that are inhibitory to plant parasitic nematodes. Particular advantages of the promoters include, but are not limited to, providing for expression of the operably linked nucleic acid sequences at nematode feeding sites within the plant while limiting expression of the gene in other parts of the plant where such expression is not required or desired. As used herein in the context of a promoter, the term "operably linked" means that a promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the protein desired.

A variety of recombinant DNA molecules comprising promoters of the invention that are operably linked to heterologous genes or nucleic acids of interest are provided. Heterologous genes or nucleic acids that provide for inhibition of plant parasitic nematodes can be operably linked to the PNCLEPRG promoters. In certain embodiments, the heterologous genes or nucleic acids of interest provide for inhibition of a plant parasitic nematode gene or function. Such plant parasitic nematode genes or functions include, but are not limited to, nematode genes that are essential or required for nematode viability or nematode genes involved in any aspect of plant host parasitism. In certain embodiments, the promoters are used to drive expression of heterologous genes or nucleic acids that are inhibitory to nematode genes disclosed in US Patent Application publication US20090012029, which discloses inhibitory nucleic acid specific for one or more cyst nematode esophageal gland cell proteins and which is incorporated herein by reference in its entirety.

In certain embodiments, the promoters are used to drive expression of genes or nucleic acids that inhibit formation and/or maintenance of the plant cells of the nematode feeding site. In certain embodiments, the promoters are thus used to: i) drive expression of heterologous genes or nucleic acids that are inhibitory to endogenous plant genes involved in formation and/or maintenance of the plant cells of the nematode feeding site; and/or, ii) drive expression of heterologous genes that comprise endogenous plant genes that are downregulated during the formation and/or maintenance of the plant cells of the nematode feeding site. Endogenous plant genes involved in formation and/or maintenance of the plant cells of the nematode feeding site that include, but are not limited to, genes involved in the cell wall architectural modifications during feeding site formation/maintenance, genes involved in sugar or carbohydrate, metal ion, and amino acid transport, and genes involved in plant phytohormone signaling and biosynthesis. A variety of soybean plant genes suitable for use with the promoters of the invention are disclosed in Ithal et al., Molec. Plant. Microb. Interact. Vol. 20, No. 5, 2007, pp. 510-525, incorporated herein by reference in its entirety.

PNCLEPRG promoters useful in the methods and plants of this invention include, but are not limited to, the RPK2 promoters of *Arabidopsis* and the orthologous RPK2 promoters of crop and ornamental plants subject to nematode infestation. Such orthologous promoters are referred to herein as "RPK2-like" promoters. As used herein, the terms "orthologous" and "-like" (when appended to a promoter) thus refer to promoters that at least have a similar role or expression pattern in plant nematode CLE peptide signal transduction in their respective plant species of origin. In certain embodiments, the PNCLEPRG promoters are obtained from a plant that is a monocot or dicot plant, or that is a crop plant such as a tobacco, cereal, sugar beet, cotton, fruit, fiber, oilseed, potato, rice, corn, soybean, vegetable, and wheat plant. Exemplary vegetable plants include, but are not limited to, carrot, pepper, cucurbit, and tomato plants.

In certain embodiments, a recombinant DNA construct comprising a PNCLEPRG promoter that is operably linked to a heterologous gene, or a plant, plant cell, plant part, or processed plant product comprising the same, is provided. In certain embodiments, the PNCLEPRG promoter comprises any one of an *Arabidopsis* RPK2 promoter (SEQ ID NO: 15), potato RPK2 promoter (SEQ ID NO: 24), a potato RPK2 promoter of SEQ ID NO:60, a tomato RPK2 promoter (SEQ ID NO: 25), or a soybean (SEQ ID NOs: 17 or 20) RPK2 promoter. Also provided are recombinant DNA constructs comprising a variant PNCLEPRG promoter that has at least 70%, 85%, 90%, 95%, or 99% sequence identity to any one of an *Arabidopsis* RPK2 promoter (SEQ ID NO: 15), potato RPK2 promoter (SEQ ID NO: 24), a potato RPK2 promoter of SEQ ID NO:60, a tomato RPK2 promoter (SEQ ID NO: 25), or a soybean (SEQ ID NO: 17 or 20) RPK2 promoter.

In certain embodiments, recombinant DNA constructs comprising a PNCLEPRG promoter comprising a deletion of about up to about 10, 50, 100, 200, 500, 700, 1000, or 1500 nucleotides of the 5' nucleotides of any one of an *Arabidopsis* RPK2 promoter (SEQ ID NO: 15), potato RPK2 promoter (SEQ ID NO: 24), a potato RPK2 promoter of SEQ ID NO:60, a tomato RPK2 promoter (SEQ ID NO: 25), or a soybean RPK2 (SEQ ID NO: 17 or 20) promoter is provided. Those skilled in the art will appreciate that promoter and 5'UT regions of PNCLEPRG provided herewith as genomic sequences in association with the coding regions can be dissociated from those coding regions and operably linked to heterologous nucleic acids or genes by transcriptional or translational fusions. In certain embodiments, a soybean (SEQ ID NO: 17 or 20) RPK2 promoter comprises the nucleic acid sequences located 5' to the start codon of those genomic sequences.

In certain embodiments, variants of any of the aforementioned PNCLEPRG promoters comprising at least about 300, 500, 800, 900, 1,000, 1,500, 2,500, or 3,000 nucleotides of the nucleic acid sequence located 5' to the start codon or located 5' to mRNA 5' cap site of the endogenous gene associated with the promoter are provided. Also provided are recombinant DNA constructs wherein any of the aforementioned RPK2 promoters is operably linked to a gene encoding a gene product that is inhibitory to a plant parasitic nematode.

In addition to nematode resistant plants comprising the recombinant DNA constructs of the aforementioned RPK2 promoters, the instant invention also provides for parts of those plants and plant cells. Plant parts provided herein include, but are not limited to, seeds, tubers, roots, leaves, stalks, lint, and the like. Also provided herein are processed products of the nematode resistant plants. Such processed products include, but are not limited to, a ground meal, a feed, a cake, and the like. In certain embodiments, such processed product would comprise a detectable amount of a recombinant DNA comprising a RPK2 promoter that is operably linked to a heterologous gene or is operably linked to a gene encoding a gene product that is inhibitory to a plant parasitic nematode.

EXAMPLES

The disclosed embodiments are merely representative of the invention, which may be embodied in various forms. Thus, specific structural and functional details disclosed herein are not to be interpreted as limiting.

Example 1. Experimental Procedures

Peptide Assays

*Arabidopsis* seeds were sterilized using the chlorine gas method (Wang et al., 2010b). Sterilized seeds were germinated on vertical plates in a growth chamber at 22° C. under long-day conditions (16 h light/8 h dark) containing synthetic peptides (Sigma-Genosys) as previously described (Wang et al., 2010b). The clv2-1 mutant in the Ler background (Koornneef et al., 1983) was obtained from the *Arabidopsis* Biological Resource Center. The crn-1 mutant in the Ler background (Muller, 2008) and the sol2-1 mutant in the Utr background (Miwa et al., 2008) have been described previously. The HgCLEp, HsCLE1p, and HsCLE2p peptides used in this study were as described (Wang et al., 2010b). Two days after germination, root length was marked each day for nine days. Plates were scanned using an Epson Perfection V200 PHOTO scanner and total root length was determined using Scion Image. Primary root tips of *Arabidopsis* were mounted on glass slides and visualized with an Olympus Vanox AHBT3 microscope equipped with Nomarski optics.

Overexpression in Mutant Backgrounds

The CLE gene sequences from the soybean cyst nematode (HgCLE2$^{ASP}$) and the beet cyst nematode (HsCLE1 and HsCLE2) used to generate the overexpression constructs were previously described (Wang et al., 2010a; Wang et al., 2010b). Constructs were transformed into the mutant backgrounds using the *Arabidopsis* floral dip method (Clough and Bent, 1998). Seeds from primary *Arabidopsis* transformants (T1) were selected on 0.5×MS media [MS basal nutrients salts (Caisson Laboratories), 2% sucrose, 0.8% Type A agar (Sigma), pH 5.7] containing 50 µg/mL timentin (GlaxoSmithKline) to control *Agrobacterium* contamination, and 50 µg/mL kanamycin and grown under the same conditions as above. Seedlings resistant to kanamycin were transplanted to soil seven days after germination. Two weeks after transplanting to soil the shoot phenotypes were observed.

Promoter-Reporter Lines

CRN:GUS has been previously described and characterized (Muller et al., 2008). To generate CLV2:H2B-mCherry, vector pMDC99 (Curtis and Grossniklaus, 2003) was modified by introducing the CDS of chimeric construct mCherry-H2B at the 3' site of the gateway cassette using the unique PacI restriction site to give pAB 149. To analyze the expression of CLV2 1252 bp of the 5' region and 9 bp of the CDS was amplified using the primers AB_CLV2_Pro_F (5' CACCAGACACAAAGCCCTTTCCATTGTC 3'; SEQ ID NO:1) and AB_CLV2_Pro_R (5' CTTTATCATAGCTCA-GAGGA 3'; SEQ ID NO:2)) to give a CACC-TOPO containing amplicon, which was cloned into pENTR/D-TOPO (Invitrogen™). This entry clone was used in a LR reaction with pAB 149 to give pAB 183 (CLV2:H2B-mCherry). Expression of CLV2 under the control of the endogenous promoter, using 1252 bp of the CLV2 5' region was sufficient to rescue the clv2-1 mutant in all isolated lines (N=20).

Nematode Infection of Promoter-Reporter Lines

The beet cyst nematode (BCN) *Heterodera schachtii* was propagated on greenhouse-grown sugar beets (*Beta vulgaris* cv Monohi). BCN eggs were isolated and hatched as previously described (Mitchum et al., 2004). After 2 days, second stage juveniles (J2) were collected and surfaced sterilized according to Wang et al. (2007) except 0.004% mercuric chloride, 0.004% sodium azide, and 0.002% Triton X-100 were used. Sterilized seeds were grown on modified Knop's medium (Brunschwig Chemie) (Sijmons et al., 1991). Ten days after germination seedlings were inoculated with 20 sterilized J2/root.

Histochemical β-glucuronidase (GUS) Assays

At the indicated time points, freshly excised CRN: GUS tissues were infiltrated with GUS substrate buffer (0.5 mM 5-bromo-4-chloro-3-indolyl glucuronide, 100 mM Tris, pH 7.0, 50 mM NaCl, 0.06% Triton X-100, 3 mM potassium ferricyanide) and incubated overnight at 37° C. (Jefferson et al., 1987). Stained roots were placed in glass Petri dishes and visualized with a Nikon Eclipse TS100 inverted microscope.

Confocal Microscopy

CLV2:H2B-mCherry seed was sterilized, grown, and inoculated with nematodes as described above. At the indicated time points, infected roots were mounted on glass slides and visualized with a 510 META confocal scanning microscope (Carl Zeiss, Thornwood, N.Y., USA) excited at 543 nm.

Infection Assay with Receptor Mutants

Sterilized receptor mutants were plated in 12-well Falcon tissue culture plates (BD Biosciences) containing modified Knop's medium with 0.8% Daishin agar in a randomized block design. Plants were grown at 24° C. with a 12 hour photoperiod. Fourteen days after germination, seedlings were inoculated with 200 surface-sterilized BCN J2. J4 females were counted at 14 days post-inoculation (dpi) and adult females were counted at 30 dpi. The average values were calculated and significant differences were determined by using Student's t test (P<0.05). To measure syncytia size, receptor mutants were germinated on modified Knop's medium in vertical square plates and inoculated at 10 days after germination with 10 surface-sterilized BCN J2. At 14 dpi, syncytia that were transparent and only fed upon by only one nematode were visualized with a Nikon Eclipse TS100 inverted microscope. Area of syncytia was measured using Adobe Photoshop CS5 and significant differences were determined by using Student's t test (P<0.05).
Results CLV2 and CRN are required for nematode CLE perception We have previously shown that exogenously applied 12-aa peptides corresponding to the CLE motifs of the SCN (HgCLEs) and the BCN (HsCLEs) CLEs can function as plant CLE peptide mimics causing termination of the primary root meristem in a concentration dependent manner (Wang et al., 2010b). In *Arabidopsis*, it has been shown that the short root phenotype caused by overexpression or exogenous application of some plant CLE peptides is dependent on CLV2 signaling (Fiers et al., 2005; Miwa et al., 2008; Muller, 2008; Meng et al., 2010). More recent evidence indicates that CLV2 forms a complex with CRN and can transmit the signal from CLV3 binding in a CLV1-independent manner (Miwa et al., 2008; Muller, 2008; Bleckmann et al., 2010; Zhu et al., 2010). To determine whether or not CLV2 and CRN might play a role in cyst nematode CLE perception we screened the *Arabidopsis* clv2-1 null mutant and the crn-1 amorphic allele for resistance to the HgCLE, HsCLE1, and HsCLE2 12-aa peptides. Seeds were grown on vertical plates in the absence of exogenous peptide or in the presence of 1 µM HgCLE or 10 µM of the HsCLEs and roots were measured 9 days after germination. Wild-type seedlings (Landsberg erecta [Ler]) had significantly shorter roots when grown on plates with any of the CLE peptides in comparison to the no peptide control (FIG. 1a). In contrast, clv2-1 and crn-1 root growth was relatively unimpaired in the presence of the different CLE peptides (FIG. 1a). The same observation was made with sol2-1, another mutant allele of CRN (Miwa et al., 2008) (FIG. S1). Previous reports have indicated that the short root phenotype can be attributed to a decrease in the number of meristematic cells (Fiers et al., 2005). Using Nomarski optics we confirmed that clv2-1 and crn-1 were insensitive to peptide application resulting in root meristems that were indistinguishable from the no peptide control (FIGS. 1b-d).

Nematode CLEs Function in Planta Through a CLV2- and CRN-Dependent Pathway

Overexpression of HgCLE2, HsCLE1, and HsCLE2 in wild-type *Arabidopsis* has been shown to cause wus-like phenotypes similar to other plant CLEs (Strabala et al., 2006; Meng et al., 2010; Wang et al., 2005; Wang et al., 2010a; Wang et al., 2010b). If CLV2 and/or CRN are involved in nematode CLE perception then we would expect the phenotypes to be diminished or abolished when overexpressed in clv2-1 and/or crn-1. Each of the nematode CLE genes was cloned into an overexpression vector and transformed into the mutant backgrounds. Transgenic seedlings in the T1 generation were screened and characterized in soil. In contrast to the overexpression phenotypes seen in wild-type *Arabidopsis* where a high percentage of wus-like phenotypes were observed (Wang et al., 2010a; Wang et al., 2010b), no wus-like phenotypes were observed when HgCLE2, HsCLE1, and HsCLE2 were overexpressed in clv2-1 or crn-1 (Table 1). These results demonstrate that mutations in CRN and CLV2 suppress nematode CLE overexpression phenotypes.

TABLE 1

Summary of nematode CLE overexpression phenotypes in clv2-1 and crn-1.

| | | T1 Shoot Phenotypes | | |
|---|---|---|---|---|
| Background | Construct | wus-like (%) | WT (%) | Total T1 (#) |
| clv2-1 | HgCLE2 | 0 | 100 | 96 |
| | HsCLE1 | 0 | 100 | 67 |
| | HsCLE2 | 0 | 100 | 28 |
| crn-1 | HgCLE2 | 0 | 100 | 85 |
| | HsCLE1 | 0 | 100 | 41 |
| | HsCLE2 | 0 | 100 | 37 |

Spatial and temporal relationship between CLV2, CRN, and nematode feeding sites.

Cyst nematodes enter the root near the zone of elongation, migrate through root cortical cells using their stylet to puncture through cell walls, and begin feeding from a single cell near the vascular cylinder. Once cyst nematodes initiate a feeding site the dorsal esophageal gland cell becomes active and the secreted CLE peptides are delivered to the host root cells (Wang et al., 2010a). In order for CLV2 and CRN to be able to perceive the nematode CLE as a ligand mimic they must be expressed in the correct spatial and temporal context.

Using a CRN:GUS transgene in *Arabidopsis*, CRN expression was previously shown to be expressed throughout the root including the vasculature where the nematode initiates feeding (FIGS. 2a-c; Muller et al., 2008). To confirm whether CRN is expressed in nematode feeding sites, transgenic *Arabidopsis* seedlings expressing CRN: GUS were infected with BCN and monitored during nematode development. GUS expression was detected in feeding sites as soon as early second-stage juveniles (J2) began to feed. (FIG. 2d). GUS expression reached its peak once nematodes reached late J2 parasitic stages, but remained detectable in the feeding sites of third stage juvenile (J3) parasitic nematodes (FIGS. 2e and f). By the time the nematodes reached the fourth stage juvenile (J4) life stage, GUS expression was either weak or absent in feeding sites (FIG. 2g).

Similar to CRN, CLV2 is expressed in many different vegetative tissues (Jeong et al., 1999). However little is known about the expression pattern of CLV2 in roots. To visualize CLV2 expression in roots and nematode feeding sites, mCherry was fused to the C-terminus of the *Arabidopsis* Histone 2B (H2B) gene and placed under the transcriptional control of the CLV2 promoter. The H2B protein has been shown to be a valid marker for chromatin organization in plant nuclei and has been used to describe development of the syncytial endosperm in *Arabidopsis* (Boisnard-Lorig et al., 2001). In uninfected roots, CLV2:H2B-mCherry fluorescence was detected throughout the root vasculature with the strongest expression detected in lateral root primordia and the zone of elongation extending down to the root apical meristem (A. Bleckmann and R. Simon, unpublished). Upon nematode infection, increased expression of CLV2:H2B-mCherry fluorescence was detected in the nuclei of syncytia fed upon by parasitic J2s (FIGS. 3a-b). At the J3 life stage CLV2:H2B-mCherry continued to be specifically expressed within feeding sites (FIGS. 3c-d). No fluorescence was detected in nuclei of syncytia fed upon by parasitic J2s in wild-type plants (FIGS. S2a-b).

Mutant alleles of CLV2 and CRN cause a reduction in nematode infection and defects in syncytial size.

By using an RNAi approach targeting nematode CLE genes, previous reports have shown that nematode CLE peptides are important for successful infection of host plants roots (Bakhetia et al., 2007; Patel et al., 2008). To determine if nematode CLE perception by CLV2 or CRN is required, root infection assays with nematodes were performed on the clv2-1 and crn-1 single mutants, and the crn-1 clv2-1 double mutant. According to Muller et al. (2008), crn-1 clv2-1 is morphologically indistinguishable from either of the single mutants, indicating that they act in the same pathway. The mutant alleles and the wild-type Ler were randomized in 12-well plates and grown on modified Knop's medium. Two weeks after germination seedlings were inoculated with infective J2s. J4 females were counted at 14 days post-inoculation (dpi) and adult females were counted at 30 dpi. Both the single and double mutants showed a statistically significant reduction in nematode infection with the exception of crn-1 at 14 dpi (FIG. 4a). At 30 dpi nematode infection was reduced by approximately 25% in all receptor mutants tested. A similar reduction in nematode infection across all mutant lines supports the hypothesis that CLV2 and CRN are acting in the same signaling pathway. Using sol2-1, we observed a 40% reduction in nematode infection (FIG. S3a). Since the establishment of a feeding site is required for nematode development and reproduction, the above observations motivated us to determine if there were any defects in syncytial size between the receptor mutants and wild-type. The mutant alleles and the wild-type Ler were grown on vertical square plates and inoculated with infective J2s. At 14 dpi, syncytia that were transparent and fed upon by only one nematode were measured. The average area of wild-type (Ler) syncytia was 1402±147 µm2 (FIG. 4b). In contrast, the syncytia of the receptor mutant alleles were reduced by approximately 40%. The average area of crn-1, clv2-1, and crn-1 clv2-1 was 797±89 µm2, 745±61 µm2, and 808±57 µm2, respectively (FIG. 4b). The same reduction in syncytia size was seen in the sol2-1 mutant allele (FIG. S3b).

Nematode CLE genes have been found to be upregulated in the dorsal esophageal gland cell at the onset of parasitism and remain on through the adult female life stage. CLE genes are turned off in adult males that are no longer feeding (Wang et al., 2005; Patel et al., 2008; Lu et al., 2009; Wang et al., 2010a). In SCN and BCN, immunolocalization studies have localized nematode CLEs along the dorsal gland extension and in the ampulla at the base of the nematode stylet indicating they are secreted into host plant roots via the stylet (Wang et al., 2005; Patel et al., 2008; Wang et al., 2010a). Consistent with these results an immunofluorescence study found that SCN CLEs are secreted directly into host plant root cytoplasm (Wang et al., 2010a). The variable domain of SCN CLEs is then able to redirect the proteins into the apoplast where they can act as plant CLE ligand mimics by interacting with extracellular membrane bound plant CLE receptors. However, thus far, host plant receptors that perceive nematode CLE signals have not been identified.

Many studies have used synthetic CLE peptides to help determine the roles that plant CLE peptides play in plant growth and development. Previous studies have shown that nematode CLE peptides cause root growth phenotypes similar to other plant CLEs (Lu et al., 2009; Wang et al., 2010a; Wang et al., 2010b). Other studies have also shown that these peptide screens can identify receptors that may be involved in certain CLE signaling pathways by utilizing receptor mutants (Fiers et al., 2005; Stahl et al., 2009; Meng et al., 2010). To identify potential nematode CLE receptors we tested plant CLE receptors implicated in CLE signaling in the RAM for a role in nematode CLE perception. In the root, exogenous peptide assays and overexpression studies have shown that CLV2 is required for proper proximal meristem function (Stahl et al., 2009; Meng et al., 2010). It has also been shown that a new member of the receptor kinase family, CRN, forms a heterodimer with CLV2 and is required for proper localization of the CLV2/CRN complex to the plasma membrane (Bleckmann et al., 2010; Zhu et al., 2010). In *Arabidopsis*, CRN has been found to be widely expressed in both shoot and root tissues suggesting dual roles in shoot and root development (Muller et al., 2008). CLV2 has been found to be expressed in shoot tissues (Jeong et al., 1999), but less is known about its expression in the root. In this paper we screened a null mutant allele of CLV2 and an amorphic mutant allele of CRN for resistance to the nematode CLE peptides. Both clv2-1 and crn-1 were resistant to HgCLEp, HsCLE1p, and HsCLE2p (FIGS. 1 and S1). Similar to synthetic peptide assays, overexpression of HgCLE, HsCLE1, and HsCLE2 in the clv2-1 and crn-1 mutant backgrounds abolished the wus-like phenotypes seen when the nematode CLEs are overexpressed in wild-type backgrounds (Wang et al., 2005; Wang et al., 2010a; Wang et al., 2010b). Taken together, the peptide assays and overexpression data indicate that CLV2 and CRN are required for nematode CLE perception.

In order to serve as a receptor complex for nematode CLE peptides, CLV2 and CRN would most likely need to be expressed in feeding cell initials as well as the developing feeding sites. With the use of promoter-reporter lines we confirmed that both CLV2 and CRN were expressed in nematode-induced feeding sites (FIGS. 2 and 3), consistent with a role in nematode CLE perception. It is also possible that nematode CLE receptors are expressed in the cells adjacent to the expanding syncytium. As the nematode CLEs are redirected to the host root apoplast, extracellular receptors of the adjacent cells that are primed for incorporation could trigger plant CLE signaling pathways needed to fully form the syncytium. In the future it will be interesting to more precisely localize the CLV2 and CRN proteins within syncytia using immunofluorescence techniques. This will aid in determining whether or not these nematode CLE receptors are expressed within the cell wall openings that occur during syncytium formation or if they are expressed on the outer plasma membrane of the syncytium and/or adjacent cells.

Previous reports have demonstrated that SCN and BCN CLEs are important for nematode parasitism by showing a reduction in nematode infection after knocking down CLE expression in the worm using RNAi approaches (Bakhetia et al., 2007; Patel et al., 2008). To directly test for a role of CLV2/CRN in nematode CLE perception we performed infection assays on the receptor mutants. We showed that a reduction in nematode infection occurs on the receptor mutants (FIGS. 4a and S2). Concurrently, we also saw a reduction in syncytium size in the receptor mutants (FIGS. 4b and S3). The fact that we saw a similar reduction in both nematode infection and syncytia size in both the single and double mutants is consistent with genetic and biochemical data that CLV2 and CRN are acting in the same pathway (Muller et al., 2008; Bleckmann et al., 2010; Zhu et al., 2010). These data indicate that not only is nematode CLE perception by CLV2 and CRN important for successful nematode infection, but demonstrates that CLE signaling also plays a role feeding cell formation.

The involvement of CRN in nematode CLE signaling also opens up the interesting possibility that nematode CLE signaling may be directly or indirectly suppressing host plant defense responses. It has been reported that in root tips of sol2-1, another mutant allele of CRN, plant disease resistance-related and stress responsive genes were upregulated (Miwa et al., 2008). Therefore, when nematode CLEs are secreted they could activate the CLV2/CRN signaling pathway leading to a suppression of plant disease resistance-related and plant stress responsive genes. One might speculate that the main target for nematode CLEs is a signaling pathway which allows developmental programming of root cells for syncytium formation to occur and that suppression of plant defense responses is just an added benefit to the nematode. Alternatively, the nematode may require suppression of plant defense responses through plant CLE signaling in order for the syncytium to form properly. Further studies will need to be performed to investigate this possibility. Several possibilities exist for why we only see a partial reduction in nematode numbers and syncytia size in the clv2-1 and crn-1 mutant backgrounds. First, besides CLEs, nematodes secrete many different effectors that likely play an important role in feeding cell formation (Wang et al., 2001; Gao et al., 2003). For example, when BCN CLEs were targeted with RNAi a similar partial reduction in nematode infection was observed (Patel et al., 2008), either as a consequence of limited reductions in transcript levels or an indication that the other effectors still active in the nematode allow infection to proceed. A second possibility for the partial reduction in the receptor mutants is that there could be multiple nematode CLE receptors. So far, the nematode CLEs reported belong to gene families (Lu et al., 2009; Wang et al., 2010a; Wang et al., 2010b). In addition, PCN CLEs have multiple CLE motifs that may be simultaneously processed to release different CLE peptides (Lu et al., 2009). This leaves the possibility that nematode CLE peptides may activate multiple plant CLE signaling pathways concurrently to function in an antagonistic or synergistic fashion as reported for plant CLEs (Whitford et al., 2008). The current plant CLV3 signaling pathway in the shoot indicates that there are parallel signaling pathways. Genetic evidence indicates that CLV1 acts in a separate pathway from the CLV2/CRN pathway (Muller et al., 2008). In support of the genetic data, recent reports using luciferase complementation assays and FRET analysis have shown that CLV1 forms a homodimer and that CLV2 and CRN form a heterodimer without CLV3 stimulation (Bleckmann et al., 2010; Zhu et al., 2010). These reports also found evidence for CLV1 interacting with the CLV2/CRN complex leading to the possibility that different signaling pathways could be activated depending on which receptor in the complex interacts with the CLE ligand (Bleckmann et al., 2010; Zhu et al., 2010). Thus it is possible that in the crn-1 clv2-1 double mutants, nematodes are still able to signal through other receptors in the roots. Unlike CLV2, which has a broad expression pattern in plants, CLV1 expression is thought to be restricted to the center of the SAM and its function is thought to be confined to stem cell specification in the shoot (Clark et al., 1997; Fletcher et al., 1999). Therefore, in order to utilize CLV1 as a receptor, nematodes would have to activate CLV1 expression in the roots. Recently, CLV1-related Barely Any Meristem (BAM) 1 and BAM2 have been shown to act redundantly in the SAM and are widely expressed throughout the plant, including root tissues (DeYoung et al., 2006; DeYoung and Clark, 2008). We have found that bam1 is also resistant to exogenous application of synthetic nematode CLE peptides (A. Replogle, S. Chen, X. Wang and M. G. Mitchum, unpublished data). Moreover, there are over 200 LRR-RLKs in Arabidopsis and only a few receptor-CLE ligand pairs have been identified (Shiu and Bleecker, 2001). Thus, further studies using a combination of mutants will need to be performed to investigate the possible involvement of other host plant receptors in nematode CLE signaling.

It is shown here that nematode CLE signaling through the CLV2/CRN receptor complex is important for proper syncytium formation and ultimately successful nematode infection. These findings open the door for identifying the downstream signaling components regulated by CLV2/CRN to uncover the role nematode CLE signaling plays in syncytium formation.

REFERENCES

Bakhetia, M., Urwin, P. E. and Atkinson, H. J. (2007) qPCR analysis and RNAi define pharyngeal gland cell-expressed genes of Heterodera glycines required for initial interactions with the host. Mol. Plant. Microbe Interact. 20, 306-312.

Bleckmann, A., Weidtkamp-Peters, S., Seidel, C. A. and Simon, R. (2010) Stem cell signaling in Arabidopsis requires CRN to localize CLV2 to the plasma membrane. Plant Physiol. 152, 166-176.

Boisnard-Lorig, C., Colon-Carmona, A., Bauch, M., Hodge, S., Doerner, P., Bancharel, E., Dumas, C., Haseloff, J. and Berger, F. (2001) Dynamic analyses of the expression of the HISTONE::YFP fusion protein in Arabidopsis show that syncytial endosperm is divided in mitotic domains. Plant Cell, 13, 495-509.

Casamitjana-Martinez, E., Hofhuis, H. F., Xu, J., Liu, C. M., Heidstra, R. and Scheres, B. (2003) Root-specific CLE19 overexpression and the sol1/2 suppressors implicate a CLV-like pathway in the control of Arabidopsis root meristem maintenance. Curr. Biol. 13, 1435-1441.

Clark, S. E., Running, M. P. and Meyerowitz, E. M. (1993) CLAVATA1, a regulator of meristem and flower development in Arabidopsis. Development, 119, 397-418.

Clark, S. E., Williams, R. W. and Meyerowitz, E. M. (1997) The CLAVATA1 gene encodes a putative receptor kinase that controls shoot and floral meristem size in Arabidopsis. Cell, 89, 575-585.

Clough, S. J. and Bent, A. F. (1998) Floral dip: a simplified method for Agrobacterium-mediated transformation of Arabidopsis thaliana. Plant J. 16, 735-743.

Curtis, M. D. and Grossniklaus, U. (2003) A gateway cloning vector set for high-throughput functional analysis of genes in planta. Plant Physiol. 133, 462-469.

Davis, E. L., Hussey, R. S, and Baum, T. J. (2004) Getting to the roots of parasitism by nematodes. Trends Parasitol. 20, 134-141.

Davis, E. L., Hussey, R. S., Mitchum, M. G. and Baum, T. J. (2008) Parasitism proteins in nematode-plant interactions. Curr. Opin. Plant Biol. 11, 360-366.

DeYoung, B. J., Bickle, K. L., Schrage, K. J., Muskett, P., Patel, K. and Clark, S. E. (2006) The CLAVATA1-related BAM1, BAM2 and BAM3 receptor kinase-like proteins are required for meristem function in Arabidopsis. Plant J. 45, 1-16.

Deyoung, B. J. and Clark, S. E. (2008) BAM receptors regulate stem cell specification and organ development through complex interactions with CLAVATA signaling. Genetics, 180, 895-904.

Endo, B. Y. (1964) Penetration and development of Heterodera glycines in soybean roots and related anatomical changes. Phytopathology, 54, 79-88.

Fiers, M., Hause, G., Boutilier, K., Casamitjana-Martinez, E., Weijers, D., Offring a, R., van der Geest, L., van Lookeren Campagne, M. and Liu, C. M. (2004) Misexpression of the CLV3/ESR-like gene CLE19 in *Arabidopsis* leads to a consumption of root meristem. *Gene*, 327, 37-49.

Fiers, M., Golemiec, E., Xu, J., van der Geest, L., Heidstra, R., Stiekema, W. and Liu, C. M. (2005) The 14-amino acid CLV3, CLE19, and CLE40 peptides trigger consumption of the root meristem in *Arabidopsis* through a CLAVATA2-dependent pathway. *Plant Cell*, 17, 2542-2553.

Fletcher, L. C., Brand, U., Running, M. P., Simon, R. and Meyerowitz, E. M. (1999) Signaling of cell fate decisions by CLAVATA3 in *Arabidopsis* shoot meristems. *Science*, 283, 1911-1914.

Gao, B., Allen, R., Maier, T., Davis, E. L., Baum, T. J. and Hussey, R. S. (2003) The parasitome of the phytonematode *Heterodera glycines*. *Mol. Plant. Microbe Interact.* 16, 720-726.

Jefferson, R. A., Kavanagh, T. A. and Bevan, M. W. (1987) GUS fusions: β-glucuronidase as a sensitive and versatile gene fusion marker in higher plants. *EMBO J*, 6, 3901-3907.

Jeong, S., Trotochaud, A. E. and Clark, S. E. (1999) The *Arabidopsis* CLAVATA2 gene encodes a receptor-like protein required for the stability of the CLAVATA1 receptor-like kinase. *Plant Cell*, 11, 1925-1934.

Kayes, J. M. and Clark, S. E. (1998) CLAVATA2, a regulator of meristem and organ development in *Arabidopsis*. *Development*, 125, 3843-3851.

Koornneef, M., Van Eden, J., Hanhart, C. J., Stam, P., Braaksma, F. J. and Feenstra, W. J. (1983) Linkage Map of *Arabidopsis thaliana*. *J. Hered.* 74, 265-272.

Laux, T., Mayer, K. F. X., Berger, J. and Jurgens, G. (1996) The WUSCHEL gene is required for shoot and floral meristem integrity in *Arabidopsis*. *Development*, 122, 87-96.

Lu, S. W., Chen, S., Wang, J., Yu, H., Chronis, D., Mitchum, M. G. and Wang, X. (2009) Structural and functional diversity of CLAVATA3/ESR(CLE)-like genes from the potato cyst nematode *Globodera rostochiensis*. *Mol. Plant. Microbe Interact.* 22, 1128-1142.

Meng, L., Ruth, K. C., Fletcher, J. C. and Feldman, L. (2010) The roles of different CLE domains in *Arabidopsis* CLE polypeptide activity and functional specificity. *Mol. Plant*, doi:10.1093/mp/ssq021

Mitchum, M. G., Sukno, S., Wang, X., Shani, Z., Tsabary, G., Shoseyov, 0. and Davis, E. L. (2004) The promoter of the *Arabidopsis thaliana Cell* endo-1,4-beta glucanase gene is differentially expressed in plant feeding cells induced by root-knot and cyst nematodes. *Mol. Plant. Pathol.* 5, 175-181.

Mitchum, M. G., Wang, X. H. and Davis, E. L. (2008) Diverse and conserved roles of CLE peptides. *Curr. Opin in Plant Biol.* 11, 75-81.

Miwa, H., Betsuyaku, S., Iwamoto, K., Kinoshita, A., Fukuda, H. and Sawa, S. (2008) The receptor-like kinase SOL2 mediates CLE signaling in *Arabidopsis*. *Plant Cell Physiol.* 49, 1752-1757.

Muller, R., Bleckmann, A. and Simon, R. (2008) The receptor kinase CORYNE of *Arabidopsis* transmits the stem cell-limiting signal CLAVATA3 independently of CLAVATA1. *Plant Cell*, 20, 934-946.

Ogawa, M., Shinohara, H., Sakagami, Y. and Matsubayashi, Y. (2008) *Arabidopsis* CLV3 peptide directly binds CLV1 ectodomain. *Science*, 319, 294.

Patel, N., Hamamouch, N., Chunying, L., Hussey, R., Mitchum, M., Baum, T., Wang, X. and Davis, E. L. (2008) Similarity and functional analyses of expressed parasitism genes in *Heterodera schachtii* and *Heterodera glycines*. *J. Nematol.* 40, 299-310.

Rojo, E., Sharma, V. K., Kovaleva, V., Raikhel, N. V. and Fletcher, J. C. (2002) CLV3 is localized to the extracellular space, where it activates the *Arabidopsis* CLAVATA stem cell signaling pathway. *Plant Cell*, 14, 969-977.

Sarkar, A. K., Luijten, M., Miyashima, S., Lenhard, M., Hashimoto, T., Nakajima, K., Scheres, B., Heidstra, R. and Laux, T. (2007) Conserved factors regulate signaling in *Arabidopsis thaliana* shoot and root stem cell organizers. *Nature*, 446, 811-814.

Sasser, J. N. and Freckman, D. W. (1987) A world perspective on Nematology: the role of the society. Vistas on nematology. Veech, J. A. and Dickson, D. W., Hyatssville, Md., USA: Society of Nematologists.

Sharma, V. K., Ramirez, J. and Fletcher, J. C. (2003) The *Arabidopsis* CLV3-like (CLE) genes are expressed in diverse tissues and encode secreted proteins. *Plant Mol. Biol.* 51, 415-425.

Shiu, S. H. and Bleecker, A. B. (2001) Plant receptor-like kinase gene family: diversity, function, and signaling. *Sci STKE*, 2001, re22.

Sijmons, P. C., Grundler, F. M. W., Von Mende, N., Burrows, P. R. and Wyss, U. (1991) *Arabidopsis thaliana* as a new model host for plant parasitic nematodes. *Plant J.* 1, 245-254.

Simon, R. and Stahl, T. (2006) Plant Cells CLEave Their Way to Differentiation. *Science*, 313, 773-774.

Stahl, Y., Wink, R. H., Ingram, G. C. and Simon, R. (2009) A signaling module controlling the stem cell niche in *Arabidopsis* root meristems. *Curr. Biol.* 19, 909-914.

Strabala, T. J., O'Donnell, P. J., Smit, A. M., Ampomah-Dwamena, C., Martin, E. J., Netzler, N., Nieuwenhuizen, N. J., Quinn, B. D., Foote, H. C. C. and Hudson, K. R. (2006) Gain-of-function phenotypes of many CLAVATA3/ESR genes, including four new family members, correlate with tandem variations in the conserved CLAVATA3/ESR domain. *Plant Physiol.* 140, 1331-1344.

Trotochaud, A. E., Hao, T., Wu, G., Yang, Z. and Clark, S. E. (1999) The CLAVATA1 receptor-like kinase requires CLAVATA3 for its assembly into a signaling complex that includes KAPP and a Rho-related protein. *Plant Cell*, 11, 393-406.

Wang, J., Lee, C., Replogle, A., Joshi, S., Korkin, D., Hussey, R., Baum, T. J., Davis, E. L., Wang, X. and Mitchum, M. G. (2010a) Dual roles for the variable domain in protein trafficking and host-specific recognition of *Heterodera glycines* CLE effector proteins. *New Phytol.* 10.1111/j.1469-8137.2010.03300.x Wang, J., Replogle, A., Hussey, R., Baum, T., Wang, X., Davis, E. L. and Mitchum, M. G. (2010b) Identification of potential host plant mimics of CLV3/ESR(CLE)-like peptides from the plant-parasitic nematode *Heterodera schachtii*. *Mol. Plant. Pathol.* (under review).

Wang, X., Allen, R., Ding, X., Goellner, M., Maier, T., de Boer, J. M., Baum, T. J., Hussey, R. S, and Davis, E. L. (2001) Signal peptide-selection of cDNA cloned directly from the esophageal gland cells of the soybean cyst nematode *Heterodera glycines*. *Mol. Plant Microbe Interact.* 14, 536-544.

Wang, X., Mitchum, M. G., Gao, B., Li, C., Diab, H., Baum, T. J., Hussey, R. S, and Davis, E. L. (2005) A parasitism gene from a plant-parasitic nematode with function similar to CLAVATA3/ESR(CLE) of *Arabidopsis thaliana*. *Mol. Plant. Pathol.* 6, 187-191.

Wang, X., Replogle, A., Davis, E. L. and Mitchum, M. G. (2007) The tobacco Ccl1 gene promoter is auxin-responsive and locally induced in nematode feeding sites of heterologous plants. *Mol. Plant. Pathol.* 8, 423-436.

Whitford, R., Fernandez, A., De Groodt, R., Ortega, E. and Hilson, P. (2008) Plant CLE peptides from two distinct functional classes synergistically induce division of vascular cells. *Proc. Natl. Acad. Sci. USA,* 105, 18625-18630.

Zhu, Y., Wang, Y., Li, R., Song, X., Wang, Q., Huang, S., Jin, J. B., Liu, C. M. and Lin, J. (2010) Analysis of interactions among the CLAVATA3 receptors reveals a direct interaction between CLAVATA2 and CORYNE in *Arabidopsis. Plant J.* 61, 223-233.

Example 2

Screening of plant CLE receptor mutants for resistance to nematode CLE peptides, overexpression of the nematode CLEs in the receptor mutant background, and infection assays of plant receptor mutants, has identified several receptors involved in nematode CLE peptide signaling. Plant receptor mutants, exhibiting resistance to exogenous treatment of nematode CLE peptides include CLAVATA2 (CLV2; At1g65380), CORYNE (CRN; At5g13290), BARELY ANY MERISTEM (BAM1; At5g65700), and ERECTA-LIKE2 (ERL2; At5g07180) (FIGS. 8 and 9). Overexpression of nematode CLEs in the clv2 and crn mutant background abolished all phenotypes (Table 2) that are observed when nematode CLEs are overexpressed in wild type plants (Wang et al., 2005; 2010: Lu et al., 2009). Additionally, nematode infection is significantly reduced on several of the receptor mutants including cly1, clv2, and crn (FIG. 10). Expression of receptors in nematode feeding cells was confirmed by infection of transgenic plants containing promoter-reporter fusions (FIGS. 11-13) and upregulation of candidate soybean and potato receptor genes in *H. glycines*-induced syncytia and *G. rostochiensis*-infected potato roots were revealed by microarray analysis of laser-captured syncytia (Table 2, 5% FDR; Ithal et al., 2007) and qRT-PCR analysis (FIG. 14). Thus, the disruption or modulation of the host plant receptor proteins that perceive the nematode CLE peptides can be used to develop a novel management tactic to reduce cyst nematode parasitism in crop plants including, but not limited to potato or soybean. Nematode control can thus be obtained by inhibiting rece -continued SEQ ID NO: 5
CORYNE (CRN; At5g13290)-promoter sequence;.

Example 4. Potato PNCLEPRG Gene Sequences

Sequences of various candidate potato nematode CLE receptor genes are provided. Sequences correspond to potato genes analyzed in FIG. 14 and as described in the claims and Example 2.
StCRN cDNA (From clone 4-3) SEQ ID NO: 6.
StBam1 SEQ ID NO: 7.
StBam2 (from clone 6-4) SEQ ID NO: 8.
StER (From 8-16) SEQ ID NO: 9.
StCLV1 (From clv1 clone 11-1 041710; SEQ ID NO: 10).
StCLV2 (From clv2-7; SEQ ID NO: 11).
StACR4 (From ACRO-3; SEQ ID NO: 12).
StERL2; SEQ ID NO: 13 and SEQ ID NO:63.

Example 5. Inhibition of Plant Responses to Nematode CLE Peptides and Inhibition of Nematode Infections by Inhibition of a Plant RPK2-2 or RPK2-5 Gene Mutant *Arabidopsis* plants homozygous for the recessive rpk2-5 mutation were exposed to various nematode CLE peptides and assayed for a response as described in Example 1. More specifically, *Arabidopsis* seeds were sterilized using the chlorine gas method (Wang et al., 2010b). Sterilized seeds were germinated on vertical plates in a growth chamber at 22° C. under long-day conditions (16 h light/8 h dark) containing synthetic peptides (Sigma-Genosys) as previously described (Wang et al., 2010b). The rpk2-5 mutation is in the RPK2 receptor-like kinase gene and has been described previously (Kinoshita et al., Development 137: 3911-3920, 2010). The HgCLEp, HsCLE1p, and HsCLE2p peptides used in this study were as described (Wang et al., 2010b). Two days after germination, root length was marked each day for nine days. Plates were scanned using an Epson Perfection V200 PHOTO scanner and total root length was determined using Scion Image. Primary root tips of *Arabidopsis* were mounted on glass slides and visualized with an Olympus Vanox AHBT3 microscope equipped with Nomarski optics. The rpk2-5 plants were resistant to 1 HgCLEp12, 10 µM HsCLE1p12, and 10 µM HsCLE2p12 (FIG. 15).

Mutant *Arabidopsis* plants i) homozygous for the recessive rpk2-5 mutation; ii) homozygous for the recessive rpk2-2 mutation; iii) homozygous for the recessive c/v/40/ mutation; iv) homozygous for the recessive clv2-101 mutation; v) homozygous for both the recessive clv1-10/and clv2-101 mutations; and vi) homozygous or heterozygous for the recessive rpk2-2 mutation in plants homozygous for both the recessive c/v/-101 and clv2-101 mutations were exposed to the cyst nematode *Heterodera schachtii* and assayed for a response as described in Example 1. More specifically, sterilized receptor mutants were plated in 12-well Falcon tissue culture plates (BD Biosciences) containing modified Knop's medium with 0.8% Daishin agar in a randomized block design. Plants were grown at 24° C. with a 12 hour photoperiod. Fourteen days after germination, seedlings were inoculated with 200 surface-sterilized BCN (Beet Cyst Nematodes; i.e. *Heterodera schachtii*) J2. J4 females were counted at 14 days post-inoculation (dpi) and adult females were counted at 30 dpi. The average values were calculated and significant differences were determined by using Student's t test (P<0.05). To measure syncytia size, receptor mutants were germinated on modified Knop's medium in vertical square plates and inoculated at 10 days after germination with 10 surface-sterilized BCN J2. At 14 dpi (days post infection) and 30 dpi, syncytia that were transparent and only fed upon by only one nematode were visualized with a Nikon Eclipse TS100 inverted microscope. Area of syncytia was measured using Adobe Photoshop CS5 and significant differences were determined by using Student's t test (P<0.05). The rpk2-5 mutant plants exhibited a 20% reduction in BCN infection relative to the Columbia wild type control plants that was statistically significant (FIG. 16). Both the rpk2-2 and rpk2-5 single mutants show a 20-25% reduction in nematode infection, similar to clv1, clv2, and crn-1 single mutants (FIG. 17). The clv1-101, clv2-101 double mutant shows a 30-35% reduction in nematode infection (FIG. 17). The most significant inhibition of nematode infection was obtained in the clv1-101, clv2-101, rpk2-2 triple mutant, which showed a 60% reduction in nematode infection (FIG. 17, clv1-101, clv2-101, rpk2-2 at right of bar graph).

Sequences of the *Arabidopsis* RPK2 gene and RPK2-like genes from other plants useful in practicing the methods and making the plants of this invention are provided below in Example 7.

Example 6. Use of a RPK2 Promoter to Drive Expression of Heterologous Genes in Nematode Infected Roots The promoter for the *Arabidopsis* RPK2 gene was operably linked to a Green Fluorescent Protein gene (GFP) and introduced into transgenic *Arabidopsis* plants. The transgenic plants were then infected with BCN and expression of the GFP observed. It was determined that the pRPK2 promoter can provide for nematode inducible expression in plant roots (FIG. 19). The sequence of the pRPK2 promoter is provided in Example 7.

Example 7. Sequences of Various RPK2 Genes and Promoters

Start and stop codons are underlined in the genomic and cDNA sequences provided. The soybean RPK2 promoters and 5'UT in the following table thus comprise the nucleic acid sequences located 5' to the start codon of those genomic sequences. It is further understood that sequences located 5' to the 5' cap site of the genomic clones also comprise promoter sequences.

TABLE 3

| SEQ ID | TYPE | SPECIES |
| --- | --- | --- |
| 14 | PROMOTER | *Arabidopsis thaliana* RPK2 Promoter (SEQ ID NO: 14) |
| 15 | Genomic | *Arabidopsis thaliana* RPK2 genomic and cDNA sequence (gene lacks introns) (SEQ ID NO: 15) |
| 16 | protein | *Arabidopsis thaliana* RPK2 protein (SEQ ID NO: 16) |
| 17 | | Soybean RPK2 ortholog Glyma13g06210 (genomic clone including about 5 kB of sequence that is located 5' to the ATG start codon; SEQ ID NO: 17) |
| 18 | cDNA | Soybean RPK2 ortholog Glyma13g06210 (cDNA; start and stop codons in bold and underlined (SEQ ID NO: 18) |

TABLE 3-continued

| SEQ ID | TYPE | SPECIES |
|---|---|---|
| 19 | protein | Soybean RPK2 ortholog Glyma13g06210 (protein; SEQ ID NO: 19) |
| 20 | genomic | Soybean RPK2 ortholog Glyma19g03710 (genomic clone with about 5 kB of sequence 5' to the start codon; SEQ ID NO: 20) |
| 21 | cDNA | Soybean RPK2 ortholog Glyma19g03710 (cDNA; SEQ ID NO: 21) |

Example 8. Soybean Nematode CLE Receptor Genes

Sequences of various candidate soybean nematode CLE receptor genes are provided. Inhibition of the expression of one or more of the following soybean genes in parallel with inhibition of a soybean RPK2 gene can be used to control of nematode infections in transgenic soybean plants. The soybean PNCLEPRG promoters and 5'UT in the following table thus comprise the nucleic acid sequences located 5' to the start codon of those genomic sequences.

TABLE 4

Soybean Genomic DNA sequences, cDNA sequences, and protein sequences
Sequence Description Glyma09g29840 gDNA and about 2.8 kb of promoter and 5'UT Sequence (SEQ ID NO: 26); Soybean BAM1-like gene;
Glyma09g29840 cDNA (SEQ ID NO: 27); Soybean BAM1-like gene;
Glyma09g29840 pprotein (SEQ ID NO: 28); Soybean BAM1-like gene;
Glyma16g34360 gDNA + about 2.7 kb promoter and 5'UT sequence (SEQ ID NO: 29) Soybean BAM1-like gene;
Glyma16g34360 cDNA (SEQ ID NO: 30)Soybean BAM1-like gene;
Glyma16g34360 protein (SEQ ID NO: 31) Soybean BAM1-like gene
Glyma01g40590 gDNA + about 5 kb upstream promoter and 5'UT sequence (start and stop codons underlined; SEQ ID NO: 32); Soybean BAM2-like gene
Glyma01g40590 cDNA(SEQ ID NO: 33); Soybean BAM2-like gene
Glyma01g40590 protein(SEQ ID NO: 34); Soybean BAM2-like gene
Glyma11g04700 gDNA + about 5 kb promoter and 5'UT sequence (SEQ ID NO: 35) Soybean BAM2-like gene
Glyma11g04700 cDNA (SEQ ID NO: 36) Soybean BAM2-like gene
Glyma11g04700 protein (SEQ ID NO: 37) Soybean BAM2-like gene
Glyma09g38720 gDNA + about 1 kb of promoter and 5'UT sequence (SEQ ID NO: 38) Soybean CLV2-like gene
Glyma09g38720 cDNA (SEQ ID NO: 39) Soybean CLV2-like gene
Glyma09g38720 protein (SEQ ID NO: 40) Soybean CLV2-like gene
GmNARK: Glyma12g04390 gDNA + 5 kb promoter and 5'UT (SEQ ID NO: 41) Soybean CLV1-like gene
GmNARK: Glyma12g04390 cDNA (SEQ ID NO: 42) Soybean CLV1-like gene
GmNARK: Glyma12g04390 protein (SEQ ID NO: 43) Soybean CLV1-like gene
GmCLV1A: Glyma11g12190 gDNA + about 1.6 kb promoter and 5'UT sequence (SEQ ID NO: 44) Soybean CLV1-like gene
GmCLV1A: Glyma11g12190 cDNA (SEQ ID NO: 45) Soybean CLV1-like gene
GmCLV1A: Glyma11g12190 protein (SEQ ID NO: 46) Soybean CLV1-like gene
Glyma18g51820 gDNA + about 3.7 kb promoter and 5'UT (SEQ ID NO: 47) Soybean CRN-like gene
Glyma18g51820 cDNA (SEQ ID NO: 48) Soybean CRN-like gene
Glyma18g51820 protein (SEQ ID NO: 49) Soybean CRN-like gene
Glyma08g28900 gDNA + about 2.8 kb promoter and 5'UT sequence (SEQ ID NO: 50) Soybean CRN-like gene
Glyma08g28900 cDNA (SEQ ID NO: 51) Soybean CRN-like gene
Glyma08g28900 protein (SEQ ID NO: 52) Soybean CRN-like gene
Glyma18g47610 gDNA + about 4 kb of promoter and 5'UT sequence (SEQ ID NO: 53) Soybean CLV2-like sequence
Glyma18g47610 cDNA (SEQ ID NO: 54) Soybean CLV2-like sequence
Glyma18g47610 protein (SEQ ID NO: 55) Soybean CLV2-like sequence

TABLE 3-continued

| SEQ ID | TYPE | SPECIES |
|---|---|---|
| 22 | protein | Soybean RPK2 ortholog Glyma19g03710 (protein; SEQ ID NO: 22) |
| 23 | | Potato RPK2 cDNA (SEQ ID NO: 23) |
| 24 | promoter | Potato StRPK2 promoter sequence (SEQ ID NO: 24) |
| 25 | promoter | Tomato RPK2 Promoter Sequence (SEQ ID NO: 25) |
| 60 | promoter | Potato StRPK2 promoter sequence (SEQ ID NO: 60) |
| 61 | cDNA | Tomato RPK2 coding sequence |

Example 9. Use of a RPK2 Promoter to Drive Expression of Heterologous Genes in Nematode Infected Roots The promoter for the potato RPK2 gene (SEQ ID NO: 23) was operably linked to a beta-glucuronidase gene (GUS) and introduced into transgenic potato plants. To prepare the promoter-GUS construct, a 2484-bp DNA fragment upstream of the start codon of the StRPK2 gene was amplified from potato cultivar Desiree using the primer set StRPK2_-2484F (5'-TCA TGA TAA GTG TGG GAA GTC G-3') (SEQ ID NO: 56) and StRPK2_-1R (5'-TAG TAA AAC CCC AAA AGG GTC CTC-3') (SEQ ID NO: 57) and cloned into the pGEM-T easy vector. After the sequence was verified, primers (5'-GCG TCG ACT CAT GAT AAG TGT GGG AAG-3' and 5'-CTG GTG GAT CCT AGT AAA ACC CCA AAA GG-3') (SEQ ID NOs: 58 and 59, respectively)

that incorporated the SalI and BamHI restriction sites were used to amplify the promoter sequence from the recombinant pGEM-T plasmid and the amplified PCR product was then cloned into the promoterless binary vector pBI101.2 at SalI and BamHI sites to create the pStRPK2-GUS construct. Potato cultivar Desiree was transformed using *Agrobacterium tumefaciens* strain LBA4404 harboring the pStRPK2-GUS construct. The obtained transgenic plants were then infected with PCN (*Globodera rostochiensis*) and expression of GUS was observed in nematode infection sites. It was determined that the StRPK2 promoter can provide for nematode inducible expression in potato roots. The sequence of the StRPK2 promoter is provided in the Sequence Listing as SEQ ID NO: 60.

Example 10. Suppression of SlRPK2 Expression by Artificial microRNA (amiRNA) in Transgenic Tomato Plants Resulted in Reduced Susceptibility to *G. rostochiensis* Infection The Web microRNA Designer (Schwab et al., 2006) was used to design a 21-mer amiRNA that targets a region in the in the open reading frame of SlRPK2 (NCBI accession no. AB645834). The SlRPK2-amiRNA sequence (5'-GGGAATCTACCTGTCTTTTAA-3'; SEQ ID NO:62) was introduced into the *Arabidopsis* miR319a precursor (Schwab et al., 2006) by overlapping PCR and the resultant SlRPK2-amiRNA precursor was then cloned into the binary vector pSMD that contains the Superpromoter (Lee et al., 2007). Tomato cultivar Moneymaker was transformed using *Agrobacterium tumefaciens* strain LBA4404 harboring the SlRPK2-amiRNA construct or the empty vector pSMD that was used as a control. qRT-PCR was used to evaluate SlRPK2 expression in obtained transgenic tomato lines in comparison with the vector control lines. Vector control lines and transgenic tomato lines confirmed to have a dramatic reduction in SlRPK2 expression were further tested for *G. rostochiensis* infection (FIG. 21). SlRPK2 expression was reduced in transgenic lines of 15d#23, 15d#27, and 15d#28 compared to the vector control line (FIG. 21A). Reduced numbers of nematode cysts were recovered from the three SlRPK2 knock-down lines compared to the vector control line, indicating that SlRPK2 can be used to control *G. rostochiensis* parasitism (FIG. 21B).

The SlRPK2 coding (cDNA) sequence is provided in the sequence listing (SEQ ID NO: 61; NCBI accession no. AB645834).

REFERENCES

1. Schwab, R. et al., (2006). Highly specific gene silencing by artificial microRNAs in *Arabidopsis*. Plant Cell 18:1121-1133.
2. Lee, L.-Y. et al., (2007). Novel plant transformation vectors containing the Superpromoter. Plant Physiology 145:1294-1300.

Example 11. Tomato Nematode CLE Receptor Genes

Sequences of various tomato nematode CLE receptor genes are provided. Inhibition of the expression of one or more of the following tomato genes in parallel with inhibition of a tomato RPK2 gene can be used to control of nematode infections in transgenic tomato plants.

TABLE 5

Tomato cDNA sequences
Sequence Description

Tomato CLV2 cDNA: >SlCLV2|Solyc04g056640.1.1 (SEQ ID NO: 64)
Tomato CLV2 cDNA: >SlCLV2|gi|339790476|dbj|AB645830.1| *Solanum lycopersicum* SlpCLV2 mRNA for leucine rich repeat receptor like protein CLAVATA2, complete cds, cultivar: Pritz (SEQ ID NO: 65)
Tomato CLV2 cDNA: >SlCLV2|gi|339790470|dbj|AB645827.1| *Solanum lycopersicum* SlmCLV2 mRNA for leucine rich repeat receptor like protein CLAVATA2, complete cds, cultivar: Micro-Tom (SEQ ID NO: 66)
Tomato CLV1 cDNA: >SlCLV1|Solyc04g081590.1.1 (SEQ ID NO: 67)
Tomato BAM1 cDNA: >SlBAM1|Solyc02g091840.1.1 (SEQ ID NO: 68)
Tomato BAM2 cDNA: >SlBAM2|gi|339790462|dbj|AB645823.1| *Solanum lycopersicum* SlmCLV1 mRNA for leucine rich repeat receptor protein kinase CLAVATA1, complete cds, cultivar: Micro-Tom (SEQ ID NO: 69)
Tomato BAM3 cDNA: >SlBAM3|Solyc01g080770.1.1 (SEQ ID NO: 70)
Tomato CRN cDNA: >SlCRN|Solyc05g023760.1.1 (SEQ ID NO: 71)
Tomato CRN cDNA: >SlCRN|gi|339790486|dbj|AB645835.1| *Solanum lycopersicum* SlmSOL2 mRNA for receptor like protein kinase SOL2, complete cds, cultivar: Micro-Tom (SEQ ID NO: 72)
Tomato ER cDNA: >SlER|Solyc08g061560.1.1 (SEQ ID NO: 73)
Tomato ERL2 cDNA: >SlERL2|Solyc03g007050.1.1 (SEQ ID NO: 74)
Tomato ACR4 cDNA: >SlACR4|Solyc11g044940.1.1 (SEQ ID NO: 75)

Example 12. Seedling Root Growth in *Arabidopsis*. clv1-101 clv2-101 rpk2-2 Triple Mutants Seedlings of wild-type Col-0 and clv1-101 clv2-101 rpk2-2/+ were grown vertically for 10 days on modified Knop's media (FIG. 22; asterisks denote clv1-101 clv2-101 rpk2-2 triple mutants confirmed by genotyping). No gross root morphological or growth phenotypes were observed in the double and triple mutants.

What is claimed is:

1. A method for inhibiting plant parasitic nematode damage to a soybean plant, said method comprising:
   (1) reducing the expression of an endogenous plant RECEPTOR-LIKE PROTEIN KINASE 2 (RPK2)-like gene by expressing in said soybean plant RNAi to silence said RPK2-like gene, wherein said RPK2-like gene is set forth in SEQ ID NO:17, SEQ ID NO: 18, SEQ ID NO: 20 or SEQ ID NO: 21; and
   (2) growing said soybean plant expressing said RNAi, thereby inhibiting plant parasitic nematode damage to said soybean plant.

2. The method of claim 1, further comprising reducing the expression of an endogenous CLAVATA2 (CLV2) gene by introducing into said soybean plant one or more non-natural mutations in said CLV2 gene, or by expressing in said soybean plant RNAi to silence said CLV2 gene.

3. The method of claim 1, further comprising the step of harvesting a product of said soybean plant.

4. The method of claim 3, wherein said product is a leaf, stem, flower, seed, root, or tuber.

5. The method of claim 3, wherein the yield and/or quality of said product is increased relative to a control plant not expressing said RNAi.

6. The method of claim 1, wherein said plant parasitic nematode is a cyst nematode.

7. The method of claim 6, wherein said cyst nematode is a *Heterodera* spp.

8. The method of claim 6, wherein said plant parasitic nematode is *Heterodera glycines*.

9. A genetically modified nematode resistant soybean plant produced by the method of claim 1, wherein said soybean plant expresses said RNAi.

* * * * *

SEQUENCE LISTING

<160> NUMBER OF SEQ ID NOS: 75

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
caccagacac aaagcccttt ccattgtc                                              28

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctttatcata gctcagagga                                                       20

<210> SEQ ID NO 3
<211> LENGTH: 2000
<212> TYPE: DNA
<213> ORGANISM: Arabidopsis thaliana

<400> SEQUENCE: 3
tctcattaag cacctacttc ccacatcttt cttaaagttt cttacataaa gctcccttca           60
cacgtgctta ccaaatcaga ttgtcaataa ttcttgctca ataattttc gaaatttatt           120 tgaatttatc taataaaaat acattgtttg agtatgatat tttgcttaag aaggttgatt          180
attctcccta tcaaagtcta aaaagaagat tacaaaacaa ttgtatggtt aaattcatat          240
aaatttgtga ctagtatttt aatatttaca tatatacaaa tacttataga tgaaacgaga          300
atgcagaaat gattatagat agatcagtga cagtgaactg tagcaaccgg caaagaaacc          360
tcgttagctg gacacacgat tacgatcatg ccccagtct cctctgtcca gacggctgca           420
ttaataacaa cgagctagag ggtgttttcg tcttttcgat acttatccca aaaccgacaa          480
tctctggttt ggactcgaag gctgatttgg tcaattcata gcaaccgaac gagcagtcca         540
ttcaagtcca aagagctcct tagtggtaaa agatgtaatt acgtagatgt tccatggtca         600
agaatgtatt cagtcaaaat aaatatttga ccaaaacttt cggttaattt cctaccacca         660
gcaaaattat aacttttcct aataattatc aatcattttc aatctctttt aattttcttt          720 ttcactttt tttattaatt aaagtcaatt cacactatac aaaaagaagg aagtctaaat           780
atttttttac tttcatgttg cttttctaac ttttatattt tgctcttctc aacagatttt         840
gctggttttt gtattagaaa tattattatg tttccagaaa tgaatttttt atatgtcgtc         900
tggattcgta tatatatatt ggaaagtgaa attaattcat ttgatttttt tctttgatat         960
atcgaccaaa tcaaataaat acgaccccat tgtggcattg ttaatgcaaa aaggcacaag         1020
tacaaaaaaa acataataat tcactatttt atttacagac acatgggccc aattcatacg         1080
gcccaattac cataaacctc tcttttaaag agtgggttcc acagtggtaa acttttgac          1140 tatccattgg aatgattgca tctggaccgt tcatctacat taattattgg gttttttcgc         1200
tttaaagcat caattaactt attacgtata ggattagatt accaataacg atcttttag          1260 cttttgtcgt tttccgataa aaccatacga ttaagaatat gacctcttgt atcttttgag          1320
ggattttagt taatctttct acatttattt tgttggatgc tcatacaatt atcctgtgtc         1380

```
tctcaaaata aaacaaaaat tactctattt attagtacat tacacatgat tatttagaaa    1440
atgtatattg tggtcatatg aaatgagaaa ttaaaggaaa tttgtcaata cttgagaaca    1500
tcaccattca aatgtttcaa gaacaacatg actccaaaac aaaataaatg aaccttcccc    1560
taataatagt atattctcca tcgtacaaag ttctaaataa tacaatattc atttcgtcaa    1620
agcatatgat gtgttggaat cagaattatc tgcaaatgtt tgaatttcaa atgttagtat    1680
caggctattt ttactgtttt atcaaatatc gtttcttctg caatctatca cttgattgtt    1740
ttatcaaatc agcactagta ttattgattt tgtaatttgt gtttgtctac ctccaattac    1800 ttttagtgt tatgattagt aatgtaataa atcacaaat ctgacgtggc acctatatac    1860
aattccaaaa acaagtggaa cgaatataaa acaaattcac accttcctca tcttcttctt    1920
cgtcttcact taccttctct ctacactcac accatctcac aacctaatc tctcccacac    1980 aagagagata gagagaaaca                                                2000
```

<210> SEQ ID NO 4
<211> LENGTH: 1261
<212> TYPE: DNA
<213> ORGANISM: Arabidopsis thaliana

<400> SEQUENCE: 4

```
cacatacata gacacaaagc cctttccatt gtcctcttcg tttccttttg ggtaaacaac      60
caatctcctg attttacaa aaaaggcaac atttcttagt tatatatgct tgtagtgaag     120
aaagatgtga agtctgaca agagaacaag acgaaggagg agtctttctc caagtcttca     180
acattgcaga atctgatgca tatgaaccca ttttctctac aaaatgttgc aaccctagag     240
agcaaaacaa aacatacccca taatcagaaa tgatctgacg aaaatcgagt tacaatacac     300
aagagaacat ttttttaga attctcagat attaaaaatg acacagaaag ctttatgctt     360
tttcctctta aaagactaaa caagttgaaa tctagagaaa gaactgacca acctgagaca     420
acgagagaga cttgagagat tcttcggca cttactatta gatctagggt ttagataccat    480 tttatataga gaaagtttta gagttgcaca aaacataaat taatgtgtta gaatgggcct    540
aaagctacaa agctggcctg gttttgtttt aaattgttgg tttcatggac attttcgaca    600
tcttcgaaca tgttattttt tgagactatg caaacttgaa gctctttact cgagttgaaa    660
tcgtatgact tatagtgaaa ttgtacattt ggtttcgatt tttcttttac actcttttctt    720 ctttgagccg gtaaatttgg aattttctt catagtggaa tcatatgctg tttttttttt    780
ttatagtaaa cgttacaaga atgaatggta actttatcca aaaaaaaga atcatattat    840 tttgaaatga ttttaagtaa attctaggtt caataacata agatttgaga ctaaatttaa    900
aatttcttag taaatatat gatttttta taaatacctta taaattagt aattaacaat    960 acggattacg tactgaatca aacccctttgt attttgtttt tcctagaaat aagtgtagat   1020
ttttggaatt ttgcattaat taatcacttc ttgggtctga aaggctaaaa caaaggaac   1080 cgaaagagaa tgttctctct gtctttatct tccacttcca cttccaggtc gcgttgcttc   1140
actctccatt gcaaagagag gtctctgcga tttctgcaac tcacccctga aaccttctta   1200
atttacttca actgccgcta tacctaaaaa cttcatcttt tcctctgag ctatgataaa   1260 g                                                                   1261
```

<210> SEQ ID NO 5
<211> LENGTH: 1706
<212> TYPE: DNA

<213> ORGANISM: Arabidopsis thaliana

<400> SEQUENCE: 5

```
aaagatgcat aggcttgcgg acataaaaat tccggagcta tgtttcatcg ttgctttcac        60
ggtctgaaga gccaatcaac actaaagaag gacctctaat ggtctctagc aagtttagcc       120
cccaattaag tattgtattg atgttttttgt gatggatgga tataggctgc atattgggaa      180
attatagtgt attgtattgt gtcgtgttgt gtgtatgtgg gactatagca tcctgagttt       240
gtcatgtcca gacgttgtaa cttgtaagca attacttatg gttttgttca cttcgtatta       300
acgtatttaa tttgtggctc gattttggtt ttgaatctgt gtcaaaacta agataaattta      360
cgtgttaaac caggcccaag tttgaaagtt aattgtcaat tttcagacca gagtacatat       420
tggtccactt attcccatta cattcatagt ttttgagtct tttgataatag tgttaccatt      480
tcaattaggc taatcttttt tcaacccaag atatttttat aaaaaggaat gtggttcaaa       540
tcggaaaaca agacctaact ttgaataaaa gcactacagc ataaagcttt tacctttaac       600
aaaaaaaata taataatttt ttacaaggaa aaagaagaga aagcaattat tctcagacaa       660
acaaaggaac cacttttgta ggtgtagtag taatctcaca cgctaagaca aaagtgcaca       720
aattctcgag actctcttct atccaacggt ccatatctca ctaaccgcat ctaaataacg       780
gacaagatct tcttttggct tcagctctct ttagtcttta ccttccctca agctcggtac       840
tcgatgtctt gctttcggcc actcatgaaa gcaacgagag cttccccttt catccgccta       900
cgtggctatg ggacccagtc taaccacgac cacctgacat cgtgggcccc actgtaaggc       960
gggaacccca ttttttttttg gctgtaagta acgattctc ggtcatgctt ttttgtgagg      1020
atagagagag agactgagag agagagagag tgtgtcacgg tctcgcagat actgtgtatt      1080
gaaaagagag ttctagagag agagtgtgtt atgtgtgtgt gtgtgtgtgt gtgtgtgtgt      1140
gtgtgtgttt ggttactggg attaattgag ctgaaacagt ttggatagtt ttgtttgttc      1200
tgtttcatct ttcaaccaca gatatagtaa tattgtgaaa acccctcatt gaagtttgtt      1260
ctctgctctc tcttttttggg tttagcactg agttttgggg tttatttcga gacatacccca    1320
tacaaagttt gatactttttg tgtccccccct tatcaagaaa attgtggggt ttttttttttt   1380
tttttaataag cttcctttaa attttcaatt tttattttgg aggaaaagag tgagaatttc     1440
agataagaat ctatgagcca atgatattct aattcatctt cttcgtgaag attttgagtt      1500
gaattccatt ttccttttttg tcttggtggt ttctcattgg ttttctcgag aatatttgtg     1560
gttttgggag aagaggcttc actgtagcat tgaaaaagtc ttaaacttttt ctgtgtcttt     1620
ttatgtaagc tttgaacagc ttcacctttc tgggttttct cagattgtgt ctaatcttga     1680
aaaaccttttt attcgtagaa gcagca                                         1706
```

<210> SEQ ID NO 6
<211> LENGTH: 1658
<212> TYPE: DNA
<213> ORGANISM: Solanum tuberosum

<400> SEQUENCE: 6

```
atcgcatggt tcatggagc tccttgtttt tttgttggaa tttgatgatt ttccaatttg        60
gttattatgt tgttcattgt tgttgttgag tctatttttgt ggtggtgcgg aggtgtgagc     120
tttaaattgg agttgggggtg attgttgttt tgttcgccgg agaagccatc tccagtgagg     180
ttggttggag aaggagagag atgaggagag caatgagtaa tttcaactat taaagattcg     240
tttcagaaag agaaaaaaag aagaaaatgg tcacattgtc gtccttgtgt aacattcaga     300
```

```
ggagtgaacc ctaaacttgc cgacccacag agaaaaacaa ccctagtttc catgggacc     360 tgctgtaaca gtagcacagt tctcaagctt tgttttttgt ggctacaact aatctgtgtg    420
caatgccatg gaaggatact caaggatgat acctcctcat ctgatcagtt taagaacaga    480
tttcaaagga tttttctgag tatacttttt ggtatgttta caggattgat tgtgcactt     540 gttttttgctt ggcttgttcg gagttttgtt cgttacatta acaaagcccc aattctcaaa   600
ggccctgttg tattctctcc taaaattcca tccaaaactc tgcaatcagc tcttgctaat    660
gatacccagt tgatagggtc aagtagttct ggaaaatact acagaactgt tcttgataat    720
gggcttactg ttgcagttaa gagaatggaa cctggttctc cacagttaca taccaagtca    780
tttaagagaa gaatacaaca cgaacttgaa cttattgcta gtttgaggca taggaatttg    840
atgagtttaa gggcttatgt tcgtgaatcg aatacgttct ttctggttta cgattatgta    900
aacactggca gtcttgaaga tgtaatgaac aaagttaggg aaaatcaatt gcaacttacc    960
tgggaagtca ggctccgaat tgcagttggg attgttaagg ctcttcagta tcttcatttc    1020
tcttgtaacc ccacagtttt gcatcggaat ttgaaaccca caatgtaat gttggatgct     1080 gagtttgagc ctaggttggc tgattgtggt ttggctaaaa tcattcccac tttaaatctc    1140
cctgctgcat caaactatgg tcctccagaa tcattccaga gttgcagcag gtataccgat    1200
aaaagtgatg tatttagctt tggggttata ttgggtgttc tattaactgg aaagtaccca    1260
acagatccct tctttgggga tacatctact ggaggaagtc tagcacgttg gcttcaacgc    1320
ttgcaggaag caggcgatgc tcgagaagca ttggataaga gtattctagg ggaagaggtt    1380
gaggaagatg agatgttaat ggcagtaaaa atagcagcgg tatgcttatc agacatgcct    1440
gctgatcgac cttccagtga tgagctcgtt tccatgctca cccaattaaa tagcttctga    1500
ttaattactt tggtcgagag ggaaagcagt caaggattca ataatcaca agatctttaa     1560 ggttgttctt ttggctttct aaggtgatag tttgctgtgt gcttttggta gttgagcaat    1620
gccttttggt tatcgcaatg agcacgagtg tagttggc                            1658
```

<210> SEQ ID NO 7
<211> LENGTH: 2931
<212> TYPE: DNA
<213> ORGANISM: Solanum tuberosum

<400> SEQUENCE: 7

```
ttctcactct cactgagtga atctgcaaac caaacagttg gtgggcatta gattaaggaa     60
ggaaaaatgc gtcttctttt tcttcttctt cttgttatgc attttactga cttttccgcc    120
ggtaaacaac ctcggttacc ggaatatcag gctttgcttg ccctgaaaac tgccattacc    180
gatgacccac agttaacact tgcctcatgg aacatctcca ccagtcactg tacgtggaat    240
ggtgtcacgt gcgacacgca tcgtcacgtg acctctcttg atatttctgg gtttaatctt    300
accggtactc ttccgccgga agttgggaat cttcgtttct acaaaatct gtctgttgct    360 gttaaccagt ttactggacc cattcctgtt gaaatctcct ttattccaaa tctcggttac    420
cttaatcttt ctaataacat attcgggatg gaattccctc cgcagttaac ccgtctgcgt    480
aacctccaag tccttgacct ttacaacaac aatatgaccg tgaacttcc ccttgaggtg     540 tatcagatga ctaaccttcg acatctacac ctcggcggga acttttcgg tggccgcatt     600 cctccggagt atgaaggtt cccgtctcta gagtacctcg cagttcagg caatgcactg      660 gtaggagaga taccaccgga gattggaaac atcactacac ttcagcagtt gtatgtagga    720
```

```
tactacaata ccttcaccgg tgggattccc ccggcaatag ggaacttatc gcagctcctc      780
cggtttgatg ctgctaactg tggactttcg ggggagattc caccggagat tgggaagctt      840
cagaaccttg acactctctt cctgcaagtg aattctctgt ctgggtcatt aactccggag      900
ataggttatc tgaagagctt gaaatctttg gatctgtcga ataacatgtt ctctggcgag      960
ataccgccaa catttgcgga gcttaagaat atcactcttg ttaatctttt tcggaataag     1020
ctttatgggt caataccaga gttcatagag gacttgccgg agctagaggt gttgcaactt     1080
tgggaaaata actttacggg aagcattcca caggggttag gcacaaagag caagctcaaa     1140
aatgttgatc tcagttccaa taaattgact ggaaatttac ccccaaacat gtgttccggt     1200
aacaatctgc agacaattat cactctaggg aacttcttgt ttggcccaat tcctgaatct     1260
ttgggtaggt gtgaatcact taatcggatt aggatgggag agaattatct gaatgggtca     1320
attccaaagg ggctcttaag cttgccacgt ctgtcacaaa ttgaacttca gaataatatt     1380
ctcactggta catttcctga tatttcttcc aaatctaata gtcttgggca gattatcctt     1440
tcaaataatc gcctaactgg acctttgccg ccaagcattg gaaactttgc tgtagcccaa     1500
aaattgcttc ttgatgggaa caaattttcg ggacgaattc cagcagaaat aggaaagctt     1560
caacagctat ccaaaattga tttcagtcac aacaactttt ctggacccat ggctccggag     1620
attagccagt gcaagttgct gacttatgtt gatctcagca ggaaccaact tcgggtgag      1680 attccttctg agatcacagg tatgaggata ctcaactact tgaacttatc gagaaaccac     1740
ttagttggga gtattccttc ccctatttct agtatgcaga gtttaacttc tgttgatttc     1800
tcatataaca acttttctgg tttagttcct ggaaccgggc aatttagtta tttcaactac     1860
acctcatttc tgggcaatcc agatctttgc ggaccctatt tgggcccttg caaagagggt     1920
gttgttgatg gggttagtca acctcatcaa cgaggagcct tatcgccttc gatgaagctt     1980
ttacttgtta ttggtttgct tgtctgttct attgtgtttg ctgttgctgc aattataaag     2040
gcccgatctt taaagaaggc aagtgaagct cgtgcctgga agctcactgc ttttcagcgc     2100
ctagatttta cttgtgatga tattttggac agcttgaagg aggataacat tattggaaaa     2160
ggaggtgctg gtatagtcta caaggggta atgccgagcg gggaacatgt agcagttaag      2220
aggttgccag ctatgagcag gggttcctct catgatcatg ggttcaatgc agagatacag     2280
actcttggga ggatccgaca caggcacatt gttagattat taggattttg ctcgaatcat     2340
gagacaaatc tttggtttta tgagtacatg cctaatggaa gtcttgggga aatgcttcat     2400
ggcaagaaag gcggtcatct acattgggat accaggtata agatagccgt ggagtctgca     2460
aagggtcttt gctatctcca tcacgattgc tctcctttga tcctccatcg tgatgtgaaa     2520
tcaaacaaca ttctgctaga ctccagcttt gaagctcatg ttgctgattt tggacttgct     2580
aaattcttgc aagattcagg gacatcagaa tgcatgtctg ctattgctgg ttcttatggg     2640
tacattgctc cagaatatgc ttacacgctt aaggttgatg agaaaagtga gtatatagc      2700 ttcggtgtgg tgctattaga actggtaagt ggcaaaaagc cagttggaga atttggtgat     2760
ggtgttgaca tagtccaatg ggttaggaaa atgactgatg ggaaaaagga tggagttctc     2820
aagatccttg acccaagact ctcaacggtt cccttaatg aggtgatgca tgtcttctat      2880
gtcgcattgt tgtgtgttga agagcaggct gtggaacgcc ccaccatgcg a             2931
```

<210> SEQ ID NO 8
<211> LENGTH: 3114
<212> TYPE: DNA
<213> ORGANISM: Solanum tuberosum

<400> SEQUENCE: 8

```
ccaccattga agaaacatgc gttttcttct cctcttcttc ctttcccttta ttctccattt      60
ccatctcctc cacttcacca ccgcaaaacc accttacgtg ccagaatacc gggcattact     120
ctccctgaaa actgccatta ccgatgaccc acaatctgct cttctttcat ggaatatctc     180
aacaagtcat tgtacatgga gaggtgtcac gtgcgaccgg tatcgtcacg tgacttctct     240
cgacatctct ggttttaatc tcaccggtac tctcacgccg gaagttggtc atctccgttt     300
tttgctcaat ctttctgtag ctgttaacca gttctctgga cccattccta tagagctctc     360
gtttatacca aatctgagtt accttaacct ctctaacaac attttcaatt tgagtttccc     420
tccccagctt acccatctcc ggtacttgaa agttctcgat atttataata acaatatgac     480
cggtgacctt ccggttgggg tttacaattt gactaatctt cgacatcttc atttgggtgg     540
caatttttt agtggcagta ttccaccgga gtatggtaga ttcccattcc tagaatacct     600
tgcagtttct ggaaatgcgc tcgtcggtat gataccaccg gagatcggaa atattaccac     660
acttcgtgag ctttacattg gatactacaa cacgttttcc ggtgggttac cggcggaaat     720
agggaacttg tcggagctca ttcggttaga tgctgcaaac tgtggacttt ccggtgggat     780
tccgccggag atagggaagc ttcagaaatt agatacactg ttcttgcaag tgaatggtct     840
ttctgggtct gttacaccgg aattgggaa tttaaaaagc ttgaaatctt tagatctatc     900
aaacaatatg ctctccggtg aaataccgtt cacattcaca gagctgaaga atctaactct     960
gctaaatctt ttccgtaaca agctttacgg gtcgataccg gagttcatag aaaatttgcc    1020
gaaactggaa gtattgcagc tttgggaaaa caactttacc ggaagtattc cacaaggttt    1080
aggcaaaaac agtaagttaa caaacgttga catcagtacc gacaaattaa ccggaaattt    1140
gcccccaaac atgtgttccg gcaacaagtt acagacgttg atcactcttg gaaacttctt    1200
gtttggccca attccagaat ctttaggtga gtgtcaatca cttaatagga ttagaatggg    1260
agaaaatttt ctaaatgggt ctattccaaa agggctattc agtttgccca agctttcaca    1320
agtagaactt caagataatc ttctcactgg tacatttcca gtgactggtt ctgtttcatc    1380
aagtcttgga cagatttgtc tgtcgaataa tcgtttcacg gggcctttgc catcgagcat    1440
tggaaatttg actggtgttc aaaagttgct tcttgatggg aacaagtttt ctggtcaaat    1500
tccagctgaa ttagggaaat tgcagcagct gtcgaaaatg gattttagtg gtaacagttt    1560
ttcaggcctg attccaccgg agataagcca gtgcaaggct ttaacttatg ttgatcttag    1620
taggaataag ctatctggtg aagttcctac tgagatcact ggtatgagga tactgaatta    1680
cttgaatgta tcgcggaatc agttagttgg gagtattcct gcacctattg cagcaatgca    1740
gagtttaacc tcggttgatt tttcgtataa caacttatct ggattggttc cgggtactgg    1800
tcagttcagt tacttcaatt acacatcatt tattggtaat ccagatcttt gcggaccccta    1860
tttgggtcct tgcaaagaag gtattgttga tggggttagt cgacctcatg agagaggtgc    1920
attttcgcct tctatgaagc ttttacttgt tatcggggttg cttgtttgct cgattgtgtt    1980
tgctatcgct gcaattatta aggctagatc gttaaagaag gcgagtcagg ctcgtgcctg    2040
gaagcttact gctttccaac gcctggattt cacttgtgat gatgtattgg aatgtttgaa    2100
agaggataac attattggta aaggaggtgc tggaatagta tacaaggggg taatgccaaa    2160
tggtgaactt gttgctgtta aaaggttgcc ggttatgagc cgtggttctt cccatgatca    2220
cgggtttaat gccgagatac agacacttgg gagtattcga catagacata ttgttagatt    2280
```

| | |
|---|---|
| attaggattt tgctcaaatc atgaaacaaa tcttttggtt tatgagtaca tgcctaatgg | 2340 |
| gagccttggt gaaatgcttc atggaaagaa aggaggtcac ttgcattggg ataccaggca | 2400 |
| taagatagca ttggaggctg caaagggact tgttatctt catcacgatt gctcgccttt | 2460 |
| gatcctccat cgtgatgtaa aatcaaacaa cattcttctg gattccagct tcgaagctca | 2520 |
| cgttgctgat tttgggcttg ccaagttttt gcaagactcg ggaacatcag aatgcatgtc | 2580 |
| tgcaattgct ggttcttatg ctacattgc accagaatat gcatacacac tcaaggtaga | 2640 |
| tgagaagagt gatgtataca gctttggtgt ggttctgtta gaattggtga gcgggaaaaa | 2700 |
| gccagtgggg gaatttggtg atggcgttga catagtccaa tgggtaagga ggatgaccga | 2760 |
| tgggaaaaaa gaaggagttc taaagatcct tgatccaaga ctctcaacag ttccccttca | 2820 |
| tgaggtgatg catgtgttct atgttgcaat gctgtgtgtc gaagagcaag ctgttgaacg | 2880 |
| ccccaaaatg cgtgaggttg tgcaaatgct aactgagctt cccaagccat ctggtccaaa | 2940 |
| aacagaagat tcaacaatca ccgagtcgcc cccatcatca ggtcctgcat tagagtctcc | 3000 |
| cacttcgact cccggagaca cgaaagacca gtaccaccat cagccatcac ctcaatctcc | 3060 |
| tccacctgac ctactcagca tatgacctac aatgttccct tctaatagag gatg | 3114 |

<210> SEQ ID NO 9
<211> LENGTH: 3362
<212> TYPE: DNA
<213> ORGANISM: Solanum tuberosum

<400> SEQUENCE: 9

| | |
|---|---|
| gtcggtaagt ccaagaactg gttttcaat tcaaaggagc tgagttagtg taaacacttt | 60 |
| tggttttgag ttttgacaga gacttgagtc tcagagaaac taccatggca tcatttttac | 120 |
| ttcaaagatg taatctttc tttgaggttc ttcttctttt ggggttcttg attttcttca | 180 |
| gctttggttc tgtggtgtct gatgatggtt ctgcattgtt ggagattaag aagtcaatta | 240 |
| gggacatgga gaatgtgttg tatgactgga ctgattctcc ttcatctgat tactgtgcct | 300 |
| ggagaggtgt tacctgtgat aatgtcacct tcaatgttgt tcaacttaat ctttcgagtt | 360 |
| taaatcttga tggggagttg tctcctgcaa ttggacagct caaaggcctt atatctattg | 420 |
| atgttagggg aaatcgcctt tctggccaga taccagatga gattggtgac tgttcagcac | 480 |
| tgaaaaactt ggacctatcc ttcaatgagc tttatggtga tattccgttt tccatatcaa | 540 |
| aacttaagca actggaatat ctgattataa agaacaatca gttgattgga ccaattccat | 600 |
| cgacattgtc acagatcccc aacttgaagg tcttggacct ggctcaaaat aggttaagtg | 660 |
| gagaaattcc taggctgata tactggaatg gagtcctgca gtatttggga ctgcgtggca | 720 |
| acaacttggg tggatcactt tctcctgata tgtgtcagct caccggcctg tggtactttg | 780 |
| atgttcggaa caatagtttg actggttcca ttcctcaaaa tattggcaac tgtactgctt | 840 |
| tccaggttct agatttgtct tataatgact tgactggaga gattcctttc aacattggtt | 900 |
| tcctgcaagt agcgaccttg tctttgcaag gtaatcgcct ttcagggcag atcccttctg | 960 |
| tcattggatt gatgcaagct cttgcagttt tggacttgag ctgcaatatg ttgagtggaa | 1020 |
| caattccttc aattcttggg aatttgactt acacagaaaa attgtatcta catgggaaca | 1080 |
| agctatctgg ttccattcct ccagagctgg gaaatatgac aaagcttcac tacttagaat | 1140 |
| tgaatgataa ccaacttact ggacgcatac caccagaact tggaaagctg acggagttgt | 1200 |
| ttgacttaaa tgctgcaaac aaccaccttg atgggcccat tccttccaat cttagctcat | 1260 |
| gtaccaattt gaatagtctc aacgttcatg gaaacaaatt gaatggtacg attccacctg | 1320 |

```
cttttcaaaa gctggaaagt atgacctatc ttaatctctc ctccaacaac ctcaaaggcc    1380
caattccaat tgagctttct cgtattggga atgtagatac actggacttg tcaaacaaca    1440
ggatcagtgg tcctatacct ttgtccctcg gtgatttgga acatcttctt aaactgaact    1500
tgagcaagaa cgaaataaat ggaaacttgc cagctaaatt tggcaattta aggagcatca    1560
tggagattga tctgtcaagc aatcacctct ctggtccctt gcctcaggaa cttggtcagc    1620
ttccaaatct gtacttgctg aaactggaaa acaacaattt atcaggcgat gtgatgtcct    1680
tagccagttg tctcagtcta aatgtcctaa atgtctcgta caataatctg ggagggaata    1740
ttccaacagg caataatttc tctagatttt caccagacag cttcatagga aatccagatc    1800
tgtgtgggta ttggctcact tctccttgtc atgcatctca tccagcagag cgagtttcaa    1860
tttctaaagc tgctatactt ggtattgctc tgggtggctc ggtgattctt ctgatgatac    1920
tagtagcagc atgccggcca cagaatcctg caccttttcat ggaaggatct attgataaac    1980
```

-continued

```
agactaaact aacagtgtaa taatgtcact ccccaaaaaa atatccctttt tcctccaaat    60
tttcattttt tttgttttct ccattaatgc aaactctgat cttgaaaccc ttttgaagct   120
caaagaatcc atggttgctc ctggaacttc tgcacttctt gattggaaca acaacacaaa   180
ttacccttt tcccattgtt cttttctgg tgttacatgt aacaataacc ctcatgttat     240
atctataaac atcactaatg ttcctctatt tggtactatt ccacctgaaa ttggtctttt   300
acaaaatctt gaaatctta ttattttgg tgataatatt actggtacac tcccttaga     360
aatgtcacaa ctttcttcta ttaaacatgt taatctttct tacaacaact tttctggtcc   420
ttttcctaga gaaatcttgt tggggttaat aaagcttgaa tcttttgaca tttataacaa   480
caatttcact ggtgaacttc ctactgagtt tgtaaagttg aaaaagttgg aaactttaca   540
tcttggtgga aactattttc atggtgaaat accagaagtt tattctcata ttgtaagttt   600
aaagtggttg ggtttagagg gaaattcact aactgggaaa ataccaaaga gtttggtttt   660
gttaccaaat cttgaagaac ttagattggg ctattataat agttatgaag ggggtattcc   720
atctgagttt ggtaatatta gtacacttaa acttcttgat cttggaaatt gtaatcttga   780
tggtgaagtt cctccaagtc ttggaaattt gaagaagttg catactttgt ttctacaagt   840
gaacagactt acaggtcgca taccttctga actatctggt ttagagagtt tgatgtcgtt   900
tgatttgtct tttaatcaac tgaccggaga ataccagag agttttgtga agttgcagaa   960
tttgacattg attaacttgt ttagaaacaa cttgcatgct ccaattcccc cttttattgg  1020
tgaccttcca aatcttgaag tgttgcagat ttggggaaac aattttactc ttgaattgcc  1080
cgaaaatctt gggcgtaacg ggaggttttt gtttcttgat atttctatta atcattttac  1140
tggaaggata ccacctgatt tgtgtagagg agggaagtta aagacactga ttctaatgga  1200
aaattacttc tttggtccaa ttcctgaaca acttggtgag tgcaaatcgc ttgctcgaat  1260
tcgcgttagg aagaattact taaatggtac tattccagct ggtttttttca agttacctgc  1320
attggatatg cttgaacttg acaacaacta tttcactggt gagctgccaa cggagataaa  1380
cgcgaataat ctcactaaac ttgtactttc caacaactgg atcacgggga acattcctcc  1440
atcattaggg aacttgaaga atctagtcac tctatcactt gatatgaaca ggttatctgg  1500
tgaaattcct caagaaattg cgagtttgaa taaactcgtg accatcaact gagtggcaa   1560
caatttaaca ggtgaaatcc caagttcaat tgcgctttgt tcagagctaa cattggttga  1620
cttgagcaga aaccaactgg ttggtgaagt gccaaaagaa atcaccaagt taaatagctt  1680
gaacgctctg aacttgtcaa gaaaccaact gagtggcgcc attcctggag aagtcggagt  1740
gatgaatggc ttgacagttt tagatctttc ttacaatgat ctttctggaa ggagaccgac  1800
caacggacaa ctaaagttct tcaatgacac ttattttgta ggaaatccaa aactctgttc  1860
acctcatgct actttttgcc cgtcagcctc caattcacca caaaacgcgc tcaaaatcca  1920
tgctgggaag ttcacaacta tccaattggt gattacaata atcatcttag tcactgttgc  1980
attgctgttg gcagttaccg tgttgttcat caagaaggaa aagttcaaga attcgaaact  2040
ttggaagtta acagcattcc agaaacttga tttcagagct gaggatgttt tggagtgttt  2100
aaaagaggag aacataattg ggaaaggtgg agctggcgtt gtgtaccgag ggtctatgtc  2160
aaatggcatc gacgttgcaa ttaagaaact tgtaggccga ggaactggac accatgatca  2220
tggattctca gctgaaatcc aaacactagg aaggatcagg cacagaaaca tcgtacgatt  2280
actaggatat gtctcaaaca aagacacaaa cttgttgttg tacgaatacg tgtcgaatgg  2340
gagcttaggt gaaatgttac atggtgccaa aggagcacat ttgaaatggg agacgaggta  2400
```

```
ccgtattgct gtggaagctg caaagggatt gtgttatttg caccatgatt gttcgccttc    2460
gattattcat agagatgtca agtccaataa tattccgctg gattccgatt acgaggctca    2520
tgttgctgat tttggcctag ccaaattctt gcaggatgct ggtgcatcag agtgcatgtc    2580
ctctattgct ggctcatatg gttacattgc tccagagtat gcatacacat tgaaagttga    2640
ccaaaagagt gatgtataca gttttggagt tgtactgttg aacttatca caggtcacaa     2700 gccagttggt gaattcgggg acggtgtaga tatagtcaga tgggtaaata aacaatgtc     2760 cgaattatct cagccgtctg atgcagcctc agttttagca gtcgttgact cgaggctaca    2820
tagttaccct cttgcaagtg ttgtaaattt gttcaagatt gctataatgt gtgttgaaga    2880
agagagttgt gctaggccta ctatgaggga agttgttcac atgcttacaa atcttcctca    2940
gtctactact actactacta ctactctcct tgccctttga aattgcaccg atatcaagtg    3000
tctggttgaa aactcgtgga gtttgaggcc gggaacacga gtctcatgag tctatttggg    3060
tacggggaac aa                                                         3072
```

<210> SEQ ID NO 11
<211> LENGTH: 2241
<212> TYPE: DNA
<213> ORGANISM: Solanum tuberosum

<400> SEQUENCE: 11

```
atggcagaat cagttcttga accttgtaca acctcttatt ccttcaaagt ttcaatcttt    60
atcctattct tcttgatttt ccctttcttg aacccatttt catctgcatt tcctcttttct  120 tttgatacta atgcaactga ggctgtcaat cttgaaacag aagaggacat gggtttgctt    180
ttgttcttca agttacagtt tcgagaaacc cctttaccaa gctgggatgt caatgttcct    240
ctatcaaact ggactggtgt tacccggtct aaccagaccg gacgggtcac tggacttaac    300
ctcacaaggt ttaacttgtc aggacaggtt catccttgtt tgtgtaatct tacttttctt    360
gaaacccttg tgttgtctca taatagcttt aacaattcaa taccttcttg tttatggaag    420
ttgtggagcc ttaagacctt agatcttagc tataatatgc ttactcttct tattcctagt    480
acatttgcaa caactatgag taagttaatt gagcttgacc ttagtcataa catgttgagt    540
gatgaaatcc caatgtggat agggaatgtc tcaatgtcac ttgaaaaact taacttaggg    600
tttaatagtt tcatgggga tatacctaag agcttgttga atttgatgtc tttgaagtat    660
cttgacttgt ctcacaatag tttgatggga aatgtgggtg attttaacca agaattggtc    720
tcacttaatc ttgagtctaa tttattatcg ggtactttgc cttgtttata ttcgtcaagg    780
gaatcactta cacttcttaa tttagcaaac aattcgattc ttggaggtat accaacgtgt    840
atctcgagtc ttgggggttt gacacagctc aacttgtcac gtaatgaatt acgatatggt    900
atctcgccta gactggtttt tcagagagg ttatgtttgt tggacttgag ttataatgag    960
ctatcaggga agattccaag taggattgtt gaggcatcgg acaagtctgg acttctactt   1020
cttgacctgt ctcacaatca gttctctggt aatattcctg taacgataac agaattgaag   1080
agcttgcaag cattgttttct gtcttataat cttcttgtgg gcgaaatacc agaaaggatt   1140
ggtaatttga cctatctaca ggtgattgat ctctcacata acttcctcac cggctcgatt   1200 ccttttgaaca tcgtaggatg tttccaacta ctggtgctga tactaaacag taataatctt   1260
tctggggaaa ttcagccagt gcttgatgcg ttggatagtc ttaagatatt tgatataggaa  1320 aacaacaaga tttctggtga gatcccactg acattggcag gctgcaagtc gttggaagtt   1380
```

-continued

```
gttgacttga gctctaacaa tctctcaggg tctctaaatg gtgcaataac caaatggtcg      1440
aacctcaaat tcctctccct tgctcggaac aagttcagtg gatctctgcc aagttggttg      1500
tttacatttc aggctattca tactctggat tttttctgga acaagttctc gggatatata      1560
ccagatggta actttaacac tagtccaaat ttctacaacg gcgacattag gaaaaccatt      1620
cctgcagtac catcaatttc agctcgaagc ctggatatca aactttcact cattgctgat      1680
gaaactagtt tgagcttcaa ctataacctg acaaccacaa ttggaattga tctgtctgac      1740
aatttgcttc atggtgaaat tccagagggt ctgttcggat tacatggttt ggagtaccct      1800
aatttgtcat acaattttct taatggtcca gttccaggga gtttagggaa gttgcagaag      1860
ctaaaagcac ttgatttatc acataattct ttatctggcc catccctga aaacattact       1920 gtcctcagaa atttgacagt tttaaatctg tcttataatt gtttctctgg tgttattccg      1980
acaaagcgag gttattggaa atttcctgga gcatttgctg ggaatccaga cttatgtatg      2040
gaatcatctg gtaatgtctg tcaaagaact ttgcctgtag agccagggaa gaaatttgaa      2100
gaggaaatgg aagagggacc attatcagtt tggatttttct gtataagtgc tttagttagc     2160
ttctatgttg gcattgttgt tttatttttgt tcatctcgaa caagaagctg tattctgcaa     2220
acaaaaagtt tagcaggttg a                                                2241
```

<210> SEQ ID NO 12
<211> LENGTH: 2583
<212> TYPE: DNA
<213> ORGANISM: Solanum tuberosum

<400> SEQUENCE: 12

```
atgtcttcaa ttgctatttc atatggtgaa tatggttctg ttttttgtgg gttgaagtca      60
gatggatctc atttggtcag ctgctatggc tctacttctt ctataatata ttcaactcca      120
gctcatttcc cttttattgg tcttactgct ggaaatggct ttgtatgtgg acttttgatg      180
gattcttacc agccttattg ttgggggaaa agtaattttg tacaaatggg agtgcctcag      240
cctatgatca aagggtctca atacttggaa atatctgcag gtgaaaatca tttgtgtgga      300
ctaaggcaac ctttaatggg gaagcatagg aacacttcac ttgttgattg ctgggggttat     360 aacatgacca caaataatga gtttgaaggt cagatccact ctatttcagc tggttctgag      420
tttaattgtg ctttgttttc tgtcaataaa agtgttttat gttgggggga tgaaactagt      480
agccaggtta ttaccctagc accaaaagat ttgagattta ttaagattgc agctggggga      540
tatcatgttt gtgggatcct agaagggtg aattctcaag tgtattgctg gggaaggagc       600
atgaaccttg aagaagaatt ctctgttgct caactcaatg ttgaattggc agcccctagt      660
gatccaatta tatctgttgt tggtggtaag tttcatgctt gtgggattag gagctatgac      720
cgtcatgtcg tttgctgggg ttacagagtt gagaaaagca caccacctcc tagtggagtt      780
aggctttatg agatagcagc tggtgactac ttcacttgtg gtatccttgc ggaaatttca      840
cttttgcctg tttgttgggg gtttggtttt ccctcatcgc taccactcgc tgtttctcct      900
ggagtctgca agcctagacc ctgtgcatct ggcttctatg agtttaacaa cggaagtgca      960
acttgcaagt ctcctgattc tcgcatttgc cttccctgca ccaatggctg ccctgctgaa      1020
atgtatcaac aggttcaatg cacttcatct acggacagtc agtgcacgta taattgttca      1080
agttgtacct ctgttgactg cctaaacagc tgttctactg ctatttctgg gaagaagaac      1140
gctaaatttt ggtcactcca gttaccagta attgttgctg aggttgcatt tgcagtattc      1200
ttggtgagtg ttgtatctct aacttcgatc gtatatgttc gctacaaatt aaggaactgt      1260
```

```
agatgttcag ggaaaggtcc tagtcctagg aagaatggta ctttcccaaa ggaaattgct    1320
aaagataggg ctgatttgga tgatcttaaa ataaggagac ctcagatgtt tacttatgaa    1380
gatcttgaga gagcaactga gggattcaaa gaagaatcac aagttggaaa gggtagcttt    1440
tcgtgtgttt tcaagggcgt tttgaaggac ggtactgtgg ttgctgtcaa gagggctata    1500
atgtcatctg acatgaagaa gaattcaaag gagttccaca atgagctaga cttgctgtcc    1560
aggttgaatc atgctcattt gctcaatttg ctaggttatt gtgaagaagg tggagagaga    1620
cttctagttt atgagtacat ggctaatgac tcgttgcatg aacatctaca tgggaaaaag    1680
aaggagcaat tggattggat aagaagggta accattgcag tccaagctgc tcggggaatc    1740
gaatatttgc atggttatgc atgtccacct gtgattcaca gagacatcaa gtcctcaaac    1800
atccttatag atgaagaaca caatgctcga gtagctgatt tgggctttc cttgcttgga    1860 cctgctaata gcagttcccc attagctgag ttaccagcag ggacacttgg gtaccttgat    1920
cccgagtact acagactaca ttatcttaca accaaatctg atgtctatag ctttggtgtt    1980 ttgctttgg aaattctcag tggtcggaaa gctattgaca tgcaatacga tgaagggaac    2040
atagtggaat gggcagtccc attaatcaaa gctggtgaaa tagaggcaat actggatcca    2100
gttttgaaat caccttctga tgctgaagct cttagaagaa tcgctaatat agccagcaaa    2160
tgcgtgagga tgagagggaa agagaggccg tcaatggata aagtaacaac agctttggag    2220
agagcacttg ctcaattgat gggtagtcca agcaatgacc agcctatctt gccaacagag    2280
gttgttctag gaagcagcag aatgcacaag aagtcctcat caaatcgatc aacatcagaa    2340
acaacagatg ttgcagaaac tgaggatcag tggtatgtcg aattcagagc tccttcgtgg    2400
attacattcc caagtgtagc atcatctcag agaagaaagt cttcagtatc ggacgcagat    2460
gttgaagcaa agaatttaga aagtaggaac tgtggaaatg gaactgatgg attgagaagt    2520
ttggaagaag aaattggacc agcttctcct catgaacatt tgttcttgaa acacaacttc    2580
taa                                                                 2583

<210> SEQ ID NO 13
<211> LENGTH: 2598
<212> TYPE: DNA
<213> ORGANISM: Solanum tuberosum

<400> SEQUENCE: 13
atggaggtga gcgtgaagat gaaattcccc tcacaagcac tactgttggc tctattgctt     60
gttttaccga tcgtttttagc tctcaccgaa gaaggcaaag cattaatgtc gatcaaggca    120
tcgtttagca acgtggcaaa cgtgttgcta gattgggatg atgtccacga cgaggatttt    180
tgctcatggc gaggcgtgtt gtgtggaaat ttctccattt ccgtcgttgc ccttgatttg    240
tctgataact tgctctatgg agatatacct ttctcaattt ctaagctcaa gcagctagag    300
ttattgaacc tgaaaaacaa ccagttgtct ggcccaatcc catccacatt aactcaaatc    360
cctaatctaa agacgcttgg cttaagaggc aacatgttga caggaacatt gtcccctgat    420
atgtgccagt tgactggttt gtgtgatgtg cggggcaata acctcagtgg aatagttcca    480
gataatattg gaattgtac aagttttgag atactggata tctcatacaa tcagataact    540
ggagaaattc cctacaatat tggatttta caagtggcta ccttgtcttt gcaaggaaat    600
aggctaactg gaaagatccc agaagtgatt ggtctaatgc aagctcttgc tgttctggac    660
ttgagtgaaa atgagttggt gggaccaatt cctccaatct ttggcaattt atcctacact    720
```

| | |
|---|---|
| gggaaactgt acctgcacgg caacaaactt acagggccaa taccaccgga gctaggaaat | 780 |
| atgtctaaac ttagttactt gcaattaaat gacaatcagc taatgggcg aattccctcc | 840 |
| gaacttggca aactggacca gttatttgaa ttgaatcttg caaataacaa gttggaggga | 900 |
| ccaattcctg aaaatatcag ctcctgctcg gcattgaatc aacttaatgt tcatggcaac | 960 |
| aacttaaacg ggtccattcc ttcagggttt aagaatcttg agagcctgac atatctggat | 1020 |
| ctctctggca atgaattttc tgggtctatc cctggttcta ttggagattt ggagcatctc | 1080 |
| ctcacactga atctgagcag caatcatctt gatggacaaa ttcctgtaga atttggcaat | 1140 |
| ctgaaaagta tacagaccat tgatatgtca tgcaacaaga tttctggtgc catcccaaaa | 1200 |
| gagctgggac agctgcagac catgataact ctgaatatat cctacaacaa tttagtggt | 1260 |
| gttgttcctc tttcacgaa tttctcgcgg tttgcacctg acagcttttt ggggaaccca | 1320 |
| tttctttgtg gcaactggaa aggctcaata tgtgaccct atgcaccaag gtctaacgcc | 1380 |
| ttgttctcta aacagctgt tgtttgcaca gcattgggtt tcatagcact cttatccatg | 1440 |
| gttatagtgg cagtgtacaa gtccaaccaa ccacaccagt ttctgaaggg gcctaagacc | 1500 |
| aatcaaggtt ccccccaaact tgtggttctt cacatggata tggccatcca tacatatgat | 1560 |
| gacattatga ggattactga gaacttcaat gagaaattca tcataggata tggtgcttcc | 1620 |
| agcactgtat ataaatgtgt tttgaaagat tcccgaccga ttgccgttaa gcgactttac | 1680 |
| actacacatc cgcacagctt gcgagagttt gagactgaac tggagaccat tggaagcatc | 1740 |
| aggcatagaa accttgttag cttgcatggt tactccctt ccctcatgg gaatctcctt | 1800 |
| tgttacgact acttggagaa tggttcactc tgggatctac ttcatgggcc ttccaaaaag | 1860 |
| gtgaagcttg actgggaaac acgtctgagg attgctgttg gtgctgctca gggtcttgct | 1920 |
| tatcttcacc acgattgcaa cccaagaatc atccacagag atgtgaaatc ttcaaacatt | 1980 |
| cttgttgatg aaaattttga ggctcatctt tctgattttg gggttgcaaa atgcatccct | 2040 |
| tctgcaaaaa ctcatgcatc aactttggtg ttgggcacca taggttacat tgaccctgag | 2100 |
| tatgccagga cttccaggtt aactgaaaaa tcagacgtct acagctttgg cattgttctc | 2160 |
| ctagagcttt tgacaggaaa gaaaccggtt gataatgact tgaacctgca tcagctgata | 2220 |
| atgtcaaagg cggatgataa caccgtgatg gatgctgttg atcctgaggt atctgttaca | 2280 |
| tgtatggact taacacatgt gaggaaaact tttcagcttg cgttgctgtg cacaaaaaga | 2340 |
| tttccatgtg agaggccaac gatgcatgag gttgctaggg tacttgtttc cttgcttcct | 2400 |
| cccccgccaa ccaaaccttg tttagaccca cctcccaaat ccattgatta tacaaagttt | 2460 |
| gtgattggga aaggactacc gcaagttcag cagggtgatg attcctccga agcacagtgg | 2520 |
| ctttttttctta gatatttagc tgctgcactg gttcaatgga acgagtttga agatggtgaa | 2580 |
| gaattgcatc tatgttga | 2598 |

<210> SEQ ID NO 14
<211> LENGTH: 1343
<212> TYPE: DNA
<213> ORGANISM: Arabidopsis thaliana

<400> SEQUENCE: 14

| | |
|---|---|
| aggagacttt tagcgtttgc gtttgaagcg attcctcttc ttatgtgtaa attgtacgga | 60 |
| tgaaaatagt tgtaaaccaa gagtgatgat ccaaaccgag ttctggtttt caggattaac | 120 |
| accatatttt ggttcgatta atttcggtta ccggatgttg taaaccggtt gatgatgat | 180 |
| ataactctta tgtcatggtg atgcatacat acaaggacca catttcatta ttactttatt | 240 |

```
tcaatacgta tcattattat aagtagtagc taaaagacag atatatttca ctaaaagaaa      300
aacaaacctt ttttcttct aattgaaaag gttataaact cagtctttt atccccataa       360 atgtggctaa tgtgttgtgt acatgacaaa attataaatt tatatttaag aaaaaacatt     420
ttaatttgct ttatcttgaa gcttccttta gttatatcct tgaaaagagg cgattctgtc     480
cctttttcac tttacaattt ctcaatattt ttgttataaa gaaacacatc tttgtcacat     540
gcatttatgt atagtggcag gcgatttttc ttttagcgtg agattatgaa attttcctaa    600
tataatgcat gtccatatac atatatctat ctgtaataaa tgttagcttc aagatcttag    660
cataacattg gtcgatgaga gattgatacg tctaggagag ttgaaatatt gttacattta    720
ttgtgactca acatatttta tttcatcact tcgaataaac aaaaaattta aataatctg     780 tcctcaaatt tagtgataag ataatcttgc atctacctac tgttatcaat catgtaccta    840
ttgcgatttg atgtggtgag actacaatga tcgatgttaa aaactttaaa tgttaacttc    900
actacatgat cgataaataa tcaaaaattg cttcttccaa gttaaaatta cactaaagag    960
tttgttagcc aataggaaat aaggaaagtg gacccactct ctcattcaca gaacgatttt    1020
ttattttttt ctgcataaat taaattaaaa acatttttaa gatcttttat caaaaaaaaa    1080 aaaaagaga gagagaagaa aaaaacgcgt cttcctcagt gacagtgttg aattctctca    1140 tctcttctc tctctgcttc atcagtttct ctcactacaa agcttctcat catctcccta    1200
aattagggtt aaagggtcga gcttgggatt gtttcgcacg gtaaaggaa ggatcttttg     1260 ctcgtcaatt gctatattag cagaccttgc gaggtgggtt tagggttttg ttgtaaaaac    1320
atttttgggg ataagttacg aag                                            1343

<210> SEQ ID NO 15
<211> LENGTH: 3456
<212> TYPE: DNA
<213> ORGANISM: Arabidopsis thaliana

<400> SEQUENCE: 15
atgacttctt tgccttcttc agtgatcaaa tggcgttttt ccgcagaca gatgccttca      60 gacgttgtct tctcgctctg cttactctgt ttcgcctcct gtctcgccgg aaaaatcact    120
gttttagctg attcggacaa atccgtgttg cttcggttta agaaaacggt atcggaccct    180
ggttcgattc tagctagctg ggtcgaagag agtgaagatt actgctcctg gtttggtgta    240
tcttgcgatt cgagctctcg agtcatggct cttaacatta gtggctctgg aagttctgaa    300
attagtcgaa atcgtttcac ttgtggtgat attggtaagt ttccgttgta tgggtttggt    360
gttcggaggg attgtaccgg aaatcatgga gctttggcgg ggaatttgcc ttctgtaatc    420
atgagtctca caggacttag ggttttgtct ctgccttta attcgtttag tggagagatt    480
cctgtaggaa tctggggaat ggagaagctt gaagttcttg atctggaagg gaatttgatg    540
acggggtcat tgccggatca gtttactggg ttacggaatt tgcgggttat gaatttgggg    600
tttaacagag tttcaggtga atccctaat tcgctgcaga atctgacaaa gttggagatt     660
ttgaatttgg gtggtaataa gttgaatgga actgttcctg gttttgttgg agattcaga     720 gtgttgcatt tgccgttaaa ctggcttcaa ggctctttgc ctaaagatat tggggatagc    780
tgtggaaagc ttgagcattt agatttgtct ggtaatttct tgactgggag gattccagag    840
agtttgggga atgtgctgg tttaaggtcg ttgttgttgt atatgaatac gttggaggag    900
actatccctt tagaatttgg gagtcttcag aagcttgagg ttttggatgt ttctaggaac   960
```

```
actcttagtg gtccattacc tgttgaactt ggaaattgct cttcgttgtc tgttctcgtt      1020
ctatcaaatc tgtacaatgt gtatgaagac attaatagtg taagagggga agctgatctt      1080
cctccaggcg ctgatttaac ctcgatgacc gaggatttca atttctatca aggaggaatc      1140
ccggaggaaa tcactaggct tccgaaacta aagatacttt gggtgcccag agctacgtta      1200
gaaggtagat ttccaggaga ttggggttca tgtcaaaact tggagatggt taatttgggt      1260
cagaacttct ttaaaggcga aattcctgtc ggtcttagta aatgcaagaa ccttcgtctt      1320
cttgatttga gctcgaatag gcttactggg gagcttctca aagagatttc ggtcccatgc      1380
atgagtgttt ttgatgttgg tggaaacagc ttatcgggtg taatccctga ttttctcaac      1440
aataccacaa gccattgtcc tcctgttgtt tactttgaca ggttttctat tgaatcttac      1500
agcgacccgt cgtctgttta tctctccttc tttaccgaga aggctcaagt tggaacttcc      1560
ctgatagatc ttggaagtga tggaggtccg gccgtgtttc ataattttgc agacaacaac      1620
ttcactggta ctctcaagtc tataccactt gcacaggagc ggttgggaaa gcgagtctct      1680
tacatatttt ctgctggagg gaatcggttg tacgggcaat ttccgggaaa tctgttttgat     1740 aactgcgacg aactcaaagc tgtttatgtc aatgtaagct tcaacaagct ctcaggtcgg      1800
attcctcagg gactaaacaa catgtgcact tctcttaaga ttcttgatgc ctcggtgaat      1860
cagatcttcg ggccaatccc aacaagtctc ggggatctag cttcacttgt tgctcttaat      1920
ctgagctgga atcagttgca aggtcagata ccgggtagcc tcgggaagaa gatggcagct      1980
ttgacatatc tttcgattgc gaataacaac ctcacggggc aaattcctca gagctttggt      2040
cagttacatt ccttggatgt tcttgatctc tcttcaaatc atctatctgg cggtattcct      2100
catgatttcg taaacttgaa gaatctcact gtcctgcttc tcaacaataa caacctctct      2160
ggcccaatcc cgtcgggttt tgcgacattt gctgttttca atgtttcctc caacaatctg      2220
tctggtccag ttccttcaac caatggactg acgaaatgca gcactgttag tggaaacccc      2280
tatcttcgac cttgccatgt gttttctctg acaacaccgt cttcggattc ccagagactcc      2340 acgggtgatt ctatcacgca ggattacgca tcttcgcctg ttgaaaacgc tccatctcag      2400
tcgccaggaa agggtggatt caactcgcta gagatcgcct caatcgcatc agcttcagcg      2460
attgtctcgg tactaattgc tcttgtaatt ctcttcttct acacaaggaa atggcatccg      2520
aaatcgaaga tcatggccac tacaaaaacga gaagtcacta tgttcatgga tatcggagtt      2580 ccaataaacct ttgacaacgt ggttagagcc acaggaaact tcaacgcaag caatctgatt      2640
ggaaatggtg gatttggagc gacctacaaa gcagaaatct ctcaagatgt ggttgtcgca      2700
atcaaacgcc tctcgatcgg acggtttcag ggagtccaac agttccacgc agaaatcaaa      2760
actcttggta gacttcgaca cccgaacctc gtgactctca tcggttacca cgctagcgaa      2820
actgagatgt tcttggtgta caactatctc ccaggaggca acctcgagaa attcatccaa      2880
gaaagatcca caagagattg gagagttctt cataagatcg ctctggacat agctcgagca      2940
ctcgcttacc tccacgacca atgcgtccca cgggtgcttc accgagatgt taaaccgagt      3000
aacatcctcc tagatgatga ctgcaatgcg tatttatcag atttcgggtt agcgagattg      3060
cttgggacat cggaaacgca cgcaacaact ggtgtggcgg gtacgtttgg gtatgtagct      3120
cccgagtacg caatgacatg cagggtatca gacaaagcag atgtatacag ctacggagtg      3180
gtgcttctag agctgctttc ggacaagaaa gcacttgatc cgtcatttgt gtcgtatggt      3240
aatggtttca acatagtgca atgggcttgt atgttgttga caaggaag ggcaaaggag      3300 tttttcacag cgggattgtg ggacgcaggt ccgcatgatg atctagtaga ggttctgcat      3360
```

```
ttagcggttg tttgtacggt ggattctctg tcgacgaggc cgacgatgaa gcaagttgta    3420
agacggttga agcagctaca acctccgtcg tgttag                              3456
```

<210> SEQ ID NO 16
<211> LENGTH: 1151
<212> TYPE: PRT
<213> ORGANISM: Arabidopsis thaliana

<400> SEQUENCE: 16

```
Met Thr Ser Leu Pro Ser Ser Val Ile Lys Trp Arg Phe Phe Arg Arg
1               5                   10                  15

Gln Met Pro Ser Asp Val Val Phe Ser Leu Cys Leu Leu Cys Phe Ala
            20                  25                  30

Ser Cys Leu Ala Gly Lys Ile Thr Val Leu Ala Asp Ser Asp Lys Ser
        35                  40                  45

Val Leu Leu Arg Phe Lys Lys Thr Val Ser Asp Pro Gly Ser Ile Leu
    50                  55                  60

Ala Ser Trp Val Glu Glu Ser Glu Asp Tyr Cys Ser Trp Phe Gly Val
65                  70                  75                  80

Ser Cys Asp Ser Ser Arg Val Met Ala Leu Asn Ile Ser Gly Ser
            85                  90                  95

Gly Ser Ser Glu Ile Ser Arg Asn Arg Phe Thr Cys Gly Asp Ile Gly
            100                 105                 110

Lys Phe Pro Leu Tyr Gly Phe Gly Val Arg Arg Asp Cys Thr Gly Asn
        115                 120                 125

His Gly Ala Leu Ala Gly Asn Leu Pro Ser Val Ile Met Ser Leu Thr
    130                 135                 140

Gly Leu Arg Val Leu Ser Leu Pro Phe Asn Ser Phe Ser Gly Glu Ile
145                 150                 155                 160

Pro Val Gly Ile Trp Gly Met Glu Lys Leu Glu Val Leu Asp Leu Glu
                165                 170                 175

Gly Asn Leu Met Thr Gly Ser Leu Pro Asp Gln Phe Thr Gly Leu Arg
            180                 185                 190

Asn Leu Arg Val Met Asn Leu Gly Phe Asn Arg Val Ser Gly Glu Ile
        195                 200                 205

Pro Asn Ser Leu Gln Asn Leu Thr Lys Leu Glu Ile Leu Asn Leu Gly
    210                 215                 220

Gly Asn Lys Leu Asn Gly Thr Val Pro Gly Phe Val Gly Arg Phe Arg
225                 230                 235                 240

Val Leu His Leu Pro Leu Asn Trp Leu Gln Gly Ser Leu Pro Lys Asp
                245                 250                 255

Ile Gly Asp Ser Cys Gly Lys Leu Glu His Leu Asp Leu Ser Gly Asn
            260                 265                 270

Phe Leu Thr Gly Arg Ile Pro Glu Ser Leu Gly Lys Cys Ala Gly Leu
        275                 280                 285

Arg Ser Leu Leu Leu Tyr Met Asn Thr Leu Glu Glu Thr Ile Pro Leu
    290                 295                 300

Glu Phe Gly Ser Leu Gln Lys Leu Glu Val Leu Asp Val Ser Arg Asn
305                 310                 315                 320

Thr Leu Ser Gly Pro Leu Pro Val Glu Leu Gly Asn Cys Ser Ser Leu
                325                 330                 335

Ser Val Leu Val Leu Ser Asn Leu Tyr Asn Val Tyr Glu Asp Ile Asn
            340                 345                 350
```

```
Ser Val Arg Gly Glu Ala Asp Leu Pro Pro Gly Ala Asp Leu Thr Ser
        355                 360                 365
Met Thr Glu Asp Phe Asn Phe Tyr Gln Gly Gly Ile Pro Glu Glu Ile
370                 375                 380
Thr Arg Leu Pro Lys Leu Lys Ile Leu Trp Val Pro Arg Ala Thr Leu
385                 390                 395                 400
Glu Gly Arg Phe Pro Gly Asp Trp Gly Ser Cys Gln Asn Leu Glu Met
                405                 410                 415
Val Asn Leu Gly Gln Asn Phe Phe Lys Gly Glu Ile Pro Val Gly Leu
            420                 425                 430
Ser Lys Cys Lys Asn Leu Arg Leu Leu Asp Leu Ser Ser Asn Arg Leu
        435                 440                 445
Thr Gly Glu Leu Leu Lys Glu Ile Ser Val Pro Cys Met Ser Val Phe
    450                 455                 460
Asp Val Gly Gly Asn Ser Leu Ser Gly Val Ile Pro Asp Phe Leu Asn
465                 470                 475                 480
Asn Thr Thr Ser His Cys Pro Pro Val Val Tyr Phe Asp Arg Phe Ser
                485                 490                 495
Ile Glu Ser Tyr Ser Asp Pro Ser Ser Val Tyr Leu Ser Phe Phe Thr
            500                 505                 510
Glu Lys Ala Gln Val Gly Thr Ser Leu Ile Asp Leu Gly Ser Asp Gly
        515                 520                 525
Gly Pro Ala Val Phe His Asn Phe Ala Asp Asn Asn Phe Thr Gly Thr
    530                 535                 540
Leu Lys Ser Ile Pro Leu Ala Gln Glu Arg Leu Gly Lys Arg Val Ser
545                 550                 555                 560
Tyr Ile Phe Ser Ala Gly Gly Asn Arg Leu Tyr Gly Gln Phe Pro Gly
                565                 570                 575
Asn Leu Phe Asp Asn Cys Asp Glu Leu Lys Ala Val Tyr Val Asn Val
            580                 585                 590
Ser Phe Asn Lys Leu Ser Gly Arg Ile Pro Gln Gly Leu Asn Asn Met
        595                 600                 605
Cys Thr Ser Leu Lys Ile Leu Asp Ala Ser Val Asn Gln Ile Phe Gly
    610                 615                 620
Pro Ile Pro Thr Ser Leu Gly Asp Leu Ala Ser Leu Val Ala Leu Asn
625                 630                 635                 640
Leu Ser Trp Asn Gln Leu Gln Gly Gln Ile Pro Gly Ser Leu Gly Lys
                645                 650                 655
Lys Met Ala Ala Leu Thr Tyr Leu Ser Ile Ala Asn Asn Asn Leu Thr
            660                 665                 670
Gly Gln Ile Pro Gln Ser Phe Gly Gln Leu His Ser Leu Asp Val Leu
        675                 680                 685
Asp Leu Ser Ser Asn His Leu Ser Gly Gly Ile Pro His Asp Phe Val
    690                 695                 700
Asn Leu Lys Asn Leu Thr Val Leu Leu Asn Asn Asn Asn Leu Ser
705                 710                 715                 720
Gly Pro Ile Pro Ser Gly Phe Ala Thr Phe Ala Val Phe Asn Val Ser
                725                 730                 735
Ser Asn Asn Leu Ser Gly Pro Val Pro Ser Thr Asn Gly Leu Thr Lys
            740                 745                 750
Cys Ser Thr Val Ser Gly Asn Pro Tyr Leu Arg Pro Cys His Val Phe
        755                 760                 765
Ser Leu Thr Thr Pro Ser Ser Asp Ser Arg Asp Ser Thr Gly Asp Ser
```

```
             770                 775                 780
Ile Thr Gln Asp Tyr Ala Ser Ser Pro Val Glu Asn Ala Pro Ser Gln
785                 790                 795                 800

Ser Pro Gly Lys Gly Gly Phe Asn Ser Leu Glu Ile Ala Ser Ile Ala
                805                 810                 815

Ser Ala Ser Ala Ile Val Ser Val Leu Ile Ala Leu Val Ile Leu Phe
                    820                 825                 830

Phe Tyr Thr Arg Lys Trp His Pro Lys Ser Lys Ile Met Ala Thr Thr
                835                 840                 845

Lys Arg Glu Val Thr Met Phe Met Asp Ile Gly Val Pro Ile Thr Phe
                850                 855                 860

Asp Asn Val Val Arg Ala Thr Gly Asn Phe Asn Ala Ser Asn Leu Ile
865                 870                 875                 880

Gly Asn Gly Gly Phe Gly Ala Thr Tyr Lys Ala Glu Ile Ser Gln Asp
                    885                 890                 895

Val Val Val Ala Ile Lys Arg Leu Ser Ile Gly Arg Phe Gln Gly Val
                900                 905                 910

Gln Gln Phe His Ala Glu Ile Lys Thr Leu Gly Arg Leu Arg His Pro
                915                 920                 925

Asn Leu Val Thr Leu Ile Gly Tyr His Ala Ser Glu Thr Glu Met Phe
930                 935                 940

Leu Val Tyr Asn Tyr Leu Pro Gly Gly Asn Leu Glu Lys Phe Ile Gln
945                 950                 955                 960

Glu Arg Ser Thr Arg Asp Trp Arg Val Leu His Lys Ile Ala Leu Asp
                965                 970                 975

Ile Ala Arg Ala Leu Ala Tyr Leu His Asp Gln Cys Val Pro Arg Val
                980                 985                 990

Leu His Arg Asp Val Lys Pro Ser Asn Ile Leu Leu Asp Asp Asp Cys
                995                 1000                1005

Asn Ala Tyr Leu Ser Asp Phe Gly Leu Ala Arg Leu Leu Gly Thr
    1010                1015                1020

Ser Glu Thr His Ala Thr Thr Gly Val Ala Gly Thr Phe Gly Tyr
    1025                1030                1035

Val Ala Pro Glu Tyr Ala Met Thr Cys Arg Val Ser Asp Lys Ala
    1040                1045                1050

Asp Val Tyr Ser Tyr Gly Val Val Leu Leu Glu Leu Leu Ser Asp
    1055                1060                1065

Lys Lys Ala Leu Asp Pro Ser Phe Val Ser Tyr Gly Asn Gly Phe
    1070                1075                1080

Asn Ile Val Gln Trp Ala Cys Met Leu Leu Arg Gln Gly Arg Ala
    1085                1090                1095

Lys Glu Phe Phe Thr Ala Gly Leu Trp Asp Ala Gly Pro His Asp
    1100                1105                1110

Asp Leu Val Glu Val Leu His Leu Ala Val Val Cys Thr Val Asp
    1115                1120                1125

Ser Leu Ser Thr Arg Pro Thr Met Lys Gln Val Val Arg Arg Leu
    1130                1135                1140

Lys Gln Leu Gln Pro Pro Ser Cys
    1145                1150

<210> SEQ ID NO 17
<211> LENGTH: 8801
<212> TYPE: DNA
<213> ORGANISM: Glycine max
```

<400> SEQUENCE: 17

```
tattcaacta agtcaagcca tcatatgtca tagattgatt tgcatttgac ttcgtaaagt        60
tttgcataat gctaattatc tgacttttat gttacatttc tctgcttacc tgtccttgaa       120
attagggaca aaatatttac ctgcattagt gggttttgtg tccatgaatg ttttttctta       180
tagttttcc taaagttttt taatgatcca tgaccatggt cttaaattca atcaacaaat        240
gacttggcat tgtactctat gtgatgtgat gtgatttgta atgtctttgc tcaccttaaa       300
tttggtgaaa taatcattta ttttttaaaa gttttacat ctcacacaag aatcctttga        360
gtttaaagcc taaaaagata cacaattcac ctttagtctc tcaagtgttg agcctaaaat       420
gtatgggtgc ttgttatgct tggtgttatt tagttgaacg gtccatagcc cctcaaatgt       480
tcgatcgacc ttcttggttg gatgatctat atctcaattt tcatttgagc aacactttga       540
tttgtcgaaa ttaagaagc aacacacaat ttcacactca ttcactatgt tgaatatcat        600
tttaggattg ttattatcta tgagctgaaa tggttaattg gacttatttc tagcctcaat       660
atgtcacatt ctcaacctag gtgcctttat tgtaattgtc aaacaatact ccacatttcc       720
aagaacctat tttttctttg agtgtaccaa atatttcagt gttgattgtc attttgtttt       780
tctttgagtg taccaaatat ttcagtgttg attgtcattt tgttccagat gagattttaa       840
agggcaacat ttgacttgct tatgtttcta ccactacaca attggtcaac acttgatctt       900
gcttggtgta tgttcgaccc gctttatttt ttagctttta tttgttttta gtacaaatta       960
cacataccctt tcattactca agttaagtag gatcattatg aatgacaaaa cttttttgtt     1020
gaaataaaaa aaaagtcaa gtggtccagt ggtttagtgc ctagtctttg tataatgttt      1080
tatcaaacaa cttttaaatt aaaggaagct tttgagctaa aagaaataaa aattatcaag      1140
caacttctat tgtattttta aagaatatat tttaacatgt gtagatcaaa ttgttctcac      1200
ttaaacaaaa tcctgacatg caagtacgtt taatactttg agaggagagc tttactgatt      1260
cattatgctc ctattcaagt tgagcaagat tgccttctat agaaaaaata gatgtgttat      1320
atatatataa cttatttga gctttaacta taatataact tttaggctaa aaaaaaaatt       1380
gagtcaaacg taaccgtagt ttacaggatt ggattccatg acattgtgat gggaactgta      1440
ggatgtggtt acttggttct caacagctag attaaaatag cttatagaat tttgccacca      1500
gtcttctta tttttatttt aatcaaagga tcctaaccaa agtgatttcg agatttttt       1560
tatgcttttg atgaaatgat tttaggatct ttaggaatga catagcaacc cattttatt       1620
tatttttaa aatattaaaa gtagaaggag tgtgtgaacc agttgtgaaa aacgtgggta       1680
ggtgaggaac ggtcaaagac tcaatacaat gtagactctt ttcttttggt cttatgcaat      1740
gcaatggtga cgttagtgat acgtaacttg tttaatccct tttgtacaaa ctaaactaca      1800
aattacagcg ctcataattc aaacagctag gtaagttatt cagcaaaata taagattaac      1860
tgaatgatta aaaaaaaaag agagagaaaa gaaaaaaagg aagaaaaaga taaaggttc       1920
gaatctctct aataaatatt tttaataaaa ttaatatatt aatatttatc aataaaaaaa      1980
tattcaactt tacatacgtg ttgagtgtgt tctagctcaa acaactaggt gtgtatttga      2040
ttctcaggtc aaattgtgat aggacgaagt ccaaaaccac tacaaaaata aggatatttt      2100
tggtgacctc aacttatatt tgcatcgaga ttgaaactcc cgtataaagg tattttataga     2160
taaaaaagga tcactttaga tttcacacct caatggattt ttatttttt ttacttaatc       2220
gcatatattt ttttacacta cataatagca tatatatata tatatatata tatatatata      2280
```

```
tatatatata tatatatata tatatatata tatatatata tatatatatt ggaaaagaaa    2340
aaatatcaag aaatagaaat aagataaata taaattagag aaaatatttt ttaatgcact    2400
cttttaagta cttttttatta tcatgttatt aatatgaaat atttatcaac attttttaatg  2460 ataatctcta taaaaatttt aattaatcac ttttagtaag atttgaatcc taaattacat    2520
gattaaataa cacaaactac tactagttag gctaactgtt gcttgtacaa attatattat    2580
ttcccgtaat ataaataaag aaagtctgtt attttttttgt ttcaaatata agtaaatatc   2640
aattatctat accttattaa ataagactct ttcaaaatac catttattta ctgaaatcaa    2700
aaacttgatg tttaatatgg agtttcaata aaaagataat ttaggaaaat tatttattta    2760
tttatttgaa atgaaacaat ataatgaaat taattaattt tttaataaat atgaaatatt    2820
tttttataat caagactaaa aggaagtatt gtctaactaa caattgtata atttcgcatt    2880
catttgttgt ctattatgtc accaaataac ttttttttaga tgattgataa aaaaaattga   2940
attagcatgt cctaaaatta tttttctaaa ttaatagaga agaatgtgga tgctgccgtt    3000
ttccaataag aatgcaaatt cggtgttgtt tcctgcatta ggaactcaaa cggtcacttg    3060
tcacggaggc cgagccacat gctatcctta cagcaatttg atgggtcagt catctccaat    3120
tagtcaacca acttgatttt tctcttgtct cttttttaat tgtttttatg ttattttttt    3180
aaaattacat aattttaaaa ttgaattata aaattaaata ttaacaaaat taaatattaa    3240
cataactata taaacagtat cgagacaacg gaaagaatga caaaagaaaa actaatttca    3300
tttgacaaca tgaatatttg aaagttgaaa caaattgcaa actggttgat gataggcatc    3360
aactggtagc ggtttcatca ttctgatgct agttttatcc tcacgacaaa cttagtcaat    3420
gtttgtttca gagagagaga gaaacagagt acataaaaat aagaaaaaga aaaatagagt    3480
agaataaaat aaaatgttaa gctatttgat ttaagagaaa taaaaagaaa taagtcaagt    3540
tacaaaatga tacaaacacc actccttgaa cttaagtcac gggaacaaaa agacaaataa    3600
gggtaagctt gaatcttgga gactgttgga tttggtttgg aagtgcaaat tgaatttaaa    3660
taataaacaa aagattgctt ataattatat atatatatat atatatatat atcattaaag    3720
gattaattta atatagttca aataaatttt aagaacagaa actaaaaatt gaattaaatt    3780
gagatagaaa tgttttcaa ttttcaattt tcttgttagt aaattgaggg atttcaatgt     3840 tttatttta aaatgatatg tataattttt ctttacagta tcaatcaata aaaaaaaatc     3900
atatataaaa ttaaaattat tttaaaaatt atcgttagca taatttataa ttgagtaata    3960
atacagtaaa aaataattaa ataataataa taatatagaa attaaaaccc ttttgatatt    4020
ttgacgaact gcgccaacca tgttagaatt ctaatgtgat gtgtggtttc ctcatttctt    4080
tactgcgtgt ggtccccaca tgaccctact tgccatgtcc tgtgggtccc atcaccaccc    4140
agtcccaatt tccaaacacc acgaaactct tttccatgta gaaattttaa actaaaaagt    4200
actaaaaaaa tctccataat cattccttga aactttaaca acagacaggt caattcgtaa    4260
gaattttatc ttaattttaa aacatttcac atcaattatt tttaaagtct aatacacctg    4320
cacttatgaa ttaatataag aatataaata tatacacatg ctgagtctgt ttaactttac    4380
aataaagtta ttttgaata tgatttttta attaatcgag agtatacatt ctgttatatt     4440
aataatacat gtctttttaa gagattgtaa atagttttta caaagaaact atcctaatca    4500
aatttagtaa caaaaaagtt tctcttaaat attgaatgca gttgcataat tattgctcaa    4560
actcaccatt aatcaaactg gaataattat gtaacatttg attcactcac ttttgatcaa    4620
ttggtgtatg actgtatgtt tcttacttaa aaattaataa cctaattaca gattcttttta   4680
```

```
atttaagact taattaaaag ttccaaattg ttcaggcctt cacagttcag ggtctactta      4740
tgtgtcaaaa catttaaaaa agacatttt aaaattaaaa aacaaaaaga aaaaaaaga       4800 aaggaagaaa aacgcgttat gcgaagacga cacagttgtg ttgttcctcc gtcttctcca     4860
tcgattccat cttttccccc ctcaacacca cacaatatca aattagggtt ttcagaaaaa     4920 cccttttcttt tcttctcttc aacttcactc caaaacggg gaacaagggt tttgggtctc     4980
acagttcaat tcaattttct tccactgtga gatgttttct ttttcttctt cttttcttc     5040 ctcttcctct tctcatagca gttcagtgat caaatggaat tctctcgcgc aatttctctt    5100
cctcgttttc ttcctcttct tcgcgtcgcg aaacgacgcc gtttcggaca aatccacgct    5160
ccttcgcctg aaggcctcgt tctccgaccc cgccggcgtc tctccacgt ggacctccgc     5220 cggcgccgct gactccggcc actgttcctt ctccggcgtc ctatgcgact tgaactctcg    5280
agtcgtcgcc gtcaacgtca ccggcgccgg cggcaaaaac cgaacctcgc acccgtgctc    5340
aaatttctcc caattccctc tctacggctt cggaattcgg cgaacctgtt ccggtagcaa    5400
aggttctctc ttcggaaatg tttcttctct gagtttgatc gccgagctca cggagcttag    5460
ggttttgtct ctccccttca acgcgttgga gggtgaaatc cccgaagcga tttgggcat     5520 ggagaacctc gaggttctcg atttagaagg gaatttgatt agtggctatc ttcccttgag    5580
agtcgatggc ttgaagaatt tgagggtttt gaatctgggg tttaatagga ttgttggaga    5640
gatacctagt tcaattgggt ctcttgagag attggaggtt ttgaatttgg ctggtaatga    5700
attgaatggt tctgttcccg gttttgtagg gaggcttaga ggggtgtatc tgtcttttaa    5760
tcagttaagt ggggttattc ccagagagat tggggagaat tgtgagaagc ttgagcattt    5820
ggatttgtct gtgaattcga tggttggagt gattccgggg agtttgggga attgtgggag    5880
gttgaagacg ctgttgttgt attccaattt gttggaagag ggcattccgg gtgagctagg    5940
gagcctcaag agccttgagg tgttggatgt ttccaggaac attctcagca gctctgtgcc    6000
gagggagctt gggaattgct tggagttgag ggttctcgtg ctgtcaaatc tattcgatcc    6060
acgaggggat gttgctgata gtgatttggg gaagttgggg tctgtggata atcagttgaa    6120
ttattttgaa ggggcaatgc cagcggaaat tttgttgctt ccgaagttga ggatattgtg    6180
ggctcccatg gtgaatttgg aaggcggttt acagagaagt tggggcggtt gtgagagctt    6240
ggagatggtg aatttggctc agaattttt cagtgggaag tttccaaacc agcttggtgt     6300
ttgcaagaag ctgcattttg ttgatttaag cgcgaacaat ctcactgggg agctttctca    6360
ggaacttcgt gttccctgta tgagtgtgtt tgatgttagt ggcaacatgt tatctggttc    6420
agttcctgat ttctccgaca atgcttgtcc ccctgttcct tcctggaatg gcactctgtt    6480
tgcggatggc gacctatccc tgccatatgc atcctttttt atgtcaaagg ttcgtgagag    6540 atcactttc acatcaatgg agggagttgg tacttctgtt gttcacaact ttgggcaaaa     6600 cagcttact ggcattcagt cattgccaat agcacgtgac aggctgggga agaagagcgg     6660
ttacacgttt cttgttggtg aaaataatct tacaggacct tttcctactt ttttatttga    6720
gaaatgtgat gaattagaag cactgctttt aaacgtcagt tataatagga tatctggtca    6780
gattccttcc aattttggtg gaatatgcag atcattgaaa ttcttagatg catctggaaa    6840
tgaacttgca ggaccgattc cccttgattt agggaatttg gtctctcttg tatctctgaa    6900
cctcagtagg aatcagttac aaggccagat tcccaccagc cttggccaga tgaagaacct    6960
gaagtttctt tctttggctg gtaataggtt aaatggttta attcctacca gcctgggggca   7020
```

| | |
|---|---|
| gttgtactct tgaaagtct tggacctttc gtcaaactct cttactggtg agattcccaa | 7080 |
| ggctattgag aacatgagaa atctgactga tgttttgctc aacaacaaca atctttctgg | 7140 |
| tcacattcct aatggtttgg cacatgtcgc tacactctca gcattcaatg tgtctttcaa | 7200 |
| caacttatct ggatccttgc cttcaaatag tggcttgatt aaatgcagca gtgctgttgg | 7260 |
| gaatccgttt ctaagtccct gccatggagt ttctctgagt gtgccatcag tgaatcaacc | 7320 |
| agggccacct gatggcaact cgtataaatac ggcaacagct caagctaatg acaagaagag | 7380 |
| tgggaatggc ttcagttcta ttgaaatagc atctataact tctgcttcag ccattgtttc | 7440 |
| ggttcttata gccctgattg ttctattctt ttacactcgg aagtggaagc caaggtccag | 7500 |
| ggttgttggt tctataagaa aagaagttac agtgtttact gatattgggg tcccgttgac | 7560 |
| gtttgaaacg gtagtccaag ccacaggaaa cttcaatgca ggtaactgta ttggcaatgg | 7620 |
| aggttttggc gcaacataca aggcagagat atcacccgga atcctggtgg ctgtcaaacg | 7680 |
| actcgcagtt ggacgtttcc aaggtgttca acaattccat gctgagatca agacccttgg | 7740 |
| gaggcttcat catccaaatc tagtcactct gataggttat catgcttgtg aaacagagat | 7800 |
| gtttctcata tacaactatt tgtcaggtgg taatctggaa aagtttatcc aggagaggtc | 7860 |
| aacaagggct gtggattgga aaattcttta caagatcgca ttggacatag cccgtgcact | 7920 |
| tgcctatctg catgatacgt gtgttccccg tgttcttcac cgcgatgtca agcccagcaa | 7980 |
| catcttgttg gatgatgatt caacgcttca tctatctgac tttggattgg ctagacttct | 8040 |
| ggggacttca gagacacatg ctacaactgg tgtggccgga acattcggtt atgttgctcc | 8100 |
| cgaatatgcc atgacgtgcc gtgtttctga taaggctgat gtgtacagct atggtgtggt | 8160 |
| gcttctggag ttgctctcag acaagaaggc attggaccct tcattttctt cttatggaaa | 8220 |
| tggtttcaac atagtggcat gggcatgcat gctactgaag caaggaaggg caaggagtt | 8280 |
| cttcactgct gggttatggg aagcaggacc aggagatgat ttggtagaag tgcttcactt | 8340 |
| agcagttgtg tgtactgttg actctctctc taccagacct acaatgaaac aggttgtaag | 8400 |
| aagacttaag caacttcaac ccccatcatg ctagcccctt gtgtggctgt gttccttta | 8460 |
| cattattaat cttagaaatg ttcccttgg aatttaattt agcattttg tggatttagg | 8520 |
| ttgagctccc gatttgtact tattcccctc cttgtacatt tttatatagt tgtattgtat | 8580 |
| ccccaatttt ccatgctctt ttcttgattt ggtattattt aggtttgggg ccttggtgtt | 8640 |
| gattctgctg aagaatgcag atatttgatt tccccttcat acacgtgtat tccatgtcta | 8700 |
| tctgttcagt aaaattgaag aatagaattt gttttttgaa tttttgttgt tggtgctaaa | 8760 |
| ttaatttgag gaaaggaatg gattggatta agattttaaa a | 8801 |

<210> SEQ ID NO 18
<211> LENGTH: 3423
<212> TYPE: DNA
<213> ORGANISM: Glycine max

<400> SEQUENCE: 18

| | |
|---|---|
| atgttttctt tttcttcttc ttttttcttcc tcttcctctt ctcatagcag ttcagtgatc | 60 |
| aaatggaatt ctctcgcgca atttctcttc ctcgttttct tcctcttctt cgcgtcgcga | 120 |
| aacgacgccg tttcggacaa atccacgctc cttcgcctga aggcctcgtt ctccgacccc | 180 |
| gccggcgtcc tctccacgtg gacctccgcc ggcgccgctg actccggcca ctgttccttc | 240 |
| tccggcgtcc tatgcgactt gaactctcga gtcgtcgccg tcaacgtcac cggcgccggc | 300 |
| ggcaaaaacc gaacctcgca cccgtgctca aatttctccc aattccctct ctacggcttc | 360 |

```
ggaattcggc gaacctgttc cggtagcaaa ggttctctct tcggaaatgt ttcttctctg    420
agtttgatcg ccgagctcac ggagcttagg gttttgtctc tccccttcaa cgcgttggag    480
ggtgaaatcc ccgaagcgat ttggggcatg gagaacctcg aggttctcga tttagaaggg    540
aatttgatta gtggctatct tcccttgaga gtcgatggct gaagaatttg agggttttg     600 aatctggggt ttaataggat tgttggagag atacctagtt caattgggtc tcttgagaga    660
ttggaggttt tgaatttggc tggtaatgaa ttgaatggtt ctgttccgg ttttgtaggg     720 aggcttagag gggtgtatct gtctttaat cagttaagtg gggttattcc cagagagatt     780
ggggagaatt gtgagaagct tgagcatttg gatttgtctg tgaattcgat ggttggagtg    840
attccgggga gtttggggaa ttgtgggagg ttgaagacgc tgttgttgta ttccaatttg    900
ttggaagagg gcattccggg tgagctaggg agcctcaaga gccttgaggt gttggatgtt    960
tccaggaaca ttctcagcag ctctgtgccg agggagcttg ggaattgctt ggagttgagg   1020
gttctcgtgc tgtcaaatct attcgatcca cgaggggatg ttgctgatag tgatttgggg   1080
aagttggggt ctgtggataa tcagttgaat tattttgaag gggcaatgcc agcggaaatt   1140
ttgttgcttc cgaagttgag gatattgtgg gctcccatgg tgaatttgga aggcggtta     1200 cagagaagtt ggggcggttg tgagagcttg gagatggtga atttggctca gaattttttc   1260
agtgggaagt ttccaaacca gcttggtgtt tgcaagaagc tgcattttgt tgatttaagc   1320
gcgaacaatc tcactgggga gctttctcag gaacttcgtg ttccctgtat gagtgtgttt   1380
gatgttagtg gcaacatgtt atctggttca gttcctgatt tctccgacaa tgcttgtccc   1440
cctgttcctt cctggaatgg cactctgttt gcggatggcg acctatccct gccatatgca   1500 tccttttta tgtcaaaggt tcgtgagaga tcacttttca catcaatgga gggagttggt    1560
acttctgttg ttcacaactt tgggcaaaac agctttactg gcattcagtc attgccaata   1620
gcacgtgaca ggctggggaa gaagagcggt tacacgtttc ttgttggtga aaataatctt   1680
acaggacctt ttcctacttt tttatttgag aaatgtgatg aattagaagc actgctttta   1740
aacgtcagtt ataataggat atctggtcag attccttcca atttggtgg aatatgcaga    1800 tcattgaaat tcttagatgc atctggaaat gaacttgcag gaccgattcc ccttgattta   1860
gggaatttgg tctctcttgt atctctgaac ctcagtagga atcagttaca aggccagatt   1920
cccaccagcc ttggccagat gaagaacctg aagtttcttt ctttggctgg taataggtta   1980
aatggtttaa ttcctaccag cctggggcag ttgtactctt tgaaagtctt ggacctttcg   2040
tcaaactctc ttactggtga gattcccaag gctattgaga acatgagaaa tctgactgat   2100
gttttgctca caacaacaa tctttctggt cacattccta atggtttggc acatgtcgct    2160
acactctcag cattcaatgt gtcttttcaac aacttatctg gatccttgcc ttcaaatagt   2220
ggcttgatta aatgcagcag tgctgttggg aatccgtttc taagtccctg ccatggagtt   2280
tctctgagtg tgccatcagt gaatcaacca gggccacctg atggcaactc gtataatacg   2340
gcaacagctc aagctaatga caagaagagt gggaatggct tcagttctat tgaaatagca   2400
tctataactt ctgcttcagc cattgttttcg gttcttatag ccctgattgt tctattcttt   2460
tacactcgga agtggaagcc aaggtccagg gttgttggtt ctataagaaa agaagttaca   2520
gtgtttactg atattggggt cccgttgacg tttgaaacgg tagtccaagc cacaggaaac   2580
ttcaatgcag gtaactgtat tggcaatgga ggttttggcg caacatacaa ggcagagata   2640
tcacccggaa tcctggtggc tgtcaaacga ctcgcagttg gacgtttcca aggtgttcaa   2700
```

```
caattccatg ctgagatcaa gacccttggg aggcttcatc atccaaatct agtcactctg    2760
ataggttatc atgcttgtga acagagatg tttctcatat acaactatt gtcaggtggt      2820 aatctggaaa agtttatcca ggagaggtca acaagggctg tggattggaa aattctttac    2880
aagatcgcat tggacatagc ccgtgcactt gcctatctgc atgatacgtg tgttccccgt    2940
gttcttcacc gcgatgtcaa gcccagcaac atcttgttgg atgatgattt caacgcttat    3000
ctatctgact ttggattggc tagacttctg gggacttcag agacacatgc tacaactggt    3060
gtggccggaa cattcggtta tgttgctccc gaatatgcca tgacgtgccg tgtttctgat    3120
aaggctgatg tgtacagcta tggtgtggtg cttctggagt tgctctcaga caagaaggca    3180
ttggacccct cattttcttc ttatggaaat ggtttcaaca tagtggcatg gcatgcatg    3240 ctactgaagc aaggaagggc aaaggagttc ttcactgctg ggttatggga agcaggacca    3300
ggagatgatt tggtagaagt gcttcactta gcagttgtgt gtactgttga ctctctctct    3360
accagaccta caatgaaaca ggttgtaaga agacttaagc aacttcaacc cccatcatgc    3420
tag                                                                  3423
```

<210> SEQ ID NO 19
<211> LENGTH: 1140
<212> TYPE: PRT
<213> ORGANISM: Glycine max

<400> SEQUENCE: 19

```
Met Phe Ser Phe Ser Ser Phe Ser Ser Ser Ser Ser His Ser
1               5                   10                  15

Ser Ser Val Ile Lys Trp Asn Ser Leu Ala Gln Phe Leu Phe Leu Val
            20                  25                  30

Phe Phe Leu Phe Phe Ala Ser Arg Asn Asp Ala Val Ser Asp Lys Ser
        35                  40                  45

Thr Leu Leu Arg Leu Lys Ala Ser Phe Ser Asp Pro Ala Gly Val Leu
    50                  55                  60

Ser Thr Trp Thr Ser Ala Gly Ala Ala Asp Ser Gly His Cys Ser Phe
65                  70                  75                  80

Ser Gly Val Leu Cys Asp Leu Asn Ser Arg Val Val Ala Val Asn Val
                85                  90                  95

Thr Gly Ala Gly Gly Lys Asn Arg Thr Ser His Pro Cys Ser Asn Phe
            100                 105                 110

Ser Gln Phe Pro Leu Tyr Gly Phe Gly Ile Arg Arg Thr Cys Ser Gly
        115                 120                 125

Ser Lys Gly Ser Leu Phe Gly Asn Val Ser Ser Leu Ser Leu Ile Ala
    130                 135                 140

Glu Leu Thr Glu Leu Arg Val Leu Ser Leu Pro Phe Asn Ala Leu Glu
145                 150                 155                 160

Gly Glu Ile Pro Glu Ala Ile Trp Gly Met Glu Asn Leu Glu Val Leu
                165                 170                 175

Asp Leu Glu Gly Asn Leu Ile Ser Gly Tyr Leu Pro Leu Arg Val Asp
            180                 185                 190

Gly Leu Lys Asn Leu Arg Val Leu Asn Leu Gly Phe Asn Arg Ile Val
        195                 200                 205

Gly Glu Ile Pro Ser Ser Ile Gly Ser Leu Glu Arg Leu Glu Val Leu
    210                 215                 220

Asn Leu Ala Gly Asn Glu Leu Asn Gly Ser Val Pro Gly Phe Val Gly
225                 230                 235                 240
```

-continued

```
Arg Leu Arg Gly Val Tyr Leu Ser Phe Asn Gln Leu Ser Gly Val Ile
                245                 250                 255
Pro Arg Glu Ile Gly Glu Asn Cys Glu Lys Leu Glu His Leu Asp Leu
            260                 265                 270
Ser Val Asn Ser Met Val Gly Val Ile Pro Gly Ser Leu Gly Asn Cys
        275                 280                 285
Gly Arg Leu Lys Thr Leu Leu Leu Tyr Ser Asn Leu Leu Glu Glu Gly
    290                 295                 300
Ile Pro Gly Glu Leu Gly Ser Leu Lys Ser Leu Glu Val Leu Asp Val
305                 310                 315                 320
Ser Arg Asn Ile Leu Ser Ser Val Pro Arg Glu Leu Gly Asn Cys
                325                 330                 335
Leu Glu Leu Arg Val Leu Val Leu Ser Asn Leu Phe Asp Pro Arg Gly
            340                 345                 350
Asp Val Ala Asp Ser Asp Leu Gly Lys Leu Gly Ser Val Asp Asn Gln
        355                 360                 365
Leu Asn Tyr Phe Glu Gly Ala Met Pro Ala Glu Ile Leu Leu Leu Pro
    370                 375                 380
Lys Leu Arg Ile Leu Trp Ala Pro Met Val Asn Leu Glu Gly Gly Leu
385                 390                 395                 400
Gln Arg Ser Trp Gly Gly Cys Glu Ser Leu Glu Met Val Asn Leu Ala
                405                 410                 415
Gln Asn Phe Phe Ser Gly Lys Phe Pro Asn Gln Leu Gly Val Cys Lys
            420                 425                 430
Lys Leu His Phe Val Asp Leu Ser Ala Asn Asn Leu Thr Gly Glu Leu
        435                 440                 445
Ser Gln Glu Leu Arg Val Pro Cys Met Ser Val Phe Asp Val Ser Gly
    450                 455                 460
Asn Met Leu Ser Gly Ser Val Pro Asp Phe Ser Asp Asn Ala Cys Pro
465                 470                 475                 480
Pro Val Pro Ser Trp Asn Gly Thr Leu Phe Ala Asp Gly Asp Leu Ser
                485                 490                 495
Leu Pro Tyr Ala Ser Phe Phe Met Ser Lys Val Arg Glu Arg Ser Leu
            500                 505                 510
Phe Thr Ser Met Glu Gly Val Gly Thr Ser Val Val His Asn Phe Gly
        515                 520                 525
Gln Asn Ser Phe Thr Gly Ile Gln Ser Leu Pro Ile Ala Arg Asp Arg
    530                 535                 540
Leu Gly Lys Lys Ser Gly Tyr Thr Phe Leu Val Gly Glu Asn Asn Leu
545                 550                 555                 560
Thr Gly Pro Phe Pro Thr Phe Leu Phe Glu Lys Cys Asp Glu Leu Glu
                565                 570                 575
Ala Leu Leu Leu Asn Val Ser Tyr Asn Arg Ile Ser Gly Gln Ile Pro
            580                 585                 590
Ser Asn Phe Gly Gly Ile Cys Arg Ser Leu Lys Phe Leu Asp Ala Ser
        595                 600                 605
Gly Asn Glu Leu Ala Gly Pro Ile Pro Leu Asp Leu Gly Asn Leu Val
    610                 615                 620
Ser Leu Val Ser Leu Asn Leu Ser Arg Asn Gln Leu Gly Gln Ile
625                 630                 635                 640
Pro Thr Ser Leu Gly Gln Met Lys Asn Leu Lys Phe Leu Ser Leu Ala
                645                 650                 655
Gly Asn Arg Leu Asn Gly Leu Ile Pro Thr Ser Leu Gly Gln Leu Tyr
```

```
                  660                 665                 670
Ser Leu Lys Val Leu Asp Leu Ser Ser Asn Ser Leu Thr Gly Glu Ile
                675                 680                 685
Pro Lys Ala Ile Glu Asn Met Arg Asn Leu Thr Asp Val Leu Leu Asn
            690                 695                 700
Asn Asn Asn Leu Ser Gly His Ile Pro Asn Gly Leu Ala His Val Ala
705                 710                 715                 720
Thr Leu Ser Ala Phe Asn Val Ser Phe Asn Asn Leu Ser Gly Ser Leu
                    725                 730                 735
Pro Ser Asn Ser Gly Leu Ile Lys Cys Ser Ser Ala Val Gly Asn Pro
                740                 745                 750
Phe Leu Ser Pro Cys His Gly Val Ser Leu Ser Val Pro Ser Val Asn
                755                 760                 765
Gln Pro Gly Pro Pro Asp Gly Asn Ser Tyr Asn Thr Ala Thr Ala Gln
            770                 775                 780
Ala Asn Asp Lys Lys Ser Gly Asn Gly Phe Ser Ser Ile Glu Ile Ala
785                 790                 795                 800
Ser Ile Thr Ser Ala Ser Ala Ile Val Ser Val Leu Ile Ala Leu Ile
                    805                 810                 815
Val Leu Phe Phe Tyr Thr Arg Lys Trp Lys Pro Arg Ser Arg Val Val
                820                 825                 830
Gly Ser Ile Arg Lys Glu Val Thr Val Phe Thr Asp Ile Gly Val Pro
                835                 840                 845
Leu Thr Phe Glu Thr Val Val Gln Ala Thr Gly Asn Phe Asn Ala Gly
            850                 855                 860
Asn Cys Ile Gly Asn Gly Gly Phe Gly Ala Thr Tyr Lys Ala Glu Ile
865                 870                 875                 880
Ser Pro Gly Ile Leu Val Ala Val Lys Arg Leu Ala Val Gly Arg Phe
                    885                 890                 895
Gln Gly Val Gln Gln Phe His Ala Glu Ile Lys Thr Leu Gly Arg Leu
                900                 905                 910
His His Pro Asn Leu Val Thr Leu Ile Gly Tyr His Ala Cys Glu Thr
                915                 920                 925
Glu Met Phe Leu Ile Tyr Asn Tyr Leu Ser Gly Gly Asn Leu Glu Lys
            930                 935                 940
Phe Ile Gln Glu Arg Ser Thr Arg Ala Val Asp Trp Lys Ile Leu Tyr
945                 950                 955                 960
Lys Ile Ala Leu Asp Ile Ala Arg Ala Leu Ala Tyr Leu His Asp Thr
                    965                 970                 975
Cys Val Pro Arg Val Leu His Arg Asp Val Lys Pro Ser Asn Ile Leu
                980                 985                 990
Leu Asp Asp Asp Phe Asn Ala Tyr Leu Ser Asp Phe Gly Leu Ala Arg
                995                 1000                1005
Leu Leu Gly Thr Ser Glu Thr His Ala Thr Thr Gly Val Ala Gly
            1010                1015                1020
Thr Phe Gly Tyr Val Ala Pro Glu Tyr Ala Met Thr Cys Arg Val
            1025                1030                1035
Ser Asp Lys Ala Asp Val Tyr Ser Tyr Gly Val Val Leu Leu Glu
            1040                1045                1050
Leu Leu Ser Asp Lys Lys Ala Leu Asp Pro Ser Phe Ser Ser Tyr
            1055                1060                1065
Gly Asn Gly Phe Asn Ile Val Ala Trp Ala Cys Met Leu Leu Lys
            1070                1075                1080
```

Gln Gly Arg Ala Lys Glu Phe Phe Thr Ala Gly Leu Trp Glu Ala
    1085                1090                1095

Gly Pro Gly Asp Asp Leu Val Glu Val Leu His Leu Ala Val Val
    1100                1105                1110

Cys Thr Val Asp Ser Leu Ser Thr Arg Pro Thr Met Lys Gln Val
    1115                1120                1125

Val Arg Arg Leu Lys Gln Leu Gln Pro Pro Ser Cys
    1130                1135                1140

<210> SEQ ID NO 20
<211> LENGTH: 8701
<212> TYPE: DNA
<213> ORGANISM: Glycine max

<400> SEQUENCE: 20
ataaaacata aaccaaatgg ggaggtagcc aagtacaagg ctaggatggt ggcaaaagga      60
tttttgcaca aagagaggat tgactataat gaggtgtttg ccctatggc aagattggag     120 acagtgagga tgattgtagc tgctgccagt aatagggtt ggcctatgta ccaaatggat     180
gttaaatcaa ccttcttgaa tggatatcta ggagaagaag tgtacatact acaaccaccg    240
ggctttgaga agaaaagca tgaagataaa gtgtaggctt agaaaagccc tatatggttt     300
aaagcagtca ccaagggcct ggaatatgag gattgatgga gtcttagcca aacaaaaatt    360
cagcaaatgc aagagtgagc atggtgtgta tgtaagagcc aattgctcaa ccaatttact    420
actggtttgt ctatatgtag atgatctact tgtgactggc agcagtgaag aggagattca    480
tggtttcaag cagttcatga tgattgagtt tgagatgact aatctaggga aattatcaca    540
tttccttgga ttagagttta accaagtcca gaagggagtg cttatgcact aaagtagata    600
tgcacaggag attctcaaga gatttggtat gctgaattgc aattctgctt ccacactagc    660
taaaccatgg cttaagttgg agaaggatcc tgaagaggaa ctggctgatg caactgagtt    720
caggaaattg attggatccc tgagatactt atgcaatagc agacctgata tctgctttac    780
agtaagcttg atcaacagat tcatgaaaca gcctagagtg tcacacatgc aagcagccaa    840
aaaagtgttg aggtttgtta aagggaaat tgataatggt gtgttgttcc cttttgaagt    900
tgaatcagga aaaccagatc tgtttggtta cacagattct gattggaaaa gagatccaaa    960
acatgagaaa agcattgggg atgtctattc atgtattatg atgcaccaat ggcttggagt   1020
tctagaaaat aggatgtggt agccttatcc acttgtgaag ctgagtatgt ggcagcatca   1080
cttggtgcat gttaagcagt ttggatgatg aatctactcg aagaattgaa gctaagggaa   1140
aggaaaccta tctgcttgat gattgacaac aagtctacta ttaatttggc caaacatcct   1200
accctgcatg gcagaagcaa acatattgag cttaggtttc attatatcag agaacaagtt   1260
ttgaaaggta atgtagttaa ggaatactgt taagcagaag aacaactagc aaatttaatg   1320
acaaagccat ttcaagtttc aaggttcaat tagatttgta gtaaactggt caatagcttg   1380
aaggatctga attgaggggg agtgttgaag cttggagttt gttatagtta tcaattcagc   1440
ccttgataag ttgtacatgg tagttagttt gttagattta tgttatttca ggtatttttg   1500
ttatttcagg taattttgtt tgagaattga tctgcaactt ggttttagaa tgcagagttc   1560
ctatgctaac tgtataaatg tgaaactatt gtttctgtaa aaggttaatg caatctttct   1620
gttcatttac acaatttagt ttccttgctc actatcttcc tcatttgtct tcatcattca   1680
agactcaatt ttggtttcta gcttgatggt gttgtaagcg tcaggcctat cacatttgc   1740

```
agcattgggt taggtacaag attgatttta tattagaatt ggccaactat attatgatca    1800
agcgaacccc atacatattc tcttttcgtt catccacaca ccaacaagta aaagtaatt    1860 atttttaggt gaaaaatgaa gaaattaaag aaggccctat gtagtaaaca tgtaaaagca    1920
tacacgaaag cattaaaaaa tgtaagaaca ctaaccatga agatattgtt atattttaag    1980
attaaatatg tttttatccc taataaatac tcaatttttg tgtttatttc ctaataaaaa    2040
atttctttat gttgagtctc taataaaata attttatttt tagtctttaa tactattttt    2100
tagtccaaat aaattagtaa aatttgtttt aagtccgact aattacatat gaaagtatca    2160
atgataataa aacccaattt atcaagaact aaaaaaagta tcaatgataa taaataaaat    2220
aattatttta ttaaaaattc aatacaagat aaaaatttat aaaaaaaaat aaacacaaaa    2280
gtcaaatatt tattagatat taaaaacata tttaagtcta ttttaattag ttgattacta    2340
attcaactcc catttgattc tatatcatat agcaataaac attccaatgt aatagaaatt    2400
gaacttcaat gatagacaat aaaatataag taaatgcttt aaaaaattta cctttatgag    2460
ttctacctac acgccatctt cagcttcaaa cctctttgtg tgtggactcc aagaaaatcc    2520
actaagccca ctaaataagt catggactta actccatcta tctttcattt ttttttttaat    2580 ttattcgtga catgttttt ggtaacatcc ttcaatcctg attctcaatg ttttgacaat    2640
atttacaata gcttaacttg tccaacttcc atgtattcta tggcctagtc ttgttttatc    2700
tatcattgca tgaagtagac gattgtcttg ttccttcatc attttctttg ttcattttcc    2760
agcctataaa attaatataa agatttgtcc atacaacaat aaacataatg atgcttataa    2820
taaatacaca tctcataaaa gggaatattg ttcatacaca acaaaaatgt caaaatgcaa    2880
taaggttcat acttcatatt tcatactcat tttgtaattt attttgaaaa ttttcgatta    2940
gtctataatc attatcacat tgttgcgttt gagatctatc tgtctcactc tgatcaaatt    3000
catgatcaac ttatttaaat aagaagtcat gattacccat gttccataaa aaattgtgta    3060
gattacaata tattaataca atattttca tagtttcaaa tccatagtgt ggttctgagc    3120
cactagctat aatggaaaat ctcttctttt gaaacaccaa ttattctctc aattacattc    3180
ctaagagatg catgtctcag gttgaataac tcttttcagat tttgctgccc tctagctgag    3240
tattccttta agtggtaaag aacaccatga tacggtgtta gaatttgatg tttaagcatc    3300
aaacctgcat cccctagata aaacttgcct acatacacaa gggatcatat aacttaagat    3360
agtacatatg aacaagtcat ttgaactgaa aaggaatttg tactcatctt caggtattct    3420
tagtggatct tcctagttaa tgcatccttt acttctcatc tcaataatta ttaagatga    3480 gaagtaagga ctaaattgat cttttatctt aattaattaa taataataat aactattttg    3540
atatttttca tgtgcagacg aacagggcca gccatgttag aatttatgt gatgtgtggt    3600 ttcctcgttt cttgactacg tgtggtcccc acatgaccat aattgccatg tcctgcgggc    3660
ccatcaccac ccagtcccaa tttccaaaca ccacgaaact cttctccatc tagaaatttt    3720
aaactaaaaa ttatataaaa aaaaaactcc acccttgaag ctttaacaac agacaggtca    3780
attctaagaa tttcatcttg attttaataa atttcacatc aattattttt aaagactaat    3840
acaccctgaa tattaatata agaatataaa tatacacatg ttaagtctgt ttaactttac    3900
aataaagtta ttttttgaata tgatttgctg attaaaaaaa attgaaaatg attttttaat    3960
taatcaaggg tataatttt ttatattgat aataaggttt tttaagagat tataaatatt    4020
ttttaaaaaa acaatcctaa tcaaattgag taaaattatt atatgtcatt ttttctcta    4080 aagcattgaa tacaactaca taattataac tcaatctcac cattaataaa actgaaataa    4140
```

```
ttatgtacta atatttcatt cactcacttt tgatcaattg gtgtattttc ctaaattatt    4200
attatagttt atagtttata agaatgattt tgaaatttat ataggattaa tttataacct    4260
aaaatatcac tcataatttt tagaaacata tttaaaaagg tttaatacaa caacagtttc    4320
tttaattatt ttaaatctat caattaaaaa aattgtaatt tctttaatat ttttttagtt    4380
cgacttttag aattaatgtc cagaaattca aagattgaca ccaccttagc tcacataaat    4440 gaaaagatc tatttatgaa ataaaattct tgagccgatc acaatcatat accgtgagcc     4500
aatgaatatt ggatacccaa attaatccaa cctagaaaat aattaattcc taacagtttt    4560
actaacttta atctttaatc actaagttat aaaactggta ggaaattaat aacctaatta    4620
tatttttaat ttgagactta attaaaattt tccaaattgt tcaggccttc agagttcagt    4680
tcagggtcta cttatgtgtc aaagcaatta aaaaaacaat ttatatgaaa aaaaaaaaca    4740
aaaacgaaga aaaaacgcgt tttgcgaaga caatactgtt gtgttgttga gtctctgagt    4800
cttgttcctc cgtcttctcc atcattttct atcgtctttt cccccctca acaccacaca    4860 aaatcaaaat tagggttttt cagaaacggg taacaaggtt ggttttgggt ctcacagttc    4920
gattcaattt tcttccactg tgagatgttt tcttcttctt tttctcacag cagttcagcg    4980
atcaaatgga attccctcac acaatttctc ttccttgttt tcttcctctt ctccgcgtcg    5040
cgaaacgacg ccgtttcgcc cttttcggac aaatccgcgc tcctccgcct taaagcctcg    5100
ttctccaacc ccgccggcgt tctctccacg tggacctccg ccaccgccac ctctgactcc    5160
ggccactgct ccttctccgg cgtcctctgc gacgcgaact cccgagtcgt cgccgtcaac    5220
gtcaccggcg ccggcggcaa caaccgaaca tctcccccgt gctcaaattt ctcccaattc    5280
cctctctacg gcttcggaat tcggcgaacc tgttccggta gcaaaggttc tctcttcgga    5340
aacgcttctt ctctgagctt catcgccgag ctcacggagc ttagggtttt gtcgctcccc    5400
ttcaatgcgt tggagggtga aatccccgaa gcgatttggg gcatggagaa cctcgaggtt    5460
ctcgacttag aagggaattt gataagtggc tgtcttcctt tcagaatcaa tggcttgaag    5520
aatttaaggg ttttgaatct cgcgtttaat aggattgttg gggatatacc tagttcaatt    5580
gggtctcttg agagattgga ggttttgaat ttggctggta atgaattgaa tggttctgtt    5640
cccggttttg tagggaggct tagaggggtg tatctgtctt ttaatcagtt aagtgggatt    5700
attccaagag agattgggga gaattgtggg aaccttgagc atttggattt gtctgcgaat    5760
tcgattgttc gagcgattcc aaggagtttg gggaattgtg ggaggttgag gacgcttttg    5820
ttgtattcca atttgttgaa agagggtatt ccgggtgagc ttgggagact aagagcctt    5880 gaggtgttgg atgtttccag gaacactctc agcggctctg tgccgcggga gcttgggaat    5940
tgcttggagt tgagagtgct tgtgctgtcg aatctattcg atccacgtgg ggatgttgat    6000
gctggtgatt tggagaaatt ggggtctgtg aatgatcagt tgaattattt tgaaggggca    6060
atgcctgtgg aggttttgtc gcttcccaag ttgaggatat tgtgggctcc catggtgaat    6120
ttggaaggtg gtttacaggg aagttgggc ggttgtgaga gcttggagat ggtgaatttg     6180
gctcagaatt ttttcagtgg ggagtttcca aaccagcttg gtgtttgcaa gaagctgcat    6240
tttgttgatt taagctctaa caatcttaca ggggagcttt ctgaggaact ccgagttccc    6300
tgtatgagtg tgtttgatgt tagtgggaac atgttatctg gttcagttcc tgatttctcc    6360
aacaatgttt gtcccctgt tccttcctgg aatggaaatc tgtttgcaga tggcaatgct     6420
tccccgcggt atgcatcctt ttttatgtca aaggttcgtg agagatcact tttcacgtca    6480
```

```
atgggggggag ttggcacttc tgttgttcac aactttgggc aaaacagctt tactgacatt    6540
cactcgttgc cagtagcaca tgacaggctg ggaaagaagt gcggttacac atttcttgtt    6600
ggtgaaaata atcttacagg acctttcct acttttttat ttgagaaatg tgatgaatta    6660
gatgcattgc ttttaaatgt cagttataat aggatatctg gtcagattcc ttccaatttt    6720
ggtggaatat gcagatcatt gaaattttg gatgcgtctg gaaatgaact tgcaggaacg    6780
attccccttg atgtagggaa tttggtctct cttgtatttc tgaacctcag taggaatcag    6840
ttacaaggcc agattcccac caaccttggc cagatgaaga atctgaagtt tctttctttg    6900
gctggtaata agttgaatgg ctcaattcct atcagcctgg ggcagttgta ctctttagaa    6960
gtcttggacc tttcttcaaa ctctcttact ggtgagattc caaaggctat tgaaaacatg    7020
agaaatctga cagatgtttt gctcaataac aacaatcttt ctggtcacat tcctaatggt    7080
ttggcacatg tcactacact ctccgcattc aatgtgtctt caacaacttt atctggatcc    7140
ttgccttcaa atagtggctt gattaaatgc agaagtgctg ttgggaatcc gtttctaagt    7200
ccctgccgtg gagtttcgct gaccgtgcca tcagggcaac tagggccact tgatgcaaca    7260
gcaccagcta ctacaggcaa gaagagtggg aatggcttca gttctattga aatagcatct    7320
ataacttctg cttcagccat tgttttggtc cttatagccc tgattgttct attcttttac    7380
actcggaagt ggaagccaag gtccagggtt attagttcta taagaaaaga agttacagtg    7440
ttcactgata ttgggttccc attgacgttt gaaactgtag tccaagccac aggaaacttc    7500
aatgcaggta actgtattgg gaatggaggt tttggcacaa catacaaggc agagatatca    7560
ccaggaatcc tggtggcagt caaacgactt gcagttggac gtttccaagg tgtccaacaa    7620
ttccatgctg agatcaagac ccttgggagg cttcatcatc caaatcttgt cactctgatt    7680
ggttatcatg cttgtgaaac agagatgttt ctcatataca ttttttatc aggtggtaat    7740
ctcgaaaagt ttatccagga gaggtccaca agggatgtgg agtggaaaat tcttcacaag    7800
atcgcattag acatagcccg tgcactcgcc tatctgcatg atacgtgtgt tccccgcgtt    7860
cttcaccgcg atgtcaagcc cagcaacatc ttgttggatg atgatttcaa tgcttatcta    7920
tctgactttg ggttggctag acttctgggg acttcagaga cacatgctac cactggtgta    7980
gccggaacat tcggctatgt tgcacctgaa tatgccatga cgtgccgtgt ttctgataag    8040
gctgatgtgt acagctacgg tgtggtgctt ctggagttgc tctcagacaa gaaggcattg    8100
gatccttcgt tttcttctta tagaaatggt ttcaacatag tggcatgggc atgcatgcta    8160
ctgaagcaag gaagggcaaa ggagttcttc actgctgggt tgtgggaagc aggacctgga    8220
gatgatttgg tagaagtgct tcacttagca gttgtgtgta ctgttgacat tctctctacc    8280
agacctacaa tgaaacaggt tgtaagaagg cttaagcaac ttcaaccct aacatgctag    8340
ccccttgtgt gtgtggctgt gttcctttaa cattattaat cttagaaata ttcccttgg    8400
aatttgtaat ctgtaattta gcattttttg tggatttagg ttgagttccc aatttgtact    8460
tattccccc gtgtacattt ttatatagtt gtgtccccaa ttttccatgc tcttgactag    8520
gtatatttag gtttgggggc ttggtgttga ttctgcagaa gaatgcagat atttgatttc    8580
cccttcatac acgtgcattc catgtctatt tgttcaataa aattgaagaa tagaatatgt    8640
attttgaaag gaaaaacatt ggtgcagttc tgctaaattt gagtaaatgt cttgagtata    8700
a                                                                    8701
```

<210> SEQ ID NO 21
<211> LENGTH: 3396

<212> TYPE: DNA
<213> ORGANISM: Glycine max

<400> SEQUENCE: 21

```
atgttttctt cttcttttc tcacagcagt tcagcgatca aatggaattc cctcacacaa      60
tttctcttcc ttgttttctt cctcttctcc gcgtcgcgaa acgacgccgt ttcgcccttt     120
tcggacaaat ccgcgctcct ccgccttaaa gcctcgttct ccaacccgc cggcgttctc     180
tccacgtgga cctccgccac cgccacctct gactccggcc actgctcctt ctccggcgtc    240
ctctgcgacg cgaactcccg agtcgtcgcc gtcaacgtca ccggcgccgg cggcaacaac    300
cgaacatctc ccccgtgctc aaatttctcc caattccctc tctacggctt cggaattcgg    360
cgaacctgtt ccggtagcaa aggttctctc ttcggaaacg cttcttctct gagcttcatc    420
gccgagctca cggagcttag ggttttgtcg ctcccctca atgcgttgga gggtgaaatc     480
cccgaagcga tttgggcat ggagaacctc gaggttctcg acttagaagg gaatttgata     540
agtggctgtc ttcctttcag aatcaatggc ttgaagaatt taagggtttt gaatctcgcg    600
tttaatagga ttgttgggga tatacctagt tcaattgggt ctcttgagag attggaggtt    660
ttgaatttgg ctggtaatga attgaatggt tctgttcccg ttttgtagg gaggcttaga     720
ggggtgtatc tgtcttttaa tcagttaagt gggattattc aagagagat tggggagaat     780
tgtgggaacc ttgagcattt ggatttgtct gcgaattcga ttgttcgagc gattccaagg    840
agtttgggga attgtgggag gttgaggacg cttttgttgt attccaattt gttgaaagag    900
ggtattccgg gtgagcttgg gagacttaag agccttgagg tgttggatgt ttccaggaac    960
actctcagcg gctctgtgcc gcgggagctt gggaattgct tggagttgag agtgcttgtg   1020
ctgtcgaatc tattcgatcc acgtggggat gttgatgctg gtgatttgga gaaattgggg   1080
tctgtgaatg atcagttgaa ttattttgaa ggggcaatgc ctgtggaggt tttgtcgctt   1140
cccaagttga ggatattgtg ggctcccatg gtgaatttgg aaggtggttt acagggaagt   1200
tggggcggtt gtgagagctt ggagatggtg aatttggctc agaattttt cagtggggag   1260
tttccaaacc agcttggtgt ttgcaagaag ctgcattttg ttgatttaag ctctaacaat   1320
cttacagggg agctttctga ggaactccga gttccctgta tgagtgtgtt tgatgttagt   1380
gggaacatgt tatctggttc agttcctgat ttctccaaca atgtttgtcc cctgttcct    1440
tcctggaatg gaaatctgtt tgcagatggc aatgcttccc cgcggtatgc atccttttt    1500
atgtcaaagg ttcgtgagag atcactttc acgtcaatgg ggggagttgg cacttctgtt   1560
gttcacaact ttgggcaaaa cagcttact gacattcact cgttgccagt agcacatgac    1620
aggctgggaa agaagtgcgg ttacacattt cttgttggtg aaaataatct tacaggacct   1680
tttcctactt ttttatttga aaatgtgat gaattagatg cattgctttt aaatgtcagt    1740
tataatagga tatctggtca gattccttcc aatttggtg aatatgcag atcattgaaa    1800
tttttggatg cgtctggaaa tgaacttgca ggaacgattc cccttgatgt agggaatttg   1860
gtctctcttg tatttctgaa cctcagtagg aatcagttac aaggccagat tcccaccaac   1920
cttggccaga tgaagaatct gaagtttctt tctttggctg gtaataagtt gaatggctca   1980
attcctatca gcctggggca gttgtactct ttagaagtct tggaccttc ttcaaactct   2040
cttactggtg agattccaaa ggctattgaa aacatgagaa atctgacaga tgttttgctc   2100
aataacaaca atctttctgg tcacattcct aatggtttgg cacatgtcac tacactctcc   2160
gcattcaatg tgtctttcaa caacttatct ggatccttgc cttcaaatag tggcttgatt   2220
```

```
aaatgcagaa gtgctgttgg gaatccgttt ctaagtccct gccgtggagt ttcgctgacc    2280
gtgccatcag ggcaactagg gccacttgat gcaacagcac cagctactac aggcaagaag    2340
agtgggaatg gcttcagttc tattgaaata gcatctataa cttctgcttc agccattgtt    2400
ttggtcctta tagccctgat tgttctattc ttttacactc ggaagtggaa gccaaggtcc    2460
agggttatta gttctataag aaaagaagtt acagtgttca ctgatattgg gttcccattg    2520
acgtttgaaa ctgtagtcca agccacagga aacttcaatg caggtaactg tattgggaat    2580
ggaggttttg gcacaacata caaggcagag atatcaccag gaatcctggt ggcagtcaaa    2640
cgacttgcag ttggacgttt ccaaggtgtc caacaattcc atgctgagat caagacccct    2700
gggaggcttc atcatccaaa tcttgtcact ctgattggtt atcatgcttg tgaaacagag    2760
atgtttctca tatacaattt tttatcaggt ggtaatctcg aaaagtttat ccaggagagg    2820
tccacaaggg atgtggagtg gaaaattctt cacaagatcg cattagacat agcccgtgca    2880
ctcgcctatc tgcatgatac gtgtgttccc cgcgttcttc accgcgatgt caagcccagc    2940
aacatcttgt tggatgatga tttcaatgct tatctatctg actttgggtt ggctagactt    3000
ctggggactt cagagacaca tgctaccact ggtgtagccg gaacattcgg ctatgttgca    3060
cctgaatatg ccatgacgtg ccgtgtttct gataaggctg atgtgtacag ctacggtgtg    3120
gtgcttctgg agttgctctc agacaagaag gcattggatc cttcgttttc ttcttataga    3180
aatggtttca acatagtggc atgggcatgc atgctactga agcaaggaag ggcaaaggag    3240
ttcttcactg ctgggttgtg ggaagcagga cctggagatg atttggtaga agtgcttcac    3300
ttagcagttg tgtgtactgt tgacattctc tctaccagac ctacaatgaa acaggttgta    3360
agaaggctta agcaacttca accectaaca tgctag                             3396
```

<210> SEQ ID NO 22
<211> LENGTH: 1131
<212> TYPE: PRT
<213> ORGANISM: Glycine max

<400> SEQUENCE: 22

```
Met Phe Ser Ser Phe Ser His Ser Ser Ala Ile Lys Trp Asn
1               5                   10                  15

Ser Leu Thr Gln Phe Leu Phe Leu Val Phe Leu Phe Ser Ala Ser
            20                  25                  30

Arg Asn Asp Ala Val Ser Pro Phe Ser Asp Lys Ser Ala Leu Leu Arg
        35                  40                  45

Leu Lys Ala Ser Phe Ser Asn Pro Ala Gly Val Leu Ser Thr Trp Thr
    50                  55                  60

Ser Ala Thr Ala Thr Ser Asp Ser Gly His Cys Ser Phe Ser Gly Val
65                  70                  75                  80

Leu Cys Asp Ala Asn Ser Arg Val Val Ala Val Asn Val Thr Gly Ala
                85                  90                  95

Gly Gly Asn Asn Arg Thr Ser Pro Pro Cys Ser Asn Phe Ser Gln Phe
            100                 105                 110

Pro Leu Tyr Gly Phe Gly Ile Arg Arg Thr Cys Ser Gly Ser Lys Gly
        115                 120                 125

Ser Leu Phe Gly Asn Ala Ser Ser Leu Ser Phe Ile Ala Glu Leu Thr
    130                 135                 140

Glu Leu Arg Val Leu Ser Leu Pro Phe Asn Ala Leu Glu Gly Glu Ile
145                 150                 155                 160

Pro Glu Ala Ile Trp Gly Met Glu Asn Leu Glu Val Leu Asp Leu Glu
```

|     |     |     |     |     | 165 |     |     |     | 170 |     |     |     | 175 |     |
| --- | --- | --- | --- | --- | --- | --- | --- | --- | --- | --- | --- | --- | --- | --- |
| Gly | Asn | Leu | Ile | Ser | Gly | Cys | Leu | Pro | Phe | Arg | Ile | Asn | Gly | Leu | Lys |

Asn Leu Arg Val Leu Asn Leu Ala Phe Asn Arg Ile Val Gly Asp Ile
    195                 200                 205

Pro Ser Ser Ile Gly Ser Leu Glu Arg Leu Glu Val Leu Asn Leu Ala
    210                 215                 220

Gly Asn Glu Leu Asn Gly Ser Val Pro Gly Phe Val Gly Arg Leu Arg
225                 230                 235                 240

Gly Val Tyr Leu Ser Phe Asn Gln Leu Ser Gly Ile Ile Pro Arg Glu
            245                 250                 255

Ile Gly Glu Asn Cys Gly Asn Leu Glu His Leu Asp Leu Ser Ala Asn
                260                 265                 270

Ser Ile Val Arg Ala Ile Pro Arg Ser Leu Gly Asn Cys Gly Arg Leu
        275                 280                 285

Arg Thr Leu Leu Leu Tyr Ser Asn Leu Leu Lys Glu Gly Ile Pro Gly
    290                 295                 300

Glu Leu Gly Arg Leu Lys Ser Leu Glu Val Leu Asp Val Ser Arg Asn
305                 310                 315                 320

Thr Leu Ser Gly Ser Val Pro Arg Glu Leu Gly Asn Cys Leu Glu Leu
            325                 330                 335

Arg Val Leu Val Leu Ser Asn Leu Phe Asp Pro Arg Gly Asp Val Asp
                340                 345                 350

Ala Gly Asp Leu Glu Lys Leu Gly Ser Val Asn Asp Gln Leu Asn Tyr
        355                 360                 365

Phe Glu Gly Ala Met Pro Val Glu Val Leu Ser Leu Pro Lys Leu Arg
    370                 375                 380

Ile Leu Trp Ala Pro Met Val Asn Leu Glu Gly Gly Leu Gln Gly Ser
385                 390                 395                 400

Trp Gly Gly Cys Glu Ser Leu Glu Met Val Asn Leu Ala Gln Asn Phe
            405                 410                 415

Phe Ser Gly Glu Phe Pro Asn Gln Leu Gly Val Cys Lys Lys Leu His
                420                 425                 430

Phe Val Asp Leu Ser Ser Asn Asn Leu Thr Gly Glu Leu Ser Glu Glu
        435                 440                 445

Leu Arg Val Pro Cys Met Ser Val Phe Asp Val Ser Gly Asn Met Leu
    450                 455                 460

Ser Gly Ser Val Pro Asp Phe Ser Asn Asn Val Cys Pro Pro Val Pro
465                 470                 475                 480

Ser Trp Asn Gly Asn Leu Phe Ala Asp Gly Asn Ala Ser Pro Arg Tyr
            485                 490                 495

Ala Ser Phe Phe Met Ser Lys Val Arg Glu Arg Ser Leu Phe Thr Ser
                500                 505                 510

Met Gly Gly Val Gly Thr Ser Val Val His Asn Phe Gly Gln Asn Ser
        515                 520                 525

Phe Thr Asp Ile His Ser Leu Pro Val Ala His Asp Arg Leu Gly Lys
    530                 535                 540

Lys Cys Gly Tyr Thr Phe Leu Val Gly Glu Asn Asn Leu Thr Gly Pro
545                 550                 555                 560

Phe Pro Thr Phe Leu Phe Glu Lys Cys Asp Glu Leu Asp Ala Leu Leu
            565                 570                 575

Leu Asn Val Ser Tyr Asn Arg Ile Ser Gly Gln Ile Pro Ser Asn Phe
                580                 585                 590

```
Gly Gly Ile Cys Arg Ser Leu Lys Phe Leu Asp Ala Ser Gly Asn Glu
            595                 600                 605

Leu Ala Gly Thr Ile Pro Leu Asp Val Gly Asn Leu Val Ser Leu Val
610                 615                 620

Phe Leu Asn Leu Ser Arg Asn Gln Leu Gln Gly Gln Ile Pro Thr Asn
625                 630                 635                 640

Leu Gly Gln Met Lys Asn Leu Lys Phe Leu Ser Leu Ala Gly Asn Lys
            645                 650                 655

Leu Asn Gly Ser Ile Pro Ile Ser Leu Gly Gln Leu Tyr Ser Leu Glu
            660                 665                 670

Val Leu Asp Leu Ser Ser Asn Ser Leu Thr Gly Glu Ile Pro Lys Ala
            675                 680                 685

Ile Glu Asn Met Arg Asn Leu Thr Asp Val Leu Leu Asn Asn Asn Asn
            690                 695                 700

Leu Ser Gly His Ile Pro Asn Gly Leu Ala His Val Thr Thr Leu Ser
705                 710                 715                 720

Ala Phe Asn Val Ser Phe Asn Asn Leu Ser Gly Ser Leu Pro Ser Asn
                725                 730                 735

Ser Gly Leu Ile Lys Cys Arg Ser Ala Val Gly Asn Pro Phe Leu Ser
            740                 745                 750

Pro Cys Arg Gly Val Ser Leu Thr Val Pro Ser Gly Gln Leu Gly Pro
            755                 760                 765

Leu Asp Ala Thr Ala Pro Ala Thr Thr Gly Lys Lys Ser Gly Asn Gly
            770                 775                 780

Phe Ser Ser Ile Glu Ile Ala Ser Ile Thr Ser Ala Ser Ala Ile Val
785                 790                 795                 800

Leu Val Leu Ile Ala Leu Ile Val Leu Phe Phe Tyr Thr Arg Lys Trp
                805                 810                 815

Lys Pro Arg Ser Arg Val Ile Ser Ser Ile Arg Lys Glu Val Thr Val
            820                 825                 830

Phe Thr Asp Ile Gly Phe Pro Leu Thr Phe Glu Thr Val Val Gln Ala
            835                 840                 845

Thr Gly Asn Phe Asn Ala Gly Asn Cys Ile Gly Asn Gly Gly Phe Gly
            850                 855                 860

Thr Thr Tyr Lys Ala Glu Ile Ser Pro Gly Ile Leu Val Ala Val Lys
865                 870                 875                 880

Arg Leu Ala Val Gly Arg Phe Gln Gly Val Gln Gln Phe His Ala Glu
                885                 890                 895

Ile Lys Thr Leu Gly Arg Leu His His Pro Asn Leu Val Thr Leu Ile
            900                 905                 910

Gly Tyr His Ala Cys Glu Thr Glu Met Phe Leu Ile Tyr Asn Phe Leu
            915                 920                 925

Ser Gly Gly Asn Leu Glu Lys Phe Ile Gln Glu Arg Ser Thr Arg Asp
            930                 935                 940

Val Glu Trp Lys Ile Leu His Lys Ile Ala Leu Asp Ile Ala Arg Ala
945                 950                 955                 960

Leu Ala Tyr Leu His Asp Thr Cys Val Pro Arg Val Leu His Arg Asp
                965                 970                 975

Val Lys Pro Ser Asn Ile Leu Leu Asp Asp Asp Phe Asn Ala Tyr Leu
            980                 985                 990

Ser Asp Phe Gly Leu Ala Arg Leu  Leu Gly Thr Ser Glu  Thr His Ala
            995                 1000                1005
```

```
Thr Thr Gly Val Ala Gly Thr Phe Gly Tyr Val Ala Pro Glu Tyr
    1010            1015                1020

Ala Met Thr Cys Arg Val Ser Asp Lys Ala Asp Val Tyr Ser Tyr
    1025            1030                1035

Gly Val Val Leu Leu Glu Leu Leu Ser Asp Lys Lys Ala Leu Asp
    1040            1045                1050

Pro Ser Phe Ser Ser Tyr Arg Asn Gly Phe Asn Ile Val Ala Trp
    1055            1060                1065

Ala Cys Met Leu Leu Lys Gln Gly Arg Ala Lys Glu Phe Phe Thr
    1070            1075                1080

Ala Gly Leu Trp Glu Ala Gly Pro Gly Asp Asp Leu Val Glu Val
    1085            1090                1095

Leu His Leu Ala Val Val Cys Thr Val Asp Ile Leu Ser Thr Arg
    1100            1105                1110

Pro Thr Met Lys Gln Val Val Arg Arg Leu Lys Gln Leu Gln Pro
    1115            1120                1125

Leu Thr Cys
    1130

<210> SEQ ID NO 23
<211> LENGTH: 3381
<212> TYPE: DNA
<213> ORGANISM: Solanum tuberosum

<400> SEQUENCE: 23
atgggtcgtt gttgttttgt catcaaatgg tactatcatg acataccctt gaaggctttt      60
ctcatccttt gtgttttctt cttagttcat gggtatgcac tttcctcgga ttcggataaa     120
tcagcgctct tggagttaaa ggcctcactt ttagactcct ctggagtgat ttctagctgg     180
agctcgagaa atactgatca ctgttcatgg tttggtgtct cctgtgattc cgattcacgt     240
gttgtggctt tgaacatcac tggaggtaat ttgggttctt tatcttgtgc taaaattgct     300
caatttcctt tgtatggctt tggaattaca agggtttgtg ccaataatag tgtcaagctt     360
gttggtaaag tacctctcgc aatatcaaag ttaactgaac taagggtttt atccttgcct     420
tttaatgaat tgcgtggtga aattccactg gaatttggg atatggagaa acttgaagtt     480
ttggatctgg aagggaattt aattactggg tctttgccat ggagtttaa ggggttgagg     540 aaattgaggg ttttaaactt gggttttaat gagattgtgg gtgccatacc caattccttg     600
tcgaattgcc ttgctctaca aatcttgaat cttgctggaa atagggtaaa tgggaccatt     660
ccagcattca ttggtggatt tggagatctg aggggaatct acctgtcttt taataagctt     720
agcgggtcta ttcctggtga gattgggcgt tcttgtgaga aacttcaaag tctagagatg     780
gcaggtaata tcttaggtgg taatattcca aaaagtttag gaactgcac atggttgcag     840 tcacttgtct tatattcaaa tttgttggag gagggtattc cagctgaatt tggtcaacta     900
actgagctca agattcttga tgtgtctagg aacagcctaa gtggacgact accatctgag     960
ctgggaaact gctcgaaact atccattctt gtactgtcaa gtttgtggga tcctcttcca    1020
aatgtgtctg attcatctcg tactactgat gagtttaact ttttttgaagg cacaatccca    1080 tcagagatca ccaggcttcc tagttttgaga atgtatatggg ctcccaggtc aactctttca    1140
ggaaaatttc ctggcagttg gggtgcttgt gacaacttgg agattgtgaa tttggctcaa    1200
aattattata ctggagtgat ttctgaggaa ttgggtagct gccagaagtt gcattttctt    1260
gacttgagct caaataggct gactggacag cttgttgaga aactgccagt tccttgcatg    1320
```

| | |
|---|---|
| tttgtgttcg atgtgagtgg gaattatctg tctggttcaa ttcccaggtt ttccaattac | 1380 |
| agttgtgctc atgttgtttc cagcggtgga gatccatttg ggccctatga tacatcatct | 1440 |
| gcatatctag cacatttcac cagtagaagt gttctagaaa ctacttcatt atttggaggt | 1500 |
| gatggtgacc atgcagtatt tcataatttc ggtggtaaca acttcacagg aaatttaccg | 1560 |
| ccttccatgc taactgcacc tgaaatgtta ggcaaacaaa ttgtttatgc ctttcttgct | 1620 |
| ggtagtaaca ggtttactgg acctttgct ggtaacttgt ttgagaaatg tcatgaattg | 1680 |
| aaaggtatga ttgttaatgt aagcaataat gcattgtcgg gtcaaatccc agaggatatt | 1740 |
| ggtgcgattt gtgggtctct taggctgttg gatggatcca aaaatcagat tggtgggaca | 1800 |
| gtccctccga gtataggag tctggtttct ttagtttctc tcaatttaag ttggaaccac | 1860 |
| ctgcgaggtc agattcctag cagtcttggc cagataaagg atctcagtta cctctctttg | 1920 |
| gctggcaata atctggttgg ctccatcccc tcaagtttcg ggcaattgca ctctttagaa | 1980 |
| acgcttgaac tttcttcgaa ttcgttgtct ggtgaaattc caaataatct ggtaaatttg | 2040 |
| aggaatttga ctaaccttct tcttaacaac aacaatttat cagggaatat accttcaggc | 2100 |
| ttggccaatg tgaccacact ggctgcattt aacgtttctt tcaataatct gtctgggcca | 2160 |
| ctgcctctta caaagatttt gatgaaatgc aatagtgttc agggaaaccc ttttctgcaa | 2220 |
| tcgtgccatg tatttctct atcaacacct tctacagatc agcagggaag aataggggac | 2280 |
| tcacaagatt ctgctgcgtc tccttcaggt tcaacccaaa aaggagggag cagtggtttc | 2340 |
| aactccatag agattgcatc cataacatct gcagcagcta ttgtgtcagt tcttcttgct | 2400 |
| ctgatagtcc tgttctttta caccagaaaa tggaatccaa gatctagagt tgctggatct | 2460 |
| accaggaaag aagttacagt ttttacagaa gttccagttc ctttgacatt tgaaaatgtc | 2520 |
| gtgcgggcca cagggagctt caatgctagc aattgcatag gcagtggagg ttttggagca | 2580 |
| acatacaaag cggagattgc accagggttc ctagtggcag taaagcgact tgctgtagga | 2640 |
| cgttttcagg ggattcaaca gtttgatgca gaaatcagaa ctctggggag gcttcgacat | 2700 |
| ccaaaccttg taactctgat aggatatcat aatagtgaaa cagaaatgtt tctgatctat | 2760 |
| aacttttgc caggtggtaa tttggaaaag tttattcagg agaggtctac aagggctgtg | 2820 |
| gactggaggg ttcttcacaa gattgctttg gatgtagccc gtgcacttgc ttatctgcat | 2880 |
| gatcagtgtg taccacgtgt gcttcatcgt gatgtgaagc caagcaacat cctattggat | 2940 |
| gaggagtata atgcatattt atctgatttt ggtttggcta gattactggg aacttcagag | 3000 |
| gcccatgcga ctactggtgt ggcgggaact tttggatatg ttgctcctga atatgccatg | 3060 |
| acttgccgcg tctcggacaa ggctgatgtc tacagttatg gggttgtgtt gcttgagtta | 3120 |
| atatcagata agaaagcact tgatccctct ttctcttctt atggaaatgg attcaatatt | 3180 |
| gttgcttggg catgcatgct tttacgccag ggccgtgcca aggagttctt tactgctggt | 3240 |
| ctatgggatt caggtccaca tgatgatttg gttgaggtcc tacacttggc tgtggtctgc | 3300 |
| acggttgact ctctttctac tagacctaca atgaagcaag tagtaagacg gttgaggcaa | 3360 |
| cttcaaccac cgtcgtgtta a | 3381 |

<210> SEQ ID NO 24
<211> LENGTH: 2051
<212> TYPE: DNA
<213> ORGANISM: Solanum tuberosum

<400> SEQUENCE: 24

| | |
|---|---|
| attacaataa ttaactactt aaatatttaa aaactttaa aaaaatgtga gtgacttttt | 60 |

```
gaaatttcat tgtatcaca taaactggga gggagtaggg ctgtgaaaaa atcgaatcga      120
aaaaaatgtt attggattat tcttatttgt acgggtttta atggttttat aaaaaaatca     180
tcgggttatc gatttgatat tagttttaa tattgggtta ctgagtaaat cgataacaca      240
ttaagactat agtaatttac tacttttaca tgtacagaaa tattaaatat taatctcaat     300
accttaatag ttactgtatg tgccatttag ccttcaattc acacttcaca gtgtctttga     360
gttcacaaat tctcattata caaatgtca aagcctaaag taagaatctt attcctctta      420
atttctcttt gtgttacact tgtatagttc ttttcatctt agttattatt gtttctattt     480
tatgagcatt tataaagtaa cactattgtc ttattgcgtc aaatttgtta gagaagtcat     540
atatttattt tataagcatt ttcttattag ttaaaccaaa aatcaaaccg ttaaagacta     600
aaacgataaa ccaaagtcga gctgaacgga tgcacacccc taggatggag taacatatat    660
tatgtgaaaa aattatgttc aaaacatact ataaatcatt ataattaaca atttaagata    720
ttttttttaa aaaagcata tgattttta tggactctcg aaattcatct gtggcacata      780
aattgttaca aatgaagtaa tatatattgg gtgaaaatta ctttgaaata gtaaaaaaat    840
cataataatt aacaacttaa aatactttta aaaacatata atttttttg attaaatcta      900 agctttatct gtgtaacata aaatttaaat aaaaaaataa tactccctcc gcttcaaaat    960
aattgaatta ttgagacttt ttcatatttc aaattaactt aattgttgaa tcttcaagac    1020
tactttaaaa atattctctc atttttttt ctttcttttg gattttctat gtgatgagtt     1080
taagaaattt aattattta aattattcta aagataaatt taacaataac taataagtgc    1140 aaaaagaaa aataatattt aaattatgtc caatttttt atcttaaaaa gatgtggaac      1200
atcttcaaca attcaatgaa tctatgtcct aaactttttt tcttaaaaat gtataaaata    1260
acttgaacaa ttcaattatt ttgaaatgaa aataacatat attaaatacg tgccgcacga    1320
agggtgtatg tagtagatta tatagtttgg aaaaatcttt ttggccagaa aatttggcca    1380
gaatgatatt ttatctatgt tatttttactt tctaaaaata ttttttaccct tttaacttta  1440 atatattta actaaaaagt gaaaacaata tcaattatt ttaaaattaa aaaaatatta     1500
taattttttt aatttttaa ccatttagca cctcccatat attttttacgg tggtccatat     1560 taatgagcga ggggagggta gatgatgcat ttattgtgcg gcatggtgtc cattttttt     1620 taccgaagta tgtacaccag accccaccaa tccatcactc tcttcaactg accccacact    1680
ttctctattt aacaaaatac taatcaaat taataatctt gagacgagaa caaaaacgaa     1740
aacagttgag caaagaatta atggaaaatg aacgtacaaa aagaagaag agacaattca     1800 tagaaaaatg agaaattgaa aaaaacagca gcaacgcgtt ttctctcttg tctctctttt    1860
aagtcttctt ctctctcctc ttcttgactc tctctctctg ttcacaacca agcagcccca    1920
aaaactaggg ttagggctag ggttttgag tttcaaaacc ccatttctgc ttcctataat     1980
cttcacatac aagggaatt tgggtctgta tttttttg cattttgag gacccttttg       2040 gggttttact a                                                         2051
```

<210> SEQ ID NO 25
<211> LENGTH: 1405
<212> TYPE: DNA
<213> ORGANISM: Lycopersicon esculentum

<400> SEQUENCE: 25

```
tgtgttcttc aagatactcc ttctatatat aaatgttgag tgaattagca actcggttgg      60
```

```
agaaaaatga ggaaaaaaaa tcatatgggt aatgagggaa acttcaaatt cagggggtaat      120
gaatatttt  gtcaataata aaaaaggaa  gattttacgt  tttttcactc  ttgtagcttt     180
ataacgtggc aaaaaatcac tctcactggc ctagtagagt gcgatttaaa tttctacgac      240
aggtggccag aaaaggtgca tgtgttggat gaataaacaa gttcgtgggg ggggagtgtt      300
ttaaacgaaa taaagttatt aaatatacac cgaacaaaaa gcttcaagtt taggggggtaa     360
tgaatacttt tgcctatatt aagtgctcgt ttggccatag attatttggg gaaaaacttg      420
acaaatagtg tttgtctata cacgttgcca ttatttggca atattttttg gaaaatattc      480
cgaatttttc aagtactagt tttatttaat atttgggtca atctcatta  ttttaaattt      540
ttttaaaatt aaaatttac  cacaaatttt tatttttac  aaaaacactc tctataattg      600
gtgtttacgt tgtactacat aattttttac attaatccca aagtggtggt gaaatatata      660
tagtgaatgt taaatgatga tatggttatt aatgaaaatg atgaacaatc ggttcaaaat      720
aagaaagtca tatgtttat  ctatttcacg atatatgaaa ttatgcttgt cgcacttact      780
ttaattatc  atactacttt aatgtcatga atattatttg ttattgttgt aaaaaagatc      840
taataaactt ataatacaaa cttatgatta aacaaatggt aaaattttat ctaaataata      900
tttattaaaa atataaaaaa tatataatca acgctagtc  gcatgtgtat ttaattgagt      960
gtatgtatta ctattttta  ctgtggtcca tattgatgag ggggaggtag atgcatttat     1020
tgtgcggcat ggtatccatt tttttaaatt tatttaccaa agtatgtact ccgaccccac     1080
actctttcta tgtaagaaaa tgctagtaat caaaattgaa ataatttca  gttgagcaaa     1140
agaattaatg gaaaatgtac gtacaaaaaa gagacaaatt catagaaatt gaaaaaaaca     1200
gcagcaacgc gttttctctc tcttaagtct tcttctctct cctcttcttg actctctctg     1260
tctctctctg ttcgcagccc caaaaagtag ggttagggct agggttttg  agtttcaaaa     1320
ccccatttct ggttcctata atcttcacat acaaggggag tttgtctctg ttgcattctt     1380
tgaagaccct tttgggggttt tacta                                           1405

<210> SEQ ID NO 26
<211> LENGTH: 6639
<212> TYPE: DNA
<213> ORGANISM: Glycine max

<400> SEQUENCE: 26
cagttcgaat ccaggttgca tggagataca ggaagaaacg taaaaattgt gttgatacct       60
caaaattaga tcaatcattt aactcatagg ttgtataatc acctgaattg cttgtaatta      120
ccatgcacaa ttcctttaaa aattaaacaa caagcaaatg ttactgttgg agagcaattc      180
aaatttcaaa ataaatggaa cttgtgaaaa ttcaaggaga tatttttagg aatttgttat      240
gttaatttca atctttaga  attttatcta gatttaaata ttttattaat ttgttaact      300
tattttaggg atttgtttcc ttttttaaaa gattagaata tgataatatt taaattttgt      360
attgttattt agctttatat atagagccaa gaaatacaaa ttttataatg tgttccatct      420
aagatttctt gaacgtgtga aattttgtt  gtgtagaaaa ttttttccaa cggttaacat      480
tttattagta gtgctttgct tataatgcaa agagccttct cctttatttt atgtctacaa      540
taagtaatga atttataagg aatgaaaata actcttaact ctcaagagag gaaagaactt      600
tggtaaacaa gatttcatat gttacagcca gacttacaca gaatatttca tttcacacag      660
ctcagatgat ttttagagaa aatgtacccg atatatattc ttcttttaaa ggcagagttg      720
aaatctaaat tatatgagca aaatatacaa cctatacagt atagacagaa tcagaaataa      780
```

-continued

| | |
|---|---|
| agttcatatt tcttagatta cggtatgaga gtcactgagt caataacttt ttactacgag | 840 |
| aataaagaaa tggaatgatt gaatgagcaa aatataccc tgaattccat tttcctagaa | 900 |
| agagaaatag catgcgattg aataagagaa tggcaccatc aagattgtga atgagaaaga | 960 |
| agaaatggag gaaacttgtg aatggaaaga gagtgagaat gggagagagc atagtgttgg | 1020 |
| acaatgacat tgtgactgta aggaaattaa tgagtaacta gagaacggaa cggaactaac | 1080 |
| aagcttcttg ttgtgtttgt gatttaagtg tttgatggag ttttaaggat tcaatacaat | 1140 |
| gaaagctacg tgacagttaa atatatgata gattcatcct ttgagttcca agcagtatac | 1200 |
| gtgaacggaa tcaacgttga tctttaggaa gatcattctc tccgctcgga agatctttta | 1260 |
| tcgtttaatc gaatcatttt ttaaaatttt cagttttcat tatcatggta agtttattga | 1320 |
| tttttttataa taattttttt tgaagtcata taaaatataa tattttattg attagaaatg | 1380 |
| taaaataatt tacaataagg gaaaatattt attgaacatt tttataatat tagaaataga | 1440 |
| ttaaactaat acagtatttc ggtattgtat tgcatatatg tttatctata actattattt | 1500 |
| ttaaattatc ttttaatata taacgatt tttttttat aaactttcaa aatgtagatg | 1560 |
| ttactatttt ttcctaaaac aatattatca ctatttttc attttttttc ttttgaaaaa | 1620 |
| aaaagaaaat aaagataaat atatgaagtg tctttctttc aactggtctt atgtaagaac | 1680 |
| aaattcacact ctatgctcag gactattat acttatactt cctacgttaa aatgtatttt | 1740 |
| ttttatctct tctaaagtaa attatcatcg tttaactttt gagaaaaatg tcaaaaaaaa | 1800 |
| atccatacac ttaactctca caatctgatt cttctccatc tttattggcc tcttctttgt | 1860 |
| catccaccct cccggtcagc taatttttt gttataatat tattaatatg aaatattcat | 1920 |
| caactttatc gataaataat ttttattaaa atacttaatt aaatattttt atgatgatat | 1980 |
| tttttttcttt taattatatt tttattttttc ttcacaagat taaaatttaa tatctttctt | 2040 |
| aacgagatta aataaatatt tcatcaacat atttttatttt tatatatata tatttttaa | 2100 |
| ctcatcatat cacttatcat atctatattt atttttatgt atcttaatac atcatttag | 2160 |
| atgggcaaat taaatatatt tatccaaaag taatgtcatg agaatgagaa gaaaagttac | 2220 |
| atcacgcctc cttctggcct tctcctaaat tatcgagatt aataccttgt gcctgtaaat | 2280 |
| ttggtaacca gaaaaagaa aaatcatgtg aggtagagga tttttcgaa tgtgtaaaaa | 2340 |
| tagatttctt gagtgcctaa ggtgtttgca ttcagcaatg gcacaacacg tgtcaagtcc | 2400 |
| caatcttaca agaaccttcc ttcctaccga aagtcccgtc acgacacgtg agcagtcaca | 2460 |
| tccgtcacgt gtcacctttt catcgaccat gggaagatct ttcggcaccg cactttctgg | 2520 |
| tatcttcacg cgcaatcccc atcccaccgt ccattctctc acacgctcga gccatcgtag | 2580 |
| ccgtcgcccc ctcacccgtc cccaactccg ccacgcatcc aaatgacacg tggcgctaaa | 2640 |
| gtaacggtca aatccacaat attacttatt gtaaccttat cctctcctca cccctcaccc | 2700 |
| ccccccttcc ccctataaat ccccctttcc ctccctccaa tttcaacctc actctgcatt | 2760 |
| cgctaaaccc aaaacactat tttattatct tcttcgtctg ttctttgcat tgaagaaaat | 2820 |
| ttctttgaat tgaagaaaac ttgaaatcga attgtgaaac agaaaataaa ccaaaggaaa | 2880 |
| tttttactga ttgaattgta gagattggaa aaatggcgtt gagtatgact caacagatcg | 2940 |
| ggaccctagc tggtgcgacg gtgccggatt cctcggccgg agaatcgacc gcggcggtga | 3000 |
| gtgctgccgc ggtgtggaag tcaccgacgg cgagtctgaa gtgcaaggta atgaggacgg | 3060 |
| atggctgcgc ggagggggctt tcgccgccgc tgagtccgtg caggtcgccg gtgctgcggg | 3120 |

-continued

```
cggatctgtc ggcggcgtgt caggcattca cggcggaggt ggcggaggag gagtacgttg    3180
ccggagggaa ggaggagaag gggaagggga aggagggagt gccggtgttt gtgatgatgc    3240
ctttggacag cgtgacggcg gggaacgcgg tgaaccggaa aaaggcgatg aacgcggcga    3300
tggctgcgct gaagagcgcg ggggtggagg gggtgatgat ggacgtgtgg tggggtttgg    3360
tggagagaga gaagcctggg gagtataatt ggggagggta cgtggaactc atggaaatgg    3420
cgaagaagca tggcctcaag gtgcaggctg ttatgtcatt tcaccaatgt ggcggtaacg    3480
tcggagactc ttgcacgtga gtcttatgca atcccttctt cttccttctt ttttttcttt    3540
tatttgtcat ttgtgatttt tattttttact ggcgaaatct tattagattc tagattaatt    3600
ggttttaaca attagaattg ttactagtat ttttttttaa gtttaatttc tgcgaattgg    3660
ttttgaaatc tgaaaactaa ttgagtgaca ccatgaaaag attttacgtt tttgatacat    3720
tcttgttggt ttttttttaac gttaagtttt tgcttttaat tcaatttacc atgaaattca    3780
catctttatc tttattggta aatatgtggt gttattatta tatggtgttt tcgttgatta    3840
tgattgaaaa tgagaggcgt gcccagcacg gtgcagctcg tttgtgaaaa ataaaataaa    3900
cgttttaaaa ggggttttgt gatgggaaat gaagccatgc catgtgatgt tggacttgta    3960
tcactttgat tcgaagtata gtattttttct tttctattga atattcaact acgaacctgg    4020
aataattgaa tcttgagaat tgtgtatatg atattgataa ttatttagcc atttctcttt    4080
aactgaaatt ttaatgtttc atttttatta gtacttgaag attctgaatt taattaaatt    4140
ttaatccttt ttttacagaa attaattttt aatctttgta ctatacagaa tgagttaaca    4200
ttcttttata attagggata atgacaattt taatttagta ttttaaacat gatgattata    4260
tttattttta tcataataac aacaattttc ctgaaaaaaa aataaaaata atttcataaa    4320
tctttatatt atgattaaa gaggcgtaat gagcacggtg atgctagtct tatttttcttt    4380 cattttttgt ggtccttatg taaaaagtaa atacaaaata catgagaaaa gagtgtgctt    4440
tcgtgatggg aagtgccaaa gtgggaccac gtgaggatgg acttctagtt ctactgattc    4500
acgtcggcat cgccacatac agtagactaa cttttaagga caccttaaat ttagtggacc    4560
cgatatctta atttattttt cggtccattt tttgaaaaag tattcctcaa attctctcca    4620 ttttttcttaa aacatgttat tcgaaacaaa taatccaggc atagtttctg tttatatatt    4680
ttatgtaaat tattttttgac agttataaga ttatctaatg gtttcgaatt cgaatcatgg    4740
acatgtggta atgttgatac taaacagttg gaggagagtt tagcatccat aatgattcta    4800
ttcggtttcg agtagaatta tctcttatta gagatacatc tgatctacta aaaaatataa    4860
atagttagtg taattttaga tattactgcc attaattttg ctataagtta gcactgtgtt    4920
ggaataccag ttgtcttatt ggtgggctta tcagatagtt tgtcctgtgt tcagtattcc    4980
tttgcccaaa tgggttgtgg aggagattga taatgaccac gatcttgcat atactgatca    5040
atggggaaga agaaactatg aatatatatc acttggatgt gatactttgc cggtgctcaa    5100
gggacgatcc ccagttcaat gttatgctga tttcatgcgt gctttcagag acactttcaa    5160
gcacctcctt ggtgatacca ttgtggtaaa tatcattctc agtgcacttt tacatcatgc    5220
tgtgatttgt tgtgctattt aaatataact tctcatctga acttctttta ctggcaatat    5280
ttcaggaaat ccaagttggg atgggaccag caggtgagtt gcgttaccct tcgtacccag    5340
agcaaaatgg gacatggaaa ttcccaggaa ttggtgcttt ccaatgctat gacaaggtat    5400
atatatttat gttttttttt tccttctcct tgttgtagtc cttatatatat aattgtctta    5460 ggatttgttt ggataaataa atttcttcat gaacaaagag gagaaaacaa ggtaaaatgt    5520
```

-continued

```
gttctaaacc tctaatactt aattatgcta tggtgcagta tatgttgagt agcttaaaag    5580
ctgctgctga agctcacggt aagcctgaat ggggaagcac aggccctact gatgctggcc    5640
actataacaa ctggccagaa gacactcaat ttttccgcaa agaaggtggt ggatgggatg    5700
gtccatatgg tgagttttc ctcacttggt actctcagat gctgttggaa catggtgaca    5760
ggattctctc atcagccacg tcgatctttg acaacactgg agttaagatc tcagtgaagg    5820
ttgccggcat tcactggcac tatggtacaa ggtctcacgc cccagaactc actgcagggt    5880
attacaacac ccgattccgt gatggctacc tccccattgc tcaaatgctg gcgcgccacg    5940
gtgccatctt taacttcacc tgtatcgaga tgcgcgatca cgagcagcca caagaggccc    6000
tttgtgcacc tgagaagctg gtgaagcaag tggctctggc aacgcagaag gcacaggttc    6060
cacttgccgg cgaaaacgcg ctgccacggt acgacgagta tgcacatgag cagatcataa    6120
gggcatcaca attggatgtt gatggtgagt ctggtgatag agagatgtgt gccttcacat    6180
acctgaggat gaatccgcat ttgtttgaac caaataactg gaggaagttt gtggggtttg    6240
tgaagaagat gaaagaaggg aagagtgcac acaagtgttg gaagaggtg gagagggaag     6300
ctgagcattt tgtgcatgtt acacagcctc ttgtgcaaga ggctgcagtg ctgatgcact    6360
gagaattgtt gaacatcctt gtggtaatag ggcttaggaa taagtcacaa ggaggctgtg    6420
tgaaagtttt agtgaaccaa cagcccaggt ttgtggcttt gaagatgtaa aatttttgtat   6480
tatattgttt tgtattgtat gcacctaaaa cttctatttg tgaccctttt acattgtgta    6540
cgtaatcata gactttgggg tactgtttcc ttaaaagtta ctctactttg tacaagtagt    6600
tacttaatct ggtttaaaaa aatgtcatcc cttaatctg                           6639
```

<210> SEQ ID NO 27
<211> LENGTH: 1710
<212> TYPE: DNA
<213> ORGANISM: Glycine max

<400> SEQUENCE: 27

```
atggcgttga gtatgactca acagatcggg accctagctg gtgcgacggt gccggattcc     60
tcggccggag aatcgaccgc ggcggtgagt gctgccgcgg tgtggaagtc accgacggcg    120
agtctgaagt gcaaggtaat gaggacggat ggctgcgcgg aggggctttc gccgccgctg    180
agtccgtgca ggtcgccggt gctgcgggcg gatctgtcgg cggcgtgtca ggcattcacg    240
gcggaggtgg cggaggagga gtacgttgcc ggagggaagg aggagaaggg gaaggggaag    300
gagggagtgc cggtgtttgt gatgatgcct ttggacagcg tgacggcggg gaacgcggtg    360
aaccggaaaa aggcgatgaa cgcggcgatg gctgcgctga agagcgcggg ggtggagggg    420
gtgatgatga acgtgtggtg gggtttggtg gagagagaga agcctgggga gtataattgg    480
ggagggtacg tggaactcat ggaaatggcg aagaagcatg gcctcaaggt gcaggctgtt    540
atgtcatttc accaatgtgg cggtaacgtc ggagactctt gcactattcc tttgcccaaa    600
tgggttgtgg aggagattga taatgaccac gatcttgcat atactgatca atggggaaga    660
agaaactatg aatatatatc acttggatgt gatactttgc cggtgctcaa gggacgatcc    720
ccagttcaat gttatgctga tttcatgcgt gctttcagag acactttcaa gcacctcctt    780
ggtgatacca ttgtggaaat ccaagttggg atgggaccag caggtgagtt cgttaccct    840
tcgtacccag agcaaaatgg gacatggaaa ttcccaggaa ttggtgcttt ccaatgctat    900
gacaagtata tgttgagtag cttaaaagct gctgctgaag ctcacggtaa gcctgaatgg    960
```

```
ggaagcacag gccctactga tgctggccac tataacaact ggccagaaga cactcaattt    1020
ttccgcaaag aagtggtgg atgggatggt ccatatggtg agttttcct cacttggtac      1080 tctcagatgc tgttggaaca tggtgacagg attctctcat cagccacgtc gatctttgac    1140
aacactggag ttaagatctc agtgaaggtt gccggcattc actggcacta tggtacaagg    1200
tctcacgccc cagaactcac tgcagggtat tacaacaccc gattccgtga tggctacctc    1260
cccattgctc aaatgctggc gcgccacggt gccatcttta acttcacctg tatcgagatg    1320
cgcgatcacg agcagccaca agaggccctt tgtgcacctg agaagctggt gaagcaagtg    1380
gctctggcaa cgcagaaggc acaggttcca cttgccggcg aaaacgcgct gccacggtac    1440
gacgagtatg cacatgagca gatcataagg gcatcacaat tggatgttga tggtgagtct    1500
ggtgatagag agatgtgtgc cttcacatac ctgaggatga atccgcattt gtttgaacca    1560
aataactgga ggaagtttgt ggggtttgtg aagaagatga agaagggaa gagtgcacac     1620 aagtgttggg aagaggtgga gagggaagct gagcattttg tgcatgttac acagcctctt    1680
gtgcaagagg ctgcagtgct gatgcactga                                     1710
```

<210> SEQ ID NO 28
<211> LENGTH: 569
<212> TYPE: PRT
<213> ORGANISM: Glycine max

<400> SEQUENCE: 28

```
Met Ala Leu Ser Met Thr Gln Gln Ile Gly Thr Leu Ala Gly Ala Thr
1               5                   10                  15

Val Pro Asp Ser Ser Ala Gly Glu Ser Thr Ala Ala Val Ser Ala Ala
            20                  25                  30

Ala Val Trp Lys Ser Pro Thr Ala Ser Leu Lys Cys Lys Val Met Arg
        35                  40                  45

Thr Asp Gly Cys Ala Glu Gly Leu Ser Pro Pro Leu Ser Pro Cys Arg
    50                  55                  60

Ser Pro Val Leu Arg Ala Asp Leu Ser Ala Ala Cys Gln Ala Phe Thr
65                  70                  75                  80

Ala Glu Val Ala Glu Glu Tyr Val Ala Gly Gly Lys Glu Glu Lys
                85                  90                  95

Gly Lys Gly Lys Glu Gly Val Pro Val Phe Val Met Met Pro Leu Asp
            100                 105                 110

Ser Val Thr Ala Gly Asn Ala Val Asn Arg Lys Lys Ala Met Asn Ala
        115                 120                 125

Ala Met Ala Ala Leu Lys Ser Ala Gly Val Glu Gly Val Met Met Asp
    130                 135                 140

Val Trp Trp Gly Leu Val Glu Arg Glu Lys Pro Gly Glu Tyr Asn Trp
145                 150                 155                 160

Gly Gly Tyr Val Glu Leu Met Glu Met Ala Lys His Gly Leu Lys
                165                 170                 175

Val Gln Ala Val Met Ser Phe His Gln Cys Gly Gly Asn Val Gly Asp
            180                 185                 190

Ser Cys Thr Ile Pro Leu Pro Lys Trp Val Glu Glu Ile Asp Asn
        195                 200                 205

Asp His Asp Leu Ala Tyr Thr Asp Gln Trp Gly Arg Arg Asn Tyr Glu
    210                 215                 220

Tyr Ile Ser Leu Gly Cys Asp Thr Leu Pro Val Leu Lys Gly Arg Ser
225                 230                 235                 240
```

```
Pro Val Gln Cys Tyr Ala Asp Phe Met Arg Ala Phe Arg Asp Thr Phe
                245                 250                 255

Lys His Leu Leu Gly Asp Thr Ile Val Glu Ile Gln Val Gly Met Gly
        260                 265                 270

Pro Ala Gly Glu Leu Arg Tyr Pro Ser Tyr Pro Glu Gln Asn Gly Thr
    275                 280                 285

Trp Lys Phe Pro Gly Ile Gly Ala Phe Gln Cys Tyr Asp Lys Tyr Met
290                 295                 300

Leu Ser Ser Leu Lys Ala Ala Glu Ala His Gly Lys Pro Glu Trp
305                 310                 315                 320

Gly Ser Thr Gly Pro Thr Asp Ala Gly His Tyr Asn Asn Trp Pro Glu
                325                 330                 335

Asp Thr Gln Phe Phe Arg Lys Glu Gly Gly Trp Asp Gly Pro Tyr
        340                 345                 350

Gly Glu Phe Phe Leu Thr Trp Tyr Ser Gln Met Leu Leu Glu His Gly
    355                 360                 365

Asp Arg Ile Leu Ser Ser Ala Thr Ser Ile Phe Asp Asn Thr Gly Val
370                 375                 380

Lys Ile Ser Val Lys Val Ala Gly Ile His Trp His Tyr Gly Thr Arg
385                 390                 395                 400

Ser His Ala Pro Glu Leu Thr Ala Gly Tyr Tyr Asn Thr Arg Phe Arg
                405                 410                 415

Asp Gly Tyr Leu Pro Ile Ala Gln Met Leu Ala Arg His Gly Ala Ile
        420                 425                 430

Phe Asn Phe Thr Cys Ile Glu Met Arg Asp His Glu Gln Pro Gln Glu
435                 440                 445

Ala Leu Cys Ala Pro Glu Lys Leu Val Lys Gln Val Ala Leu Ala Thr
450                 455                 460

Gln Lys Ala Gln Val Pro Leu Ala Gly Glu Asn Ala Leu Pro Arg Tyr
465                 470                 475                 480

Asp Glu Tyr Ala His Glu Gln Ile Ile Arg Ala Ser Gln Leu Asp Val
                485                 490                 495

Asp Gly Glu Ser Gly Asp Arg Glu Met Cys Ala Phe Thr Tyr Leu Arg
        500                 505                 510

Met Asn Pro His Leu Phe Glu Pro Asn Asn Trp Arg Lys Phe Val Gly
    515                 520                 525

Phe Val Lys Lys Met Lys Glu Gly Lys Ser Ala His Lys Cys Trp Glu
530                 535                 540

Glu Val Glu Arg Glu Ala Glu His Phe Val His Val Thr Gln Pro Leu
545                 550                 555                 560

Val Gln Glu Ala Ala Val Leu Met His
                565
```

<210> SEQ ID NO 29
<211> LENGTH: 6509
<212> TYPE: DNA
<213> ORGANISM: Glycine max

<400> SEQUENCE: 29

```
tattagctaa actttgtcat aggttgtacg attataaaat atctttgata gtttcactta      60
tttccatgta caaatgttcc ttctaaaagg catgtattaa gcgtcaagaa cttaattaaa     120
aaattgagaa ttggataact cgccagaagc agccatgaat tttaacatga atcagatgag     180
caagttccat ttcttacttc ccctacataa ttggtccaac aaaatacata agaacaataa     240
```

```
acatagaact attgttgagg aatcaggaag acaaacaatg accatctaat atccttttag      300
agtagtagtt gaagatgcca atggcagttg acaactagaa gaacatgttg aaaagcaaac      360
gaatagttct taattgagaa caagcatcaa agcaccctca catgattttt agagaaaatg      420
tacccgatat ttattcttct tttaaaggaa gggttaaaat ttaaattata tgagcaaaat      480
ataactgttg tttttttaat aagagtaggc agaaatatta acaataaaa gggagcataa       540 agaaaaaaaa aattgagatt gcaaaggttt atttaaaag cagagaaaag atagtaactg        600
ctaacaaaaa gataacatca ctcactaaca aatcatgcct agagaatagg atcaaaactg      660
ttttatccta tcagtcaaat gacttttatt tttcctaaaa aaatagcata aaagtcttat      720
ctactgtagt ttcaacagtc aaatcttaac aataaccta aatttaaggt ggatgatgac        780
attcatcctt tgagctcgca gtaaatata cctcaacaca agttattata gactcattct        840
atgccttcgg agttcgcact cctaataatt atacgctaac ggattcattt atccatcata     900
tttttaaatt tcaatttct aatgaaaaaa tactataact actcactttt tatttacact       960
gtgatttaat aataaattaa aaaaatattt tttagatcat catccaatta taatttttta    1020
atgtataata aatttgttga ctttcatgat acttatttta aaaaaattat taatattgaa    1080
ttctgattag atgatattaa actcaaataa attatcattt atgtttaatt tattgatttt    1140
tataataatt atatttaaaa ttacataaaa tataaatttt tattgattaa aaagtgtaaa    1200 agcttttac agaaatggtg gatatctatt aaactctttt ataatagaat caaactaata     1260
ttttagtacg tgaattgaat agagtaaatg tttatcttat aaaactatcc tttataataa    1320
taataataag gcatgcccga tattattatt actattattg aaggaatata taagcatacg    1380
catttaaaaa aaataccaaa tatactagtt taatttgtaa tcacaatttt taatctctaa    1440
tcatcttcaa tctaggaata agtctctagc tatcatattt aaactgagtt taaaatattt    1500
cacatatttt gttaatgtca aatgacaatg tttatttgtt atgaagtaat caaaaccacg    1560
aaacaacaaa accaaatcta gctctatatt aatcacaaaa taagtattat attaaaaata   1620
tctcaaaata aatattatat taattttca atgtaatatt aattttctta tattaacatc    1680
tttgataagt atcactttaa atttcaatgt aatactaaaa gttagattta taaaattatt    1740
attctctttt atttgtttat taacttttgt aaataattta tgtcaacatt ttttaaacaa    1800
aaaagagtag ctattatatt atactatttt taaaacatct actttaaaaa agtatatcat    1860
ctatttatta ctggtttaat catgattgaa tcacaattga atcattaaaa tttaaataag    1920
tatcatcact ttttttgtcc tacctattat agtctgcaac tcatattaag ttgaatagct    1980
aattttggga tgtgaaaaaa tagatttcat gaccattggc cgatgacatg acacttgccg    2040
tgttcccaat ctcacaagat ccttctcctc ccatatttc tcttggctcc tacatcgaca      2100
cgtgaccaca catctctcac gtgtcacctt tccatggacc atcaccttca cgcgcaatcc    2160
ccatcccacc gtccattctc ccaaatgaca cgtggcgcaa aactaacggt catacccaaa    2220
atattaatat tacttattgt aaccttatcc tcaccacccc cttccccta taaatatcct     2280 tcccctcac tgcattcgct aaacccaata aattgttatt ttctgttctt tgcatttgaa      2340
tcaaagcaaa ttttgattga ttgattagaa aatggcgttg aatatgactc accagatcgg    2400
gaccctggct gctgcgacgg tgccggtgcc gaattcgtct gccggagaat caaccgcggc    2460
gatgagtgcc gccactctgt ggaagccgcc ggcggtgagt ctgaagtgca aggtcacgag    2520
gacggagggc ggcgctgagg ggctgtcgcc gccgctgagc ccgtgcaggt cgccggtgct    2580
acgggcggat ctgtcggcag cgtgtcaggc gttcacggcg gaggtggcgg cggaggagta    2640
```

```
cattgccgga gggaaggaga aaggagaggg gaaggaggga gtgccgctgt tgtgatgat    2700 gccgttggac agcgtaaaga cgggaaacgc ggtgaaccgg aagaaggcga tgaacgcggc    2760
gatggcggcg ctgaagagtg cggggtgga ggggtaatg atggacgtgt ggtgggttt      2820 ggtggagaga gagaagcctg gggagtataa ttggggaggg tacgttgaac tcatggagat    2880
ggcgaagaag catggcctga aggtgcaggc cgttatgtca tttcaccaat gtggcggtaa    2940
cgtcggagac tcttgcacgt gagtattatt atgcaatctc tctcattctt ttttgtcatt    3000
gctgattgaa tgttattaga ttctggatca attggtttta acaattagaa ttgttactat    3060
tagattctgg agtactttaa aggtttcttt taggtttaat ttctgtgaat tcgtattgaa    3120
atctgaaaat caattgagtg acaccatgaa attttttac gttttggaaa cattcttatt     3180
taaaaaaatt ttaacgtcgt gtttttgctt ttaattatat ttgtagtttt ttaaaataag    3240
caattatatt ttattagtat taaaattgct ggacacgtga acaaaacgg ctggatacat     3300 tcttattaaa aaaatttaac gtcaagttta gatacctaaa tattgttata cgatatatat    3360
ctataatgtt tggataatga aattggtcgg acaagcaatt tggatgaaaa ttcatgcagt    3420
gtgaaaatgt taatttttg tgaaagtaat tcgtttaatt tatatttaa ttttatagt       3480 ttaaaattaa tattttagt tcttataatt tacatttaa atattaacat atattttaat      3540
taatttcata tatttatctt tataggaaaa tatgtggtta ttaattatat ggagttttcg    3600
atgattatga ttgaaaatgg gaggcgtgcc cagcacgatg cagcctgttt gtgaaaaata    3660
aaataaacgg ataaaggggg ttttgtgatg ggaaatgaag ccaatactgc catgtgaatg    3720
atgtgatatt ggacttgtat cactttgctt ctaagtgtag tattagtttt ctctattgaa    3780
tgaactagga acctggaata attgaatctt gagaattgtg tatattcata attatttagc    3840 catttcccctt ttactgaaat tttagtgttt catttttatt actactattt tgatcgaaga    3900
ttatgaagtt aattaaattt taatccttgt gctattacga atgagctggc attctcttaa    3960
aattagggat aacaacaata ttaatttagt attttaagc atgattatta tgcttattaa     4020
aaaaacataa ttattatatc tatttttaaca taataacaat gattaaaaat aatttcataa   4080
atgtttatat tttgatatga tttaaagagg cgtaatgagc acggtgcaga gtcttatttt    4140
ctttcatctt tcgtggtcct tgtgtgtagt aaatacaaaa tacgtgagaa aagagtgtgc    4200
tttcgtgatg gaaagtgcca aagtgggacc acgtgaggta gcacttgtag ttctactgat    4260
tcacgtcggt atcgccacaa acagtagact aactttttaa ggatctacta cctttaatca    4320
agtggacccg agatcttaat ttgttttca gtctatttt tgaaaatgta tttgtaaaat      4380
attttcattt gtttaaaatg ttatttgaaa caaataatcc agatatattt tctgtttata    4440
tatttcatgt aaattatttc aacggctatc aattatagta aactagtttt catttatcag    4500
tgatcgcata aatcaactat tgatttcgaa tttgagtctt ggacatgcgg tagttaaata    4560
gttggaggag ggtttaaaat tcacagtgat tctatctggt tccagtaaga gataatccag    4620
tagaattatc tcttacagga gatagctgtg gtttattaaa aaaaaaaaaa ctagttcata    4680 ttttatgat tttagatatt attgccatca gttttgctgt aagttagcat agtgttggaa      4740
taccagttgt cttattggtt ggcttatcag attgtttgtc ttgtgtgcag tattcccttta    4800 cccaaatggg ttgtggagga gattgataat gaccccgatc ttgcatatac tgatcaatgg    4860
ggaagaagaa actatgaata tatatcactt ggatgtgata cttcgccagt gctcaagggc    4920
cgaaccccag ttcaatgtta tgctgatttc atgcgtgctt tcagagacac tttcaagcac    4980
```

-continued

```
ctccttggtg acaccattgt ggtaaatatc tttctcagtg cacttttaca tcatggtgtg    5040
atttttgttg ctatataact tctcatctaa actcctttta ctggcatatt tcaggaaatt    5100
caagttggga tgggaccggc aggtgagctg cgttacccct cttacccaga gcaaaatggg    5160
acatggaatt tcccaggaat tggtggtttc caatgctatg acaaggtata tatatttacg    5220
ttttttttc cttctccttc ttgtactctt ttatatataa ttgttttagg atttgtttgg    5280
ataaatttct tgatgaacga agaggagaaa attaggtaaa atgtgttcta atacttaaat    5340
tatgctacgg tgcagtatat gttgagtagc ttaaaagctg ctgctgaagc tgagggtaag    5400
cctgaatggg gaagcacagg ccctactgat gctggacact ataacaactg ccagaagac     5460
actcaatttt tccgcaaaga aggtggaggc tgggatggtc catatggtga ttttttcctc    5520
acctggtact ctcagatgct gttgaccac ggtgacagga ttctctcatc agccacgtca     5580
atctttgaca acactggagt gaagatctca gtgaaggttg ctggcattca ctggcactat    5640
ggctcaaggt ctcacgcccc agaactcaca gcagggtatt acaacacccg gttccgtgat    5700
ggctacatcc ccattgctca aatgttggca cgccacggtg ccatcttcaa cttcacctgt    5760
attgagatgc gcgatcacga gcagccacaa gatgcccttt gtgcacccga gaagcttgtg    5820
aagcaagtgg ctctggcaac gcagaaggca caggttccac ttgctggtga aaatgcgctg    5880
ccacggtacg atgagtatgc tcatgagcag atcataaggg catcacagtt ggatgttgat    5940
ggtgactctg gtgaagaga gatgtgtgca ttcacttacc tgagaatgaa cccgcatttg     6000
tttgaaccaa ataactggag gaagtttgtg gggtttgtga agaaaatgaa agaagggaag    6060
agtgcacaca gtgttggga agaggtggag agggaagctg agcattttgt gcatgttaca    6120
cagcctcttg tgcaagaagc tgcagtgctg atgcactgag aattgttgaa caatcttgtg    6180
ctgatagatg gcttagaaaa ggtcacaagt aggctgtgtg aaagttttag tgaaccagca    6240
gcccaggttt gtggctttga agatgtaaaa ttttgtatta tattgttgtt ttatattcta    6300
tgcacctaaa acttctattt gttaccctt tatattgtgt acgtaatcat tgactttggg     6360
gtactatttt cttaaaagtt actctacttt gtacaagtag ttacttattt ctgcatcatg    6420
aaactgttac atggcgtaac agcaacaaga gatgctattt tcttctatag ggaaaaatga    6480
atttaaaatc aatgattttc gttgtgttt                                       6509
```

<210> SEQ ID NO 30
<211> LENGTH: 1389
<212> TYPE: DNA
<213> ORGANISM: Glycine max

<400> SEQUENCE: 30

```
atgatgccgt tggacagcgt aaagacggga aacgcggtga accggaagaa ggcgatgaac      60
gcggcgatgg cggcgctgaa gagtgcgggg gtggagggg taatgatgga cgtgtggtgg      120
ggtttggtgg agagagagaa gcctggggag tataattggg gagggtacgt tgaactcatg      180
gagatggcga agaagcatgg cctgaaggtg caggccgtta tgtcatttca ccaatgtggc      240
ggtaacgtcg gagactcttg cactattcct ttacccaaat gggttgtgga ggagattgat      300
aatgaccccg atcttgcata tactgatcaa tggggaagaa gaaactatga atatatatca      360
cttggatgtg atacttcgcc agtgctcaag ggccgaaccc cagttcaatg ttatgctgat      420
ttcatgcgtg ctttcagaga cacttttcaag cacctccttg gtgacaccat tgtggaaatt    480
caagttggga tgggaccggc aggtgagctg cgttacccct cttacccaga gcaaaatggg     540
acatggaatt tcccaggaat tggtggtttc caatgctatg acaagtatat gttgagtagc     600
```

```
ttaaaagctg ctgctgaagc tgagggtaag cctgaatggg gaagcacagg ccctactgat      660
gctggacact ataacaactg gccagaagac actcaatttt tccgcaaaga aggtggaggc      720
tgggatggtc catatggtga gttttcctc acctggtact ctcagatgct gttggaccac       780
ggtgacagga ttctctcatc agccacgtca atctttgaca acactggagt gaagatctca      840
gtgaaggttg ctggcattca ctggcactat ggctcaaggt ctcacgcccc agaactcaca      900
gcagggtatt acaacacccg gttccgtgat ggctacatcc ccattgctca aatgttggca      960
cgccacggtg ccatcttcaa cttcacctgt attgagatgc gcgatcacga gcagccacaa     1020
gatgcccttt gtgcacccga gaagcttgtg aagcaagtgg ctctggcaac gcagaaggca     1080
caggttccac ttgctggtga aaatgcgctg ccacggtacg atgagtatgc tcatgagcag     1140
atcataaggg catcacagtt ggatgttgat ggtgactctg gtggaagaga gatgtgtgca     1200
ttcacttacc tgagaatgaa cccgcatttg tttgaaccaa ataactggag gaagtttgtg     1260
gggtttgtga agaaaatgaa agaagggaag agtgcacaca agtgttggga agaggtggag     1320
agggaagctg agcattttgt gcatgttaca cagcctcttg tgcaagaagc tgcagtgctg     1380
atgcactga                                                            1389
```

<210> SEQ ID NO 31
<211> LENGTH: 462
<212> TYPE: PRT
<213> ORGANISM: Glycine max

<400> SEQUENCE: 31

```
Met Met Pro Leu Asp Ser Val Lys Thr Gly Asn Ala Val Asn Arg Lys
1               5                   10                  15

Lys Ala Met Asn Ala Ala Met Ala Ala Leu Lys Ser Ala Gly Val Glu
            20                  25                  30

Gly Val Met Met Asp Val Trp Trp Gly Leu Val Glu Arg Glu Lys Pro
        35                  40                  45

Gly Glu Tyr Asn Trp Gly Tyr Val Glu Leu Met Glu Met Ala Lys
    50                  55                  60

Lys His Gly Leu Lys Val Gln Ala Val Met Ser Phe His Gln Cys Gly
65                  70                  75                  80

Gly Asn Val Gly Asp Ser Cys Thr Ile Pro Leu Pro Lys Trp Val Val
                85                  90                  95

Glu Glu Ile Asp Asn Asp Pro Asp Leu Ala Tyr Thr Asp Gln Trp Gly
            100                 105                 110

Arg Arg Asn Tyr Glu Tyr Ile Ser Leu Gly Cys Asp Thr Ser Pro Val
        115                 120                 125

Leu Lys Gly Arg Thr Pro Val Gln Cys Tyr Ala Asp Phe Met Arg Ala
    130                 135                 140

Phe Arg Asp Thr Phe Lys His Leu Leu Gly Asp Thr Ile Val Glu Ile
145                 150                 155                 160

Gln Val Gly Met Gly Pro Ala Gly Glu Leu Arg Tyr Pro Ser Tyr Pro
                165                 170                 175

Glu Gln Asn Gly Thr Trp Asn Phe Pro Gly Ile Gly Gly Phe Gln Cys
            180                 185                 190

Tyr Asp Lys Tyr Met Leu Ser Ser Leu Lys Ala Ala Ala Glu Ala Glu
        195                 200                 205

Gly Lys Pro Glu Trp Gly Ser Thr Gly Pro Thr Asp Ala Gly His Tyr
    210                 215                 220
```

```
Asn Asn Trp Pro Glu Asp Thr Gln Phe Phe Arg Lys Glu Gly Gly Gly
225                 230                 235                 240

Trp Asp Gly Pro Tyr Gly Glu Phe Phe Leu Thr Trp Tyr Ser Gln Met
            245                 250                 255

Leu Leu Asp His Gly Asp Arg Ile Leu Ser Ser Ala Thr Ser Ile Phe
                260                 265                 270

Asp Asn Thr Gly Val Lys Ile Ser Val Lys Val Ala Gly Ile His Trp
            275                 280                 285

His Tyr Gly Ser Arg Ser His Ala Pro Glu Leu Thr Ala Gly Tyr Tyr
        290                 295                 300

Asn Thr Arg Phe Arg Asp Gly Tyr Ile Pro Ile Ala Gln Met Leu Ala
305                 310                 315                 320

Arg His Gly Ala Ile Phe Asn Phe Thr Cys Ile Glu Met Arg Asp His
                325                 330                 335

Glu Gln Pro Gln Asp Ala Leu Cys Ala Pro Glu Lys Leu Val Lys Gln
            340                 345                 350

Val Ala Leu Ala Thr Gln Lys Ala Gln Val Pro Leu Ala Gly Glu Asn
        355                 360                 365

Ala Leu Pro Arg Tyr Asp Glu Tyr Ala His Glu Gln Ile Ile Arg Ala
370                 375                 380

Ser Gln Leu Asp Val Asp Gly Asp Ser Gly Gly Arg Glu Met Cys Ala
385                 390                 395                 400

Phe Thr Tyr Leu Arg Met Asn Pro His Leu Phe Glu Pro Asn Asn Trp
                405                 410                 415

Arg Lys Phe Val Gly Phe Val Lys Lys Met Lys Glu Gly Lys Ser Ala
            420                 425                 430

His Lys Cys Trp Glu Glu Val Glu Arg Glu Ala Glu His Phe Val His
        435                 440                 445

Val Thr Gln Pro Leu Val Gln Glu Ala Ala Val Leu Met His
450                 455                 460
```

<210> SEQ ID NO 32
<211> LENGTH: 8834
<212> TYPE: DNA
<213> ORGANISM: Glycine max

<400> SEQUENCE: 32

```
ttgagaactt aacctactaa aattattctt tgatgtaatg ttaatgattt ttttatttat      60
aattattcta atttaaatat gcatctacta gtatattcta attttactcc ccaacataaa     120
aaagtctaat ttatctattt tctctctcaa atcccttttac aaaactaaaa tagtaaattg    180
cattaaaaat atagatgtat aacatgctaa agaaaaatta atgtttcccc atgttacccc     240
taaaacttat catgcaaatg gatgatcaag tcataagaaa tgtaatattc ataaatagat     300
aagaagataa attacatcaa aagtagttga cggtcaaatt ttcaacaaaa aaggtttagc    360
ctcttattgt catggagatt ttataattgc aagagtaaaa tatttagtaa aggggagaaa     420
ataaaaaagg gaataaagga aatgaatgac tctcaatatt tatttctcct tcttctagtc    480
tttgccttct ataatgaagt gtattctctc ttaaaaattt tcctttgttt tttcttattc     540
tctccttttc ttttatagat gcatattagt gggcttcttg cattaagtct aagtctgtct    600
ttatttttct taattagtca tattttctt aattagttcg ctttccttaa ttattcctct      660
cttcttgaat tatcctactt ttttttttact cactaagcat aataaattca tcatttttaa   720
tatttgttgc acaaaaaata aaataatgtt aatttaacaa ttatttgctt aaaaaaaatt    780
```

```
agaagaaaaa aattacaaat tcttatatat tttaaccctc aaaatatact tataattagt      840
tgttattgat tttaaagtta acctattttt tcaagatatc catggtaggt attttcaaat      900
tacacacttc acatgtaaac tttgaggttg caagggtgaa acaggtaaaa agaataaca      960 gctagcaaag acatttaaaa taattctagc aatataagtc caatctaaag cggatacgtc     1020
cagcaatatt catccctcac caactccaac ttcactctca ataaactgga aaattataac     1080
caaacatgct gaatcgtgaa ggcatcccta caattccttc ctagccaacc agcccaacaa     1140
ttttcttagc ttttagaaat attatcgtgt gcaatgtgat acactgcagt aagcatcaac     1200
aagaatagta acctgacctt tcatgccata tatgatcgaa gtggtcaaga atggcaagta     1260
gaagtgaggt tcatgctctt taatgattaa tctaatggga taaaaaggac aaagacaaac     1320
agaactctta atagaaaaga aaaaaactaa gtgggtcaac aatgcatatt ttggattcaa     1380
aaccaccact gtccaatcga caacattgtt ctacaaaacc ggaatgattg tgattcatcc     1440
ggagggtatt tgctcattca tgttccttat tgtcgatatg gcatgccta actagctaag     1500 tacaatttcc ttaatttcta ttttggcact tacaatcgta attaaaactg aaatcaggtt     1560
tatatatata tatatatata tatatatata tatatatata tatatatata tataaaatt     1620 agcatgcatt atatatttaa ggggtacggg taacgtgtgt acaatatact ccttacaaaa     1680
ggtttatatc tctgctcggc ttcttatccc aaaattagca agcattaaat gaagggtaac     1740
gtgtgttttg ttcttattaa aaaaaaaaca tagtacaatt ttttaagtgg aaacatggaa     1800 atattttttca ctcttttttaa tgattttttt ataacataaa attaaaatat taattctaaa     1860
gtagccaata attataaaatt tttcactaac tatgtattgt aatgaaaaaa aatattttta     1920
tattttactt ttggaaaatt ttaaatttat ttgttagcaa atgatctgtt catgatatat     1980
ttttattaat tttaaatatt ataatttaaa acatatatat ttaaatttaa ttttctgata     2040
caacattgga ggattatata tataactgct cagatagacc cctccaatag tccaattgta     2100
ataagagttt gagaacataa gaaaaaaaat cttgtaatta ctaatctata ttgtggcttt     2160
cctcatacaa ttgatccatg gagagaagga gtaattcaca ataataatag taattattag     2220
tattataata aatgttaatg ttggtgactg cttggtcatt ttctcttcca gaaaaacaga     2280
taagctgtga cctgttagta aggccatggt gggagggacc actgcatggc atctttctca     2340
gtgctactag tgcttcactt attacatgat tttgaagttg tcagtgagcg ggtagaagat     2400
ggaggccatg gtccacactt tgttgccgca ttgcaagaaa atggtaaaaa tgatattgaa     2460
tctgcaaccc cccaatgtaa gggcctcttg taataatgga agcagcacag gggcgaagtc     2520
acacattgat aatagggttt atcgaaaaca ccacatcaca ccataccact tcacttacca     2580
cgccccctct ctttcgtgt caacaatctt tgaccacctt tatccaacct aacaaaatca     2640
ttactgttta ttaatttat actcttgttt tactagtaat tttctatatt gatttcgttc     2700
atttgttatg caggtgtgaa aatgaacacg atcaataaaa gaaaggaaga aaaatctagc     2760
ctttagtgat gatatcggac ttcttttttg ttttttcaaa aggagggctt gcaattcgac     2820
aataactaag caaaattaac aaaaattaaa gaaacaataa tccattttct gtcataattt     2880
cgtgctttga taaatttaat actgcaatat tattgtagaa cccgtgatta tgaagtataa     2940
gaacataaac ttcatgtgat aaattttcac tgcaaataga atgtctatat gttttcatt      3000 taagacacac tattcaaaaa acaatctttt gaacgacgat tcattgacac atttaataat     3060
tgtttttaac cgttattgaa gtgaatgtaa tgagaaatat tatattttttt acgataattt     3120 cttaatcatc ttagaagatc tcatcttta agataacttt tatgttaaaa ccgttgtaga      3180
```

```
agacccacca tcctaaaaga acactaacta gaaaaagaat ggtggagagg gtgaaatagc    3240
tacgggttcc ttggcttagt gtacagtttg gcgggacctt actccttggg aaggctagac    3300
agtagaagga tactccgaga tcacttcaaa gagaatacga cacccatgat tatcaaaagg    3360
ttagacaagt tgatgcgcaa tttccttgtt ttcagtcata attttggact aattaaactc    3420
cacacagaac gacaagcatg cttattttct aggcttttgc tttgctgaat actagaagat    3480
aaatctcata gctttagccc attgccaaac gctggatttt actctcttcc tcacaagatg    3540
gtaacaagtt agataatcta agatttgtga ccttattcgt cttatgtttg ggttaatatt    3600
catgttgtac cgagtatcat gtgctctaaa acatgcagtt ttggcttggc aatgaattag    3660
aagtattcca tcaaagtaat tcataccata ccccattttt aaagctcaaa atgagcaaga    3720
taaaaacttt aaacgtatct tagggcattc attattatca aaagccttta tattcattag    3780
aactctttgc atgtatagac cattttctct tttttaaata aaaaacatat taacatatgt    3840
atctcaggga atttattaaa caattaaaaa tgaaaatatt tatataaaaa tattatcgac    3900
ataatattat tattattatt attattatta ttattattat tattatatat cgtgagtttt    3960
aattaaaaaa aattcattga tactctttaa agtagaaacg cttgttagta aaaatgatat    4020
ttttgaattt aaaaggttat acattttat attattgtta aaatttaaaa cttaataatg    4080
aaaattaaaa atatttattt ttatcctcaa atgactagac actacaacaa aataaataat    4140
aaataagaca aggaaaacta acaaaagaac taaccgttgt ccttgacctt ccttggaaaa    4200
taaggcaata gcataggacc tacttcaaaa aagacattcg actacaaaaa catgcaaaat    4260
ggacaaagat gaacagaaaa actaagaaga cgttgcattt atttttttcaa tttcacgtat    4320 tttcattgaa aattatattt taacattatt catttatttg ttaacaggcc tattttaaaa    4380
ttcgaaacct cggtatttta ttaaactcat taaaatatct acaccatttt ttattaaaaa    4440
tataataata ataattttaa tatagtttct taataataaa atctctaata actgcgaaaa    4500
aagtattttt ctaaaaatac cataattaaa tacgtacaac aacgaagtat taaacatata    4560
aaactaaaga accacgacac atttatgtct ttcctatcac aatcataagt aatgcttgat    4620
ttgtgagcac actctccata accaacaaca cacacataac attcttttat taaaatcatt    4680
ttaaattatg tcacataata actactgtaa caacacacat tagcatgaaa ctggtattag    4740
tagcacatac aataaataaa tattgattat tatctgatgt aattatgtaa gtattatgag    4800
tggttgatta aaaaaacaaa atagagttgg taaggggtg gatccacatc caccgcttct    4860
gcaccaaact cagcatagca gtgggtcaat gattgattgg taattgtaat tctattcaaa    4920
aagtgaaaag agttgaatga gaattcgtat attcagaaaa tcccccctcc tttaagataa    4980
gagaataggc ctcactcttt cttctcttc cattcccaaa atgcgtgtcc tctttctttt    5040
tctgtttttc cagtttctcc attttcattt ccccaaaacc ctttcagccc caatctcaga    5100
gtaccgtgcc cttctctctc tccgttcagc cattaccgac gccacccac ctcttctcac    5160 ttcgtggaac tcctccaccc cttactgttc ctggctcggc gtcacctgcg acaaccgccg    5220
ccacgtcacc tccctagacc tcaccggcct cgaccctctc ggccccctct ccgccgacgt    5280
cgcccacctc ccattcctct ccaacctctc cctcgcctcg aataagttct ccggcccat    5340 tcctcctca ctctccgctc tctccggcct ccgcttcctc aacctctcca acaatgtctt    5400
caacgaaacc ttcccctcgg agctctcgcg cctccagaac ctcgaggtcc tcgacctcta    5460
caacaacaac atgaccggcg tgcttccct cgccgtcgcg cagatgcaga atcttcgtca    5520
```

```
tttgcatctc ggcggcaact tcttctccgg ccagatcccg ccggagtatg gacgctggca    5580
gcgcctccag tacctcgccg tctccggcaa cgagctcgag gggactatcc ctccggagat    5640
cggaaacttg tccagcctcc gggagctcta catcggctac tacaacacct acaccggggg    5700
cattccgccg gagatcggaa atttgtcgga gctggtgagg ctcgacgccg cctactgtgg    5760
gttgtccggc gagattccgg cggcgctggg aaagcttcag aagctggaca cgctgttcct    5820
tcaggtgaat gcattgtcag ggtctttgac tcccgagctg gggaacctga agagcctgaa    5880
atccatggat ttgtctaaca acatgctctc cggtgagatt ccggcgagat cggcgagct    5940
gaagaatatt actcttctga atctgttcag gaacaagctt cacggagcta taccagagtt    6000
tatagggag cttccagcgt tggaagttgt gcaactgtgg gagaataact tcacaggtag    6060
cattccagag ggtttgggca aaacgggag actcaaccctt gttgatcttt cttctaacaa    6120
gttaactggg actttgccta cttatctctg ttctgggaat actcttcaga ctctgataac    6180
tcttgggaat tttctttttg gtccaattcc tgagtcgctt ggtagttgtg aatcccttac    6240
acggattaga atgggagaga actttttgaa tggttccatt ccgagagggc ttttttggact   6300
tcccaaacta acacaggttg agcttcagga taattatctc tctggagagt ttcctgaggt    6360
gggttctgtt gctgttaatc ttggtcagat tactctctct aacaaccagc tttctggggt    6420
tctacctccc tccattggta acttctccag cgtgcagaag ctccttcttg atggcaacat    6480
gttcacgggt cggatacctc cccagattgg gaggttgcaa cagctttcta agattgattt    6540
tagtggcaac aagttctcgg gtcctattgt gcctgagatc agtcagtgta agctgttaac    6600
tttccttgac cttagccgca atgagctatc tggagacatc ccaaatgaga taactggcat    6660
gaggatattg aattacttga atctttctag gaatcattta gtgggtggca ttccctcttc    6720
gatatcatct atgcaaagct tgacttctgt tgattttca tacaacaacc tgtctggttt    6780
ggtgcctggt accggtcaat tcagctactt caattacacg tctttcttgg gaaaccctga    6840
cctctgtggc ccctatttgg gtgcttgcaa ggatggggtt gccaatggcg cacaccaacc    6900
tcatgttaaa ggtctctcct cttcttttaa gctgctactt gttgttgggt tgctactatg    6960
ttccattgct tttgctgtgg ctgcaatatt caaggcccgg tcactgaaga aggccagtgg    7020
ggctcgtgca tggaagttga ctgcgttcca acgtttggac ttcactgtcg atgatgtttt    7080
gcattgcttg aaggaggata atattatagg gaaaggaggt gctggcattg tctacaaagg    7140
ggctatgcct aatggggatc atgttgctgt gaaaaggctt ccggctatga gtagaggctc    7200
ttcacatgat catggcttca atgctgagat tcaaacattg gggcgaatcc gacacaggca    7260
cattgttagg ttgttgggct tctgttcaaa tcatgagaca aacctttttgg tctatgagta    7320
catgcccaat ggaagtttag gcgaggttct tcatggaaag aaaggggggtc atttgcattg    7380
ggatacaagg tataaaattg cggtggaggc tgccaagggg ctttgctatc tgcaccatga    7440
ttgttcgcca ctcattgtcc atcgtgatgt gaagtcaaac aacatccttc ttgattctaa    7500
tcatgaagcc catgttgctg attttgggct tgctaagttc ctgcaagatt ctgggacatc    7560
tgaatgcatg tctgctattg ctggttcata tggatacata gctccaggta ccgtccaatt    7620
tcgacataat taatgcatta tttacatggt tgtggaaaat tttcttttac ccgcctgttc    7680
ataattgtac gtttaatcat tgttcagaat ttgactcttt gacttatcat catgttttag    7740
gtgtagactg ttgatattga ggtgatgtcc ctaaattaat taacattgct atgtggtttt    7800
tcttgacttt ggttttctat cataccccaaa tgatctcttg atttcgaccc cttatttagt    7860
ctatttcaag ccaagtactg aaagtaaatg gtagatagct ctgcaacgtt agagtcattc    7920
```

```
acgaccggaa actgatgatt atgggcaaaa tatcggataa aaagacctat tatgttactt    7980
tacacttatt gcctttgttt aacttatagt ttcaaattca agtgtcttgc tttattttag    8040
tttatgatac atgttcgatg tttgattgca gagtatgcct acacattgaa agttgatgag    8100
aaaagcgatg tgtacagttt tggtgtggtt ctcttagaac ttataacagg caggaaacca    8160
gttggagaat tggtgatgg cgtggacata gtgcaatggg tgaggaaaat gacggattct    8220
aacaaggaag gagttcttaa agttcttgat cctagacttc cctcagttcc ccttcacgaa    8280
gtgatgcatg ttttctatgt agccatgctg tgcgttgaag aacaggctgt agagagacca    8340
actatgcgtg aagttgttca aatactgaca gagcttccaa agccacctga ctctaaagag    8400
gggaacttaa caataacgga atcatctttg tcatcatcaa acgctttaga atctccatcc    8460
tcagcctcta aggaagatca aaatcctcct caatccccac cacccgatct tcttagcatt    8520
taaagtgctc tgttgggtgt ttcatcttag ttcccttggg ttgtgatcgc ttatccattt    8580
actttctttt tctgtctctc ttctgggatt ggttttttt tttttcccta actgaaggtg    8640
ttaatgtttg gattttttaa tggttttgta cagtaggatt gatgggggta ttttcttata    8700
aagtcactgt cttcatcatg tagtactgct ttttaatttt tatttgcgac cgttgttggg    8760
gaggattcaa gggatacaat taaattactc gtttgtttcc tgaaatttca ttattcatac    8820
ttttttagtt tatg                                                      8834

<210> SEQ ID NO 33
<211> LENGTH: 3039
<212> TYPE: DNA
<213> ORGANISM: Glycine max

<400> SEQUENCE: 33
atgcgtgtcc tctttctttt tctgtttttc cagtttctcc attttcattt ccccaaaacc      60
ctttcagccc caatctcaga gtaccgtgcc cttctctctc tccgttcagc cattaccgac     120
gccaccccac ctcttctcac ttcgtggaac tcctccaccc cttactgttc ctggctcggc     180
gtcacctgcg acaaccgccg ccacgtcacc tccctagacc tcaccggcct cgacctctcc     240
ggccccctct ccgccgacgt cgcccacctc ccattcctct ccaacctctc cctcgcctcg     300
aataagttct ccggcccat tcctccctca ctctccgctc tctccggcct ccgcttcctc     360
aacctctcca caatgtctt caacgaaacc ttccctcgg agctctcgcg cctccagaac     420
ctcgaggtcc tcgacctcta caacaacaac atgaccggcg tgcttcccct cgccgtcgcg     480
cagatgcaga atcttcgtca tttgcatctc ggcggcaact tcttctccgg ccagatcccg     540
ccggagtatg gacgctggca gcgcctccag tacctcgccg tctccggcaa cgagctcgag     600
gggactatcc ctccggagat cggaaacttg tccagcctcc gggagctcta catcggctac     660
tacaacacct acaccggggg cattccgccg gagatcggaa atttgtcgga gctggtgagg     720
ctcgacgccg cctactgtgg gttgtccggc gagattccgg cggcgctggg aaagcttcag     780
aagctggaca cgctgttcct tcaggtgaat gcattgtcag ggtctttgac tcccgagctg     840
gggaacctga gagcctgaa atccatggat ttgtctaaca acatgctctc cggtgagatt     900
ccggcgagat tcggcgagct gaagaatatt actcttctga atctgttcag gaacaagctt     960
cacggagcta taccagagtt tatagggag cttccagcgt tggaagttgt gcaactgtgg    1020
gagaataact tcagggtag cattccgag ggttttggca aaaacgggag actcaacctt    1080
gttgatcttt cttctaacaa gttaactggg actttgccta cttatctctg ttctgggaat    1140
```

```
actcttcaga ctctgataac tcttgggaat tttcttttg gtccaattcc tgagtcgctt      1200
ggtagttgtg aatcccttac acggattaga atgggagaga acttttttgaa tggttccatt   1260 ccgagagggc tttttggact tcccaaacta acacaggttg agcttcagga taattatctc     1320
tctggagagt ttcctgaggt gggttctgtt gctgttaatc ttggtcagat tactctctct    1380
aacaaccagc tttctggggt tctacctccc tccattggta acttctccag cgtgcagaag   1440
ctccttcttg atggcaacat gttcacgggt cggatacctc cccagattgg gaggttgcaa    1500
cagctttcta agattgattt tagtggcaac aagttctcgg gtcctattgt gcctgagatc    1560
agtcagtgta agctgttaac tttccttgac cttagccgca atgagctatc tggagacatc   1620
ccaaatgaga taactggcat gaggatattg aattacttga atctttctag gaatcattta   1680
gtgggtggca ttccctcttc gatatcatct atgcaaagct tgacttctgt tgatttttca   1740
tacaacaacc tgtctggttt ggtgcctggt accggtcaat tcagctactt caattacacg    1800
tctttcttgg gaaaccctga cctctgtggc ccctatttgg gtgcttgcaa ggatgggtt    1860 gccaatggcg cacaccaacc tcatgttaaa ggtctctcct cttcttttaa gctgctactt   1920
gttgttgggt tgctactatg ttccattgct tttgctgtgg ctgcaatatt caaggcccgg   1980
tcactgaaga aggccagtgg ggctcgtgca tggaagttga ctgcgttcca acgtttggac    2040
ttcactgtcg atgatgtttt gcattgcttg aaggaggata atattatagg gaaaggaggt   2100
gctggcattg tctacaaagg ggctatgcct aatgggatc atgttgctgt gaaaaggctt     2160
ccggctatga gtagaggctc ttcacatgat catggcttca atgctgagat caaacattg    2220 gggcgaatcc gacacaggca cattgttagg ttgttgggct tctgttcaaa tcatgagaca   2280
aaccttttgg tctatgagta catgcccaat ggaagtttag gcgaggttct tcatggaaag   2340 aaaggggtc atttgcattg ggatacaagg tataaaattg cggtggaggc tgccaagggg    2400
ctttgctatc tgcaccatga ttgttcgcca ctcattgtcc atcgtgatgt gaagtcaaac   2460 aacatcctc ttgattctaa tcatgaagcc catgttgctg attttgggct tgctaagttc    2520
ctgcaagatt ctgggacatc tgaatgcatg tctgctattg ctggttcata tggatacata   2580
gctccagagt atgcctacac attgaaagtt gatgagaaaa gcgatgtgta cagttttggt   2640
gtggttctct tagaacttat aacaggcagg aaaccagttg gagaatttgg tgatggcgtg    2700
gacatagtgc aatgggtgag gaaaatgacg gattctaaca aggaaggagt tcttaaagtt   2760
cttgatccta gacttccctc agttcccctt cacgaagtga tgcatgtttt ctatgtagcc   2820
atgctgtgcg ttgaagaaca ggctgtagag agaccaacta tgcgtgaagt tgttcaaata   2880
ctgacagagc ttccaaagcc acctgactct aaagagggga acttaacaat aacggaatca   2940
tctttgtcat catcaaacgc tttagaatct ccatcctcag cctctaagga agatcaaaat   3000
cctcctcaat ccccaccacc cgatcttctt agcatttaa                          3039
```

<210> SEQ ID NO 34
<211> LENGTH: 1012
<212> TYPE: PRT
<213> ORGANISM: Glycine max

<400> SEQUENCE: 34

```
Met Arg Val Leu Phe Leu Phe Leu Phe Phe Gln Phe Leu His Phe His
1               5                   10                  15

Phe Pro Lys Thr Leu Ser Ala Pro Ile Ser Glu Tyr Arg Ala Leu Leu
            20                  25                  30

Ser Leu Arg Ser Ala Ile Thr Asp Ala Thr Pro Pro Leu Leu Thr Ser
```

```
              35                  40                  45
Trp Asn Ser Ser Thr Pro Tyr Cys Ser Trp Leu Gly Val Thr Cys Asp
 50                  55                  60

Asn Arg Arg His Val Thr Ser Leu Asp Leu Thr Gly Leu Asp Leu Ser
 65                  70                  75                  80

Gly Pro Leu Ser Ala Asp Val Ala His Leu Pro Phe Leu Ser Asn Leu
                 85                  90                  95

Ser Leu Ala Ser Asn Lys Phe Ser Gly Pro Ile Pro Pro Ser Leu Ser
                100                 105                 110

Ala Leu Ser Gly Leu Arg Phe Leu Asn Leu Ser Asn Asn Val Phe Asn
                115                 120                 125

Glu Thr Phe Pro Ser Glu Leu Ser Arg Leu Gln Asn Leu Glu Val Leu
                130                 135                 140

Asp Leu Tyr Asn Asn Met Thr Gly Val Leu Pro Leu Ala Val Ala
145                 150                 155                 160

Gln Met Gln Asn Leu Arg His Leu His Leu Gly Gly Asn Phe Phe Ser
                165                 170                 175

Gly Gln Ile Pro Pro Glu Tyr Gly Arg Trp Gln Arg Leu Gln Tyr Leu
                180                 185                 190

Ala Val Ser Gly Asn Glu Leu Glu Gly Thr Ile Pro Pro Glu Ile Gly
                195                 200                 205

Asn Leu Ser Ser Leu Arg Glu Leu Tyr Ile Gly Tyr Tyr Asn Thr Tyr
210                 215                 220

Thr Gly Gly Ile Pro Pro Glu Ile Gly Asn Leu Ser Glu Leu Val Arg
225                 230                 235                 240

Leu Asp Ala Ala Tyr Cys Gly Leu Ser Gly Glu Ile Pro Ala Ala Leu
                245                 250                 255

Gly Lys Leu Gln Lys Leu Asp Thr Leu Phe Leu Gln Val Asn Ala Leu
                260                 265                 270

Ser Gly Ser Leu Thr Pro Glu Leu Gly Asn Leu Lys Ser Leu Lys Ser
                275                 280                 285

Met Asp Leu Ser Asn Asn Met Leu Ser Gly Glu Ile Pro Ala Arg Phe
290                 295                 300

Gly Glu Leu Lys Asn Ile Thr Leu Leu Asn Leu Phe Arg Asn Lys Leu
305                 310                 315                 320

His Gly Ala Ile Pro Glu Phe Ile Gly Glu Leu Pro Ala Leu Glu Val
                325                 330                 335

Val Gln Leu Trp Glu Asn Asn Phe Thr Gly Ser Ile Pro Glu Gly Leu
                340                 345                 350

Gly Lys Asn Gly Arg Leu Asn Leu Val Asp Leu Ser Ser Asn Lys Leu
                355                 360                 365

Thr Gly Thr Leu Pro Thr Tyr Leu Cys Ser Gly Asn Thr Leu Gln Thr
                370                 375                 380

Leu Ile Thr Leu Gly Asn Phe Leu Phe Gly Pro Ile Pro Glu Ser Leu
385                 390                 395                 400

Gly Ser Cys Glu Ser Leu Thr Arg Ile Arg Met Gly Glu Asn Phe Leu
                405                 410                 415

Asn Gly Ser Ile Pro Arg Gly Leu Phe Gly Leu Pro Lys Leu Thr Gln
                420                 425                 430

Val Glu Leu Gln Asp Asn Tyr Leu Ser Gly Glu Phe Pro Glu Val Gly
                435                 440                 445

Ser Val Ala Val Asn Leu Gly Gln Ile Thr Leu Ser Asn Asn Gln Leu
                450                 455                 460
```

```
Ser Gly Val Leu Pro Pro Ser Ile Gly Asn Phe Ser Val Gln Lys
465                 470                 475                 480

Leu Leu Leu Asp Gly Asn Met Phe Thr Gly Arg Ile Pro Pro Gln Ile
            485                 490                 495

Gly Arg Leu Gln Gln Leu Ser Lys Ile Asp Phe Ser Gly Asn Lys Phe
            500                 505                 510

Ser Gly Pro Ile Val Pro Glu Ile Ser Gln Cys Lys Leu Leu Thr Phe
            515                 520                 525

Leu Asp Leu Ser Arg Asn Glu Leu Ser Gly Asp Ile Pro Asn Glu Ile
530                 535                 540

Thr Gly Met Arg Ile Leu Asn Tyr Leu Asn Leu Ser Arg Asn His Leu
545                 550                 555                 560

Val Gly Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
        595                 600                 605

Cys Gly Pro Tyr Leu Gly Ala Cys Lys Asp Gly Val Ala Asn Gly Ala
        610                 615                 620

His Gln Pro His Val Lys Gly Leu Ser Ser Ser Phe Lys Leu Leu Leu
625                 630                 635                 640

Val Val Gly Leu Leu Leu Cys Ser Ile Ala Phe Ala Val Ala Ala Ile
            645                 650                 655

Phe Lys Ala Arg Ser Leu Lys Lys Ala Ser Gly Ala Arg Ala Trp Lys
            660                 665                 670

Leu Thr Ala Phe Gln Arg Leu Asp Phe Thr Val Asp Asp Val Leu His
            675                 680                 685

Cys Leu Lys Glu Asp Asn Ile Ile Gly Lys Gly Gly Ala Gly Ile Val
        690                 695                 700

Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
            725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
        755                 760                 765

Pro Asn Gly Ser Leu Gly Glu Val Leu His Gly Lys Lys Gly Gly His
        770                 775                 780

Leu His Trp Asp Thr Arg Tyr Lys Ile Ala Val Glu Ala Ala Lys Gly
785                 790                 795                 800

Leu Cys Tyr Leu His His Asp Cys Ser Pro Leu Ile Val His Arg Asp
            805                 810                 815

Val Lys Ser Asn Asn Ile Leu Leu Asp Ser Asn His Glu Ala His Val
            820                 825                 830

Ala Asp Phe Gly Leu Ala Lys Phe Leu Gln Asp Ser Gly Thr Ser Glu
            835                 840                 845

Cys Met Ser Ala Ile Ala Gly Ser Tyr Gly Tyr Ile Ala Pro Glu Tyr
        850                 855                 860

Ala Tyr Thr Leu Lys Val Asp Glu Lys Ser Asp Val Tyr Ser Phe Gly
865                 870                 875                 880
```

```
Val Val Leu Leu Glu Leu Ile Thr Gly Arg Lys Pro Val Gly Glu Phe
            885                 890                 895

Gly Asp Gly Val Asp Ile Val Gln Trp Val Arg Lys Met Thr Asp Ser
        900                 905                 910

Asn Lys Glu Gly Val Leu Lys Val Leu Asp Pro Arg Leu Pro Ser Val
        915                 920                 925

Pro Leu His Glu Val Met His Val Phe Tyr Val Ala Met Leu Cys Val
        930                 935                 940

Glu Glu Gln Ala Val Glu Arg Pro Thr Met Arg Glu Val Val Gln Ile
945                 950                 955                 960

Leu Thr Glu Leu Pro Lys Pro Pro Asp Ser Lys Glu Gly Asn Leu Thr
                965                 970                 975

Ile Thr Glu Ser Ser Leu Ser Ser Ser Asn Ala Leu Glu Ser Pro Ser
            980                 985                 990

Ser Ala Ser Lys Glu Asp Gln Asn  Pro Pro Gln Ser Pro  Pro Pro Asp
            995                 1000                1005

Leu Leu  Ser Ile
    1010
```

```
<210> SEQ ID NO 35
<211> LENGTH: 9088
<212> TYPE: DNA
<213> ORGANISM: Glycine max

<400> SEQUENCE: 35
gttggagtaa atccaataac atcaaatcct taatatatat ttattaaatt ttattgataa      60
aactgactta ctagtacata ttttagtttg taataatatc atttgtttgg atccaatata     120
taagccaatt tttttttatgg acaaaatata tggagccaaa gccgcagctc aaaaacctat    180
gtaacaagag acactgaaga gtgaagaatc agcaacatga tcaaagccta aaattggggc    240
aaaaattcaa acacttggct ataaatacac cagatagtcc atacttagcc gctattatgt    300
caaaatataa tagtattaat attacatggc aaagtatagg ctatataatt taatgtaatt    360 tattaaatttt tacaaggtac tgattcaact ttaaacatgt atgctaattg gagtttaaaa    420
tttgtgaaca aaaagcaagt gcattttgtt gcgtgatcaa aattgctcaa ccttatcatg    480
taggaaaacg ataaccaga atttgtgtgg tcccaaacga caacaagacg catttataag      540
cttgactagt tctcttcgtc gtcaactgac attctcattt tcaatgata gttgctactt     600 gataatattt tattcgaata atctgtcgtt aacctaccta taatatatag ctggtgctat    660
taatcgaatg tttaatctca ttttaagatt tacagtgtgt ggattgatgg tgaagatcca    720
aaaatcatag tatctgatta tgatttagtt tccaccgcat cagagagtat agctagctag    780
ttttaaagtt agcatgattt tttcaagata acccaccgta gatttttca acataatata     840 atataatttt cacttgtaaa ctttgaggtt gcaaggaaga aaagcaggta aaagaataa    900 caggtagcaa agacatttaa aaattaaaat agttctaaca atataagtcc aatctaaagg    960
ggatacgtcc agcaatactc atccctcacc aactccaact tcactctcaa taaactggaa   1020
tcgtgaaagc atcattacaa ttatctccta gctaaccaaa cccaacatt tttttagctt   1080 ttagaaatat tatcgcgtgc aatgtgatgc actgctgcag ttagcatcaa caagaatagt   1140
aacctgaccc ttcatgccat tatgatcgag gtggtaaaaa atggcaagta gaagtgaggt   1200
tcatgctctt taatgattaa tctaatggga taacaagaac cagaacaaac agaactcttg   1260
gtagaaaaga aaaaaaaaag tgggtcaata atgcatattt tggattcaaa accaccactg   1320
```

```
tccaattgac atcattgttc tacaaaaccg aatgattgt gattcatccg gagggtattt    1380
gctcattcat gttccttatt atcgatatgg gcatacctga ctagccaagt acaatttcct    1440
taatttcaat tttggcactt acaatcgtga ttaaaactga gatcaggttt atatatatgc    1500
ttgtcttttt atccaaaaat tagcatgcat tctatattta tggggtacgg gtcacgtgtg    1560
tacaatatac tccttacaaa aggtttatat atctgcttgg cttttaatcc caaaattagc    1620
atgcattaaa tgaagggtaa cgtgtgtttt attcttattt aaataaataa catatagtac    1680
aatttttaag tagccaataa ttttaaaatt ttcactaact ctgtatctgt attgtaatga    1740
aaatatttt atattttact tttggatcaa tttaaattta tttgtaaaca aatggtttta    1800
cattttatta atttctttta ttaaatctgt ccataatatc tttttttttt ataagtttta    1860
aattttataa ttttaattta aatttctaat acaacgtaag aggattaata tacttagcta    1920
gttaaagatt ataataatta ttttcaactg cgttggagtt agctgggatg accacggatc    1980
ttccccccca taaattacca caaagcaccc catttgttac acagaaaggg actcttgcaa    2040
caagagaata agggacatta agtaatttgc ctattaataa tgttataagc taatataaaa    2100
ttagtttggc ggttaaaatg aaaatttaaa gattgaaggg agaagaaga agaaaagaga    2160
gttttaaatt caaatcttcc actgatcttg gttgataaaa aatgaaacc gcacacaaaa    2220
acgctctcca tcaatgcaat tgtactagta atacttaact tgtgtcttat atacagcgtg    2280
gaaatataaa ataaataaca taattatcat ttttgataa tattatatat atatatatat    2340
atatatataa ctattttta tatacgtttg agtacataag gaaacaatct tgctattacc    2400
aatctatatt agttgtggct ttcctcatag aattgatcca tgaaacgaag gagtaacact    2460
gaataataat agtgctaatg aaaaacccat tataatagta attactaata ttattatgaa    2520
atatgaaatg ttaatattcg gtgactgctt ggtcattttc tcttccagaa aaacagagct    2580
gtgacctgtt agtaaggcca tggtgggagg gaccactgca tggcatcttt ctcagtgctt    2640
cccttattac atgattttga tggcttcagt tgtcagagac cgggtgggtg ggtagaagat    2700
ggagtattgt ataggaagaa aatggtaaaa tcatattgaa tcttctgcaa tccccaatgt    2760
actctagtta gtaactgtaa tgtaagggcc tattgtaata attgaagcag cacaggggcg    2820
aagtctcaca ttcataatag ggtttatcga aaacaccaca ccataccact tgccacgccc    2880
cctctctttt cgtgacggtc aacattcttt gaccaccttt atccaaccta actaaatcat    2940
tactactgtt tattaattta tactcttgtt ttaattttct atattgaatt tcattcattt    3000
gtaatattaa tataggtgtg aaaatgacca tgatcaataa aaagaaagga agagcaatat    3060
ctagctttta gtgataacat tggacttctt ttttgtttta acaaaaatta aagaaacaac    3120
agtcattttt ctgtcataac ttgatgcctt gacaaattaa tttaatactg taagattatt    3180
gtagaacccg tgattatgca gtagaagaac ataaatttgt atgtttctca tctaagaaag    3240
gaaaagtagc tagaaaaaga atggtagaga gggtgaaata gcgaaatgca tgctatggcc    3300
aacgggttcc ttattccttg cggaggctat acagtagaat ggttgtccta gatcacttca    3360
aatagaatac gacacccatg attgtcaaaa ggctaaacaa gttgatgcgc gcaatttcct    3420
tgttttcagt cataatttg gactaaactc cacacagaac gacatgttct tttctaggct    3480
tttgctttgt tgaatactag cgttggattt tactctcttc ctcacaagat ggtaacaagt    3540
tagataatct atataagatt tctgacctta ttcgtcttaa tataataaac atgttatagc    3600
gagtatatat catgtgctcc aatacatgca gttttggcaa tggattagaa gtgttaacgt    3660
tccagcagag taattcatac catcccccat ttttaatgct caaaatgagc aagatgaaaa    3720
```

```
tttttaaaac gtatcttaat tcttagggca ttcattatta tcaaaaagcc tttatattca    3780
ttagaactct ttgcatgtat agatcatttt ctcttttttt ttattaaaaa aattaacata    3840
tatatatata tatatatata tatatatata tatatatata tatatatata tatatatata    3900
tatatatatc aggccattca ttaagcaatt aaacatgaaa atattttata caaaatatta    3960
ttatatctat tgtaagtttt aattaaaaaa ttcattgata ttcttaaaac gtttgttagt    4020
aaaaaatata ttttaaattt aaaaggttat atatagttat acattattat attattctta    4080
aaatttaaaa cttaataata ataaaataaa aaatagtatt cttaataact agacacgaca    4140
acaaaataaa taataatta agacaaggaa aactaacaga agaattagcc gttttcctcg     4200
accttccttg aaaataagg caatagcata ggacctactt aaaaaaagtt aaaacattcg     4260
actacaaaaa catacaaaat ggacaaagat aaacacgtaa gaaaaactaa gaaaaacgtt    4320 acatttttt cttttcaatt tcacgtattg ttattgaaaa ttttatttca aacattgttc      4380
atttatttgt ttttaaga gagttcattc atttgttatt aatttaacaa attatttgtt      4440
aacgatctat tttaaaattc aaaacctatt tttattaaac tcattaaatt atgtgcacca    4500
ttttttttat tataaaatata ataataactg ttatataaat ttgatgaatg acatgataaa    4560
agaccgtatt atttgcataa ttaaagaagc acgccatatt tatgtctttc ctatcacaat    4620
cataagtaaa acttgagttt accaccatcc tccgctcaat aacccagcaa cacacataac    4680
attcttttat taatgtcatt tttaagtggc ataataacta tataacaaca cacatgagtg    4740
ccgcatcata aattacacat acgataaata aatcttcatt attatcttat gcaattatat    4800
atgtattatg agtggttcat taaaaaatag tgcagcaaag tcaccatagc cgtgggtgaa    4860
tgattgatag gtaaaattgt attttttcttt ttttcccggg tatttcaaaa agtaaaaaga    4920
gttgaaggga cgaattcata tattcagaaa attccctctc ctttaagtat cggtttgtgt    4980
ttgggggcat cactcgttgt ttctctcttc catgcccaaa atgcgtgtcc tctttgtttt    5040
tctgtttttc cattttcatt tccctgaaac cctttctgcc ccaatctcag agtaccgcgc    5100
ccttctctct ctccgttcag tcattaccga cgccacacca cccgttctct cttcttggaa    5160
cgcctccatc ccttactgtt cctggctcgg cgtcacctgc gacaaccgcc gccacgtcac    5220
cgccctcaac ctcaccggcc tcgacctctc cggcacgctc tctgccgacg tcgcccacct    5280 cccttttcctc tccaacctct ccctcgccgc aaacaaattc tccggcccca ttcctccctc    5340
tctctccgcc ctctccggcc tccgctacct caacctctcc aacaatgtct tcaacgaaac    5400
cttcccctcg gagctttggc gcctccagag cctcgaggtc ctcgacctct acaacaacaa    5460
catgaccggc gtgctccctc ttgccgtcgc gcagatgcag aatcttcgtc atttgcatct    5520
cggcggcaac ttcttctccg gccagatccc gccgagtac ggacgctggc agcgcctcca     5580
gtacctcgcc gtctccggca acgaactcga cgggactatc ccgccggaga tcggaaactt    5640
gaccagcctc cggagctct acatcggcta ctacaacacc tacaccggcg gcattccgcc     5700
ggagatcgga aacttgtcgg agctggtgag gcttgacgta gcgtactgtg cgttgtccgg    5760
ggagattccg gcggcgcttg ggaagcttca gaagctggac acgctgttcc ttcaggtgaa    5820
tgcattgtca ggatcactga cgccggagct ggggaacctg aagagcctga atccatgga     5880 tttgtctaac aacatgctct ccggtgagat tccggcgagt ttcggcgagc tgaagaatat    5940
tacgcttctg aatctgttca ggaacaagct tcatggagct ataccggagt ttataggaga    6000
gcttccagcg ttggaagttg tgcaactgtg ggaaaataac ttaacaggta gcattcctga    6060
```

```
gggtttgggc aaaaatggga gactcaacct tgttgatctt tcttctaaca agttaaccgg   6120
gactttgcct ccttatctct gttctgggaa tactcttcag actctgataa ctcttgggaa   6180
ttttcttttc ggtccaattc ctgagtcgct cgggacttgt gaatctctta cacggattag   6240
aatgggagaa aacttttga atggttccat tcctaaaggg cttttttggac ttcccaaact   6300 cacccaggtt gaacttcagg ataattatct ctctggagag tttcctgagg ttggttctgt   6360
tgcggttaat cttggtcaga ttactctctc taacaaccag cttttctgggg ctctgtctcc   6420 ctccattggt aacttctcca gcgtgcagaa gctccttctt gatggcaaca tgttcaccgg   6480
tcggatacct acacagattg ggaggttgca acagctttct aagattgatt ttagtggcaa   6540
caagttctcg ggtcctattg cgcctgagat cagtcagtgt aagctgttaa cttttcctgga   6600 ccttagccgc aatgagctat ctggagacat ccctaatgag ataactggca tgaggatatt   6660
gaattacttg aatctttcta agaatcattt agtgggtagc attccctctt cgatatcatc   6720
tatgcaaagc ttgacttctg ttgattttc atacaacaac ctgtctggtt tggtgcctgg   6780
taccggtcaa ttcagctact tcaactacac gtctttcttg ggaaaccctg acctgtgtgg   6840
cccctatttg ggtgcttgca agggtggggt tgccaatggt gcacaccaac ctcatgttaa   6900
aggactctcc tcttctttga agctgctact tgttgttggg ttgctattat gttccattgc   6960
ttttgctgtg gctgcaatat tcaaggcccg gtcattaaag aaggccagtg aggctcgtgc   7020
atggaagttg actgcgttcc agcgtttgga cttcactgtt gatgatgttt tgcattgctt   7080
gaaagaggat aatattattg ggaaggagg tgctggaatt gtctacaaag gggctatgcc   7140
taatggggat catgttgctg tgaaaaggct tccagctatg agtagaggct cttcccatga   7200
tcacggattc aatgctgaga ttcagacatt ggggcgaatc cgacacaggc acattgttag   7260
gttgttgggt ttctgttcaa atcatgagac aaacctttg gtctatgagt acatgcccaa   7320
tggaagttta ggtgaggttc ttcatggaaa aaggggggt catttgcatt gggacaccag   7380
gtataaaatt gcgtggagg ctgccaaggg gctttgctat ctgcaccatg attgttcgcc   7440
actcattgtc catcgtgatg tgaagtcaaa caacatcctt cttgattcaa atcatgaagc   7500
ccatgttgct gattttggc ttgctaagtt cctgcaagat tctgggacat ctgaatgcat   7560
gtctgctatt gctggttcat atggatacat agctccaggt accgttgaat tttgacataa   7620
ttaatgcatc atatgcatgg ttgtggcaaa tttccttttt ctcgcctaat cataattgta   7680
cgtttaagca ttttgttcag aatttgactc tttgacttat gcatgatatt gaggtgatgc   7740
ccctaaattt attaacattg ctatgtggtt tttcttgact ttggttttct atcataccca   7800
attgattcgc ccccttattt tgttttttt tctaagccaa gtactgaaag taaatggtag   7860
gtatctctgc accgtttgat tttttacccct aacccctct ccccacctat gaagtagata   7920
atgctgtagt cgtaggttaa gagtcattca caatcggaaa ctgatggtta tgggcaaaaa   7980
catcagataa aaagacctat tatgttactt tatacgtatt gcctttgttt aacttattgt   8040
ttcaaattaa agtgtcttgc tttattatag tgtatgatac ctgttggatg tttgattgca   8100
gagtatgcct acacattgaa agttgatgag aaaagcgatg tgtacagttt tggtgtggtt   8160
cttttagaac ttataacagg caggaaacca gttggtgaat ttggtgatgg cgtggacatc   8220
gtgcaatggg tgaggaaaat gacggactct aacaaggaag gagttcttaa agttcttgat   8280
cctaggcttc cctcagttcc ccttcacgaa gtgatgcatg ttttctatgt ggccatgctg   8340
tgtgttgaag aacaggctgt agagagacca acaatgcgtg aagttgttca atactgacc   8400 gagcttccaa agccacctgg ctctaaagag ggagacttaa caataacaga atcctctttg   8460
```

```
tcatcatcaa acgctttaga atctccatcc tcagcctcca aggaagatca aaatcctcct    8520
caatccccac cacccgacct tcttagtatt taaagtgctc tgttgggtgt ttcatcttat    8580 tagttcccttt ggttgtgata gcttatccat ttactttctt tttctgtctc tcttctgggg   8640 ttggggctttt tcttcttctt ctaactgaag gtattaatgc tctgattttt taatggtttt   8700
gtacagtagg attggtgggg ggggttattt tcttatgaag tcactttctt catcatgtag    8760
tactgctttt taattttttat gttacggccg ttgttgtgct tcgcctaagc tggggagtgg   8820
ggagggttca agggaatgga tactctttttt ttatgcgatc actgacaggt agacacaaaa   8880
tgacgcaaac gggttgggta ttaaacagtg ggtatattgt atggtttaga atattattga    8940
tgaatcctga gtggattggc acagtgtgaa ctgtgagcct gagctgtgac tgagtctatg    9000
agtcaggttt ggataaaagc ttatttgaag aagttaacct gtttcgagaa aatcagagtg    9060
aatcaggatt caggcgtgtt ttagctttt                                       9088

<210> SEQ ID NO 36
<211> LENGTH: 3039
<212> TYPE: DNA
<213> ORGANISM: Glycine max

<400> SEQUENCE: 36
atgcccaaaa tgcgtgtcct cttttgttttt ctgtttttcc attttcattt ccctgaaacc      60
ctttctgccc caatctcaga gtaccgcgcc cttctctctc tccgttcagt cattaccgac     120
gccacaccac ccgttctctc ttcttggaac gcctccatcc cttactgttc ctggctcggc     180
gtcacctgcg acaaccgccg ccacgtcacc gccctcaacc tcaccggcct cgacctctcc     240
ggcacgctct ctgccgacgt cgcccacctc ccttttcctct ccaacctctc cctcgccgca    300
aacaaattct ccggccccat tcctccctct ctctccgccc tctccggcct ccgctacctc    360
aacctctcca acaatgtctt caacgaaacc ttccccctcgg agctttggcg cctccagagc    420
ctcgaggtcc tcgacctcta caacaacaac atgaccggcg tgctccctct tgccgtcgcg    480
cagatgcaga atcttcgtca tttgcatctc ggcggcaact tcttctccgg ccagatcccg    540
ccggagtacg gacgctggca gcgcctccag tacctcgccg tctccggcaa cgaactcgac   600
gggactatcc cgccggagat cggaaacttg accagcctcc gggagctcta catcggctac   660
tacaacacct cacccggcgg cattccgccg gagatcggaa acttgtcgga gctggtgagg   720
cttgacgtag cgtactgtgc gttgtccggg gagattccgg cggcgcttgg gaagcttcag   780
aagctggaca cgctgttcct tcaggtgaat gcattgtcag gatcactgac gccggagctg   840
gggaacctga gagcctgaaa tccatggat ttgtctaaca acatgctctc cggtgagatt    900
ccggcgagtt tcggcgagct gaagaatatt acgcttctga atctgttcag gaacaagctt   960
catggagcta taccggagtt tataggagag cttccagcgt tggaagttgt gcaactgtgg  1020
gaaaataact taacaggtag cattcctgag ggtttgggca aaaatgggag actcaacctt  1080
gttgatcttt cttctaacaa gttaaccggg acttttgcctc cttatctctg ttctgggaat  1140
actcttcaga ctctgataac tcttgggaat tttcttttcg gtccaattcc tgagtcgctc   1200
gggacttgtg aatctcttac acggattaga atgggagaaa acttttttgaa tggttccatt  1260 cctaaagggc tttttggact tcccaaactc acccaggttg aacttcagga taattatctc  1320
tctggagagt ttcctgaggt tggttctgtt gcggttaatc ttggtcagat tactctctct  1380
aacaaccagc tttctggggc tctgtctccc tccattggta acttctccag cgtgcagaag  1440
```

```
ctccttcttg atggcaacat gttcaccggt cggatacctc cacagattgg gaggttgcaa    1500
cagctttcta agattgattt tagtggcaac aagttctcgg gtcctattgc gcctgagatc    1560
agtcagtgta agctgttaac tttcctggac cttagccgca atgagctatc tggagacatc    1620
cctaatgaga taactggcat gaggatattg aattacttga atctttctaa gaatcattta    1680
gtgggtagca ttccctcttc gatatcatct atgcaaagct tgacttctgt tgatttttca    1740
tacaacaacc tgtctggttt ggtgcctggt accggtcaat tcagctactt caactacacg    1800
tctttcttgg gaaaccctga cctgtgtggc cctatttgg gtgcttgcaa gggtggggtt    1860
gccaatggtg cacaccaacc tcatgttaaa ggactctcct cttctttgaa gctgctactt    1920
gttgttgggt tgctattatg ttccattgct tttgctgtgg ctgcaatatt caaggcccgg    1980
tcattaaaga aggccagtga ggctcgtgca tggaagttga ctgcgttcca gcgtttggac    2040
ttcactgttg atgatgtttt gcattgcttg aaagaggata atattattgg gaaaggaggt    2100
gctggaattg tctacaaagg ggctatgcct aatgggatc atgttgctgt gaaaaggctt    2160
ccagctatga gtagaggctc ttcccatgat cacggattca atgctgagat tcagacattg    2220
gggcgaatcc gacacaggca cattgttagg ttgttgggtt tctgttcaaa tcatgagaca    2280
aaccttttgg tctatgagta catgcccaat ggaagtttag gtgaggttct tcatggaaaa    2340
aagggggtc atttgcattg gacaccagg tataaaattg cggtggaggc tgccaagggg    2400
cttttgctatc tgcaccatga ttgttcgcca ctcattgtcc atcgtgatgt gaagtcaaac    2460
aacatccttc ttgattcaaa tcatgaagcc catgttgctg attttgggct tgctaagttc    2520
ctgcaagatt ctgggacatc tgaatgcatg tctgctattg ctggttcata tggatacata    2580
gctccagagt atgcctacac attgaaagtt gatgagaaaa gcgatgtgta cagttttggt    2640
gtggttcttt tagaacttat aacaggcagg aaaccagttg gtgaatttgg tgatggcgtg    2700
gacatcgtgc aatgggtgag gaaaatgacg gactctaaca aggaaggagt tcttaaagtt    2760
cttgatccta ggcttccctc agttccccctt cacgaagtga tgcatgtttt ctatgtggcc    2820
atgctgtgtg ttgaagaaca ggctgtagag agaccaacaa tgcgtgaagt tgttcaaata    2880
ctgaccgagc ttccaaagcc acctggctct aaagagggag acttaacaat aacagaatcc    2940
tctttgtcat catcaaacgc tttagaatct ccatcctcag cctccaagga agatcaaaat    3000
cctcctcaat ccccaccacc cgaccttctt agtatttaa                          3039
```

<210> SEQ ID NO 37
<211> LENGTH: 1012
<212> TYPE: PRT
<213> ORGANISM: Glycine max

<400> SEQUENCE: 37

```
Met Pro Lys Met Arg Val Leu Phe Val Phe Leu Phe Phe His Phe His
1               5                   10                  15

Phe Pro Glu Thr Leu Ser Ala Pro Ile Ser Glu Tyr Arg Ala Leu Leu
            20                  25                  30

Ser Leu Arg Ser Val Ile Thr Asp Ala Thr Pro Val Leu Ser Ser
        35                  40                  45

Trp Asn Ala Ser Ile Pro Tyr Cys Ser Trp Leu Gly Val Thr Cys Asp
    50                  55                  60

Asn Arg Arg His Val Thr Ala Leu Asn Leu Thr Gly Leu Asp Leu Ser
65                  70                  75                  80

Gly Thr Leu Ser Ala Asp Val Ala His Leu Pro Phe Leu Ser Asn Leu
                85                  90                  95
```

-continued

```
Ser Leu Ala Ala Asn Lys Phe Ser Gly Pro Ile Pro Pro Ser Leu Ser
            100                 105                 110

Ala Leu Ser Gly Leu Arg Tyr Leu Asn Leu Ser Asn Val Phe Asn
        115                 120                 125

Glu Thr Phe Pro Ser Glu Leu Trp Arg Leu Gln Ser Leu Glu Val Leu
    130                 135                 140

Asp Leu Tyr Asn Asn Asn Met Thr Gly Val Leu Pro Leu Ala Val Ala
145                 150                 155                 160

Gln Met Gln Asn Leu Arg His Leu His Leu Gly Gly Asn Phe Phe Ser
                165                 170                 175

Gly Gln Ile Pro Pro Glu Tyr Gly Arg Trp Gln Arg Leu Gln Tyr Leu
            180                 185                 190

Ala Val Ser Gly Asn Glu Leu Asp Gly Thr Ile Pro Pro Glu Ile Gly
        195                 200                 205

Asn Leu Thr Ser Leu Arg Glu Leu Tyr Ile Gly Tyr Tyr Asn Thr Tyr
    210                 215                 220

Thr Gly Gly Ile Pro Pro Glu Ile Gly Asn Leu Ser Glu Leu Val Arg
225                 230                 235                 240

Leu Asp Val Ala Tyr Cys Ala Leu Ser Gly Glu Ile Pro Ala Ala Leu
                245                 250                 255

Gly Lys Leu Gln Lys Leu Asp Thr Leu Phe Leu Gln Val Asn Ala Leu
            260                 265                 270

Ser Gly Ser Leu Thr Pro Glu Leu Gly Asn Leu Lys Ser Leu Lys Ser
        275                 280                 285

Met Asp Leu Ser Asn Asn Met Leu Ser Gly Glu Ile Pro Ala Ser Phe
    290                 295                 300

Gly Glu Leu Lys Asn Ile Thr Leu Leu Asn Leu Phe Arg Asn Lys Leu
305                 310                 315                 320

His Gly Ala Ile Pro Glu Phe Ile Gly Glu Leu Pro Ala Leu Glu Val
                325                 330                 335

Val Gln Leu Trp Glu Asn Asn Leu Thr Gly Ser Ile Pro Glu Gly Leu
            340                 345                 350

Gly Lys Asn Gly Arg Leu Asn Leu Val Asp Leu Ser Ser Asn Lys Leu
        355                 360                 365

Thr Gly Thr Leu Pro Pro Tyr Leu Cys Ser Gly Asn Thr Leu Gln Thr
    370                 375                 380

Leu Ile Thr Leu Gly Asn Phe Leu Phe Gly Pro Ile Pro Glu Ser Leu
385                 390                 395                 400

Gly Thr Cys Glu Ser Leu Thr Arg Ile Arg Met Gly Glu Asn Phe Leu
                405                 410                 415

Asn Gly Ser Ile Pro Lys Gly Leu Phe Gly Leu Pro Lys Leu Thr Gln
            420                 425                 430

Val Glu Leu Gln Asp Asn Tyr Leu Ser Gly Glu Phe Pro Glu Val Gly
        435                 440                 445

Ser Val Ala Val Asn Leu Gly Gln Ile Thr Leu Ser Asn Asn Gln Leu
    450                 455                 460

Ser Gly Ala Leu Ser Pro Ser Ile Gly Asn Phe Ser Ser Val Gln Lys
465                 470                 475                 480

Leu Leu Leu Asp Gly Asn Met Phe Thr Gly Arg Ile Pro Thr Gln Ile
                485                 490                 495

Gly Arg Leu Gln Gln Leu Ser Lys Ile Asp Phe Ser Gly Asn Lys Phe
            500                 505                 510
```

```
Ser Gly Pro Ile Ala Pro Glu Ile Ser Gln Cys Lys Leu Leu Thr Phe
    515                 520                 525

Leu Asp Leu Ser Arg Asn Glu Leu Ser Gly Asp Ile Pro Asn Glu Ile
530                 535                 540

Thr Gly Met Arg Ile Leu Asn Tyr Leu Asn Leu Ser Lys Asn His Leu
545                 550                 555                 560

Val Gly Ser Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
    595                 600                 605

Cys Gly Pro Tyr Leu Gly Ala Cys Lys Gly Val Ala Asn Gly Ala
    610                 615                 620

His Gln Pro His Val Lys Gly Leu Ser Ser Ser Leu Lys Leu Leu Leu
625                 630                 635                 640

Val Val Gly Leu Leu Cys Ser Ile Ala Phe Ala Val Ala Ala Ile
                645                 650                 655

Phe Lys Ala Arg Ser Leu Lys Lys Ala Ser Glu Ala Arg Ala Trp Lys
                660                 665                 670

Leu Thr Ala Phe Gln Arg Leu Asp Phe Thr Val Asp Asp Val Leu His
            675                 680                 685

Cys Leu Lys Glu Asp Asn Ile Ile Gly Lys Gly Gly Ala Gly Ile Val
    690                 695                 700

Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
    755                 760                 765

Pro Asn Gly Ser Leu Gly Glu Val Leu His Gly Lys Lys Gly Gly His
    770                 775                 780

Leu His Trp Asp Thr Arg Tyr Lys Ile Ala Val Glu Ala Ala Lys Gly
785                 790                 795                 800

Leu Cys Tyr Leu His His Asp Cys Ser Pro Leu Ile Val His Arg Asp
                805                 810                 815

Val Lys Ser Asn Asn Ile Leu Leu Asp Ser Asn His Glu Ala His Val
                820                 825                 830

Ala Asp Phe Gly Leu Ala Lys Phe Leu Gln Asp Ser Gly Thr Ser Glu
            835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Ile Thr Gly Arg Lys Pro Val Gly Glu Phe
                885                 890                 895

Gly Asp Gly Val Asp Ile Val Gln Trp Val Arg Lys Met Thr Asp Ser
                900                 905                 910

Asn Lys Glu Gly Val Leu Lys Val Leu Asp Pro Arg Leu Pro Ser Val
            915                 920                 925

Pro Leu His Glu Val Met His Val Phe Tyr Val Ala Met Leu Cys Val
```

```
                    930             935             940
Glu Glu Gln Ala Val Glu Arg Pro Thr Met Arg Glu Val Val Gln Ile
945             950             955             960

Leu Thr Glu Leu Pro Lys Pro Pro Gly Ser Lys Glu Gly Asp Leu Thr
                965             970             975

Ile Thr Glu Ser Ser Leu Ser Ser Ser Asn Ala Leu Glu Ser Pro Ser
            980             985             990

Ser Ala Ser Lys Glu Asp Gln Asn  Pro Pro Gln Ser Pro  Pro Pro Asp
        995             1000            1005

Leu Leu  Ser Ile
    1010

<210> SEQ ID NO 38
<211> LENGTH: 4268
<212> TYPE: DNA
<213> ORGANISM: Glycine max

<400> SEQUENCE: 38
```

| | | | | | |
|---|---|---|---|---|---|
| cacgtggtac | acgaacaccg | acgccatcag | aatccaaaag | ggtatcagga | atcacaatca | 60 |
| aaaacgaatt | ttgttctagt | ttttatatcc | ttaaaaaatt | cgaaaccaga | gagagaaaaa | 120 |
| aaatggttgg | gttttttttac | tcttgtcggg | tgagagctat | aagagggtgt | ggaggaagat | 180 |
| gaggagaaga | tcgagggcgg | tgatgggatg | gcggtggagg | atcacagcag | agaaatagtt | 240 |
| tgccattgcc | atggagggag | agcgaagagg | ttgaggccca | ttcaattgaa | ttggatcaga | 300 |
| gagagttaac | tgaagaatcg | gtcactgaga | aaagggcgcg | tagcttagca | tttgatatgt | 360 |
| ggcgatttgg | tttgggtacg | tcctttcggg | gacagaagaa | gatggatcaa | agacgcttaa | 420 |
| tgcggttggg | acctgagaat | gaatgagaga | gacactcact | acactcacaa | aaggaggttc | 480 |
| aatttatcaa | ataaaaaaga | gagacacagg | ggatggatgt | gtcatgtgtg | tgtccatgtg | 540 |
| tggtgagctc | catcatatag | agaatctttt | caccttaatt | atttttttaag | gctattctta | 600 |
| atcagtaatc | ttagacattg | attaaaaaat | taaaagaaa | atataaaata | agttgtagag | 660 |
| cactataatt | taatatttta | atataaaaag | tatttagaag | aatgataaat | atatctagct | 720 |
| ttcttaatat | ataaaattaa | tataaattag | tataatatca | caaatatttt | attaaaccaa | 780 |
| acaattaaca | ttttaaaaat | tttatatttg | attttttactg | tgtctaaaat | ttttttgggtc | 840 |
| gctgataacc | acaaattaca | aacaaaatta | atctcccatt | gaattaaaaa | ataacataat | 900 |
| ctataaccta | tcaaaaagaa | aagaaaaaa | gaatctggac | ctatttctac | cccgatgcac | 960 |
| atgagaaact | taaaagggg | gtgaagtgtt | atgtagtata | gagagaaagc | gagggaaggc | 1020 |
| aaagcaagca | aacagaaca | aagccacttt | atttttttga | tctaacctaa | accatccttt | 1080 |
| ccccctgttg | cactctcact | ttatcaacgt | gacacaagca | acttatgacc | aatgtgtaag | 1140 |
| atgttgttcc | tctttcccctt | ctcttctgtc | catttcatca | agtttccatt | ctaatctcca | 1200 |
| aatctttgcc | accccagttc | ctctttttgct | tcaaacttct | cttcccctcc | ctaaaaattg | 1260 |
| caccttttact | ctcatggtga | tgggacacac | cacacccctc | acactcctct | gtatgattct | 1320 |
| tcttttttgca | acccctttctc | tctcaattga | tgttcaccca | caagacagaa | tctcactctc | 1380 |
| actgttcagg | tcatctctgc | caaaccccaa | ccagagtttg | cccagctggg | taggctccaa | 1440 |
| ctgcacttca | tggagtggaa | tcacctgcga | cagcagaact | gggagagtgc | tttccatcaa | 1500 |
| cctaactagc | atgaaccttt | caggcaaaat | ccacccccagt | ttgtgccacc | tttcatacct | 1560 |
| caacaagttg | gggttgtcac | acaacaactt | cacagcccca | cttcctgagt | gtttttggaaa | 1620 |

```
cttgcttaac ctaagagcca ttgatctcag ccacaacagg tttcatggtg gaataccaga    1680
ctctttcatg aggctcaggc acctcactga gcttgttttc agtgggaacc ctggtttggg    1740
gggtccactt cctgcttgga ttggtaactt ctctgcaaat ctggaaaagt tacatcttgg    1800
tttctgttca ttcagtggtg gcatacctga gagcttgctt tacatgaagt ccctcaagta    1860
tttggacctt gagaacaatc tcttgtttgg taatttggtt gattttcaac agcctttggt    1920
tttgctcaat cttgcttcca atcagttttgc tggtactttg ccttgctttg cagcttcagt    1980
tcagtctcta actgtgttga atttgtccaa caattctatt gcgggggat tgcctgcttg    2040
tattgcttct tttcaagctt tgactcattt gaacctttca gggaaccatt tgaagtatag    2100
aatatatcct aggcttgtgt ctcagagaa acttcttgtt ttggacttga gtaataatgc    2160
tttatctggt cctattccca gtaaaattgc tgagactact gacaaacttg gccttgttct    2220
tcttgacctt tctcacaatc agttctctgg tgaaatacct gtgaaaatta ctgagttgaa    2280
aagcttgcag gccttgtttc tctctcacaa tcttctctca ggagaaattc ctgctagaat    2340
tggaaatttg acttatctgc aggtcattga tctctcacac aactctttgt ctggaaccat    2400
tccattcagt attgttgggt gctttcagct gtatgctctg atacttaaca acaacaatct    2460
ttctggtgta attcaaccgg agtttgatgc gttggatatc ttgaggatac tggatataag    2520
caacaacagg ttttccgggg ctatcccact cactttggct ggatgcaaat ctttggagat    2580
tgtagacttt agttccaatg agctttctgg atcgttgaat gatgcaataa ccaaatggac    2640
aaacctcagg tatttgtctc ttgctcagaa caagttcagt gaaaatctgc ctagttggtt    2700
gttcacattt aacgcaatag aaatgatgga tttctcgcat aacaagttta ctggcttcat    2760
accggatatt aattttaagg gtagcttaat atttaacact aggaatgtca ctgttaaaga    2820
gccattggtt gcagcaagaa aggttcaact cagagtttcg gcggttgttt ctgatagcaa    2880
tcaactcagt ttcacttatg atctttcctc aatggttgga attgatctat ccagcaactc    2940
gcttcatggg gaaattccaa ggggcttatt tggtctatct ggcctagaat atctgaattt    3000
gtcatgcaac tttctttacg gacagcttcc ggggttgcag aaaatgcaga gtttgaaagc    3060
cttggatttg tcacataatt ccttgtcagg acatatccca ggaaacatct ctatccttca    3120
agatctgtct attttgaatc tttcctacaa ctgcttttct ggatgtgttc cccagaagca    3180
agggtatggg agatttcctg gtgcatttgc tggaaatcca gatctgtgca tggaatcttc    3240
cagtggatta tgtgatgatg aaggactca atctgcgcaa ggaagtactt ttagggaaga    3300
taggatggat gacccaattt ctgtggggat tttctttatc agtgcatttg ttagttttga    3360
ttttggtgtt gtggttctct tctgttccgc acgggcaaga aattacattc tccaaacaaa    3420
agtttgattt tgatgcttgtg acacatacaa atctcctgta aattccattt tgtaatgtgg    3480
tacctgtctt ctcagtttca agtaaacata cacttacgtg actgggaata ctatctggcc    3540
atcagcttca caagtgtttt ctcgtgatta ctgaacaagt gtctcggaat tgcaggatca    3600
aaatgccatg atatgagtaa cacaaggttt aagaacact cataacgctg gctttaacta    3660
tctgagtgaa gactagtcct gcatcattca gccaagaaaa aatggatgg ttatgatgaa    3720
aatttgatcc aagtaaagac gagtccctca tcattctgat ggttgttctc ttttgctgga    3780
acttggttgc atcaagttta ttatgcatca tcacatgcat tattcataat caggtgggtg    3840
aagggtcagc aaggaacatg cctgattgat atctggtcta gttatggtga aattttgatc    3900
ttgggacatc aaattgcaga tttgcaagca tgtttacgtg aagagaactt gtatcattct    3960
agattaaccc agctcttct tgaggtgggg aaccaagttt tccctgtaag tgtttacct    4020
```

```
taagaatgtg agttgatgag tagtggggag tggtaagtgc agacaaaata aatggagtag    4080
ttctcataaa tctaagattt gtatttgtat tactgtcttc atgccttcat cttagtgctg    4140
tgattttaaa tgaaattctc acgaaatctt tcattgaga acagaaaaga ggtaattgag    4200
caccttagct ttgttatcaa atgccaagca tgctcaacaa aaattagaaa aattatctag    4260
tttaccaa                                                             4268

<210> SEQ ID NO 39
<211> LENGTH: 2154
<212> TYPE: DNA
<213> ORGANISM: Glycine max

<400> SEQUENCE: 39
atggtgatgg acacaccac accctcaca ctcctctgta tgattcttct ttttgcaacc      60
ccttctctct caattgatgt tcacccacaa gacagaatct cactctcact gttcaggtca    120
tctctgccaa accccaacca gagtttgccc agctgggtag gctccaactg cacttcatgg    180
agtggaatca cctgcgacag cagaactggg agagtgcttt ccatcaacct aactagcatg    240
aacctttcag gcaaaatcca ccccagtttg tgccacctt catacctcaa caagttgggg    300
ttgtcacaca acaacttcac agccccactt cctgagtgtt ttggaaactt gcttaaccta    360
agagccattg atctcagcca aacaggtttt catggtggaa taccagactc tttcatgagg    420
ctcaggcacc tcactgagct tgttttcagt gggaaccctg gtttgggggg tccacttcct    480
gcttggattg gtaacttctc tgcaaatctg gaaaagttac atcttggttt ctgttcattc    540
agtggtggca tacctgagag cttgctttac atgaagtccc tcaagtattt ggaccttgag    600
aacaatctct gtttggtaa tttggttgat tttcaacagc ctttggtttt gctcaatctt    660
gcttccaatc agtttgctgg tacttgcct tgctttgcag cttcagttca gtctctaact    720
gtgttgaatt tgtccaacaa ttctattgcg ggggattgc ctgcttgtat tgcttcttt    780 caagctttga ctcatttgaa cctttcaggg aaccatttga agtatagaat atatcctagg    840
cttgtgttct cagagaaact tcttgttttg gacttgagta ataatgcttt atctggtcct    900
attcccagta aaattgctga gactactgac aaacttggcc ttgttcttct tgacctttct    960
cacaatcagt tctctggtga aatacctgtg aaaattactg agttgaaaag cttgcaggcc    1020
ttgtttctct ctcacaatct tctctcagga gaaattcctg ctagaattgg aaatttgact    1080
tatctgcagg tcattgatct ctcacacaac tctttgtctg gaaccattcc attcagtatt    1140
gttgggtgct tcagctgta tgctctgata cttaacaaca acaatctttc tggtgtaatt    1200
caaccggagt tgatgcgtt ggatatcttg aggatactgg atataagcaa caacaggttt    1260
tccggggcta tcccactcac tttggctgga tgcaaatctt ggagattgt agactttagt    1320 tccaatgagc tttctggatc gttgaatgat gcaataacca aatggacaaa cctcaggtat    1380
ttgtctcttg ctcagaacaa gttcagtgaa atctgcctta gttggttgtt cacatttaac    1440
gcaatagaaa tgatggattt ctcgcataac aagtttactg gcttcatacc ggatattaat    1500
tttaagggta gcttaatatt taacactagg aatgtcactg ttaaagagcc attggttgca    1560
gcaagaaagg ttcaactcag agtttcggcg gttgttctg atagcaatca actcagtttc    1620
acttatgatc tttcctcaat ggttggaatt gatctatcca gcaactcgct tcatgggaa    1680 attccaaggg gcttatttgg tctatctggc ctagaatatc tgaatttgtc atgcaacttt    1740
ctttacggac agcttccggg gttgcagaaa atgcagagtt tgaaagcctt ggatttgtca    1800
```

-continued

```
cataattcct tgtcaggaca tatcccagga aacatctcta tccttcaaga tctgtctatt    1860
ttgaatcttt cctacaactg cttttctgga tgtgttcccc agaagcaagg gtatgggaga    1920
tttcctggtg catttgctgg aaatccagat ctgtgcatgg aatcttccag tggattatgt    1980
gatgatggaa ggactcaatc tgcgcaagga agtactttta gggaagatag gatggatgac    2040
ccaatttctg tggggatttt ctttatcagt gcatttgtta gttttgattt tggtgttgtg    2100
gttctcttct gttccgcacg ggcaagaaat tacattctcc aaacaaaagt ttga          2154
```

<210> SEQ ID NO 40
<211> LENGTH: 717
<212> TYPE: PRT
<213> ORGANISM: Glycine max

<400> SEQUENCE: 40

```
Met Val Met Gly His Thr Thr Pro Leu Thr Leu Leu Cys Met Ile Leu
1               5                   10                  15

Leu Phe Ala Thr Pro Ser Leu Ser Ile Asp Val His Pro Gln Asp Arg
            20                  25                  30

Ile Ser Leu Ser Leu Phe Arg Ser Ser Leu Pro Asn Pro Asn Gln Ser
        35                  40                  45

Leu Pro Ser Trp Val Gly Ser Asn Cys Thr Ser Trp Ser Gly Ile Thr
    50                  55                  60

Cys Asp Ser Arg Thr Gly Arg Val Leu Ser Ile Asn Leu Thr Ser Met
65                  70                  75                  80

Asn Leu Ser Gly Lys Ile His Pro Ser Leu Cys His Leu Ser Tyr Leu
                85                  90                  95

Asn Lys Leu Gly Leu Ser His Asn Asn Phe Thr Ala Pro Leu Pro Glu
            100                 105                 110

Cys Phe Gly Asn Leu Leu Asn Leu Arg Ala Ile Asp Leu Ser His Asn
        115                 120                 125

Arg Phe His Gly Gly Ile Pro Asp Ser Phe Met Arg Leu Arg His Leu
    130                 135                 140

Thr Glu Leu Val Phe Ser Gly Asn Pro Gly Leu Gly Gly Pro Leu Pro
145                 150                 155                 160

Ala Trp Ile Gly Asn Phe Ser Ala Asn Leu Glu Lys Leu His Leu Gly
                165                 170                 175

Phe Cys Ser Phe Ser Gly Gly Ile Pro Glu Ser Leu Leu Tyr Met Lys
            180                 185                 190

Ser Leu Lys Tyr Leu Asp Leu Glu Asn Asn Leu Leu Phe Gly Asn Leu
        195                 200                 205

Val Asp Phe Gln Gln Pro Leu Val Leu Leu Asn Leu Ala Ser Asn Gln
    210                 215                 220

Phe Ala Gly Thr Leu Pro Cys Phe Ala Ala Ser Val Gln Ser Leu Thr
225                 230                 235                 240

Val Leu Asn Leu Ser Asn Asn Ser Ile Ala Gly Gly Leu Pro Ala Cys
                245                 250                 255

Ile Ala Ser Phe Gln Ala Leu Thr His Leu Asn Leu Ser Gly Asn His
            260                 265                 270

Leu Lys Tyr Arg Ile Tyr Pro Arg Leu Val Phe Ser Glu Lys Leu Leu
        275                 280                 285

Val Leu Asp Leu Ser Asn Asn Ala Leu Ser Gly Pro Ile Pro Ser Lys
    290                 295                 300

Ile Ala Glu Thr Thr Asp Lys Leu Gly Leu Val Leu Leu Asp Leu Ser
305                 310                 315                 320
```

His Asn Gln Phe Ser Gly Glu Ile Pro Val Lys Ile Thr Glu Leu Lys
                325                 330                 335

Ser Leu Gln Ala Leu Phe Leu Ser His Asn Leu Ser Gly Glu Ile
            340                 345                 350

Pro Ala Arg Ile Gly Asn Leu Thr Tyr Leu Gln Val Ile Asp Leu Ser
            355                 360                 365

His Asn Ser Leu Ser Gly Thr Ile Pro Phe Ser Ile Val Gly Cys Phe
            370                 375                 380

Gln Leu Tyr Ala Leu Ile Leu Asn Asn Asn Leu Ser Gly Val Ile
385                 390                 395                 400

Gln Pro Glu Phe Asp Ala Leu Asp Ile Leu Arg Ile Leu Asp Ile Ser
                405                 410                 415

Asn Asn Arg Phe Ser Gly Ala Ile Pro Leu Thr Leu Ala Gly Cys Lys
            420                 425                 430

Ser Leu Glu Ile Val Asp Phe Ser Asn Glu Leu Ser Gly Ser Leu
            435                 440                 445

Asn Asp Ala Ile Thr Lys Trp Thr Asn Leu Arg Tyr Leu Ser Leu Ala
450                 455                 460

Gln Asn Lys Phe Ser Glu Asn Leu Pro Ser Trp Leu Phe Thr Phe Asn
465                 470                 475                 480

Ala Ile Glu Met Met Asp Phe Ser His Asn Lys Phe Thr Gly Phe Ile
                485                 490                 495

Pro Asp Ile Asn Phe Lys Gly Ser Leu Ile Phe Asn Thr Arg Asn Val
            500                 505                 510

Thr Val Lys Glu Pro Leu Val Ala Ala Arg Lys Val Gln Leu Arg Val
            515                 520                 525

Ser Ala Val Val Ser Asp Ser Asn Gln Leu Ser Phe Thr Tyr Asp Leu
530                 535                 540

Ser Ser Met Val Gly Ile Asp Leu Ser Ser Asn Ser Leu His Gly Glu
545                 550                 555                 560

Ile Pro Arg Gly Leu Phe Gly Leu Ser Gly Leu Glu Tyr Leu Asn Leu
                565                 570                 575

Ser Cys Asn Phe Leu Tyr Gly Gln Leu Pro Gly Leu Gln Lys Met Gln
            580                 585                 590

Ser Leu Lys Ala Leu Asp Leu Ser His Asn Ser Leu Ser Gly His Ile
            595                 600                 605

Pro Gly Asn Ile Ser Ile Leu Gln Asp Leu Ser Ile Leu Asn Leu Ser
            610                 615                 620

Tyr Asn Cys Phe Ser Gly Cys Val Pro Gln Lys Gln Gly Tyr Gly Arg
625                 630                 635                 640

Phe Pro Gly Ala Phe Ala Gly Asn Pro Asp Leu Cys Met Glu Ser Ser
                645                 650                 655

Ser Gly Leu Cys Asp Asp Gly Arg Thr Gln Ser Ala Gln Gly Ser Thr
            660                 665                 670

Phe Arg Glu Asp Arg Met Asp Pro Ile Ser Val Gly Ile Phe Phe
            675                 680                 685

Ile Ser Ala Phe Val Ser Phe Asp Phe Gly Val Val Leu Phe Cys
            690                 695                 700

Ser Ala Arg Ala Arg Asn Tyr Ile Leu Gln Thr Lys Val
705                 710                 715

<210> SEQ ID NO 41
<211> LENGTH: 8656

```
<212> TYPE: DNA
<213> ORGANISM: Glycine max

<400> SEQUENCE: 41
gcacccactg ggtaagttgg taactactat gtatctatat atcgtcaggt cattgtctgt      60
ttcattctct tctcacaaga acaaaatggt aatttacatt taacttagaa atgtttggga     120
cagaacctct agcttgcgat gattctcttc tcacaagaac aaaatggtaa tttacattta     180
actttagaaa tgtttgggac cgaacctcta gcttgcgatg attctcttct cacaagaaca     240
aaatggtaat ttacatttaa ctttagaaat gtttgggacc gaaccactag cttgcgatga     300
ttcccttctc acaagaacaa aatggtaatt tacatttaac ttagaaatgt tgggacaga      360
accactggct tgcgatgatt ctcttctcac aagaacaaaa tggtaatttg catttaactt     420
agaaatgatt gggacagaac cactagcttc gatgaataat ttgctttaat ttttattaat     480
gcataatacc cttttattgt cacacataga atccgattct gcaataacta gtgcttgatc     540
ctaattgaca gaacaaatta aaacagagaa ttgatgcttt ggcttttcca tgggcaataa     600
ttatcccaat gatatactaa agcatagtaa ctaggaagac ttccatgtaa agaaactttc     660
ttttattctc cttttaaaat ttggtgaatc acttaaaacc acttttgttt cattccaagg     720
ttaggctcat ggaaagctta aacctactta actggtcacg aagagattgc atctttgttt     780
tcacaaaagt ctaactccaa gttcgtgtag ctagtattgc atgctaccat ggtgcaagtg     840
atgtacatgc atatatgata ttcaatttaa tttgctacta atatataaag gtgtatatat     900
aaatagagag tgcatgaggt gtgtggtgtc aacatataag gacgcagcaa aggtataata     960
gcgactactg cgaagcaaga tcagagacta gagagacatg ataagaagtt gttaatttgt    1020
tttcttcata tggctgcgcg tggcaacgtg ctcttcgttc actgacatgg atgcgctgct    1080
gaagctgaag gactccatga ctggaagttt tccacgtcgc tttctgcaca ctgtttcttt    1140
tcaggcgtaa actgcgacca agaacttcga gtcgttgcta tcaatgtctc gtttgttcct    1200
cttttcggct accttccgcc ggagatcgga caattggaca aactcgagaa cctcacttcc    1260
ctcaagctcc tcgacatctc tcacaacgtc ttctccggcc aaattattct tccgatgacg    1320
aaactggagg tcctcgacgt ctacgacaac aacttccggc agcataccgg agatttactc    1380
ggagtttaag agcttggagt ttttaagctt aagcaccaat aacttatcgg ggaagattcc    1440
gaagagtttg tctaagttga agacgctgag gtatctcaaa ctcggataca acaacgctta    1500
cgaaggtgaa attccaccgg agtttggcag cataaaatct gagataccttt gacctcatcg    1560
gcgagattcc acctactcta aacaataata agaaaaactt atcacatttc ttgaaacttt    1620
aaaagaccga taaaaataaa aggaggaaat gccactacaa tatttttaat ttatttttt     1680
tacttatttt atttgaatct ttaatacata tgctatttta gcattataaa aatacctggg    1740
ctatacaaaa tatacttgct agtagtatta tgtgtgtgtg aaagttaaat gagtctttaa    1800
gtatttgtaa atgtttaata agtttcgagg tttatcttga ttccaacaat gaattcctga    1860
aatctaattt atctaacttt tttttaacca aaatgttaaa tggtctagtt aagagaacaa    1920
atccttatgt gttcattttt tcacaagacc taaaatctaa aatttcactt taaaagaaac    1980
aaaatacttg ctacttgaac taacaatcat tagtacattt tttagtaat gatatacaaa     2040
catctaaaac tcctatacaa cacaacacat agaagacaat aaaaaatatc aatatgataa    2100
ataaaaatga gaaatagatg aattatttaa aataatgaaa tgtttatttta tcattacttt   2160
tttttacttt aacagttcat acatctccta caaggtaaga tgtgtaatgc aagtaagttg    2220
```

```
caacatggtt ttaaattttg acaataagaa ccatgcatgt taattagtct aatcacagag    2280
cgttcgggat acgccattag tggtctatag tagtcaactg ccgggataaa tcacgatcca    2340
catttcatag gtgtttccac catgtcaaca tcgaactaaa aggaaaaata tgtgaatggg    2400
taaaaatgat taaaaatatt tgtaaaaaat tatttgaatt tatttaaaac aatatgcaag    2460
ttgtttatag gttgagtata tttcaatggt ttttgaaaaa tctatgtaaa taaaaaaaat    2520
acaattattt atataaaata aaataatctt ttttttatta ttatgacatt gatgagagta    2580
tctaataatt tgacccataa ctaatttgga taaaaaaaaa tctgattgac cacttttaat    2640
ttaatgtatc actaaactaa ataccctttt ttaaaatagt ctaaacatga attaaatatt    2700
caaaagaaat attttacttg agattattac ctaatattaa tgataatttc attcaactcc    2760
aataaaatta attttcatgt aagatatatc taaaagaaaa gatatatata aattttattt    2820
tcactagtaa aaaaaagttg atctagttag tgaaaaacca actcatatcc tataagaata    2880
tgaatttgat ttttttttgtt aaggtgagaa ttttattgat caataattta taaatatcta    2940
tataaataat ctttagcctt atgagtcctt aggtcaattc aactcaccta aatttttat     3000 tatgaaaaaa aaaattgtat cttcacaaga taaatgtgtt ggattcaatc actccttatt    3060
agcttaatta gattataatt gtagtcccct atatatatat atgtatcatc ttgtcaaata    3120
ataatgaaat atagaatta tttagactta gagaataaaa ttaaaaactg tctgccatga     3180
aaaaagacga agttaagaaa agggccaatc atagaagatt tttatgggca cttcacggac    3240
actaactcac tgtcacaatc atcactgggg ttgacaaaag gacaatatga aacacttttg    3300
agaagcatgt accactcatc catttatcag tggctcccaa ttcccagagg ccagaactat    3360
atatgaaaga attgttgaac gcacgggcat gaacccattc ttgaagcatc attgtgtgag    3420
aatatcttga ccttgtaaga tgcaacacct ttttaagcct taaatttaaa aaaggaaaaa    3480
agaaaaatct tgtctctact ttcttttagc acaagtgtat agaaattctt aaatatatac    3540
actctccttt atattgtagt atcagtggcg caaatcatta tatttcattt ttaataataa    3600
aattaagagc attaattta tagttaaaat tgaaaataaa gataatttac agaactcatt     3660
tgacttaaac tgacaaaata tatatatata tatatatata tatatatata tatattgtga    3720
gatgaacatg ttactttttt aacatgcaaa aaggagaata tattttacat gcatgcaccc    3780
atgataactt ctatgtatat atccatacaa tacatcgttc gtatatcgtc tcgtttgtct    3840
ttattctcct ctcaaaatac gacaatagca atttacattt ttttttataa gcaaatagta    3900
atttacattt aacttagtaa tgtagggatc gaacataacc acttgcgatg aataatttgc    3960
tttaaatttt tgttgatgcg tacccttttaa ctgtcactca tggaatacga ttcttcaata    4020
tctagtgctt gatcgttgac agaacaactt aaaacagaga attgatgttt tggcttttcc    4080
atggataata attatcccag tgacatacca aagcatagta gctaagaaga ctttcacgta    4140
aaaaaaagtt tcttttattc cctttttttaa tttggtgaat cacaaaaaac cacttttgtt    4200
tggttccaaa gttaggctca tggaaagttt aaacctccat agaatggtca cgaagagatt    4260
gcatctttgt cttcacaaaa gctaactcca cgttgagtag acttaacagc cagtggcgaa    4320
tagcaaggat atttcattaa ttatacgcca ccggccaaat gttaaccaat cgtattataa    4380
ttaagttcca tcatcatcaa acaatttagt aaagtgcatg acccaaattt ctacgataca    4440
tatttattta ttaaaaatgt aagaatattt cagtcatatt taaaaatata tatatcaaga    4500
ataattaact ttgtacacac gcactgaata aaagattgt gacagacaag gcttgcataa     4560
aaatttctcc tctaaactaa ttgcttgtag gacctctccc accactatag aatcaatata    4620
```

```
attaatccgc attagaaagt tatattgtat acaattttct tgaaacataa ttatacttca    4680
tgtttcacag acttatagtg gatcttgtgt ggctagctac tgatgaatat tgtttttttt    4740
ttttcctaag catccacttt gaacaacttt tcccatttca tacaaacaga attaattagt    4800
attgcgtgcc accatatggt acagtgttgt acatgcatat aagctattta atttaataat    4860
atacaaacat aacggtgtat ataaatagag gcagcatgtg gtgtgtggtg taaaaataag    4920
gacgcaggca aatgtatgca tttggcataa gtatataaga gagagggagt agtactactg    4980
caaagcaaaa tcagagagac atgagaagct gtgtgtgcta cacgctatta ttgtttattt    5040
tcttcatatg gctgcgcgtg gcaacgtgct cttcgttcac tgacatggaa tcgcttctga    5100
agctgaagga ctccatgaaa ggagataaag ccaaagacga cgctctccat gactggaagt    5160
ttttcccctc gctttctgca cactgtttct tttcaggcgt aaaatgcgac cgagaacttc    5220
gagtcgttgc tatcaacgtc tcgtttgttc ctctcttcgg tcaccttccg ccggagatcg    5280
gacaattgga caaactcgag aacctcaccg tctcgcagaa caacctcacc ggcgtacttc    5340
ccaaggagct cgccgccctc acttccctca agcacctcaa catctctcac aacgtcttct    5400
ccggccattt ccccggccaa attatccttc cgatgacgaa actggaggtc ctcgacgtct    5460
acgacaacaa cttcaccgga ccgcttcccg tagagttggt gaaactggag aaattaaaat    5520
acctgaagct cgacggaaac tatttctccg gcagcatacc ggagagttac tcggagttta    5580
agagcttgga gttttttaagc ttaagcacca atagcttatc ggggaagatt cccaagagtt    5640
tgtcgaagtt gaagacgctg aggtacctaa aactcggata caacaacgct tacgaaggtg    5700
gaattccacc ggagtttggc agcatgaaat ctctgagata ccttgacctc tctagctgca    5760
acctcagcgg cgagattcca ccgagccttg caaatctgac aaaccttgac acgttgttcc    5820
tgcaaattaa caacctcacc ggaaccattc cgtcggagct ctccgctatg gtgagcctca    5880
tgtcacttga tctctccatc aacgacctca ccggtgagat accgatgagc ttctcacagc    5940
ttagaaacct cactctcatg aacttcttcc aaaacaatct tcgcggctca gttccgtcct    6000
tcgtcggcga gcttccgaat ctggaaacgc tgcagctctg ggataacaac ttctccttcg    6060
tgctacctcc gaaccttggg caaaacggca agttaaagtt cttcgacgtc atcaagaatc    6120
acttcaccgg gttgatccct cgagatttgt gtaagagtgg gaggttacaa acgatcatga    6180
tcacagataa cttcttccgc ggtccaatcc ctaacgagat tggtaactgc aagtctctca    6240
ccaagatccg agcctccaat aactaccttta acggcgtggt tccgtcaggg attttcaaac    6300
taccttctgt cacgataatc gagctggcca ataaccgttt taacggcgaa ctgcctcctg    6360
agatttccgg cgaatccctg ggggattctca ctctttccaa caacttattc agtgggaaaa    6420
ttcccccagc gttgaagaac ttgagggcac tgcagactct ctcacttgac gcaaacgagt    6480
tcgttggaga aataccggga gaggttttttg acctaccgat gctgactgtg gtcaacataa    6540
gcggcaacaa tctaaccgga ccaatcccaa cgacgttgac tcgctgcgtt tcactcaccg    6600
ccgtggacct cagccggaac atgcttgaag ggaagattcc gaagggaatc aaaaacctca    6660
cggacttgag cattttcaat gtgtcgataa accaaatttc agggccagtc cctgaggaga    6720
ttcgcttcat gttgagtctc accacattgg atctatccaa caacaatttc atcggcaagg    6780
tcccaaccgg gggtcagttc gcggtcttca gcgagaaatc ctttgcaggg aaccccaacc    6840
tctgtaccct cccactcttgc ccgaattcct cgttgtaccc tgacgacgcc ttgaagaaga    6900
ggcgcggccc ttggagtttg aaatccacga gggtgatagt catcgtgatt gcactgggca    6960
```

```
cagccgcgct gctggtggcg gtgacggtgt acatgatgag gaggaggaag atgaaccttg    7020
cgaagacgtg gaagctgacg gcgttccagc ggctgaactt caaagccgag gacgtggtgg    7080
agtgtctgaa ggaggagaac ataataggaa aaggaggggc agggatcgtg taccgcgggt    7140
ccatgccaaa cggaacagac gtggcgataa agccggttgg tggggcgggg agtggaagga    7200
acgattacgg attcaaagcg gagatagaaa cgctggggaa gataaggcac aggaacataa    7260
tgaggctttt aggttacgtg tcgaacaagg agacgaactt gctgctgtat gagtacatgc    7320
caaatgggag cttaggggaa tggctgcatg gtgccaaagg agggcacttg aagtgggaaa    7380
tgaggtacaa gattgcggtg gaagctgcta agggactgtg ctatttgcac catgattgtt    7440
cccctcttat cattcacagg gatgtcaagt ctaataatat attgctggat ggggacttgg    7500
aggcccatgt tgctgatttt ggccttgcca agttcttgta cgaccctggc gcctctcagt    7560
ccatgtcctc cattgctggc tcctacggct acattgctcc aggttccatt cattattatt    7620
ttctcttttc cttcttcata atcttaatat accatgcaga taacgtacaa catgcatact    7680
tatacatata attttatcct ttcaacatat aatcaaatat ttcatatcta ataataccaa    7740
cttcatatta taaacatcac ctaatataat caacatgact tgataaataa gacatataag    7800
ttcaatattt aaactcatgt gtctgaaaaa acattaattg gaaaagtcac tcttaaaaat    7860
atttgataat atatcaatat gaccatatga ttccaattac gatcacaaac tctgttaaaa    7920
attcttgctg aagatattag tccttgaata ctaatataag aatatcttgg gttagaaaag    7980
ttactatttt actgttaatt cccgtttact ttagatgggt tggaagttga aaagttgagt    8040
gatttaattt gtttctggtg gttgcgcaga gtatgcatac actttgaaag tggacgagaa    8100
aagtgatgtg tacagctttg gcgttgtgct gctggagctg ataataggga ggaagccagt    8160
gggagagttt ggagacgggg tggacatcgt tggatgggtc aacaaaacga gattggagct    8220
cgctcagccg tcggatgcag cgttggtgtt ggcagtggtg gacccaaggt tgagtgggta    8280
tccattgaca agtgtcattt acatgttcaa catagctatg atgtgtgtta aagaaatggg    8340
gcccgctagg cctaccatga gggaagtcgt tcatatgctc tcagagcctc ctcactctgc    8400
tactcacact cacaacctaa ttaatctcta gttaattaag ttatttgctc atcgatccag    8460
aatcacttct tttcaaaata aattaacaca gacgaaaact gtaggaataa ctttcatctg    8520
ttgtttgtcg gaagtgaaac aacgaatcaa atgtgaacta tgtatcaaat gtaagatagg    8580
ttttaattaa ttttgtaata ttggtgtcaa ctgtcaagta attcgaagga ttttccccat    8640
tgtgcatgta tcaaga                                                    8656
```

<210> SEQ ID NO 42
<211> LENGTH: 2964
<212> TYPE: DNA
<213> ORGANISM: Glycine max

<400> SEQUENCE: 42

```
atgagaagct gtgtgtgcta cacgctatta ttgtttattt tcttcatatg gctgcgcgtg     60
gcaacgtgct cttcgttcac tgacatggaa tcgcttctga agctgaagga ctccatgaaa    120
ggagataaag ccaagacgac cgctctccat gactggaagt ttttcccctc gctttctgca    180
cactgtttct tttcaggcgt aaaatgcgac cgagaacttc gagtcgttgc tatcaacgtc    240
tcgtttgttc ctctcttcgg tcaccttccg ccggagatcg gacaattgga caaactcgag    300
aacctcaccg tctcgcagaa caacctcacc ggcgtacttc ccaaggagct cgccgccctc    360
acttccctca agcacctcaa catctctcac aacgtcttct ccggccattt ccccggccaa    420
```

```
attatccttc cgatgacgaa actggaggtc ctcgacgtct acgacaacaa cttcaccgga    480
ccgcttcccg tagagttggt gaaactggag aaattaaaat acctgaagct cgacggaaac    540
tatttctccg gcagcatacc ggagagttac tcggagttta agagcttgga gttttaagc    600
ttaagcacca atagcttatc ggggaagatt cccaagagtt tgtcgaagtt gaagacgctg    660
aggtacctaa aactcggata caacaacgct tacgaaggtg gaattccacc ggagtttggc    720
agcatgaaat ctctgagata ccttgacctc tctagctgca acctcagcgg cgagattcca    780
ccgagccttg caaatctgac aaaccttgac acgttgttcc tgcaaattaa caacctcacc    840
ggaaccattc cgtcggagct ctccgctatg gtgagcctca tgtcacttga tctctccatc    900
aacgacctca ccggtgagat accgatgagc ttctcacagc ttagaaacct cactctcatg    960
aacttcttcc aaaacaatct tcgcggctca gttccgtcct tcgtcggcga gcttccgaat   1020
ctggaaacgc tgcagctctg ggataacaac ttctccttcg tgctacctcc gaaccttggg   1080
caaaacggca agttaaagtt cttcgacgtc atcaagaatc acttcaccgg gttgatccct   1140
cgagatttgt gtaagagtgg gaggttacaa acgatcatga tcacagataa cttcttccgc   1200
ggtccaatcc ctaacgagat tggtaactgc aagtctctca ccaagatccg agcctccaat   1260
aactaccttaa acggcgtggt tccgtcaggg attttcaaac taccttctgt cacgataatc   1320
gagctggcca ataaccgttt taacggcgaa ctgcctcctg agatttccgg cgaatccctg   1380
gggattctca ctctttccaa caacttattc agtgggaaaa ttcccccagc gttgaagaac   1440
ttgagggcac tgcagactct ctcacttgac gcaaacgagt tcgttggaga ataccgggga   1500
gaggttttg acctaccgat gctgactgtg gtcaacataa gcggcaacaa tctaaccgga   1560
ccaatcccaa cgacgttgac tcgctgcgtt tcactcaccg ccgtggacct cagccggaac   1620
atgcttgaag ggaagattcc gaagggaatc aaaaacctca cggacttgag cattttcaat   1680
gtgtcgataa accaaatttc agggccagtc cctgaggaga ttcgcttcat gttgagtctc   1740
accacattgg atctatccaa caacaatttc atcggcaagg tcccaaccgg gggtcagttc   1800
gcggtcttca gcgagaaatc ctttgcaggg aaccccaacc tctgtacctc ccactcttgc   1860
ccgaattcct cgttgtaccc tgacgacgcc ttgaagaaga ggcgcggccc ttggagtttg   1920
aaatccacga gggtgatagt catcgtgatt gcactgggca cagccgcgct gctggtggcg   1980
gtgacggtgt acatgatgag gaggaggaag atgaaccttg cgaagacgtg gaagctgacg   2040
gcgttccagc ggctgaactt caaagccgag gacgtggtgg agtgtctgaa ggaggagaac   2100
ataataggaa aaggaggggc agggatcgtg taccgcgggt ccatgccaaa cggaacagac   2160
gtggcgataa agcggttggt tggggcgggg agtggaagga acgattacgg attcaaagcg   2220
gagatagaaa cgctggggaa gataaggcac aggaacataa tgaggctttt aggttacgtg   2280
tcgaacaagg agacgaactt gctgctgtat gagtacatgc caaatgggag cttaggggaa   2340
tggctgcatg gtgccaaagg agggcacttg aagtgggaaa tgaggtacaa gattgcggtg   2400
gaagctgcta agggactgtg ctatttgcac catgattgtt cccctcttat cattcacagg   2460
gatgtcaagt ctaataatat attgctggat ggggacttgg aggcccatgt tgctgatttt   2520
ggccttgcca agttcttgta cgaccctggc gcctctcagt ccatgtcctc cattgctggc   2580
tcctacggct acattgctcc agagtatgca tacactttga agtggacga gaaaagtgat   2640
gtgtacagct ttggcgttgt gctgctggag ctgataatag ggaggaagcc agtgggagag   2700
tttggagacg gggtggacat cgttggatgg gtcaacaaaa cgagattgga gctcgctcag   2760
```

```
ccgtcggatg cagcgttggt gttggcagtg gtggacccaa ggttgagtgg gtatccattg   2820
acaagtgtca tttacatgtt caacatagct atgatgtgtg ttaaagaaat ggggcccgct   2880
aggcctacca tgagggaagt cgttcatatg ctctcagagc ctcctcactc tgctactcac   2940
actcacaacc taattaatct ctag                                          2964
```

<210> SEQ ID NO 43
<211> LENGTH: 987
<212> TYPE: PRT
<213> ORGANISM: Glycine max

<400> SEQUENCE: 43

```
Met Arg Ser Cys Val Cys Tyr Thr Leu Leu Leu Phe Ile Phe Phe Ile
1               5                   10                  15

Trp Leu Arg Val Ala Thr Cys Ser Ser Phe Thr Asp Met Glu Ser Leu
            20                  25                  30

Leu Lys Leu Lys Asp Ser Met Lys Gly Asp Lys Ala Lys Asp Asp Ala
        35                  40                  45

Leu His Asp Trp Lys Phe Phe Pro Ser Leu Ser Ala His Cys Phe Phe
    50                  55                  60

Ser Gly Val Lys Cys Asp Arg Glu Leu Arg Val Val Ala Ile Asn Val
65                  70                  75                  80

Ser Phe Val Pro Leu Phe Gly His Leu Pro Pro Glu Ile Gly Gln Leu
                85                  90                  95

Asp Lys Leu Glu Asn Leu Thr Val Ser Gln Asn Asn Leu Thr Gly Val
            100                 105                 110

Leu Pro Lys Glu Leu Ala Ala Leu Thr Ser Leu Lys His Leu Asn Ile
        115                 120                 125

Ser His Asn Val Phe Ser Gly His Phe Pro Gly Gln Ile Ile Leu Pro
    130                 135                 140

Met Thr Lys Leu Glu Val Leu Asp Val Tyr Asp Asn Asn Phe Thr Gly
145                 150                 155                 160

Pro Leu Pro Val Glu Leu Val Lys Leu Glu Lys Leu Lys Tyr Leu Lys
                165                 170                 175

Leu Asp Gly Asn Tyr Phe Ser Gly Ser Ile Pro Glu Ser Tyr Ser Glu
            180                 185                 190

Phe Lys Ser Leu Glu Phe Leu Ser Leu Ser Thr Asn Ser Leu Ser Gly
        195                 200                 205

Lys Ile Pro Lys Ser Leu Ser Lys Leu Lys Thr Leu Arg Tyr Leu Lys
    210                 215                 220

Leu Gly Tyr Asn Asn Ala Tyr Glu Gly Gly Ile Pro Pro Glu Phe Gly
225                 230                 235                 240

Ser Met Lys Ser Leu Arg Tyr Leu Asp Leu Ser Ser Cys Asn Leu Ser
                245                 250                 255

Gly Glu Ile Pro Pro Ser Leu Ala Asn Leu Thr Asn Leu Asp Thr Leu
            260                 265                 270

Phe Leu Gln Ile Asn Asn Leu Thr Gly Thr Ile Pro Ser Glu Leu Ser
        275                 280                 285

Ala Met Val Ser Leu Met Ser Leu Asp Leu Ser Ile Asn Asp Leu Thr
    290                 295                 300

Gly Glu Ile Pro Met Ser Phe Ser Gln Leu Arg Asn Leu Thr Leu Met
305                 310                 315                 320

Asn Phe Phe Gln Asn Asn Leu Arg Gly Ser Val Pro Ser Phe Val Gly
                325                 330                 335
```

```
Glu Leu Pro Asn Leu Glu Thr Leu Gln Leu Trp Asp Asn Asn Phe Ser
                340                 345                 350

Phe Val Leu Pro Pro Asn Leu Gly Gln Asn Gly Lys Leu Lys Phe Phe
            355                 360                 365

Asp Val Ile Lys Asn His Phe Thr Gly Leu Ile Pro Arg Asp Leu Cys
        370                 375                 380

Lys Ser Gly Arg Leu Gln Thr Ile Met Ile Thr Asp Asn Phe Phe Arg
385                 390                 395                 400

Gly Pro Ile Pro Asn Glu Ile Gly Asn Cys Lys Ser Leu Thr Lys Ile
                405                 410                 415

Arg Ala Ser Asn Asn Tyr Leu Asn Gly Val Val Pro Ser Gly Ile Phe
            420                 425                 430

Lys Leu Pro Ser Val Thr Ile Ile Glu Leu Ala Asn Asn Arg Phe Asn
        435                 440                 445

Gly Glu Leu Pro Pro Glu Ile Ser Gly Glu Ser Leu Gly Ile Leu Thr
                450                 455                 460

Leu Ser Asn Asn Leu Phe Ser Gly Lys Ile Pro Pro Ala Leu Lys Asn
465                 470                 475                 480

Leu Arg Ala Leu Gln Thr Leu Ser Leu Asp Ala Asn Glu Phe Val Gly
                485                 490                 495

Glu Ile Pro Gly Glu Val Phe Asp Leu Pro Met Leu Thr Val Val Asn
            500                 505                 510

Ile Ser Gly Asn Asn Leu Thr Gly Pro Ile Pro Thr Thr Leu Thr Arg
        515                 520                 525

Cys Val Ser Leu Thr Ala Val Asp Leu Ser Arg Asn Met Leu Glu Gly
        530                 535                 540

Lys Ile Pro Lys Gly Ile Lys Asn Leu Thr Asp Leu Ser Ile Phe Asn
545                 550                 555                 560

Val Ser Ile Asn Gln Ile Ser Gly Pro Val Pro Glu Glu Ile Arg Phe
                565                 570                 575

Met Leu Ser Leu Thr Thr Leu Asp Leu Ser Asn Asn Asn Phe Ile Gly
            580                 585                 590

Lys Val Pro Thr Gly Gly Gln Phe Ala Val Phe Ser Glu Lys Ser Phe
        595                 600                 605

Ala Gly Asn Pro Asn Leu Cys Thr Ser His Ser Cys Pro Asn Ser Ser
        610                 615                 620

Leu Tyr Pro Asp Asp Ala Leu Lys Lys Arg Arg Gly Pro Trp Ser Leu
625                 630                 635                 640

Lys Ser Thr Arg Val Ile Val Ile Val Ile Ala Leu Gly Thr Ala Ala
                645                 650                 655

Leu Leu Val Ala Val Thr Val Tyr Met Met Arg Arg Arg Lys Met Asn
            660                 665                 670

Leu Ala Lys Thr Trp Lys Leu Thr Ala Phe Gln Arg Leu Asn Phe Lys
        675                 680                 685

Ala Glu Asp Val Val Glu Cys Leu Lys Glu Glu Asn Ile Ile Gly Lys
        690                 695                 700

Gly Gly Ala Gly Ile Val Tyr Arg Gly Ser Met Pro Asn Gly Thr Asp
705                 710                 715                 720

Val Ala Ile Lys Arg Leu Val Gly Ala Gly Ser Gly Arg Asn Asp Tyr
                725                 730                 735

Gly Phe Lys Ala Glu Ile Glu Thr Leu Gly Lys Ile Arg His Arg Asn
            740                 745                 750

Ile Met Arg Leu Leu Gly Tyr Val Ser Asn Lys Glu Thr Asn Leu Leu
```

```
                    755                 760                 765
Leu Tyr Glu Tyr Met Pro Asn Gly Ser Leu Gly Glu Trp Leu His Gly
    770                 775                 780

Ala Lys Gly Gly His Leu Lys Trp Glu Met Arg Tyr Lys Ile Ala Val
785                 790                 795                 800

Glu Ala Ala Lys Gly Leu Cys Tyr Leu His Asp Cys Ser Pro Leu
                805                 810                 815

Ile Ile His Arg Asp Val Lys Ser Asn Asn Ile Leu Leu Asp Gly Asp
            820                 825                 830

Leu Glu Ala His Val Ala Asp Phe Gly Leu Ala Lys Phe Leu Tyr Asp
        835                 840                 845

Pro Gly Ala Ser Gln Ser Met Ser Ser Ile Ala Gly Ser Tyr Gly Tyr
    850                 855                 860

Ile Ala Pro Glu Tyr Ala Tyr Thr Leu Lys Val Asp Glu Lys Ser Asp
865                 870                 875                 880

Val Tyr Ser Phe Gly Val Val Leu Leu Glu Leu Ile Ile Gly Arg Lys
                885                 890                 895

Pro Val Gly Glu Phe Gly Asp Gly Val Asp Ile Val Gly Trp Val Asn
            900                 905                 910

Lys Thr Arg Leu Glu Leu Ala Gln Pro Ser Asp Ala Ala Leu Val Leu
        915                 920                 925

Ala Val Val Asp Pro Arg Leu Ser Gly Tyr Pro Leu Thr Ser Val Ile
    930                 935                 940

Tyr Met Phe Asn Ile Ala Met Met Cys Val Lys Glu Met Gly Pro Ala
945                 950                 955                 960

Arg Pro Thr Met Arg Glu Val Val His Met Leu Ser Glu Pro Pro His
                965                 970                 975

Ser Ala Thr His Thr His Asn Leu Ile Asn Leu
            980                 985

<210> SEQ ID NO 44
<211> LENGTH: 3525
<212> TYPE: DNA
<213> ORGANISM: Glycine max

<400> SEQUENCE: 44
agcttcgcat aagtaacgtg agtttagtta agtcgagcta gtcgcctttt tctatggttg     60
gttatgtgca gtagtgaatg ttgtgtagta tcttgcgagg ccatgtttgg tgtgacaagc    120
ccgaaagtga cttgagggga acaaatagc ttttgtccaa acatgctaac ttgtcatcat     180
gacatctact tctctggtca tggcagctct gattaataat ttaagtgatc ataatattag    240
aagttaaaaa attataacat ctttaattat tttattatt ttatataatc ttaaaaatta    300
tttcaaactt cttaaaacaa tgttgaataa gatcatgtat ttttttttt tccttacgta    360 gtagtatcct ggcagtcacc caggagcaaa tgatgtagat aaatcctttt tactaaaata    420
gtcttggagc aatatttaag aggggaccat tttatgatct tttctatctt aatagtggcg    480
ttagaataac acttttttaa gctttaaata aaaataaaa aatattatc tttactttct     540 tttagcaatt attcctacgt gtagagaaac tgttaaatac actctccttt gtattgtata    600
atgttgcatt gtatcagttg tccaaattaa tcacagtata ttagtaataa aattatgaac    660 attaattta tcttaaaat ttagttaaat attgataatt cacataactc gtgacttaat     720
ctaattatat atagaagatc atgttagtat gttacctttt taaatgcaa aatgaagaat      780 ctgttacatg cacccactgg gtaagttgat aactattatg tatctatata tcgtctggat    840
```

```
attgtctgtt tcattctctt ctcaaaagaa caaaatggta atttacattt aacttagaaa    900
tgtttgggac agaatcacta gcttgcagat gaataatttg ttttaaattc ttattgatgc    960 ataatacccct ctacttgtca ctcatagaat acgattctgc ataactagt gcttgatcct   1020 tgacagaaca aattaaaaca gagaattgat gcattggctt ttccatggac aataattatc   1080
ccattgatgt actaaagcac agtaactagg taggaagacc tccacctaaa gaaactttct   1140
tttattctcc tttaattta aatttggtga atcacttaaa acaactttg tttcattcca    1200 aagttaggct catggaaagc ttaaacctag ttaaatagcc acgaaagaga ttgcatcttt   1260
gttttcacaa aagctaactg cgcgtttgtg aagctagtga tgcatagtat atatatattt   1320
ttttctcggc atccactttg agaactactt ttttttttcat tttcatagaa acagaattga   1380
agtagtataa catgccacca tgaacagtac agtgatgtac atgaataaat gcatgctatt   1440
caatataatg tataatataa cggtgtatat ataaatagag actgcatgag gtgtgtggtg   1500
tcaacatata ataaggacgc agcgtaggta taatagtgag taccgcgaag aaagataaga   1560
gccagagcca tgagaagctg tgtgctttac acgctattat tgtttgtttt ctgcatatgg   1620
gttcccatgg caacgtgctc ttcgttcagt gacatggatg cgttactaaa gctgaaggag   1680
tccatgaaag gagacgaagc caaagacgac gcactccatg actggaagtt ttccacatcg   1740
cattctgcac actgtttctt ttcaggcgta acatgtgacc aagaccttcg agtcgttgct   1800
atcaacgtct cctttgttcc tctcttcggt cacattccgc cggagatcgg aaacttggac   1860
aagctggaaa atctcacaat cgtgaacaac aatctaaccg gtgtactccc catggagctt   1920
gccgccctca cttccctcaa gcacctcaac atatctcaca acctcttcac cggcgatttc   1980
cccggccaag ccactcttcc gatgacgaaa cttcaagtcc tcgacgtcta cgacaacaac   2040
ttcaccggac cgcttccgga agaattcgtg aaactggaga actaaaaata cctgaaactc   2100
gacggaaact attttaccgg cagcataccg gagagttact cggagtttaa gagcttggag   2160 ttttttgagct taaacaccaa cagcttatcg gggaggattc cgaagagttt gtccaagttg   2220
aagactctga ggattctcaa actcggatac agcaacgctt acgaaggtgg aattcctccg   2280
gagttcggca ccatggaatc tctgagattc ctcgacctct caagctgcaa cctcagcggc   2340
gagattccac cgagtcttgc aaatctgaca aacctagaca cgttgttctt gcaaatgaac   2400
ttcctcaccg gaagcattcc gtctgaactc tcttctttgg tgaggctcat ggcactggat   2460
ctctcctgca acagcctcac cggggagatt ccagagagct tttctcagct gagaaacctc   2520
actctcatga acttgttccg caacaatctt cacggcccta ttccgtcctt gctgagcgag   2580
cttcccaatc tgaatacgct gcagctctgg gagaataact tctcctctga gctcccgcag   2640
aacctggggc aaaacgggag gctgaagttc ttcgacgtca cgaagaatca cttcagcggg   2700
ttgatccctc gggatttgtg caagagtggg aggttacaaa tcttcattat cacagataac   2760
ttctttcatg gcccaatccc taacgagatt gctaactgca agtctctaac caagatccga   2820
gcctccaata actaccttaa cggcgcagtt ccgtcgggga ttttcaagct accttccgtc   2880
acgataatcg agttggccaa taccgttttt aacggagaac tgcctcccga aatttccggc   2940
gattcactcg ggattctcac tctttccaac aacttattca ctgggaaaat tcccccagcg   3000
ttgaagaact aagggcact gcagactctg tcacttgaca cgaacgagtt ccttggagaa   3060
atcccggggg aggtttttga cctaccaatg ctgactgtgg tcaacataag cggcaacaat   3120
ctcaccggac caatcccaac gacgtttact cgctgcgttt cactcgccgc cgttgatctc   3180
```

| | |
|---|---|
| agccggaaca tgctagttga ggatattcct aaggggatta agaacctcac ggtcttgagc | 3240 |
| tttttcaatg tctcgagaaa ccatttaaca gggccagtcc ctgacgagat aaaattcatg | 3300 |
| acgagcctca ccacgctgga tctctcctac aacaatttca caggcaaggt ccccaacgag | 3360 |
| ggtcagtttt tggtcttcaa cgacaactcg tttgcaggga accctaacct ctgttccatt | 3420 |
| cacggatgca ctttaagcat tgtgggggca gctgccccta tcaacatttt aacatttgta | 3480 |
| aatatagtat gtacaattat agtaatttat aaattgcttg tataa | 3525 |

<210> SEQ ID NO 45
<211> LENGTH: 1899
<212> TYPE: DNA
<213> ORGANISM: Glycine max

<400> SEQUENCE: 45

| | |
|---|---|
| atggcaacgt gctcttcgtt cagtgacatg gatgcgttac taaagctgaa ggagtccatg | 60 |
| aaaggagacg aagccaaaga cgacgcactc catgactgga gttttccac atcgcattct | 120 |
| gcacactgtt tcttttcagg cgtaacatgt gaccaagacc ttcgagtcgt tgctatcaac | 180 |
| gtctcctttg ttcctctctt cggtcacatt ccgccggaga tcggaaactt ggacaagctg | 240 |
| gaaaatctca aatcgtgaa caacaatcta accggtgtac tccccatgga gcttgccgcc | 300 |
| ctcacttccc tcaagcacct caacatatct cacaacctct tcaccggcga tttccccggc | 360 |
| caagccactc ttccgatgac ggaacttcaa gtcctcgacg tctacgacaa caacttcacc | 420 |
| ggaccgcttc cggaagaatt cgtgaaactg gagaaactaa aatacctgaa actcgacgga | 480 |
| aactatttta ccggcagcat accggagagt tactcggagt ttaagagctt ggagttttg | 540 |
| agcttaaaca ccaacagctt atcggggagg attccgaaga gtttgtccaa gttgaagact | 600 |
| ctgaggattc tcaaactcgg atacagcaac gcttacgaag gtggaattcc tccggagttc | 660 |
| ggcaccatgg aatctctgag attcctcgac ctctcaagct gcaacctcag cggcgagatt | 720 |
| ccaccgagtc ttgcaaatct gacaaaccta gacacgttgt tcttgcaaat gaacttcctc | 780 |
| accggaagca ttccgtctga actctcttct ttggtgaggc tcatggcact ggatctctcc | 840 |
| tgcaacagcc tcaccgggga gattccagag agcttttctc agctgagaaa cctcactctc | 900 |
| atgaacttgt tccgcaacaa tcttcacggc cctattccgt ccttgctgag cgagcttccc | 960 |
| aatctgaata cgctgcagct ctgggagaat aacttctcct ctgagctccc gcagaacctg | 1020 |
| gggcaaaacg ggaggctgaa gttcttcgac gtcacgaaga atcacttcag cgggttgatc | 1080 |
| cctcgggatt tgtgcaagag tgggaggtta caaatcttca ttatcacaga taacttcttt | 1140 |
| catggcccaa tccctaacga gattgctaac tgcaagtctc taaccaagat ccgagcctcc | 1200 |
| aataactacc ttaacggcgc agttccgtcg gggattttca agctaccttc cgtcacgata | 1260 |
| atcgagttgg ccaataaccg ttttaacgga gaactgcctc ccgaaatttc cggcgattca | 1320 |
| ctcgggattc tcactctttc caacaactta ttcactggga aaattccccc agcgttgaag | 1380 |
| aacttaaggg cactgcagac tctgtcactt gacacgaacg agttccttgg agaaatcccg | 1440 |
| ggggaggttt ttgacctacc aatgctgact gtggtcaaca taagcggcaa caatctcacc | 1500 |
| ggaccaatcc caacgacgtt tactcgctgc gtttcactcg ccgccgttga tctcagccgg | 1560 |
| aacatgctag ttgaggatat tcctaagggg attaagaacc tcacggtctt gagcttttc | 1620 |
| aatgtctcga gaaaccattt aacagggcca gtccctgacg agataaaatt catgacgagc | 1680 |
| ctcaccacgc tggatctctc ctacaacaat ttcacaggca aggtccccaa cgagggtcag | 1740 |
| tttttggtct tcaacgacaa ctcgtttgca gggaacccta acctctgttc cattcacgga | 1800 |

```
tgcactttaa gcattgtggg ggcagctgcc cctatcaaca ttttaacatt tgtaaatata   1860
gtatgtacaa ttatagtaat ttataaattg cttgtataa                          1899
```

<210> SEQ ID NO 46
<211> LENGTH: 632
<212> TYPE: PRT
<213> ORGANISM: Glycine max

<400> SEQUENCE: 46

```
Met Ala Thr Cys Ser Ser Phe Ser Asp Met Asp Ala Leu Leu Lys Leu
1               5                   10                  15

Lys Glu Ser Met Lys Gly Asp Glu Ala Lys Asp Ala Leu His Asp
            20                  25                  30

Trp Lys Phe Ser Thr Ser His Ser Ala His Cys Phe Phe Ser Gly Val
        35                  40                  45

Thr Cys Asp Gln Asp Leu Arg Val Val Ala Ile Asn Val Ser Phe Val
    50                  55                  60

Pro Leu Phe Gly His Ile Pro Pro Glu Ile Gly Asn Leu Asp Lys Leu
65                  70                  75                  80

Glu Asn Leu Thr Ile Val Asn Asn Leu Thr Gly Val Leu Pro Met
                85                  90                  95

Glu Leu Ala Ala Leu Thr Ser Leu Lys His Leu Asn Ile Ser His Asn
            100                 105                 110

Leu Phe Thr Gly Asp Phe Pro Gly Gln Ala Thr Leu Pro Met Thr Glu
        115                 120                 125

Leu Gln Val Leu Asp Val Tyr Asp Asn Asn Phe Thr Gly Pro Leu Pro
130                 135                 140

Glu Glu Phe Val Lys Leu Glu Lys Leu Lys Tyr Leu Lys Leu Asp Gly
145                 150                 155                 160

Asn Tyr Phe Thr Gly Ser Ile Pro Glu Ser Tyr Ser Glu Phe Lys Ser
                165                 170                 175

Leu Glu Phe Leu Ser Leu Asn Thr Asn Ser Leu Ser Gly Arg Ile Pro
            180                 185                 190

Lys Ser Leu Ser Lys Leu Lys Thr Leu Arg Ile Leu Lys Leu Gly Tyr
        195                 200                 205

Ser Asn Ala Tyr Glu Gly Gly Ile Pro Pro Glu Phe Gly Thr Met Glu
    210                 215                 220

Ser Leu Arg Phe Leu Asp Leu Ser Ser Cys Asn Leu Ser Gly Glu Ile
225                 230                 235                 240

Pro Pro Ser Leu Ala Asn Leu Thr Asn Leu Asp Thr Leu Phe Leu Gln
                245                 250                 255

Met Asn Phe Leu Thr Gly Ser Ile Pro Ser Glu Leu Ser Ser Leu Val
            260                 265                 270

Arg Leu Met Ala Leu Asp Leu Ser Cys Asn Ser Leu Thr Gly Glu Ile
        275                 280                 285

Pro Glu Ser Phe Ser Gln Leu Arg Asn Leu Thr Leu Met Asn Leu Phe
    290                 295                 300

Arg Asn Asn Leu His Gly Pro Ile Pro Ser Leu Leu Ser Glu Leu Pro
305                 310                 315                 320

Asn Leu Asn Thr Leu Gln Leu Trp Glu Asn Asn Phe Ser Ser Glu Leu
                325                 330                 335

Pro Gln Asn Leu Gly Gln Asn Gly Arg Leu Lys Phe Phe Asp Val Thr
            340                 345                 350
```

Lys Asn His Phe Ser Gly Leu Ile Pro Arg Asp Leu Cys Lys Ser Gly
            355                 360                 365

Arg Leu Gln Ile Phe Ile Ile Thr Asp Asn Phe His Gly Pro Ile
    370                 375                 380

Pro Asn Glu Ile Ala Asn Cys Lys Ser Leu Thr Lys Ile Arg Ala Ser
385                 390                 395                 400

Asn Asn Tyr Leu Asn Gly Ala Val Pro Ser Gly Ile Phe Lys Leu Pro
                405                 410                 415

Ser Val Thr Ile Ile Glu Leu Ala Asn Asn Arg Phe Asn Gly Glu Leu
            420                 425                 430

Pro Pro Glu Ile Ser Gly Asp Ser Leu Gly Ile Leu Thr Leu Ser Asn
        435                 440                 445

Asn Leu Phe Thr Gly Lys Ile Pro Pro Ala Leu Lys Asn Leu Arg Ala
    450                 455                 460

Leu Gln Thr Leu Ser Leu Asp Thr Asn Glu Phe Leu Gly Glu Ile Pro
465                 470                 475                 480

Gly Glu Val Phe Asp Leu Pro Met Leu Thr Val Val Asn Ile Ser Gly
                485                 490                 495

Asn Asn Leu Thr Gly Pro Ile Pro Thr Thr Phe Thr Arg Cys Val Ser
            500                 505                 510

Leu Ala Ala Val Asp Leu Ser Arg Asn Met Leu Val Glu Asp Ile Pro
        515                 520                 525

Lys Gly Ile Lys Asn Leu Thr Val Leu Ser Phe Phe Asn Val Ser Arg
    530                 535                 540

Asn His Leu Thr Gly Pro Val Pro Asp Glu Ile Lys Phe Met Thr Ser
545                 550                 555                 560

Leu Thr Thr Leu Asp Leu Ser Tyr Asn Asn Phe Thr Gly Lys Val Pro
                565                 570                 575

Asn Glu Gly Gln Phe Leu Val Phe Asn Asp Asn Ser Phe Ala Gly Asn
            580                 585                 590

Pro Asn Leu Cys Ser Ile His Gly Cys Thr Leu Ser Ile Val Gly Ala
        595                 600                 605

Ala Ala Pro Ile Asn Ile Leu Thr Phe Val Asn Ile Val Cys Thr Ile
    610                 615                 620

Ile Val Ile Tyr Lys Leu Leu Val
625                 630

<210> SEQ ID NO 47
<211> LENGTH: 5725
<212> TYPE: DNA
<213> ORGANISM: Glycine max

<400> SEQUENCE: 47
gcctgcccct tagtcatgtg caaaatagtg ctaagatctg tattgtaaaa tggccacatt      60
ggtcttagta aaagagttat gcatatgctg cactggtagc acccagcctg cacttcgtaa     120
tatgatgatt gtgtattttt gtttactttt gaggtgaagc tgcgatgcat taggctaggg     180
atttgtgtat gttgtgtaca ttggtttttg tgaaggtgtt gttgtggctg taatttacat     240
ttttgtattt ttgggattac ttggtgggac atgtgctgag gatgccatgt ccctagttct     300
ctaatgttct gatgtattat ttatttatat tgataaaaaa aattatatac tttcaaaggc     360
aaaaagataa agaaaactat caatcacctg ctattttaga ataccccccc tcccaaaaga     420 aaacccaaa ttattgtaat catataaagt ttcggtgttg aaaagacggc gtggggcacc     480
atgttgaagg cttgagaatt ttttggtcaa ttgaatcaaa aagtgaagtg gtccatttga     540

-continued

```
cccccagttt gcaatggtaa attcaagaat tgggtggaag tgtccattgt attttcgta     600 tccaacaata aagaatcaca gttgttgcac agatacaaca atcaaaggtc tagatatttt    660
gtagtcttat aataggaatt ttcactgttt tacacaaaca tttttttatc tacaaaacaa    720
accgtgagga atcttgtagg ttatagtggc caacactcat gttgcgttaa cacagctatc    780
aactaaaact caacttttgt cacgggtgac ctcaacataa ttattgatat tactgacaga    840
gtaacaacac ctgaagtggg ccctgttgaa ctgggttatg actaatgacg agaccacaac    900
ttagaggata gatacatttc taatctttca aataaataca agtgatatta acttggtctt    960
tgaaaaatat gaacatcaat tctgttttt aattataaaa acaatagtaa tttgatttga    1020
tttactgaaa aaattagcgt caatttaaaa tttcagtatt aaaaaatgat acgatttacc    1080
atcttaagta ttgcacgcaa aagattattt taatatcatt tttcaattat taagagaaaa    1140
aaagtgacgt taatatctta ggacaaaatt aatatctctg gcattttaag aaaataaaga    1200
gaatacttat aaaataagac cacaattcac gaaatcttat attaaatatg gtcctgataa    1260
ttccaatttg tataaactta ttaaaataat acttataggg aaaaaataga gaggcaaata    1320
aattaaaatc aaattatgta ttttactttt tggagaattt aaataagaga atttcttaaa    1380
acttgagtta gataagttga ttttaatttg tgggagattc ttttttatta tatgtcttta    1440 ttttttctc agtattttt tttttggaa aattttacct aaactgaaat taagcattgt    1500
ggagaatact ttcagggaaa atgactcaat gatttagcgt gtgatttaag cataaatttt    1560
ggtacaagag tttgattaac tattaattaa attaatttag aaaggtcaag gtcattttca    1620
cacaattcta ttcccttgct cgagaccact tttcaagtat aaatttatga ctaatgggtc    1680
aaaacataca atgccttgtg taaatagtta tgaacgatat taatatttt atgaaaatga    1740 tagttgcacc aaatatgtga aattcgcaat ctgaattatc tgttgcattt ggcttggttt    1800 catttgtta ggttattatt attatttttt tttaaaaagg aactgactgt atccaattat    1860
atgtctgttt ttaaaattg aaagaaatag ttttaaacca tttaatatag ctataatata    1920
tatttaagtt aatcttagct atatattttg tattaaaatg tatatttgct ataataatta    1980
actctagtaa tttaccaaat ggatattatt tgtaaaggct tgatttgggt tatactagta    2040
atttaaaatc tacgtactta ctatttctga tttcaaaatg tctcatgcca caaatgaaca    2100
aaacaatcat gataatttat tcatactatt attgcttgct cattcactca ccccacagtg    2160
ctagatcctc ggactcgaat aaatcattta ttatgcttag ataattcgat ttatttttat    2220
tcaatgcaac actcattcaa ttgcactacc ctcctattcc tatatcacat taatatgaag    2280
agttaatctt atcctctcga ttcatttct ttttaaattt aagggtata atgagaaatt    2340 aattttgact attaaatttt aaaacaatc caaaaatgtc ataagaatt tttcctattc    2400 cacgagagaa cttgaaagtt aaaatttgat taaaatctta ttaaaggcgt tcctaatcct    2460
agcaacttcc acctatcaca gagaaaaaaa aaggaaaaga aaaggtaaga tagaaagaaa    2520
gaaggaaaag taaaagcatg caaatataga attataaata ctaaaaata ttgttaagat    2580 attagttaaa aaattattaa gatacacaaa attacattat acacaatttt ttataatctt    2640
taaaataaat attttttatt ttattaatat cctaaagata ttagttaatt aacattcatg    2700
tattattatt tgaaattgaa acgtaagtag taattaaaag caaattattc tatcgaaaaa    2760
gagataactt tattaatgac acacaccaaa cataccaatc gctagagttg ttaaccactc    2820
actcatatag catatcacaa attcccatgc aaccttaatt caacggtcca gatgcagtct    2880
```

```
gatgagatca gacggtcgag acgaactgta cattctccct ctcacggatt tcgatgtttc    2940
tctttcggac caaatgtggg gcccacatag tactgtgtcc tgagtgctgg ctactcacaa    3000
aggcgggaac cagttttttgt cgcagaagag gtatggctct ttgtttgttg tcatcagatg   3060
agagagaaac aaaacaaaga gacaatcact gaatcactct cactcactct gcatgctgtg    3120
tgcgtgactc tgtcattgtg ttttgtgttt taagcacttt gcagtttagt ttctgaggag    3180
cgtttttttt ttttctttc ttatgagtgt gtgtctgttc ttagttgctg ttattgttgt     3240
tcaagtttcg gttactacta ctactaccac atgtccatgc cccttcaatt tctgttcaac    3300
tttgtgactt tttgtttggt ttctaaggaa aaagattgca acttgtttct gggtctagtt    3360
tgcttttggt tgggtttgtt agtcaccgct ggcaactcgg aatagtgggt ttttttttgg    3420
agggtgtttt ttttttcttc ttttggaggt tcaaattctt gttctgattc gtgtgaaggt    3480
ggaaaattta tgggtgctga gaggaggaaa aagatgggat ttggtggaat aaatgtaaaa    3540
ctattcggcg acaacatgtc tgcttgcttt tttgggacgg cttcttgtg aagattttgg     3600 gtttaaaagg ttgaggaaga tgcttatgcc ttatgcttat gcttgcaact tttttttaa     3660 aacccatttt agcatcaagt ataaaagttt cttcttggtc ttgtttccaa gtgtttgagg    3720
tgatgggggt tttgagcatg tgagtgattc atgcctcatt ttggagcttc tgagattggt    3780
ttctggttgt ggctttgttt gttttgtgtt gtgctttcat gtttaggaaa aggcacaccc    3840
tttcttctct tgcaagggaa ttgttggcat ttcagccact ttttcttctc ttcttgttca    3900
gcttgcacca caacactatg cagtgtcaag gaaggttgag taaacatgtt tcttctgagc    3960
ctccctcacc ttctaggtca acaccatcac caccatcttc atcaggatac aaggatgacc    4020
ctaggaagat aattttgagc atggttttag gagcagtcac tggactagtt tcttctgctc    4080
tctttgcact tgtggttcgt tgtgttgttc agtatctgaa ccgcacacca atcctcaagg    4140
gacctgtcat attctccccc aaaattgccc ccatgacact ccaatcagct ttggcaaagg    4200
aaaaccactt gctcggttcg agtcctaatg ggaagtacta caaaactgtg cttgacaatg    4260
gactcactat tgcagtcaaa aggctaacac cctttgagag taattccccg gaggctaaga    4320
gaaaatcagt gaagaggcag atacaaactg agcttgagct tcttgcaagc cttaggcata    4380
ggaacttgat gagtttaagg gcctatgttc gtgagcctga tgggttctca ttggtttatg    4440
attatgtttc cactgggagt cttgctgatg tgttgagtaa agtgagggag aatgagttgc    4500
cctttggttg ggaagttagg ctcaggattg ctgttggtgt ggtgaagggt cttcagtatc    4560
ttcatttcac ttgtgtgcct cagattctgc actacaactt gaagcccaca aatgtgatgt    4620
tggatgctga gtttgaacct agattggcag attatgggtt ggctaaactt ctacccaatt    4680
tggatggagg aagttctctc tacactcctc ctgaatgttt ccataattgc aggtaagaca    4740
aatttcaatc atactcattc actagtgttt tgaacttggt ctgtttctgt tctttcactt    4800
ttttacacca atagggtaat taggtggttg atattgggaa tttgtttgat tcgttacctt    4860
ttcaaaagct ccacacctca ttggtttttt gccccctttg tagtacccta atgaaagact    4920
cttgttttga aacgaaatta ctattctgta atctgtattg tcattgtatc atttgctgat    4980
tgaatttggt attatttaat aaagactttg ctatttgttt ttgtaactac ccattacttc    5040
ctgatgtcaa gttttagacc ttaggcagtt ggcactaagt ctggtccaaa tgaataatat    5100
agtttatagt tcacatgctg caaactacta aacctagatt ggtgagtgag accacaacta    5160
aattataata ataattgaca aaggtttttt ttcctaattt aacttggaat acttctagtt    5220
tttcagtggt gtatatttgg atgcatcaat atcaatagca ataagtaata acaataaaag    5280
```

```
attgcttgat tgatggcatt gcatatatgg gtatggtatt gccaataaga tgtttatttt      5340
aacttcattc cattcttgta tatgtggagc ttcatggtat tcagattgaa tggtgttttt      5400
tggcaatttc agcaggtaca ctgacaaaag tgacatcttt agttttggca tgatactagg      5460
tgttttgtta actggtaagg atcctacaga tccattcttt ggagaagcag ccagtggggg      5520
aagtttggga tgttggctga gacacttgca gcaagcgggc gaggcgcacg aagctctaga      5580
taagagcatg ttaggggaag aaggtgagga agatgagatg ctaatggcgg ttaggattgc      5640
tgctgcatgc ctctctgata tgcctgcaga taggccttct agtgatgagc ttgttcacat      5700
gctaacgcaa ctgcacagtt tttga                                            5725

<210> SEQ ID NO 48
<211> LENGTH: 1227
<212> TYPE: DNA
<213> ORGANISM: Glycine max

<400> SEQUENCE: 48
atgtttagga aaggcacac cctttcttct cttgcaaggg aattgttggc atttcagcca        60 cttttcttc tcttcttgtt cagcttgcac acaacacta tgcagtgtca aggaaggttg       120
agtaaacatg tttcttctga gcctccctca ccttctaggt caacaccatc accaccatct       180
tcatcaggat acaaggatga ccctaggaag ataattttga gcatggtttt aggagcagtc       240
actggactag tttcttctgc tctctttgca cttgtggttc gttgtgttgt tcagtatctg       300
aaccgcacac caatcctcaa gggacctgtc atattctccc ccaaaattgc ccccatgaca       360
ctccaatcag ctttggcaaa ggaaaaccac ttgctcggtt cgagtcctaa tgggaagtac       420
tacaaaactg tgcttgacaa tggactcact attgcagtca aaaggctaac accctttgag       480
agtaattccc cggaggctaa gagaaaatca gtgaagaggc agatacaaac tgagcttgag       540
cttcttgcaa gccttaggca taggaacttg atgagtttaa gggcctatgt tcgtgagcct       600
gatgggttct cattggttta tgattatgtt tccactggga gtcttgctga tgtgttgagt       660
aaagtgaggg agaatgagtt gccctttggt tgggaagtta ggctcaggat tgctgttggt       720
gtggtgaagg gtcttcagta tcttcatttc acttgtgtgc ctcagattct gcactacaac       780
ttgaagccca caaatgtgat gttggatgct gagtttgaac ctagattggc agattatggg       840
ttggctaaac ttctacccaa tttggatgga ggaagttctc tctacactcc tcctgaatgt       900
ttccataatt gcagcaggta cactgacaaa agtgacatct ttagttttgg catgatacta       960
ggtgttttgt taactggtaa ggatcctaca gatccattct tggagaagc agccagtggg      1020 ggaagtttgg gatgttggct gagacacttg cagcaagcgg gcgaggcgca cgaagctcta      1080
gataagagca tgttagggga agaaggtgag gaagatgaga tgctaatggc ggttaggatt      1140
gctgctgcat gcctctctga tatgcctgca gataggcctt ctagtgatga gcttgttcac      1200
atgctaacgc aactgcacag tttttga                                         1227

<210> SEQ ID NO 49
<211> LENGTH: 408
<212> TYPE: PRT
<213> ORGANISM: Glycine max

<400> SEQUENCE: 49

Met Phe Arg Lys Arg His Thr Leu Ser Ser Leu Ala Arg Glu Leu Leu
1               5                   10                  15

Ala Phe Gln Pro Leu Phe Leu Leu Phe Leu Phe Ser Leu His His Asn
```

```
            20                  25                  30
Thr Met Gln Cys Gln Gly Arg Leu Ser Lys His Val Ser Ser Glu Pro
         35                  40                  45
Pro Ser Pro Ser Arg Ser Thr Pro Ser Pro Pro Ser Ser Ser Gly Tyr
 50                  55                  60
Lys Asp Asp Pro Arg Lys Ile Ile Leu Ser Met Val Leu Gly Ala Val
 65                  70                  75                  80
Thr Gly Leu Val Ser Ser Ala Leu Phe Ala Leu Val Val Arg Cys Val
                 85                  90                  95
Val Gln Tyr Leu Asn Arg Thr Pro Ile Leu Lys Gly Pro Val Ile Phe
             100                 105                 110
Ser Pro Lys Ile Ala Pro Met Thr Leu Gln Ser Ala Leu Ala Lys Glu
         115                 120                 125
Asn His Leu Leu Gly Ser Pro Asn Gly Lys Tyr Tyr Lys Thr Val
         130                 135                 140
Leu Asp Asn Gly Leu Thr Ile Ala Val Lys Arg Leu Thr Pro Phe Glu
145                 150                 155                 160
Ser Asn Ser Pro Glu Ala Lys Arg Lys Ser Val Lys Arg Gln Ile Gln
                 165                 170                 175
Thr Glu Leu Glu Leu Ala Ser Leu Arg His Arg Asn Leu Met Ser
             180                 185                 190
Leu Arg Ala Tyr Val Arg Glu Pro Asp Gly Phe Ser Leu Val Tyr Asp
         195                 200                 205
Tyr Val Ser Thr Gly Ser Leu Ala Asp Val Leu Ser Lys Val Arg Glu
         210                 215                 220
Asn Glu Leu Pro Phe Gly Trp Glu Val Arg Leu Arg Ile Ala Val Gly
225                 230                 235                 240
Val Val Lys Gly Leu Gln Tyr Leu His Phe Thr Cys Val Pro Gln Ile
                 245                 250                 255
Leu His Tyr Asn Leu Lys Pro Thr Asn Val Met Leu Asp Ala Glu Phe
             260                 265                 270
Glu Pro Arg Leu Ala Asp Tyr Gly Leu Ala Lys Leu Leu Pro Asn Leu
         275                 280                 285
Asp Gly Gly Ser Ser Leu Tyr Thr Pro Pro Glu Cys Phe His Asn Cys
         290                 295                 300
Ser Arg Tyr Thr Asp Lys Ser Asp Ile Phe Ser Phe Gly Met Ile Leu
305                 310                 315                 320
Gly Val Leu Leu Thr Gly Lys Asp Pro Thr Asp Pro Phe Phe Gly Glu
                 325                 330                 335
Ala Ala Ser Gly Gly Ser Leu Gly Cys Trp Leu Arg His Leu Gln Gln
             340                 345                 350
Ala Gly Glu Ala His Glu Ala Leu Asp Lys Ser Met Leu Gly Glu Glu
         355                 360                 365
Gly Glu Glu Asp Glu Met Leu Met Ala Val Arg Ile Ala Ala Ala Cys
         370                 375                 380
Leu Ser Asp Met Pro Ala Asp Arg Pro Ser Ser Asp Glu Leu Val His
385                 390                 395                 400
Met Leu Thr Gln Leu His Ser Phe
                 405

<210> SEQ ID NO 50
<211> LENGTH: 4954
<212> TYPE: DNA
<213> ORGANISM: Glycine max
```

<400> SEQUENCE: 50

```
attataagaa aataatggta atttgattta ctgaaaaaat tagcgtcaat tcatcatttc    60
aatattacaa aatgatacta cgatttagta tcttaagtat tgcacgcaaa agattatttt   120
catatcattt ttcaattatt tagagaaaaa agtgacgtta atatcttagg aaaaaattaa   180
tatctctggc attttaagaa aataaagagt tacttataaa atatgaccac gattcatgaa   240
atcttatatt aaatatagtc ccgataattc caatttgtat aaactaaaag aatacttata   300
ggaaaaaaat agtgaggcaa ataaattaaa cttctttcat aaataaaaat caaattatgt   360
attttttactt ttggaaaagt taaataagag aatttcttaa aattgattag ataagttaat   420
tttaacttgt gggagatttt tatttattta tttttcatta tacctctatt ttttctgagt   480
attttttgaa aattttatct aaatttaaat taaaaattgt ggagaatact ttcaaggaaa   540
atggcctaat ggtttagcgt gtgttttaag cataaatttt ggtacccatg tttgattaac   600
tattaattaa aattaatttt aaaaggccaa ggtcattttc acacaattct attcccttgc   660
actagaccac tttttaagta taaatttatg actaatgggt caaagcatac aatgccttgt   720
gtaaatagtt gactatcaac caaaaatttg acattcaata agacaccact ggtctttgag   780
cgacatcaat attttttatga aaacgatagt tgcacctaat atgtgaaatt cgcaatctga   840
attatttata aaacgttgca tttgcgttcc aaataaaaaa ctcaacccaa caaggaaaaa   900
aaaaactgaa cttatgtctt ggttttgttt tgtttggtta ttaaaaaaag taaatggaac   960
tgactgtatc caattatatg tctgttttta gattttgaaa gaaataattt taaaccaata  1020
aatatagtta tgatatatat ttaaattaat ctcagctata tattaaaatg tatatcacgg  1080
taaaaataat taactctagt aaattatcaa atggatattt gctataataa ttatttgtaa  1140
atgcctgatt tagattatag taatttaaaa tctaagtact tgtcattttt catttcaaaa  1200
tgcctcatgc cataaattaa ccaaacaaac atgaattata tcctttgata atttattcat  1260
actattattg cttgcacctg tacatatatg tgttgctcat tcactcaccc cagactgagt  1320
gctagatcct cggactcgaa taaatcattt attatgctta aataattcga ttttatttt   1380
cctacatcac aataatctaa agagttaatc tcatactctc gattcatcct taaaaattta  1440
atgggtgtaa tgagaaatta atttttaacta ctattatatt ttaaaaaata aatagtgaaa  1500
ataatgagaa actctaatta aaattactct ttgagtaact aacttgatt ttcctcgtag   1560
aacaacccaa tcaatgtcac aacgaatttt tcctatttca cgagagaact tgaaagttaa  1620
aatttggtta aagtcgttcc taaacgtagc agaagataag atagaaagat ggaaagtaa   1680
aagcatgcaa atatataatt gaaattgaaa tgtaagtagt agtaattaaa aacaattatt  1740
tgatggaaaa agagataact ttactaatga cacacaccaa acataagatg tgttcgctag  1800
agttgttaac cacactcact catatacagc atatcacaaa ttcccatgca ccctcaattc  1860
aacggtccag atgcggtctg atgaaatcac acggtcgata cgaactgtac attctccctc  1920
tctctatcac ggatttcgat gtttcgcttt cggaccaaat gtggggccca catagtactg  1980
tgtcctgagt gctggctact cacaaaggcg ggaaccagtt tttgtcgcag aggtatggct  2040
ctttgttgtc atcggatgag agagaaagag tgtagagaga gaaacaaaac taagagacaa  2100
tcactgaatc actctcactc actctacatg ctgtgtgcgt gactctgtca ctgtgttttg  2160
tgtttaagca cattgcattt tagtttcaga ggagtttttt ttttttttt tgctgttatt   2220
gttattcaag ttttggttac tactaccgcc acatgttcat gccccttcaa tttttgttca  2280
```

```
acttttgac tttctgcttg gtttccaagg aaaaagattg caacttgttt ctgggtctag   2340
tttgcttttg gttgggtttg ttagtccctg ctggcaccctc ggaatagtgg gttttttgttt  2400 ttgtttttgt ttttttttctt cttttggagg ttcaaattct tgttctgatt cgtgtgaagg   2460
tggaaaattt atgggtggtc accggaagag gaaaaagatg ggattcgttg gaaaaaagta   2520
agactattcg gtgataacat gtctgcttgc tttttttggga cggcttttttt gttaagattt  2580 tgggttgaaa aggttgagga agatgcttat gcttgcaact ttttttttaaa cccatttttag  2640 caccaagtat aaaaagttgt tcttggtctt gtttccaagt gttgaggtag gtgatagggg   2700 tttttgagcat gtgagtgatt catgcctctc attttggagc ttctgagatt ggtttctggt  2760
tgtggcttcg tttgtttgtt tgtttgtttg ttgtgctttc atgtttagga aaaggcacat   2820
cctttcttct cttgcaaggg aattgttggc actccagcca ctttttcttc tcttcttgtt   2880
cagcttgcac cacaacactg tgcagtgtca aggaaggttg agtaagcatg tttcttcaga   2940
gcctccctca ccttctaggc catcgtcagc agcaccatct tcatcaggat acaaggatga   3000
ccctaggaag ataattttga gcatggtttt aggagcagtc actgggctag tttgttctgt   3060 tctgttttgca cttgtggttc gttgtgttgt tcagtatctg aaccgcacac caatcctcaa   3120
gggccctgtc atattctccc ccaaaattgc ctccaagaca ctccaatcag ctttggcaaa   3180
ggaaaaccac ttgcttggct cgagtcctaa tgggaagtac tataaaacta tgcttgacaa   3240
tggactcact attgcagtca aaaggctaac acccctttgag agcaattccc cggaggccaa   3300
gaggaaatca gtgaagaggc agatacaaac tgagcttgaa cttcttgcaa gccttaggaa   3360
taggaacctg atgagtttga gagcctatgt tcgtgagcct gatggattct cattggttta   3420
tgattatgcg tccactggga gtcttgctga tgtgttgaat agagtgaggg agaatgagtt   3480 gcccttggt tgggaagtta ggctcaggat tgctgttggt gtggtgaagg gtcttcagta   3540
tcttcacttc acttgtgtgc ctcagattct gcactacaac ttgaagccca ctaatgtgat   3600
gttggatgct gagtttgaac ctagattagc agattatggc ttggctaaac ttctgcctaa   3660
cttggataga ggaagttctc tctacacccc tcctgaatgt ttccacaatt gcaggtaaga   3720
caaatcaatt gctttcaatc atactcactc actagtgttt tgaacttggt ttgtttctgt   3780 tttttcacttt tttacaccaa atgggtaact agttggttga tattgggcac ttgcttgatt   3840
cgttaccttt ttaaaagctc cactcctcat tggtttttttc tccttctttg gagtacctta   3900
atcaaagact cttagtgtga aacgtgatta ttgttctgta ttgtcatggt gtcatttgct   3960
attgtttaat aattaagact ttgcaaaact aatgttttttg taactaccca ttacttgtat   4020
agttcacatg ctgcaaacta ctaaacctag attggtgatt gagaccccaa ttaaaaatta   4080
taataataat ttactaaggt tttttcttttc caatttaact tatttctagt ttttcattgt   4140
tgtgtatatc tctggataca tcaatcttaa tagtaataac ttaaaaataa gtaataacaa   4200 taaaagatt gcttgattga tgcatttcat atatgggtat ggtattgcca ataagatgtt   4260 aatttttaact tcattccatt cttgtatgtg aaacttcatg gtatttagat tggatggtgt   4320
tttttgcaat ttcagcaggt acaccgacaa aagtgatatc ttcagttttg gcatcatact   4380
aggtgtttta ttaaccagta aggaccctac agatccattc tttggagaag cagccagtgg   4440
gggaagtttg ggatgttggt tgagacactt gcagcaagcc ggtgagtcac gtgaagctct   4500
agataagagc atgttaggag aagaaggtga ggaagatgag atgctaatgg ctgttaggat   4560
tgctgctgca tgcctttctg atatgcctgc agataggcct tctagtgatg agcttgttca   4620
catgctaacg caactgcaca gttttttgaaa caaaccttga ttcttcagtt cctagatatt   4680
```

```
ttttcttttc tcttatcccc tctttctgta ataagatgat aggggaatttt ggttagtgcc      4740 catgattctg gtgtaattga ttgttttggt gtaattgatt gttttgcatg atcttggttt      4800
tcatggtgtg gtttctaata ttccattttc tctttctcta ttctatttcc ttttctttt       4860 ggctgatttt gcaggttgtg gtgggttag gtcacactat tatattttgt ttgtaaatga       4920
ctagtcatgt taacaagagt tttcttttct tgct                                  4954
```

<210> SEQ ID NO 51
<211> LENGTH: 1227
<212> TYPE: DNA
<213> ORGANISM: Glycine max

<400> SEQUENCE: 51

```
atgtttagga aaggcacat cctttcttct cttgcaaggg aattgttggc actccagcca        60 cttttcttc tcttcttgtt cagcttgcac acaacactg tgcagtgtca aggaaggttg       120
agtaagcatg tttcttcaga gcctccctca ccttctaggc atcgtcagc agcaccatct       180 tcatcaggat acaaggatga ccctaggaag ataattttga gcatggtttt aggagcagtc       240
actgggctag tttgttctgt tctgtttgca cttgtggttc gttgtgttgt tcagtatctg       300
aaccgcacac caatcctcaa gggccctgtc atattctccc ccaaaattgc ctccaagaca       360
ctccaatcag ctttggcaaa ggaaaaccac ttgcttggct cgagtcctaa tgggaagtac       420
tataaaacta tgcttgacaa tggactcact attgcagtca aaaggctaac ccctttgag       480 agcaattccc cggaggccaa gaggaaatca gtgaagaggc agatacaaac tgagcttgaa       540
cttcttgcaa gccttaggaa taggaacctg atgagtttga gagcctatgt tcgtgagcct       600
gatggattct cattggttta tgattatgcg tccactggga gtcttgctga tgtgttgaat       660
agagtgaggg agaatgagtt gccctttggt tgggaagtta ggctcaggat tgctgttggt       720
gtggtgaagg gtcttcagta tcttcacttc acttgtgtgc ctcagattct gcactacaac       780
ttgaagccca ctaatgtgat gttggatgct gagtttgaac ctagattagc agattatggc       840
ttggctaaac ttctgcctaa cttggataga ggaagttctc tctacacccc tcctgaatgt       900
ttccacaatt gcagcaggta caccgacaaa agtgatatct tcagtttgg catcatacta       960 ggtgttttat taaccagtaa ggaccctaca gatccattct ttggagaagc agccagtggg     1020
ggaagtttgg gatgttggtt gagacacttg cagcaagccg tgagtcacg tgaagctcta      1080 gataagagca tgttaggaga agaaggtgag gaagatgaga tgctaatggc tgttaggatt     1140
gctgctgcat gcctttctga tatgcctgca gataggcctt ctagtgatga gcttgttcac     1200
atgctaacgc aactgcacag ttttttga                                        1227
```

<210> SEQ ID NO 52
<211> LENGTH: 408
<212> TYPE: PRT
<213> ORGANISM: Glycine max

<400> SEQUENCE: 52

```
Met Phe Arg Lys Arg His Ile Leu Ser Ser Leu Ala Arg Glu Leu Leu
1               5                   10                  15

Ala Leu Gln Pro Leu Phe Leu Leu Phe Leu Phe Ser Leu His His Asn
            20                  25                  30

Thr Val Gln Cys Gln Gly Arg Leu Ser Lys His Val Ser Ser Glu Pro
        35                  40                  45

Pro Ser Pro Ser Arg Pro Ser Ser Ala Ala Pro Ser Ser Ser Gly Tyr
```

```
            50                  55                  60
Lys Asp Asp Pro Arg Lys Ile Ile Leu Ser Met Val Leu Gly Ala Val
 65                  70                  75                  80

Thr Gly Leu Val Cys Ser Val Leu Phe Ala Leu Val Val Arg Cys Val
                 85                  90                  95

Val Gln Tyr Leu Asn Arg Thr Pro Ile Leu Lys Gly Pro Val Ile Phe
            100                 105                 110

Ser Pro Lys Ile Ala Ser Lys Thr Leu Gln Ser Ala Leu Ala Lys Glu
        115                 120                 125

Asn His Leu Leu Gly Ser Ser Pro Asn Gly Lys Tyr Tyr Lys Thr Met
    130                 135                 140

Leu Asp Asn Gly Leu Thr Ile Ala Val Lys Arg Leu Thr Pro Phe Glu
145                 150                 155                 160

Ser Asn Ser Pro Glu Ala Lys Arg Lys Ser Val Lys Arg Gln Ile Gln
                165                 170                 175

Thr Glu Leu Glu Leu Leu Ala Ser Leu Arg Asn Arg Asn Leu Met Ser
            180                 185                 190

Leu Arg Ala Tyr Val Arg Glu Pro Asp Gly Phe Ser Leu Val Tyr Asp
        195                 200                 205

Tyr Ala Ser Thr Gly Ser Leu Ala Asp Val Leu Asn Arg Val Arg Glu
    210                 215                 220

Asn Glu Leu Pro Phe Gly Trp Glu Val Arg Leu Arg Ile Ala Val Gly
225                 230                 235                 240

Val Val Lys Gly Leu Gln Tyr Leu His Phe Thr Cys Val Pro Gln Ile
                245                 250                 255

Leu His Tyr Asn Leu Lys Pro Thr Asn Val Met Leu Asp Ala Glu Phe
            260                 265                 270

Glu Pro Arg Leu Ala Asp Tyr Gly Leu Ala Lys Leu Leu Pro Asn Leu
        275                 280                 285

Asp Arg Gly Ser Ser Leu Tyr Thr Pro Pro Glu Cys Phe His Asn Cys
    290                 295                 300

Ser Arg Tyr Thr Asp Lys Ser Asp Ile Phe Ser Phe Gly Ile Ile Leu
305                 310                 315                 320

Gly Val Leu Leu Thr Ser Lys Asp Pro Thr Asp Pro Phe Gly Glu
                325                 330                 335

Ala Ala Ser Gly Gly Ser Leu Gly Cys Trp Leu Arg His Leu Gln Gln
            340                 345                 350

Ala Gly Glu Ser Arg Glu Ala Leu Asp Lys Ser Met Leu Gly Glu Glu
        355                 360                 365

Gly Glu Glu Asp Glu Met Leu Met Ala Val Arg Ile Ala Ala Ala Cys
    370                 375                 380

Leu Ser Asp Met Pro Ala Asp Arg Pro Ser Ser Asp Glu Leu Val His
385                 390                 395                 400

Met Leu Thr Gln Leu His Ser Phe
                405

<210> SEQ ID NO 53
<211> LENGTH: 6932
<212> TYPE: DNA
<213> ORGANISM: Glycine max

<400> SEQUENCE: 53
caaatgggta tgctcccttc aggggactcc ccaatcgccc taatcgcaga ctccaccgtc      60
tcactctcgt gaaactccgc cagctccggc ttccccaccg tcagatcgcc caccacgtgg     120
```

```
tacacgaaca ccgacgccat cggaatccaa aagggtatcc ggaaccacaa tcaaaatcga    180 ttttttgttct gcttttttgta tccttaaaaa aaaaaccgaa aacagaaaga aaaaaaaaag   240 tttgctttttt ttgctttgtc gggtgagagc tataagaggg tatggaggaa gatgaggaga   300
agatcgaggg cggtgatggg agggcggtgg aggatcacgg cagagaaaga gttagccatt   360
gccatggagg gagaacgaaa aggttaaggc ccattcaatt gaatcagatc agagagagag   420
agggcgtagc ttttggggaa gatatgatat gtagagattt ggataaggta cgtcctttcg   480
gggacagcaa gagatgcaac gacagaagaa gatggatcag cgacgcttga tgcggttggg   540
acctgagaat gaatgggaca ccagacacac actaaaagga ggttcaattt atcaaataaa   600
aaagagaaag gcacagggga tgtgtcatgt gtcatgtgtc atgtgtcatg tgtatggtga   660
gctgcatcat atagagaatc ttttcacctt aattaatttg tttagtttaa tacgtttttc   720
ttttcttgtc atactcatct ttgatttcaa ttctatagac ctatatataa gttaatttat   780
ttaataagag aggataaaca aagaatgaaa ataggtaaat gagaaaaaag gagaaataaa   840
ttaaaaacaa tgcttgtttg aatttaaaga aacggaagaa aaataagaaa aatagattac   900
taatataaaa tatcctttat attacataat ttttttcata taacatagta catacggaca   960
aaacttagat acattatttt gggtgttatt ttttttattag agttaaagtt tcatttcaat  1020
gatatatata taagttttaa atgtaaaact ttattatgca aattactcaa ataaaactcc   1080
aattttcatt agagaataat acaaaccgtg taacgactac aagtttatct taaatttcca   1140
atctttgaaa ttatgttatt tgtctcccctt tcttaaaaat ataaaattga tttagtgata   1200
aagaaaaaag aggagaaggg ataagttttta aatataaatt cttcaggtta tagttcaata   1260 ggtcacccttt aattaatgac gttaattaac agattaataa tgacttcaga agcagtgtct   1320 atgaagtttta tgcgagatca ccaatgatat atgtagttaa tagcaacaag ttgaggaaag   1380
aggtttggat gaatgtgtgg ctgtttaatg ttgggtggtg gtgtggtggc tatgactacg   1440
aggttggtgt tggaaaatgt tgtcaattca attgggattc ggtttgcaaa gttgtgataa   1500
ctttgagttg aatgatggaa tattgaaatt ttctaggctt agttaggaat gattgctaca   1560
tgtaacagtg ataccacaac aacagggatg agggattgtt ggggtttact tttaaaaaat   1620
gaatgaattg aattacaatg taaaagtata catataaaac actattcttg cttcttaaaa   1680
aaaacgtgag acagagagaa agtgaagatg ataagattat agcgcacgcg ttggagcgtg   1740
catgagttta ctaggtcttg taccatgcaa aaaaatttag gacccttaga tataacaaca   1800
agacaagaag atctttaaga gtgtaacata tggataacat actgtatacc aacttttctt   1860
tttaatagta tttcttctct ctggttataa catcatttta actaatctat gtctgttaaa   1920
aaaatattaa tttaattaat tatattaaat atatcaatta tttatatttt ttattttttct   1980 atccacttaa tttttttatta atgtttttaaa aaaataatta agaataaaat aattaatgta   2040
ttaaaaatta aaaaaatctt ataaatcaag acaaataaat ttatgaaaaa catcatataa   2100
ttagtatggg attatgggat ggagtagtat ttaacttgtg gcttttgaaa attacaccat   2160
attttctctc tctcttgaca aaatgaatgc aacttaaaaa cgtgggatca ttcttcctcc   2220
tgagtccaga atgttcgacc ccattcgtac tctgatctat gtgtgtttgt ggtatatctc   2280
cgttgtcact tcaccattct agcttcatca gagaaagtaa tatatatatt tgtaaaccaa   2340
ttatatatat atttgagagg attttaattc ttactaaaat tgtaaaccaa ttagaaatca   2400
tttttctgta attttttgtga tctgaaattt tctgttcggg ttggaaatga cacaaaatcg   2460
```

```
ttgggtcttt aaatgggttg caaccggatg agaatgaccc aactcaaggt aggggatgac    2520
caaagcatag ccttttaatg ggtaatgtta aacatgatat aaatttataa caaattattt    2580
ttatggtgta gtggttaact cttttcattaa taataatata gctggttgtt ggttccatcc    2640
cacaataagt cagtttagct ttttatcttc taaagatttc ctgttttcat ttattttggt    2700 tttttttaaaa aataaacaat ttcgccttgg aatcgaactc acgatatagt gattagttat    2760
aaaaaaataa ttataaatta tttggtaatt tttttcttac attcactctt gtttgaata    2820 ctcttctctt tgtgaagtta tgaactttgt tctcttacca caaatatgat acatcttctt    2880
atgtttttta atttttagatt atatttgata aaactaacca aaaagatgaa aaatatagtc    2940
tgtttaaaat atttaagatc taagcttaac tcgttacatg tgatagactt tatttgtaga    3000
ttatacttga tttatttgaa agtttagctt aacctattag tttatttaaa gacctatttc    3060
atatgaaagt ttttatataa gtctattttt ttatattgga caataaattt ataaatcgtt    3120
gagaaaattc catgtaaaca aactataatc tataaaaaaa aaaatttct ttattcaaag    3180 cacaagatag gtgaaaatag atgaactaag ttttataagt gaaatttaac atgtcattat    3240
gatgtaagtt tatcaacttc aagataactt agttaaaaat ataattttgt aataagtcct    3300
ctaattaaaa cataaatttc gcactcaata attttttttt aatcgtggat caacactcat    3360
aatattttaa aaaagtaaat aatgtattat tttgatacat tacaataatt ttaatattac    3420
aaaatattat aatttatatt tatttaaata ggttgatcta ttaggtttaa aacactttt    3480 aaataactta aaacctaatt ttttaatcaa atagactttt attaaaactt agatatgatt    3540 tattttatt ttttaaaaa aaactaacct gacttgagtt tgatataaat taggtgtcag    3600
tttgtttaaa tttatttatt aaaataaatg tttattttaa taaaataagt aattttatat    3660
ttgtttagta tatttgtgta aattctttt ccttaaaaaa tatttttttc ttttaaaaa    3720 aaatacttat tttaaaatta tttttttta aaagagaaac ttgaaaaagg ataaagtgta    3780
atgcagtata gagagaaaga ggaggaagca aagcaaacca agcacaacac aacaaagcca    3840 ctttatttttt ttgatctaac ctaaaccctc tttttcccct gttgctctct cactttatca    3900
gcgtgataca accaacccaa gaccaatgtg gaagatcttg ttcctctttc ccttctctta    3960
tgtccatttc atcatgtttt cattctaatc tccaaaatcc atgcccaccc agttcctctt    4020
ttgcttcaaa ctcctctccc ccttcctaaa aattgcacct ttactctcat ggtgatggga    4080
cacaccacac ccctcacact tctctgtgtg attcttcttt ttgcaactcc ttctcactca    4140
attgatgttc acccacaaga cagaatctca ctttcaatgt tcaggtcatc tctgccaaac    4200
cccaaccaga gtttgcccag ctgggtgggc tccaactgca cttcatggag tggaatcacc    4260
tgtgacaaca gaactgggag ggtgcttccc atcaacctaa ccagtatgaa cctttcaggc    4320
aaaatccacc ccagtttgtg ctacctttca tatctgaaca agttgggggtt gtcccacaac    4380 aacttcacat cccctcttcc tgaatgtttt ggcaacttgc ttaacctaag agccattgat    4440
ctcagccaca acaggcttca tgggggaata ccagactctt tcatgaggct taggcacctc    4500
actgagcttg ttttgagtgg gaaccctgat ttgggggtc cactgcctgc ttggattggt    4560
aacttctctg caaatctgga aaggttacat cttggtttct gttcattcag tggtggcata    4620
ccggagagct tgcttacct gaagtccctc aagtatttgg accttgagaa caacctcttg    4680
tctggtaact tggtcaattt tcaacagcct ttggttttgc tcaatcttgc ttccaatcag    4740
tttgctggta ctttgccttg ctttgcagct tcagttcagt tctctaactgt gttgaattta    4800 tctaacaatt ctattgtggg gggactacct gcttgtattg cttcttttca agctttgact    4860
```

```
catttgaacc tgtcagggaa ccacttgaag tatagaatat atcctaggct tgtgttctcg    4920
gagaaacttc ttgttttgga cttgagtaat aatgctttgt ctggtcctat tccttgtaaa    4980
attgctgaga caactgagaa acttggcctt gttcttcttg acctttctca caatcagttc    5040
tctggtgaaa ttcctgtgaa aatcactgag ttgaaaagct tgcaggcctt gtttctctct    5100
cacaatcttc tctctggaga aattcctgct agaattggaa atttgactta tctgcaggtc    5160
attgatctct cacacaactc tttgtctgga accattccat tcagtattgt tgggtgcttt    5220
cagctgtatg ctctaatact tactaacaac aatctttctg gtgtaattca accggagttt    5280
gatgcgttgg atatcttgag gattctggat ataagcaaca acaggttttc cggggctatc    5340
ccactcactc tggctggatg caaatctctg gagattgtag attttagttc caatgagctt    5400
tctggatcct tgaatgatgc aataaccaaa tggacaaacc tcaggtattt gtctcttgct    5460
cagaacaagt tcagtggaaa tctgcctagt tggttgttca catttaacgc aatagaaatg    5520
atggatttct cgcataacaa gtttactggc ttcatacctg atattaattt taagggtagc    5580
ttaatattta acaccaggaa tgtcactgtt aaagagccat tggttgcagc aagaaaggtt    5640
caactgagag tttcggcggt tgtttctgat agcaatcagc tcagtttcac ttatgatctt    5700
tcctcaatgg ttgaattga tctatccagc aattcgcttc atggggaaat tccaagggc    5760
ttatttggtc tagctggcct agaatatctg aacttgtcat gcaactttct ttacggacag    5820
cttccggggt tgcagaaaat gcatagtttg aaagccttgg atttgtcaca taattccttg    5880
tctggacata tcccaggaaa catttctagc cttcaagatc tgtccatttt gaatctttcc    5940
tacaactgtt tttctggata tgttccccag aagcaagggt atgggagatt tcccggtgca    6000
tttgctggaa atccagatct gtgcatggaa acttccagtg gagtatgtga tgatggaagg    6060
actcaatctg cgcaaggaag ttcttccagt gaagatagga tggatggccc aatttctgtg    6120
gggattttct ttatcagtgc ctttgttagt tttgattttg tgttgtggt tctcttctgt    6180
tctgcccggg caagaaatta cattctccaa acaaaagttt gatttgatgc ttgtgacagt    6240
tacaaatctc ctgtaaattc cattttgtaa tttggtacct gtgttctcag tttcaagtaa    6300
aacatacact tatgtgacta ggaatactat ccggccatca acttcacaag tgttttcttg    6360
tgattcctga tcaagtgtct cagatttaca ggatcaaaat gccatgacat gagtaacaca    6420
aggtttaaag aacactcaac actggcttta tctatctgag tgaagactag cctggcatca    6480
ttcagccaag aaaagaatgg atgattatga tgaaatttg atccgagtaa agacgagtcc    6540
ctcatcattc tgatggttgt tctcttttgc tggaatttgg ttgcatcaag tttagaatgc    6600
atcatcacat gtattattca taatcagtgg tgggcgaagg gtcagtaggg aacatgtctg    6660
atatctggtc tagttatggt gaaattttga tcttgggcat caaattgcag atttgcaagc    6720
atgtttacgt gaagagaact tgtataattc ttgattaacc tagttctttc ttgaggtggg    6780
gaaccaagtt ttccctgtaa gtggggagta ggttctcata agtctaagat ttgtatttgt    6840
attactatct tcacaccttc atcatagtgc tgtgatttta aatgatattc tcacgaaacc    6900
ttttcattga caacagaaaa gaggttaatt ga                                  6932
```

<210> SEQ ID NO 54
<211> LENGTH: 2109
<212> TYPE: DNA
<213> ORGANISM: Glycine max

<400> SEQUENCE: 54

```
atgcccaccc agttcctctt ttgcttcaaa ctcctctccc ccttcctaaa aattgcacct      60
ttactctcat ggtcatctct gccaaacccc aaccagagtt tgcccagctg ggtgggctcc     120
aactgcactt catggagtgg aatcacctgt gacaacagaa ctgggagggt gctttccatc     180
aacctaacca gtatgaacct tcaggcaaaa tccaccccca gtttgtgcta cctttcatat     240
ctgaacaagt tggggttgtc ccacaacaac ttcacatccc ctcttcctga atgttttggc     300
aacttgctta acctaagagc cattgatctc agccacaaca ggcttcatgg gggaatacca     360
gactctttca tgaggcttag gcacctcact gagcttgttt tgagtgggaa ccctgatttg     420
gggggtccac tgcctgcttg gattggtaac ttctctgcaa atctggaaag gttacatctt     480
ggtttctgtt cattcagtgg tggcataccg gagagcttgc tttacctgaa gtccctcaag     540
tatttggacc ttgagaacaa cctcttgtct ggtaacttgg tcaattttca acagcctttg     600
gttttgctca atcttgcttc caatcagttt gctggtactt tgccttgctt tgcagcttca     660
gttcagtctc taactgtgtt gaatttatct aacaattcta ttgtgggggg actacctgct     720
tgtattgctt cttttcaagc tttgactcat ttgaacctgt cagggaacca cttgaagtat     780
agaatatatc ctaggcttgt gttctcggag aaacttcttg ttttggactt gagtaataat     840
gctttgtctg gtcctattcc ttgtaaaatt gctgagacaa ctgagaaact ggccttgtt      900 cttcttgacc tttctcacaa tcagttctct ggtgaaattc ctgtgaaaat cactgagttg     960
aaaagcttgc aggccttgtt tctctctcac aatcttctct ctggagaaat tcctgctaga    1020
attggaaatt tgacttatct gcaggtcatt gatctctcac acaactcttt gtctggaacc    1080
attccattca gtattgttgg gtgctttcag ctgtatgctc taatacttac taacaacaat    1140
ctttctggtg taattcaacc ggagtttgat gcgttggata tcttgaggat tctggatata    1200
agcaacaaca ggttttccgg ggctatccca ctcactctgg ctggatgcaa atctctggag    1260
attgtagatt ttagttccaa tgagctttct ggatccttga atgatgcaat aaccaaatgg    1320
acaaacctca ggtatttgtc tcttgctcag aacaagttca gtggaaatct gcctagttgg    1380
ttgttcacat ttaacgcaat agaaatgatg gatttctcgc ataacaagtt tactggcttc    1440
atacctgata ttaattttaa gggtagctta atatttaaca ccaggaatgt cactgttaaa    1500
gagccattgg ttgcagcaag aaaggttcaa ctgagagttt cggcggttgt tctctgatagc    1560 aatcagctca gtttcactta tgatctttcc tcaatggttg gaattgatct atccagcaat    1620
tcgcttcatg gggaaattcc aaggggctta tttggtctag ctggcctaga atatctgaac    1680
ttgtcatgca actttcttta cggacagctt ccggggttgc agaaaatgca tagtttgaaa    1740
gccttggatt tgtcacataa ttccttgtct ggacatatcc aggaaacat tctagccttt    1800 caagatctgt ccattttgaa tctttcctac aactgtttttt ctggatatgt tccccagaag    1860
caagggtatg ggagatttcc cggtgcattt gctggaaatc cagatctgtg catggaaact    1920
tccagtggag tatgtgatga tggaaggact caatctgcgc aaggaagttc tttcagtgaa    1980
gataggatgg atggcccaat ttctgtgggg attttcttta tcagtgcctt tgttagtttt    2040
gattttggtg ttgtggttct cttctgttct gcccgggcaa gaaattacat tctccaaaca    2100
aaagtttga                                                             2109
```

<210> SEQ ID NO 55
<211> LENGTH: 702
<212> TYPE: PRT
<213> ORGANISM: Glycine max

<400> SEQUENCE: 55

-continued

```
Met Pro Thr Gln Phe Leu Phe Cys Phe Lys Leu Leu Ser Pro Phe Leu
1               5                   10                  15

Lys Ile Ala Pro Leu Leu Ser Trp Ser Ser Leu Pro Asn Pro Asn Gln
            20                  25                  30

Ser Leu Pro Ser Trp Val Gly Ser Asn Cys Thr Ser Trp Ser Gly Ile
        35                  40                  45

Thr Cys Asp Asn Arg Thr Gly Arg Val Leu Ser Ile Asn Leu Thr Ser
    50                  55                  60

Met Asn Leu Ser Gly Lys Ile His Pro Ser Leu Cys Tyr Leu Ser Tyr
65                  70                  75                  80

Leu Asn Lys Leu Gly Leu Ser His Asn Asn Phe Thr Ser Pro Leu Pro
                85                  90                  95

Glu Cys Phe Gly Asn Leu Leu Asn Leu Arg Ala Ile Asp Leu Ser His
            100                 105                 110

Asn Arg Leu His Gly Ile Pro Asp Ser Phe Met Arg Leu Arg His
        115                 120                 125

Leu Thr Glu Leu Val Leu Ser Gly Asn Pro Asp Leu Gly Gly Pro Leu
130                 135                 140

Pro Ala Trp Ile Gly Asn Phe Ser Ala Asn Leu Glu Arg Leu His Leu
145                 150                 155                 160

Gly Phe Cys Ser Phe Ser Gly Gly Ile Pro Glu Ser Leu Leu Tyr Leu
            165                 170                 175

Lys Ser Leu Lys Tyr Leu Asp Leu Glu Asn Asn Leu Leu Ser Gly Asn
            180                 185                 190

Leu Val Asn Phe Gln Gln Pro Leu Val Leu Leu Asn Leu Ala Ser Asn
        195                 200                 205

Gln Phe Ala Gly Thr Leu Pro Cys Phe Ala Ala Ser Val Gln Ser Leu
210                 215                 220

Thr Val Leu Asn Leu Ser Asn Asn Ser Ile Val Gly Leu Pro Ala
225                 230                 235                 240

Cys Ile Ala Ser Phe Gln Ala Leu Thr His Leu Asn Leu Ser Gly Asn
            245                 250                 255

His Leu Lys Tyr Arg Ile Tyr Pro Arg Leu Val Phe Ser Glu Lys Leu
            260                 265                 270

Leu Val Leu Asp Leu Ser Asn Asn Ala Leu Ser Gly Pro Ile Pro Cys
            275                 280                 285

Lys Ile Ala Glu Thr Thr Glu Lys Leu Gly Leu Val Leu Leu Asp Leu
        290                 295                 300

Ser His Asn Gln Phe Ser Gly Glu Ile Pro Val Lys Ile Thr Glu Leu
305                 310                 315                 320

Lys Ser Leu Gln Ala Leu Phe Leu Ser His Asn Leu Leu Ser Gly Glu
            325                 330                 335

Ile Pro Ala Arg Ile Gly Asn Leu Thr Tyr Leu Gln Val Ile Asp Leu
        340                 345                 350

Ser His Asn Ser Leu Ser Gly Thr Ile Pro Phe Ser Ile Val Gly Cys
        355                 360                 365

Phe Gln Leu Tyr Ala Leu Ile Leu Thr Asn Asn Leu Ser Gly Val
    370                 375                 380

Ile Gln Pro Glu Phe Asp Ala Leu Asp Ile Leu Arg Ile Leu Asp Ile
385                 390                 395                 400

Ser Asn Asn Arg Phe Ser Gly Ala Ile Pro Leu Thr Leu Ala Gly Cys
                405                 410                 415
```

-continued

Lys Ser Leu Glu Ile Val Asp Phe Ser Ser Asn Glu Leu Ser Gly Ser
             420                 425                 430

Leu Asn Asp Ala Ile Thr Lys Trp Thr Asn Leu Arg Tyr Leu Ser Leu
         435                 440                 445

Ala Gln Asn Lys Phe Ser Gly Asn Leu Pro Ser Trp Leu Phe Thr Phe
450                 455                 460

Asn Ala Ile Glu Met Met Asp Phe Ser His Asn Lys Phe Thr Gly Phe
465                 470                 475                 480

Ile Pro Asp Ile Asn Phe Lys Gly Ser Leu Ile Phe Asn Thr Arg Asn
                485                 490                 495

Val Thr Val Lys Glu Pro Leu Val Ala Ala Arg Lys Val Gln Leu Arg
            500                 505                 510

Val Ser Ala Val Val Ser Asp Ser Asn Gln Leu Ser Phe Thr Tyr Asp
        515                 520                 525

Leu Ser Ser Met Val Gly Ile Asp Leu Ser Ser Asn Ser Leu His Gly
530                 535                 540

Glu Ile Pro Arg Gly Leu Phe Gly Leu Ala Gly Leu Glu Tyr Leu Asn
545                 550                 555                 560

Leu Ser Cys Asn Phe Leu Tyr Gly Gln Leu Pro Gly Leu Gln Lys Met
                565                 570                 575

His Ser Leu Lys Ala Leu Asp Leu Ser His Asn Ser Leu Ser Gly His
            580                 585                 590

Ile Pro Gly Asn Ile Ser Ser Leu Gln Asp Leu Ser Ile Leu Asn Leu
        595                 600                 605

Ser Tyr Asn Cys Phe Ser Gly Tyr Val Pro Gln Lys Gln Gly Tyr Gly
610                 615                 620

Arg Phe Pro Gly Ala Phe Ala Gly Asn Pro Asp Leu Cys Met Glu Thr
625                 630                 635                 640

Ser Ser Gly Val Cys Asp Gly Arg Thr Gln Ser Ala Gln Gly Ser
                645                 650                 655

Ser Phe Ser Glu Asp Arg Met Asp Gly Pro Ile Ser Val Gly Ile Phe
            660                 665                 670

Phe Ile Ser Ala Phe Val Ser Phe Asp Phe Gly Val Val Val Leu Phe
        675                 680                 685

Cys Ser Ala Arg Ala Arg Asn Tyr Ile Leu Gln Thr Lys Val
690                 695                 700

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
tcatgataag tgtgggaagt cg                                          22

<210> SEQ ID NO 57
<211> LENGTH: 24
<212> TYPE: DNA
<213> ORGANISM: Artificial Sequence
<220> FEATURE:
<223> OTHER INFORMATION: primer

<400> SEQUENCE: 57
tagtaaaacc ccaaagggt cctc                                         24

-continued

```
<210> SEQ ID NO 58
<211> LENGTH: 27
<212> TYPE: DNA
<213> ORGANISM: Artificial Sequence
<220> FEATURE:
<223> OTHER INFORMATION: primer

<400> SEQUENCE: 58
gcgtcgactc atgataagtg tgggaag                                          27

<210> SEQ ID NO 59
<211> LENGTH: 29
<212> TYPE: DNA
<213> ORGANISM: Artificial Sequence
<220> FEATURE:
<223> OTHER INFORMATION: primer

<400> SEQUENCE: 59
ctggtggatc ctagtaaaac cccaaaagg                                        29

<210> SEQ ID NO 60
<211> LENGTH: 2484
<212> TYPE: DNA
<213> ORGANISM: Solanum tuberosum

<400> SEQUENCE: 60
tcatgataag tgtgggaagt cgctagtgta ctcgatgatt gaatgaccta tcgacttgca      60 tcgattttg gtacaaaggt tcgaatcctt tttactccac attatgaact cccgatcgaa      120
tttgtcaaga acgagcttcc cctttcctaa gatcctgaat gtggtactga cgcatcatat     180
gtttgtcaac atgtctactt atatgtcaag gatagttaga atatttttag tgttctgttc     240 taagttttt gtattttgct attttataga aaataatgta aaaagtatta taaataataa      300
taatcaagaa aacttaaaat atctaaaaac atataaagaa aattggttta ctctaaaaat     360
tctacctatg acacataatt tgagataaac agagtaacat atttatataa aaattacata    420
aaatgtatta taaattacaa taattaacta cttaaatatt taaaaacttt taaaaaaatg    480
tgagtgactt tttgaaattt catttgtatc acataaactg ggagggagta gggctgtgaa    540
aaaatcgaat cgaaaaaaat gttattggat tattcttatt tgtacgggtt ttaatggttt    600
tataaaaaaa tcatcgggtt atcgatttga tattagtttt taatattggg ttactgagta    660
aatcgataac acattaagac tatagtaatt tactactttt acatgtacag aaatattaaa    720
tattaatctc ataccttaa tagttactgt atgtgccatt tagccttcaa ttcacacttc      780
acagtgtctt tgagttcaca aattctcatt atacaaaatg tcaaagccta agtaagaat      840 cttattcctc ttaatttctc tttgtgttac acttgtatag ttcttttcat cttagttatt    900
attgtttcta ttttatgagc atttataaag taacactatt gtcttattgc gtcaaatttg    960
ttagagaagt catatattta ttttataagc attttcttat tagttaaacc aaaaatcaaa   1020
ccgttaaaga ctaaaacgat aaaccaaagt cgagctgaac ggatgcacac ccctaggatg    1080
gagtaacata tattatgtga aaaaattatg ttcaaaacat actataaatc attataatta   1140
acaatttaag atattttttt taaaaaaagc atatgatttt ttatggactc tcgaaattca   1200
tctgtggcac ataaattgtt acaatgaag taatatatat tgggtgaaaa ttactttgaa    1260
atagtaaaaa aatcataata attaacaact taaaatactt ttaaaaacat ataattttttt   1320 ttgattaaat ctaagcttta tctgtgtaac ataaaattta aataaaaaaa taatactccc   1380
tccgcttcaa aataattgaa ttattgagac tttttcatat ttcaaattaa cttaattgtt   1440
```

```
gaatcttcaa gactactttt aaaatattct ctcattttttt tttctttctt ttggatttttc    1500 tatgtgatga gtttaagaaa tttaattatt ttaaattatt ctaaagataa atttaacaat    1560
aactaataag tgcaaaaaag aaaaataata tttaaattat gtccaattttt tttatcttaa    1620 aaagatgtgg aacatcttca acaattcaat gaatctatgt cctaaacttt ttttcttaaa    1680
aatgtataaa ataacttgaa caattcaatt attttgaaat gaaaataaca tatattaaat    1740
acgtgccgca cgaagggtgt atgtagtaga ttatatagtt tggaaaaatc ttttttggcca    1800 gaaaatttgg ccagaatgat attttatcta tgttattttta ctttctaaaa atatttttac    1860
ccttttaact ttaatatatt ttaactaaaa agtgaaaaca atatcaattt attttaaaat    1920
taaaaaaata ttataatttt tttaattttt taaccatttta gcacctccca tatatttta    1980 cggtggtcca tattaatgag cgaggggag gtagatgatg catttattgt gcggcatggt    2040 gtccatttttt ttttaccgaa gtatgtacac cagacccccac caatccatca ctctcttcaa    2100
ctgaccccac actttctcta tttaacaaaa tactaatcaa aattaataat cttgagacga    2160
gaacaaaaac gaaaacagtt gagcaaagaa ttaatggaaa atgaacgtac aaaaaagaag    2220
aagagacaat tcatagaaaa atgagaaatt gaaaaaaaca gcagcaacgc gttttctctc    2280
ttgtctctct tttaagtctt cttctctctc ctcttcttga ctctctctct ctgttcacaa    2340
ccaagcagcc ccaaaaacta gggttagggc tagggttttt gagtttcaaa accccatttc    2400
tgcttcctat aatcttcaca tacaagggga atttgggtct gtattttttt ttgcattttt    2460 gaggacccttt ttgggggttttt acta                                           2484

<210> SEQ ID NO 61
<211> LENGTH: 3378
<212> TYPE: DNA
<213> ORGANISM: Lycopersicon esculentum

<400> SEQUENCE: 61
atgggtcgtt gttgttttgt catcaaatgg tactatcatg acataccctt gaaagttttt      60
ctcatccttt gtgttttctt cttagttcat ggctatgcac tttcctcgga ttcggataaa     120
tcagcgctct tggagttaaa ggcctcattt tcagattcct ctggagtgat ttctagctgg     180
agctccagaa ataatgatca ctgttcatgg tttggtgtct cctgtgattc cgattcacgt     240
gttgtggctt tgaacatcac tggaggtaat ttggttcttt tatcttgtgc taaaattgct     300
caatttcctt tgtatggctt tggaattaca agggtttgtg ctaataatag tgtcaagctt     360
gttggtaaag tacctctcgc aatatcaaaa ttaactgaac taagggtttt atccttgcct     420
tttaatgaat tgcgtggtga tattccattg ggaatttggg atatggacaa acttgaagtt     480
ttggatctgc aagggaattt aattactggg tctttgccat ggagtttaa ggggttgagg     540 aaattgaggg ttttaaactt gggttttaat cagattgtgg gtgccatacc gaattccttg     600
tcaaattgcc ttgctctaca aatctttaat cttgctggaa atagggtaaa tgggaccatt    660
ccagcattca ttggtggatt tgaagatctg agggaatct acctgtctt taatgagctt     720 agcgggtcta ttcctggtga aattgggcgt tcttgtgaga aacttcaaag tctagagatg     780
gcaggtaata tcttaggtgg tgttattcca aaaagtttag ggaactgcac acggttgcag    840
tcacttgtct tatattcaaa tttgttggaa gaggctattc cagctgaatt tggtcaacta    900
actgagctcg agattcttga tttgtctagg aacagcctaa gtggtcgact accatctgag    960 ctgggaaaact gctcgaaact atccattctt gtactgtcaa gtttgtggga tccccttcca   1020
aatgtgtctg attcagctca tactactgat gagtttaact ttttgaagg cacaatccca   1080
```

```
tcagagatca ccaggcttcc tagtttgaga atgatatggg ctcccaggtc aactctttca    1140
ggaaaatttc ctggcagttg gggtgcttgt gacaatttgg agatcgtgaa cttggctcaa    1200
aattattata ctggagtgat ttctgaggaa ttgggtagct gccagaagtt gcattttctt    1260
gacttgagct caaataggct gactggacag cttgttgaga aactgccagt tccttgcatg    1320
tttgtgttcg atgtgagtgg gaattatctc tctggttcaa ttcccaggtt ttccaattac    1380
agttgtgctc atgttgtttc cagcggtgga gatccatttg ggccctatga tacatcatct    1440
gcatatctag cacatttcac cagtagaagt gttctagaca ctacattatt tgcaggtgat    1500
ggtaaccatg cagtatttca taatttcggt gttaacaact tcacgggaaa tttaccgcct    1560
tccatgctaa ttgcacctga aatgttaggc aaacaaattg tatacgcatt tcttgctggt    1620
agtaacaggt ttactggacc ttttgctggt aacttgttcg agaaatgtca tgaattgaat    1680
ggaatgattg ttaatgtaag caataatgcg ttgtcaggtc aaatcccaga ggatattggt    1740
gcaatttgtg ggtctcttag gctgttggat ggatccaaaa atcagattgt tgggacagtc    1800
cctccgagtt tagggagtct ggtttcatta gttgctctca atttaagttg gaaccacctg    1860
cgaggtcaga ttcctagcag acttggccag ataaaggatc tcagttacct ctctttggct    1920
ggcaataatc tggttggccc aatcccctca gttttggcc aattgcactc tttagaaacg    1980
cttgaacttt cttcgaattc tttgtctggt gaaattccaa ataatctggt aaatttgagg    2040
aatttgactt cccttcttct gaacaacaac aatttatcag ggaaaatacc ttcaggcttg    2100
gccaatgtga ccacactggc agcatttaac gtttctttca ataatctgtc tgggccactg    2160
cctcttaaca aagatttgat gaagtgtaat agtgttcagg gaaacccctt tctgcaatcg    2220
tgccatgtat tttctctatc aacaccttct acagatcagc agggaagaat aggggactca    2280
caagattctg ctgcgtctcc ttcaggttca acccagaaag gagggagcag cggtttcaac    2340
tccatagaga ttgcatccat aacatctgcg gcagctattg tgtcagttct tcttgctctg    2400
atagtcctgt tcttttacac cagaaaatgg aatccaagat ctagagttgc tggatctacc    2460
aggaaagaag tcacagtgtt tacagaagtt ccggttcctt taacatttga aaatgtagtg    2520
cgggccacag ggagcttcaa tgctagcaat tgcataggca gtggaggttt tggagcaaca    2580
tacaaagcgg agattgcacc agggttccta gtggcagtaa agcgacttgc tgtaggacgt    2640
tttcagggga ttcaacagtt tgatgcagaa atcagaactc tggggaggct cgacatcca    2700 aacctcgtaa ctctgatagg atatcataat agtgaaacag aaatgtttct gatctataac    2760
tatttgccag gtggtaattt ggaaaagttt attcaggaga ggtctacaag ggctgtggac    2820
tggagggttc ttcacaagat tgctttggat gtagcccgtg cacttgctta cctgcatgat    2880
cagtgtgtac cacgtgtgct tcatcgtgat gtgaagccga gcaacatttt attggatgag    2940
gagtataatg catatttatc tgattttggt ttggctagat tactgggaac ttcagagacc    3000
catgcaacta ctggtgtggc gggaactttt ggatatgttg ctcctgaata tgccatgact    3060
tgccgcgtct cggacaaggc tgatgtctac agttatgggg ttgtgttgct tgagttaata    3120
tcagataaga aagcacttga tccgtctttc tcttcttatg gaaatggatt caatattgtt    3180
gcttgggcat gcatgctttt acggcagggc cgtgctaagg agttctttac ggctggtcta    3240
tgggattcag gtccacatga tgatttggtt gaggtcctac acttggctgt ggtctgcacg    3300
gttgactctc tttctactag acctacaatg aagcaagtag taagacggtt gaagcaactt    3360 caaccccgt cgtgttag                                                   3378
```

<210> SEQ ID NO 62
<211> LENGTH: 21
<212> TYPE: DNA
<213> ORGANISM: Lycopersicon esculentum

<400> SEQUENCE: 62
gggaatctac ctgtctttta a                                        21

<210> SEQ ID NO 63
<211> LENGTH: 2928
<212> TYPE: DNA
<213> ORGANISM: Solanum tuberosum

<400> SEQUENCE: 63

```
atggaggtga gcgtgaagat gaaattcccc tcacaagcac tactgttggc tctattgctt    60
gttttaccga tcgttttagc tctcaccgaa gaaggcaaag cattaatgtc gatcaaggca   120
tcgtttagca acgtggcaaa cgtgttgcta gattgggatg atgtccacga cgaggatttt   180
tgctcatggc gaggcgtgtt gtgtggaaat ttctccattt ccgtcgttgc cctgaatctg   240
tctaatctta acttgggcgg ggaaatttca ccagccattg agatttgaa gaatctagag    300
acattagacc ttcagggaaa taaattaact ggtcaagtcc cagatgaaat tggcaactgc   360
atttcactga tctatcttga tttgtctgat aacttgctct atggagatat accttttctca  420
atttctaagc tcaagcagct agagttattg aacctgaaaa acaaccagtt gtctggccca   480
atcccatcca cattaactca aatccctaat ctaaagacgc ttgatctggc tcgaaaccag   540
ctcattggtg agataccaag gttgatctat tggaatgaag ttctgcaata ccttggctta   600
agaggcaaca tgttgacagg aacattgtcc cctgatatgt gccagttgac tggtttgtgg   660
tattttgatg tgcgggggcaa taacctcagt ggaatagttc cagataatat tgggaattgt  720
acaagttttg agatactgga tatctcatac aatcagataa ctggagaaat tccctacaat   780
attggatttt tacaagtggc taccttgtct ttgcgaggaa atagactaac tgggaagatc   840
ccagaagtga ttggtctaat gcaagctctt gctgttctgg acttgagtga aatgagttg    900
gtgggaccaa ttcctccaat cttttggcaat ttatcctaca ctgggaaact gtacctgcac  960
ggcaacaaac ttacagggcc aataccaccg gagctaggaa atatgtctaa acttagttac  1020
ttgcgattaa atgacaatca gctaatgggg cgaattccct ccgaacttgg caaactggac  1080
cagttatttg aattgaatct tgcaaataac aagttggagg gaccaattcc tgaaaatatc  1140
agctcctgct cggcattgaa tcaacttaat gttcatggca acaacttaaa cgggtccatt  1200
ccttcagggt ttaagaatct tgagagcctg acatatctaa atctttcagc aaataaattt  1260
aaaggtcaca taccctctca actagggcga atcatcaacc ttgatacatt ggatctctct  1320
ggcaatgaat tttctgggtc tatccctggt tctattggag atttggagca tctcctcaca  1380
ctgaatctga gcagcaatca tcttgatgga caaattcctg tagaatttgg caatctgaaa  1440
agtatacaga ccattgatat gtcatgcaac aagatttctg gtgccatccc aaaagagctg  1500
ggacagctgc agaccatgat aactcttact ttgacagcta acgatcttag tggagcaatc  1560
cctgaccaat tgaccaattg tttcagccta actagtttga atatatccta caacaatttt  1620
agtggtgttg ttcctctttc acggaatttc tcgcggtttg cacctgacag cttttggggg  1680
aacccatttc tttgtggcaa ctggaaaggc tcaatatgtg accctatgc accaaggtct  1740
aacgccttgt tctctagaac agctgttgtt tgcacagcat gggtttcat agcactctta  1800
tccatggtta tagtggcagt gtacaagtcc aaccaaccac accagtttct gaaggggcct  1860
```

```
aagaccaatc aaggttcccc caaacttgtg gttcttcaca tggatatggc catccataca    1920
tatgatgaca ttatgaggat tactgagaac ttcaatgaga aattcatcat aggatatggt    1980
gcttccagca ctgtatataa atgtgttttg aaagattccc gaccgattgc cgttaagcga    2040
ctttacacta cacatccgca cagcttgcga gagtttgaga ctgaactgga gaccattgga    2100
agcatcaggc atagaaacct tgttagcttg catggttact ccctttcccc tcgtgggaat    2160
ctcctttgtt acgactactt ggagaatggt tcactctggg atctacttca tgggccttcc    2220
aaaaaggtga agcttgactg ggaaacacgt ctgaggattg ctgttggtgc tgctcagggt    2280
cttgcttatc ttcaccacga ttgcaaccca agaatcatcc acagagatgt gaaatcttca    2340
aacattcttg ttgatgaaaa ttttgaggct catctttctg attttggggt gcaaaatgc     2400 atcccttctg caaaaactca tgcatcaact ttggtgttgg gcaccatagg ttacattgac    2460
cctgagtatg ccaggacttc ctggttaact gaaaaatcag acgtctacag ctttggcatt    2520
gttctcctag agcttttgac aggaaagaaa ccggttgata tgacttgaa cctgcatcag    2580 ctgataatgt caaaggcgga tgataacacc gtgatggatg ctgttgatcc tgaggtatct    2640
gttacatgta tggacttaac acatgtgagg aaaacttttc agcttgcgtt gctgtgtaca    2700
aaaagatttc catgtgagag gccaacgatg catgaggttg ctagggtact tgtttccttg    2760
cttcctcccc cgccaaccaa accttgttta gacccacctc ccaaatccat tgattataca    2820
aagtttgtga ttgggaaagg actaccgcaa gttcagcagg gtgatgattc ctccgaagca    2880
cagtggcttg ttagatttca agaagctata tccaaaaact ccctttga                 2928
```

<210> SEQ ID NO 64
<211> LENGTH: 2241
<212> TYPE: DNA
<213> ORGANISM: Lycopersicon esculentum

<400> SEQUENCE: 64

```
atggcagaat cacttgttga accttgtaca acctcttatc cccttaaagt ttcaatcttt     60
atcctattct tcttgatttt cccttttcttg aacccatttt catctgcatt tcctctttct    120
catgatacta atgcaactgg ggtgttcaat cttgaaacag aagaggacat gggtttgctt    180
ttgttcttca agttacagtt tcaagaaacc cctttatcaa gctgggatgt tagtgttcct    240
ctgtcaaact ggactggtgt tacccggtct aaccagacag ggcgggtcac tggacttaac    300
ctcacaaggt ttaacttgtc aggacaggtt catccttgtt tgtgtaatct tacttttctt    360
gaaacccttg tgttgtctca taatagcttt aacaattcaa taccttcttg tttatggaag    420
ttgtggagtc ttaagacctt agatcttagc tataatattt ttactcttct tgttcctagt    480
acatttgcag caactatgag taagttaatt gagcttgacc ttagtcataa catgttgagt    540
ggtgaaatcc caatgtggat agggaatgtc tcaatgtcac ttgaaaaact caacttgggg    600
tttaatagtt tcatgggga tatacctaag agcttgttga atttgatgtc tttgaagtat    660
cttgatttgt ctcataatag tttgatggga aatgtgggtg attttaacca agaattggtc    720
acacttaatc ttgagtctaa tttgttatcg ggtactttgc cttgtttata ttcgtcaaga    780
gaatcactta cacttcttaa tttagcaaac aattcgattc ttggaggtat accaacgtgt    840
ctctcgagtc ttgggggttt gacacagctc aacttgtcac acaatgaatt acgatatggt    900
atctcgccta gactggtttt ttcagagagg ttatgtttgt tggacttgag ttataatgag    960
ctatcaggga agattccaag taggattgtc gaggcatcgg acaagtctgg actactactt    1020
```

```
cttgacctgt ctcacaatca gttctctggt aatattcctg taacgataac agaattgaag    1080
agcttgcaag cgttgtttct gtcttataat cttcttgtgg gcgaaatacc agaaaggatt    1140
ggtaatttga cctatctaca ggtgattgat ctctcacata acttcctcac tggctcgatt    1200
cctttgaaca ttgtaggatg tttccaacta ctggcgctga tactaaacag taataatctt    1260
tctggggaaa ttcagccagt gcttgacgcg ttggatagtc taaagatatt tgatatagga    1320
aacaacaaga tttctggtga gatcccactg acattggcag gctgcaagtc gttggaagtt    1380
gttgacttaa gctctaacaa tctctcagga tctctaaatg atgcaataac caaatggtca    1440
aacctcaaat tcctctccct tgctaggaac aagttcagtg gatctctgcc aagttggttg    1500
tttacatttc aggctattca tactctagat tttctggaa acaaattctc aggatatata     1560
ccagatggta actttaacac tagtccaaat ttctacaacg gcgacattag gaaaaccatt    1620
tctgcagtac catcaatttc agctcgaagc ctggatatca aactttcact cgttgctgat    1680
gaaactagtt tgagcttcaa gtataacctc acaaccacaa ttggaattga tctgtctgac    1740
aatttgcttc atggtgaaat tccagaaggt ctgttcggat tacatggtct ggagtacctt    1800
aacttgtcat acaattttct taatggtcca gttccaggga gtttagggaa gttgcagaag    1860
ctaaaggcac ttgatttgtc acacaattct ttatctggcc acatccctga aaacattact    1920
tccctcagaa atttgacagt tttaaatctt tcatataatt gtttctctgg tgttatttcg    1980
acaaaacgag gttattggaa atttcctgga gcatttgctg gcaatccaga cttgtgtatg    2040
gaatcatctg gtaatgtctg tcaaagaact ttgcctgtaa agccagggaa gaaatttgaa    2100
gaggaaatgg aagagggacc attatcagtt tggattttct gtataagtgc tttagttagc    2160
ttctatgttg gcgttgtcgt tttattttgt tcatctcgaa caagaagctg tattctgcaa    2220
acaaaaaatt tagcaggttg a                                              2241
```

<210> SEQ ID NO 65
<211> LENGTH: 2241
<212> TYPE: DNA
<213> ORGANISM: Lycopersicon esculentum

<400> SEQUENCE: 65

```
atggcagaat cacttgttga accttgtaca acctcttatc cccttaaagt ttcaatcttt     60
atcctattct tcttgatttt ccctttcttg aacccatttt catctgcatt tcctcttttct   120 catgatacta atgcaactgg ggtgttcaat cttgaaacag aagaggacat gggtttgctt    180
ttgttcttca agttacagtt tcaagaaacc cctttatcaa gctgggatgt tagtgttcct    240
ctgtcaaact ggactggtgt tacccgtgtct aaccagacag ggcgggtcac tggacttaac    300
ctcacaaggt taacttgtc aggacaggtt catccttgtt tgtgtaatct tacttttctt    360
gaaacccttg tgttgtctca taatagcttt aacaattcaa taccttcttg tttatggaag    420
ttgtggagtc ttaagacctt agatcttagc tataatattt ttactcttct tgttcctagt    480
acatttgcag caactatgag taagttaatt gagcttgacc ttagtcataa catgttgagt    540
ggtgaaatcc caatgtggat agggaatgtc tcaatgtcac ttgaaaaact caacttgggg    600
tttaatagtt tcatgggga tatacctaag agcttgttga atttgatgtc tttgaagtat     660
cttgatttgt ctcataatag tttgatggga aatgtgggtg attttaacca agaattggtc    720
acacttaatc ttgagtctaa tttgttatcg ggtactttgc cttgttatat tcgtcaaga     780 gaatcactta cacttcttaa tttagcaaac aattcgattc ttggagggtat accaacgtgt   840 atctcgagtc ttgggggttt gacacagctc aacttgtcac acaatgaatt acgatatggt    900
```

| | |
|---|---|
| atctcgccta gactggtttt ttcagagagg ttatgtttgt tggacttgag ttataatgag | 960 |
| ctatcaggga agattccaag taggattgtc gaggcatcgg acaagtctgg actactactt | 1020 |
| cttgacctgt ctcacaatca gttctctggt aatattcctg taacgataac agaattgaag | 1080 |
| agcttgcaag cgttgtttct gtcttataat cttcttgtgg gcgaaatacc agaaaggatt | 1140 |
| ggtaatttga cctatctaca ggtgattgat ctctcacata acttcctcac tggctcgatt | 1200 |
| cctttgaaca ttgtaggatg tttccaacta ctggcgctga tactaaacag taataatctt | 1260 |
| tctggggaaa ttcagccagt gcttgacgcg ttggatagtc taaagatatt tgatatagga | 1320 |
| aacaacaaga tttctggtga gatcccactg acattggcag gctgcaagtc gttggaagtt | 1380 |
| gttgacttaa gctctaacaa tctctcagga tctctaaatg atgcaataac caaatggtca | 1440 |
| aacctcaaat tcctctccct tgctaggaac aagttcagtg gatctctgcc aagttggttg | 1500 |
| tttacatttc aggctattca tactctagat ttttctggaa acaaattctc aggatatata | 1560 |
| ccagatggta actttaacac tagtccaaat ttctacaacg gcgacattag gaaaaccatt | 1620 |
| tctgcagtac catcgatttc agctcgaagc ctggatatca aactttcact cgttgctgat | 1680 |
| gaaactagtt tgagcttcaa gtataacctc acaaccacaa ttggaattga tctgtctgac | 1740 |
| aatttgcttc atggtgaaat tccagaaggt ctgttcggat tacatggtct ggagtacctt | 1800 |
| aacttgtcat acaattttct taatggtcca gttccaggga gtttagggaa gttgcagaag | 1860 |
| ctaaaggcac ttgatttgtc acacaattct ttatctggcc acatccctga aaacattact | 1920 |
| tccctcagaa atttgacagt tttaaatctt tcatataatt gtttctctgg tgttatttcg | 1980 |
| acaaaacgag gttattggaa atttcctgga gcatttgctg gcaatccaga cttgtgtatg | 2040 |
| gaatcatctg gtaatgtctg tcaaagaact ttgcctgtaa agccagggaa gaaatttgaa | 2100 |
| gaggaaatgg aagagggacc attatcagtt tggatttct gtataagtgc tttagttagc | 2160 |
| ttctatgttg gcgttgtcgt tttatttgt tcatctcgaa caagaagctg tattctgcaa | 2220 |
| acaaaaaatt tagcaggttg a | 2241 |

<210> SEQ ID NO 66
<211> LENGTH: 2241
<212> TYPE: DNA
<213> ORGANISM: Lycopersicon esculentum

<400> SEQUENCE: 66

| | |
|---|---|
| atggcagaat cacttgttga accttgtaca acctcttatc cccttaaagt ttcaatcttt | 60 |
| atcctattct tcttgatttt cccttcttg aacccatttt catctgcatt tcctctttct | 120 |
| catgatacta atgcaactgg ggtgttcaat cttgaaacag aagaggacat gggtttgctt | 180 |
| ttgttcttca agttacagtt tcaagaaacc cctttatcaa gctgggatgt tagtgttcct | 240 |
| ctgtcaaact ggactggtgt tacccggtct aaccagacag ggcgggtcac tggacttaac | 300 |
| ctcacaaggt ttaacttgtc aggacaggtt catccttgtt tgtgtaatct tacttttctt | 360 |
| gaaacccttg tgttgtctca taatagcttt aacaattcaa taccttcttg tttatggaag | 420 |
| ttgtggagtc ttaagacctt agatcttagc tataatattt ttactcttct tgttcctagt | 480 |
| acatttgcag caactatgag taagttaatt gagcttgacc ttagtcataa catgttgagt | 540 |
| ggtgaaatcc caatgtggat agggaatgtc tcaatgtcac ttgaaaaact caacttgggg | 600 |
| tttaatagtt tcatgggga tatacctaag agcttgttga atttgatgtc tttgaagtat | 660 |
| cttgatttgt ctcataatag tttgatggga aatgtgggtg attttaacca agaattggtc | 720 |

-continued

| | |
|---|---|
| acacttaatc ttgagtctaa tttgttatcg ggtactttgc cttgtttata ttcgtcaaga | 780 |
| gaatcactta cacttcttaa tttagcaaac aattcgattc ttggaggtat accaacgtgt | 840 |
| ctctcgagtc ttgggggttt gacacagctc aacttgtcac acaatgaatt acgatatggt | 900 |
| atctcgccta gactggtttt ttcagagagg ttatgtttgt tggacttgag ttataatgag | 960 |
| ctatcaggga agattccaag taggattgtc gaggcatcgg acaagtctgg actactactt | 1020 |
| cttgacctgt ctcacaatca gttctctggt aatattcctg taacgataac agaattgaag | 1080 |
| agcttgcaag cgttgtttct gtcttataat cttcttgtgg gcgaaatacc agaaggatt | 1140 |
| ggtaatttga cctatctaca ggtgattgat ctctcacata acttcctcac tggctcgatt | 1200 |
| cctttgaaca ttgtaggatg tttccaacta ctggcgctga tactaaacag taataatctt | 1260 |
| tctggggaaa ttcagccagt gcttgacgcg ttggatagtc taaagatatt tgatatagga | 1320 |
| aacaacaaga tttctggtga gatcccactg acattggcag gctgcaagtc gttggaagtt | 1380 |
| gttgacttaa gctctaacaa tctctcagga tctctaaatg atgcaataac caaatggtca | 1440 |
| aacctcaaat tcctctccct tgctaggaac aagttcagtg gatctctgcc aagttggttg | 1500 |
| tttacatttc aggctattca tactctagat ttttctggaa acaaattctc aggatatata | 1560 |
| ccagatggta actttaacac tagtccaaat ttctacaacg gcgacattag gaaaaccatt | 1620 |
| tctgcagtac catcaatttc agctcgaagc ctggatatca aactttcact cgttgctgat | 1680 |
| gaaactagtt tgagcttcaa gtataacctc acaaccacac ttggaattga tctgtctgac | 1740 |
| aatttgcttc atggtgaaat tccagaaggt ctgttcggat acatggtct ggagtacctt | 1800 |
| aacttgtcat acaattttct taatggtcca gttccaggga gtttagggaa gttgcagaag | 1860 |
| ctaaaggcac ttgatttgtc acacaattct ttatctggcc acatccctga aaacattact | 1920 |
| tccctcagaa atttgacagt tttaaatctt tcatataatt gtttctctgg tgttatttcg | 1980 |
| acaaaacgag gttattggaa atttcctgga gcatttgctg gcaatccaga cttgtgtatg | 2040 |
| gaatcatctg gtaatgtctg tcaaagaact ttgcctgtaa agccagggaa gaaatttgaa | 2100 |
| gaggaaatgg aagagggacc attatcagtt tggattttct gtataagtgc tttagttagc | 2160 |
| ttctatgttg gcgttgtcgt tttatttttgt tcatctcgaa caagaagctg tattctgcaa | 2220 |
| acaaaaaatt tagcaggttg a | 2241 |

<210> SEQ ID NO 67
<211> LENGTH: 2961
<212> TYPE: DNA
<213> ORGANISM: Lycopersicon esculentum

<400> SEQUENCE: 67

| | |
|---|---|
| atgtcactac ccaaaaaaat atccctttc ctccaaattt tcatctttt tgttttcacc | 60 |
| attaatgcaa actctgatct tgaagccctt ttgaagctca agaatccat ggttgctcct | 120 |
| ggaacttctg cacttcttga ttggaacaac aacacaaaaa attacccttt ttcccattgt | 180 |
| tcttttttctg gtattacatg taacaataac tctcatgtta tatctattaa catcactaat | 240 |
| gttcctctat ttggtactat tccacctgaa attggtcttt tacaaaatct tgaaaatctt | 300 |
| actattttg gtgataatct tactggtaca ctcccttag aaatgtcaca actttcttct | 360 |
| attaaacatg ttaatctttc ttacaacaat tttttctggtc cttttccaag agaaatcctg | 420 |
| ttggggttaa taaagcttga atcttttgac atttataaca acaatttcac tggtgaactt | 480 |
| cctattgagg ttgtaaagtt gaaaaatttg gaaactttac atcttggtgg aaactattt | 540 |
| catggtgaaa taccagaagt ttattcccat attgtaagtt taaagtggtt gggtttagag | 600 |

```
ggaaattcac ttactgggaa ataccaaag  agtttggctt tgttaccaaa tcttgaagaa     660
cttagattgg gttactataa tagttatgaa gggggtattc catctgagtt tggtaatatt     720
agtacactta aacttcttga tcttggaaat tgtaatcttg atggtgaagt tcctccaagt     780
cttggaaatt tgaagaagtt gcattctttg tttctacaag tgaacagact tacaggtcac     840
ataccttctg aactatctgg tttagagagt ttgatgtcgt ttgatttgtc gtttaaccaa     900
ctgaccggag aaataccaga gagttttgtg aagttgcaga aattgacatt gattaacttg     960
tttagaaaca acttgcatgg tccaattccc tcttttattg gtgaccttcc gaatcttgaa    1020
gtgttgcaga tttggggaaa caatttact  cttgaattgc ccgaaaatct tgggcgaaac    1080
gggaggcttt tgtttctgga tatttctatt aatcatttta ctggaaggat accacctgat    1140
ttgtgtaaag gagggaagtt aaagacactg attctaatgg agaattactt ctttggccca    1200
attcctgaac aacttggtga gtgcaaatcg cttactcgaa ttcgcgttag gaagaattac    1260
ttaaatggta ctattccagc tggttttttc aagttacctg cattggatat gcttgaactt    1320
gacaacaact atttcactgg tgagctgcca acggagataa acgcgaacaa tctcactaaa    1380
cttgtacttt ccaacaactg gatcacgggg aacattcctc catcattagg gaacttgaag    1440
aatctagtca ctctgtcact tgatgtgaac agattatctg gtgagattcc tcaagaaatt    1500
gcgagtttga taaactcgt  gaccatcaac ttgagtggca acaatttaac aggtgaaatc    1560
ccgagttcaa ttgcgctttg ttcagagcta acactggttg acttgagcag aaaccaactg    1620
gttggtgaag tgccaaaaga aatcaccaag ttaaatagct tgaacgcgct gaacttgtca    1680
agaaaccaac tgagtggcgc cattcctgga gaagtcggag tgatgaatgg cttgacagtt    1740
ttggatcttt cttacaatga tctctctgga aggagaccga ccaacggaca acttaagttc    1800
ttcaatgaca cttactttgt aggaaatcca aaactctgct cgcctcatgc tacttttgc     1860 ccgtcagctt ccaattcacc acaaaacgcg cttaaaatcc atgccgggaa gttcacaact    1920
acccaattgg tgattacaat aatcatctta gtcactgttg cattgctgtt ggcagttacc    1980
gtgctgttca tcaagaagga gaaattcaag aattcgcaac tttggaagtt aacagcattc    2040
cagaaacttg atttcagagc tgacgatgtt ttggagtgtt taaaagagga gaacataatt    2100
gggaaaggtg gagctggtgt tgtgtaccga gggtctatgt caaatggcat cgacgttgca    2160
ataaagaaac ttgtaggccg aggaaccgga caccatgatc acggattctc agctgaaatc    2220
caaacactag gaaggatccg gcacagaaac atcgtacgat tactgggata tgtctcaaac    2280
aaagacacaa acttgttgtt gtacgaatac atgtcaaatg ggagcttagg tgaaatgtta    2340
catggtgcca aggggcaca  tttgaaatgg gagacaaggt accgtattgc tgtggaagct    2400
gcaaaaggat tgtgttattt gcaccatgat tgttcacctt cgattattca cagagatgtc    2460
aagtccaata atattctgct ggattccgat tacgaagcgc atgttgctga tttcggcctc    2520
gccaaattct tgcaggatgc tgtgcatca  gagtgcatgt cctctattgc tggctcatat    2580
ggttacattg ctccagagta tgcatacaca ttgaaagttg accaaaagag tgatgtatac    2640
agttttggag ttgtactgtt ggaacttatc acaggtcaca agccagtagg tgaattcggg    2700
gacggtgtat atatagtgag atgggtgaat aaaacaatgt ccgaattatc tcaaccgtct    2760
gatgcagcct cagttttagc agtcgttgac tcgaggctac atagttaccc tcttgcaagt    2820
gttgtcaatt tgttcaagat tgctatgatg tgtgttgaag aagagagttg tgctaggcct    2880
agcatgaggg aagtggttca catgcttaca aatcctcctc ctcagtctac taacactact    2940
```

```
actactctcc gtgcccttfg a                                                   2961

<210> SEQ ID NO 68
<211> LENGTH: 3051
<212> TYPE: DNA
<213> ORGANISM: Lycopersicon esculentum

<400> SEQUENCE: 68
atgcgtcttc tttttttcct tcttcttcct atgcatttta ctgacttttc tgccggtaaa         60
caaccacgct taccggaata ccaggctttg cttgccctga aaactgccat taccgatgac        120
ccgcagttaa ctcttgcctc atggaacatc tccaccagtc actgtacgtg aatggtgtc         180 acgtgcgaca cgcatcgtca cgtgacctct cttgatattt ctgggtttaa tcttaccggt        240
actcttccgc cggaagttgg aaatcttcgt ttcttacaaa atttgtctgt tgctgttaac        300
cagtttactg gacctgtacc tgttgaaatc tcctttattc caaatctgag ttaccttaat        360
ctttctaata acatattcgg gatggaattc ccttcgcagt taacacgtct gcgtaacctc        420
caagtccttg acctttacaa caacaatatg accggtgaac ttcccgttga ggtgtatcag        480
atgactaaac ttcgacatct acacctaggc gggaactttt tcagtggccg cattcctccg        540
gagtatggaa gattcccgtc tctagagtac cttgcagttt caggcaatgc attggtagga        600
gagataccac cggagattgg aaacatcgct acacttcagc agttgtatgt aggatactac        660
aataccttca ccggtgggat tccaccggca atagggaact tatcgcagct ccttcggttt        720
gatgctgcta actgtggact ttcggggaag attccaccgg agattgggaa gcttcagaac        780
cttgatcccc tcttcctgca agtgaattct ctatctggat cttttaactcc ggagataggt        840 tatctgaaga gcttgaaatc tttggatctg tcgaataaca tgttctctgg cgagataccg        900
ccgacatttg cggagcttaa gaatatcact cttgttaatc ttttccggaa taagctttat        960
gggtcaatac cagagttcat agaggacttg ccggaactag aggtgttgca actttgggaa       1020
aataacttta ctggaagcat tcctcagggg ttaggcacaa agagcaagct caaaactctt       1080
gatctcagtt ccaataaatt aacgggaaat ttaccccccaa acatgtgctc cggtaacaat       1140
ctgcagacaa ttatcactct agggaacttc ttgtttggcc caattcctga atctttgggt       1200
aggtgtgaat cacttaatcg tattagaatg ggagaaaatt atctgaatgg gtctattcca       1260
aaagggctct taagcttgcc acatctgtca caagttgaac ttcagaataa tattctcact       1320
ggtacatttc ctgatatttc ttccaaatct aacagtcttg gccagattat cctttcaaat       1380
aatcgcttaa ctggaccttt gccaccaagc attggaaact ttgctgtagc ccaaaaattg       1440
cttcttgatg ggaacaaatt ttcgggacga attccagctg aaataggaaa gcttcaacag       1500
ctatccaaaa ttgatttcag tcataacaac ttgtctggac ccattgctcc ggagattagc       1560
cagtgcaagt tgctgactta tgttgatctc agcaggaacc aactttcggg tgagattcct       1620
actgagatca caggtatgag aatactcaac tacttgaatt tatcgcgaaa ccacttagtt       1680
gggagtattc ctgcccctat ttctagtatg cagagtttaa cttctgttga tttctcgtat       1740
aacaactttt ctggtttagt tcctggaacc gggcaattta gttatttcaa ttacacctca       1800
tttctaggca atccagatct ttgcggaccc tatttgggcc cttgcaaaga gggcgttgtt       1860
gatggggtta gtcaacctca ccaacgagga gccttaacgc cttcgatgaa gcttttactt       1920
gttataggtt tgcttgtctg ttctattgtg tttgctgttg ctgcaattat aaaggcccga       1980
tctttaaaga aggcaagtga agctcgtgcc tggaagctaa ctgcttttca gcgcctggat       2040
tttacttgtg atgatatttt ggatagcttg aaggaggata acgttattgg aaaaggaggt       2100
```

```
gctggtattg tctacaaggg ggtaatgcct agcggggaac atgtagcggt taagaggttg    2160
ccagctatga gcaggggttc ctctcatgat catgggttca atgcagagat acagactctt    2220
gggaggatcc gacacaggca cattgttaga ttattagggt tttgctcgaa tcatgagaca    2280
aatcttttgg tttacgagta catgcctaat ggaagtcttg gggaaatgct tcatggcaag    2340
aaaggcggtc atttacattg ggataccagg tataagattg ccttggagtc tgctaagggt    2400
cttgtctatc tccatcacga ttgctctcct ttgatcctcc atcgtgatgt gaaatcaaac    2460
aacattctgc tggactccag ctttgaagct catgttgctg attttggact tgctaagttc    2520
ttgcaagatt cagggacatc agaatgcatg tctgctattg ctggttctta tgggtacatt    2580
gctccagaat atgcttacac acttaaggtt gatgagaaga gtgatgtata tagcttcggt    2640
gtggtgctac tagaactggt aagtggcaaa aaaccagttg gagaatttgg tgatggtgtt    2700
gacatagtcc aatgggttag gaaaatgact gatgggaaaa aggatggagt tctcaagatc    2760
cttgacccaa gactctcaac ggttccccct aatgaggtga tgcatgtctt ctatgtcgca    2820
ttgttgtgtg tcgaagagca ggctgtggaa cgtcccacca tgcgagaggt agtgcaaata    2880
ctaacggaac ttcccaagcc accaggtgca aaatcagatg actcaaccgt cactgatcag    2940
tcgcccccat cagcctctgc attagagtcc ccaacctcaa ttcccgggga cacaaaagac    3000
catcatcaac caaacctca atcacctcca cctgacctac tcagtatcta a             3051

<210> SEQ ID NO 69
<211> LENGTH: 3051
<212> TYPE: DNA
<213> ORGANISM: Lycopersicon esculentum

<400> SEQUENCE: 69
atgcgtcttc ttttttttct tcttcttctt atgcatttta ctgacttttc tgccggtaaa      60
caaccacgct taccggaata ccaggctttg cttgccctga aaactgccat taccgatgac     120
ccgcagttaa ctcttgcctc atggaacatc tccaccagtc actgtacgtg gaatggtgtc     180
acgtgcgaca cgcatcgtca cgtgacctct cttgatattt ctgggtttaa tcttaccggt     240
actcttccgc cggaagttgg aaatcttcgt ttccttacaa atttgtctgt tgctgttaac     300
cagtttactg gacctgtacc tgttgaaatc tcctttattc caaatctgag ttaccttaat     360 cttttctaata acatattcgg gatggaattc ccttcgcagt taacacgtct gcgtaacctc     420
caagtccttg acctttacaa caacaatatg accggtgaac ttcccgttga ggtgtatcag     480
atgactaaac ttcgacatct acacctaggc gggaactttt tcagtggccg cattcctccg     540
gagtatggaa gattcccgtc tctagagtac cttgcagttt caggcaatgc attggtagga     600
gagataccac cggagattgg aaacatcgct acacttcagc agttgtatgt aggatactac     660 ataccttca ccggtgggat tccaccggca atagggaact tatcgcagct ccttcggttt     720
gatgctgcta actgtggact ttcggggaag attccaccgg agattgggaa gcttcagaac     780
cttgataccc tcttcctgca agtgaattct ctatctggat ctttaactcc ggagataggt     840
tatctgaaga gcttgaaatc tttggatctg tcgaataaca tgttctctgg cgagataccg     900
ccgacatttg cggagcttaa gaatatcact cttgttaatc ttttccggaa taagctttat     960
gggtcaatac cagagttcat agaggacttg ccggaactag aggtgttgca actttgggaa    1020
ataactttta ctgaagcat tcctcagggg ttaggcacaa agagcaagct caaaactctt    1080
gatctcagtt ccaataaatt aacgggaaat ttaccccca acatgtgctc cggtaacaat    1140
```

```
ctgcagacaa ttatcactct agggaacttc ttgtttggcc caattcctga atctttgggt   1200
aggtgtgaat cacttaatcg tattagaatg ggagaaaatt atctgaatgg gtctattcca   1260
aaagggctct taagcttgcc acatctgtca caagttgaac ttcagaataa tattctcact   1320
ggtacatttc ctgatatttc ttccaaatct aacagtcttg ccagattat cctttcaaat    1380 aatcgcttaa ctggaccttt gccaccaagc attggaaact ttgctgtagc ccaaaaattg   1440
cttcttgatg ggaacaaatt tcgggacga attccagctg aaataggaaa gcttcaacag    1500
ctatccaaaa ttgatttcag tcataacaac ttgtctggac ccattgctcc ggagattagc   1560
cagtgcaagt tgctgactta tgttgatctc agcaggaacc aactttcggg tgagattcct   1620
actgagatca caggtatgag aatactcaac tacttgaatt tatcgcgaaa ccacttagtt   1680
gggagtattc ctgcccctat ttctagtatg cagagtttaa cttctgttga tttctcgtat   1740
aacaactttt ctggtttagt tcctggaacc gggcaattta gttatttcaa ttacacctca   1800
tttctaggca atccagatct tgcggaccc tatttgggcc cttgcaaaga gggcgttgtt    1860
gatggggtta gtcaacctca ccaacgagga gccttaacgc cttcgatgaa gcttttactt   1920
gttataggtt tgcttgtctg ttctattgtg tttgctgttg ctgcaattat aaaggcccga   1980
tctttaaaga aggcaagtga agctcgtgcc tggaagctaa ctgcttttca gcgcctggat   2040
tttacttgtg atgatatttt ggatagcttg aaggaggata cgttattgg aaaaggaggt    2100 gctggtattg tctacaaggg ggtaatgcct agcggggaac atgtagcggt taagaggttg   2160
ccagctatga gcaggggttc ctctcatgat catgggttca atgcagagat acagactctt   2220
gggaggatcc gacacaggca cattgttaga ttattaggt tttgctcgaa tcatgagaca    2280
aatcttttgg tttacgagta catgcctaat ggaagtcttg gggaaatgct tcatggcaag   2340
aaaggcggtc atttacattg ggataccagg tataagattg ccttggagtc tgctaagggt   2400
ctttgctatc tccatcacga ttgctctcct ttgatcctcc atcgtgatgt gaaatcaaac   2460
aacattctgc tggactccag ctttgaagct catgttgctg attttggact tgctaagttc   2520
ttgcaagatt cagggacatc agaatgcatg tctgctattg ctggttctta tgggtacatt   2580
gctccagaat atgcttacac acttaaggtt gatgagaaga gtgatgtata tagcttcggt   2640
gtggtgctac tagaactggt aagtggcaaa aaaccagttg gagaatttgg tgatggtgtt   2700
gacatagtcc aatgggttag gaaaatgact gatgggaaaa aggatggagt tctcaagatc   2760
cttgacccaa gactctcaac ggttcccctt aatgaggtga tgcatgtctt ctatgtcgca   2820
ttgttgtgtg tcgaagagca ggctgtgaa cgtcccacca tgcagaggt agtgcaaata     2880 ctaacggaac ttcccaagcc accaggtgca aaatcagatg actcaaccgt cactgatcag   2940
tcgcccccat cagcctctgc attagagtcc ccaacctcaa ttcccgggga cacaaaagac   3000
catcatcaac caacacctca atcacctcca cctgacctac tcagtatcta a            3051
```

<210> SEQ ID NO 70
<211> LENGTH: 2883
<212> TYPE: DNA
<213> ORGANISM: Lycopersicon esculentum

<400> SEQUENCE: 70

```
atggctactt ctaacacaag tctcttgttt ttcgcgtatt tcctccttgt gttccttatt    60
actccatctc aatcgcgtaa cctgtctctg agacgacagg ctaaaactct agtttcattg   120
aaatatgcat ttgtacaatc atctgttcct agtactctgt ccaattggaa catgtcgaat   180
tatatgtcta tatgttcttg gacaggtata acgtgtgatg ataccaaatc agtaacttcc   240
```

```
attgatatat ccaatctaaa catttctggc tctttatcac ctgatattca tgagctcact    300
agacttcgcg tcctgaatat ttctaacaat ttgtttagtg gaaacttaag ctgggagtat    360
cgcgagttta atgtacttca agtgttggat gcttataaca acaatttctc tggtccactc    420
cctttgggag ttactcaact tgtgcagctc aagtacttga atttcggggg taactacttt    480
tcagggaaga ttcctttgag ttatggtagt tttaatcagc ttgagttcct gtctcttgct    540
gggaatgact tgcacggtcc tataccgagg gagctgggga acgttacgag cctcaggtgg    600
ttacagttgg gttattataa tcaatttgat gaggggattc caccagagtt ggggaaactt    660
gttaatttgg ttcatctaga tctttcaagc tgtaacttaa cgggttcgat tccaccagaa    720
ttgggcaatc ttaatatgtt ggacactctt ttcttgcaaa agaatcaact tactggtgta    780
tttcctcctc agctagggaa tttgacaagg ttaaaatctc ttgatatctc ggtcaatgaa    840
ctcacaggag agatcccggt tgacttgtca ggactcaagg agctcatatt gttgaacctc    900
tttatcaaca atttgcacgg tgagattcca ggatgtatcg cggagctgcc aaagttggaa    960
atgttgaatc tttggaggaa taatttcact ggctcgattc cttctaagct tgggatgaac    1020
ggtaaactaa ttgaaattga tctgtctagt aatagactca ctggcttgat accaaaatct    1080
ctatgctttg ggaggaattt gaaaatcttg attcttcttg ataattttct gtttggacct    1140
ttacctgatg attttgggca gtgtcgaacg ttgtccagag tcagaatggg acagaattac    1200
ttgagtggat caataccaac agggtttctt tatttgcctg agttgtcact ggtggaactg    1260
cagaacaact acatcagtgg acaactctgg aacgagaaaa gctcagcgtc ttctaaactt    1320
gaagggctga acctgtcgaa caatcgcttg tctggtgcac ttcctagtgc tattggaaac    1380
tattcagggc tgaagaatct tgtgttaact ggaaatggtt tctcaggtga tatcccttct    1440
gatattggca gactaaagag catcttaaag ctggacctga gtagaaacaa cttctctggc    1500
acaatccctc ctcagattgg taactgtctt tccttaactt acttggattt gagccaaaat    1560
caactttctg gtcctatccc agttcaaatt gctcaaattc acatcttaaa ttacatcaat    1620
atttcctgga atcacttcaa cgagagcctt cccgcggaga ttggcttgat gaagagttta    1680
acttcagcag attttcccca caataactta tctggatcaa tacctgaaac aggccaatat    1740
ttatatttca actcaacttc cttcaccggc aacccttatc tctctggatc cgactcgact    1800
cctagcaaca ttacatccaa ctcaccgtca gaacttggag acggaagtga cagcagaact    1860
aaggttccta caatatacaa gttcatattt gcatttgggc tcttattctg ctccctcatt    1920
ttcgttgtct tagcaataat caagacaaga aaggggagta agaattcaaa tttgtggaag    1980
ctgacagcat ttcagaagct tgagttcgga agtgaagacg tcttgcagtg cttgaaagac    2040
aacaacgtca tagggagagg tggagcaggg atagtgtata agggaactat gccaaatggt    2100
gatcatgtcg cggtgaagaa attgggaata agcaaaggct cacatgataa cggcctatct    2160
gctgaactta aaacattagg gaagatcagg cataggtaca ttgtgagact gctcgcgttt    2220
tgttcaaaca aggaaatcaa cttgctagtt tatgagtaca tgctaaatgg aagcttaggt    2280
gaagtgcttc atgggaagaa cggcgggcaa ctccaatggg aaactaggct aaaaatagcc    2340
atagaagctg ccaagggcct ttcttatttg caccacgatt gctcccctat gataatccac    2400
cgcgatgtca agtccaacaa tatattgttg aactctgaac ttgaagctca tgttgcagat    2460
tttggattag ccaagtactt tcgtaacaat ggtacctctg agtgcatgtc tgcaattgca    2520
ggatcttatg gctacattgc tccagaatat gcatacacgc tgaaaattga tgagaaaagc    2580
```

| | |
|---|---:|
| gatgtgtata gctttggagt ggtgttgttg gagcttataa caggacgaag gccagtagga | 2640 |
| aattttggag aagaaggaat ggacattgta caatgggcga aaacggagac aaaatggagc | 2700 |
| aaagaagggg tggtgaaaat cttggatgag aggctaaaaa atgttgcaat tgttgaagct | 2760 |
| atgcaagtat tttttgtagc aatgcttgt gttgaagagt acagcattga gaggcctaca | 2820 |
| atgagggaag tagtccaaat gctttctcaa gctaaacaac caaatacttt ccaaatccaa | 2880 |
| taa | 2883 |

<210> SEQ ID NO 71
<211> LENGTH: 1131
<212> TYPE: DNA
<213> ORGANISM: Lycopersicon esculentum

<400> SEQUENCE: 71

| | |
|---|---:|
| atgggcacag ttctcaagct tgttttttg tgtctacaat taatctctgt gcattgccat | 60 |
| ggaaggatac tcaaggatga taactcttca tctgatcagt tcaaaaacag gtttcaaagg | 120 |
| attttctga gtatactttt tggtatgttt acaggtttga tttgtgcact tgtttttgct | 180 |
| tggcttgttc ggagttttgt tcgttacatt aacaaagccc caattcttaa aggccctgtt | 240 |
| gtattttctc ctaaaattcc acctaaaact ctgcaatcag ctcttgataa tgatacccag | 300 |
| ttgattgggt caagtaattc tggaaaatat ttcagaactg ttcttgataa tgggcttact | 360 |
| gttgctgtta agagaatgga acctggttct ccgcagttac atactaagtc atttaagaga | 420 |
| agaatacaac atgaacttga acttattgct ggtttaaggc ataggaattt gatgagttta | 480 |
| agggcgtatg ttcgtgaatc gaatacgttc ttttggtt atgattatgt aaacagtgga | 540 |
| agtctcgaag atgtgatgaa taaagttagg gaaaatcaat tgcaacttac ttgggaagtt | 600 |
| aggttacgaa ttgcagttgg gattgttaag gctcttcagt atcttcattt ctcttgtaat | 660 |
| cctacagttt tgcatcggaa tttgaagccc acaaatgtaa tgttggatgc tgagtttgag | 720 |
| cccaggttgg ctgattgcgg tttggctaaa atcattccca ctttaaatct ccctgctgca | 780 |
| tcaaactatg gtcctccaga atctttccag agttgcagca ggtatactga taagagtgac | 840 |
| gtatttagct ttggggttat attgggtgtt ctattaactg gaaagtaccc aacagatccc | 900 |
| ttcttcgggg atacatctac tggaggaagt ttagcatgtt ggcttcaacg tttgcaggaa | 960 |
| gcaggcgatg ctcgagaagc attggataag agtattctag gggaagaggt tgaggaagat | 1020 |
| gagatgttaa tggcagtaaa aatagcagtt gtatgcttat cagacatgcc tgctgatcga | 1080 |
| ccttccagtg atgagctcgt atccatgctc acccaattaa atagcttcta a | 1131 |

<210> SEQ ID NO 72
<211> LENGTH: 1128
<212> TYPE: DNA
<213> ORGANISM: Lycopersicon esculentum

<400> SEQUENCE: 72

| | |
|---|---:|
| atgggcacag ttctcaagct tgttttttg tgtctacaat taatctctgt gcattgccat | 60 |
| ggaaggatac tcaaggatga taactcttca tctgatcagt tcaaaaacag gtttcaaagg | 120 |
| attttctga gtatactttt tggtatgttt acaggtttga tttgtgcact tgtttttgct | 180 |
| tggcttgttc ggagttttgt tcgttacatt aacaaagccc caattcttaa aggccctgtt | 240 |
| gtattttctc ctaaaattcc acctaaaact ctgcaatcag ctcttgataa tgatacccag | 300 |
| ttgattgggt caagtaattc tggaaaatat ttcagaactg ttcttgataa tgggcttact | 360 |
| gttgctgtta agagaatgga acctggttct ccgcagttac atactaagtc atttaagaga | 420 |

```
agaatacaac atgaacttga acttattgct ggtttaaggc ataggaattt gatgagttta    480
agggcgtatg ttcgtgaatc gaatacgttc ttttttggttt atgattatgt aaacagtgga    540
agtctcgaag atgtgatgaa taaagttagg gaaaatcaat tgcaacttac ttgggaagtt    600
aggttacgaa ttgcagttgg gattgttaag gctcttcagt atcttcattt ctcttgtaat    660
cctacagttt tgcatcggaa tttgaagccc acaaatgtaa tgttggatgc tgagtttgag    720
cccaggttgg ctgattgcgg tttggctaaa atcattccca ctttaaatct ccctgctgca    780
tcaaactatg gtcctccaga atctttccag agttgcaggt atactgataa gagtgacgta    840
tttagctttg gggttatatt gggtgttcta ttaactggaa agtacccaac agatcccttc    900
ttcggggata catctactgg aggaagttta gcatgttggc ttcaacgttt gcaggaagca    960
ggcgatgctc gagaagcatt ggataagagt attctagggg aagaggttga ggaagatgag    1020
atgttaatgg cagtaaaaat agcagttgta tgcttatcag acatgcctgc tgatcgacct    1080
tccagtgatg agctcgtatc catgctcacc caattaaata gcttctaa    1128

<210> SEQ ID NO 73
<211> LENGTH: 2973
<212> TYPE: DNA
<213> ORGANISM: Lycopersicon esculentum

<400> SEQUENCE: 73
atggcatcat ttttactcca aagatgtaat cttctctttg aggttcttct tattttgggg    60
ttcttgattt tcttcagctt tggttctgtg gtgtctgatg atggttctgc attgttggaa   120
attaagaagt caattaggga cgtggagaat gtgttgtatg actggactga ttctccttca   180
tctgattact gtgcctggag aggtgttacc tgtgataatg tcaccttcaa tgttgttcaa   240
cttaatcttt cgagtttaaa tcttgatggg gagttgtctc ctgctattgg acagctcaaa   300
ggccttgtat ctattgatat gaggggaaat cgccttttctg ccagataccc agatgagatt   360
ggtgactgtt cagcactgaa aaatttggac cttttccttca atgagctttta tggtgatatt   420 cccttctcca tatctaaact caagcaactg gaatatctga ttttgaagaa taatcaattg    480
attggaccaa ttccatctac attgtcacag atccctaact tgaaggtctt ggacctggct    540
caaaataggt taagtggaga aattcctagg ctgatatact ggaacgaagt cctgcagtat    600
ctgggactgc gtggtaacaa cttgggtgga tcccttttctc ctgatatgtg tcagctcacc    660
ggcctgtggt actttgatgt tcggaacaat agtttgactg gttccattcc tcaaaatatt    720
ggcaactgta ctgccttcca ggttctagat ttgtcttata tgatttttgac cggagagatt    780 cctttcaata ttggtttcct gcaagtagcg accttgtctt tgcaaggtaa tcgtctttca    840
gggcagatcc cttctgtaat tggattgatg caagctcttg cagttttgga cttgagctgc    900
aatatgttga gtggaacaat tccttcaatt cttgggaatt tgacttacac agagaaattg    960
tatctacacg ggaacaagct atctggttcc attcctccag agctgggaaa tatgacaaag   1020
ctccactact tggaattgaa tgataaccaa cttactggac gcataccacc agaacttgga   1080
aagctgacag aattgtttga cttaaatgtt gcaaacaacc acctagatgg gcccatacct   1140
tccaatatta gctcatgtac caatttgaat agtctcaacg ttcatggaaa caaattgaat   1200
ggtactattc cacctgcttt tcagaagctg gaaagtatga cctatcttaa tctctcctcc   1260
aacaatctca aaggcccaat tccaattgag ctatctcgta ttgggaatgt agatacactg   1320
gacttatcaa acaacaggat cagtggtcct atacctatgt cccttggtga tttggaacat   1380
```

```
cttcttaaac tgaacttaag caagaatgaa ataaatggaa acttaccagc tgaatttggc    1440
aatttaagga gcatcatgga gattgatctg tcaagcaatc acctctctgg tcccttacct    1500
caggaacttg gtcagcttcc aaacctgtac ttgctgaagg tggaaaacaa caatttatca    1560
ggcgatgtga tgtccttagc cagttgcctc agtctaaata tcttaaatgt ctcatacaat    1620
aatctgggag ggaatattcc aaccggcaat aatttctcta gattttcacc agacagcttc    1680
ataggaaatc cagatctgtg tgggtattgg ctcacttctc cttgtcatgc atctcatccg    1740
gcagagcgag tttcaatttc taaagcagca atacttggta ttgctctggg tggcttggtg    1800
attcttctga tgatactagt agcagcatgc cggccacaga aacctgcacc tttcatggaa    1860
ggatctattg ataaaccagt ttattactca tctccaaaac ttgtgatcct tcatatgaac    1920
atggcacttc atgtttacga ggacattatg aggatgactg agaacttgag tgagaagtat    1980
ataattggtt gtggagcatc aagtactgta tataaatgtg ttttgaaaaa ttgcaagcct    2040
gtagctatca agaagttgta ctctcacaac ccgcaatact tgaaggaatt tgagactgaa    2100
cttgagacag ttgggagtat taagcatcgt aatcttgtct gtctccaagg atattctctt    2160
tctccatctg gccatcttct tttctatgac tacatggaaa atggtagcct ttgggatttg    2220
cttcatggtc ctacaacaaa gaagaaaaag cttgattggg ttactcgcct tcgaattgca    2280
ttgggatcag ctcaagggct tgcatatctt catcatgatt gtagccctcg aataatccac    2340
cgtgatgtta aatcatctaa tatcttgttg gacaaagact tgaggctca tctgactgat    2400 tttggcatag ctaaaagctt atgcatatca aagacctata cgtccacgta cattatggga    2460
accattggtt acattgatcc agagtatgct cgcacttctc gcttgacaga gaagtctgat    2520
gtttacagct atggtattgt tctattggaa ttgctcactg gaaggaaagc tgtagataat    2580
gaatctaatc tacatcattt gattctaact aaggcagcaa acgatgctgt aatgaaaaca    2640
gtggatcctg agataacatg cacatgcaaa gatcttgcag atgtgaagaa ggttttcag    2700 cttgcccttc tatgttccaa aagacagcct gctgagagac caacaatgca tgaagtggca    2760
agagtacttg aaagcctaat acccgtcgct gaaacgaaac agccaaatcc aacccccctca    2820 cttgcattac tcccatctgc taaggtacct tgttacatgg atgaatatgt caacctcaag    2880
acaccccacc tagtgaactg ttcatccatg agcacttcag atgcccaact tttcctcaag    2940
tttggagagg tcatatccca gaatagtggc tga                                2973

<210> SEQ ID NO 74
<211> LENGTH: 2928
<212> TYPE: DNA
<213> ORGANISM: Lycopersicon esculentum

<400> SEQUENCE: 74
atggaagtga gcctgaaaat gaaattccgc tcgcaagcgc tactgttggt tctattgctt     60
gttttcccga tcgttttggc tctcaccgaa gaaggcaaag cattaatgtc gatcaaggca    120
tcgtttagca acgtagcaaa cgtgttgctg gattgggatg atatccacga cgaggatttt    180
tgctcatgga gaggcgtgtt gtgtggaaat ttctccatgt ccgtcgttgc actgaatctg    240
tctaatctga acttgggcgg ggaaatttca ccagacattg gagagttgaa gaatctggag    300
acattagacc ttcagggaaa taattaact ggtcaagtcc cagatgaaat tggcaactgc    360
atttcactga tctatcttga tttgtctgat aacttgttct atggagatat accattctca    420
atttctaagc tcaagcagct agagttgtta aacttaaaa acaaccagtt gtccggccca    480
atcccgtcca cattaactca aattcctaat ctaaagacgc ttgatctggc tcgaaaccag    540
```

-continued

```
ctcattggtg agataccaag gttgatctat tggaatgaag ttctacaata tctaggatta    600
agaggcaaca tgttgacagg aacattgtcc cctgatatgt gccagttgac tggcttgtgg    660
tattttgatg tgcggggcaa taacctcagc ggaataattc cagataatat tgggaattgt    720
acaagctttg agatactgga tatctcatac aatcagataa ctggagaaat tccctacaat    780
attgggtttt tacaagtggc taccttgtct ttgcaaggaa ataggctaac tggcaggatc    840
ccagaagtga ttggtcttat gcaagctctt gctgttctgg acttgagtga aaatgagttg    900
gtgggaccaa tccctccaat ctttggcaat ttatcttaca cagggaagct gtacctgcac    960
ggcaacaaac ttacagggcc agttccaccg gagctaggaa atatgtctaa acttagttac   1020
ttgcaattaa atgacaatca gctaatgggt cgaattcccc ctgaacttgg caaactggac   1080
cagttatttg aattgaatct tgcaaataac aagttggagg gaccaattcc tgaaaatatc   1140
agctcctgtt ctgcattgaa tcagcttaat gttcatggca acaacttaaa cgagtccatt   1200
ccttcagggt taagaatct ggagagcttg acgtatctaa atctttcagc taataaattt   1260
aagggtcaca taccttctca acttgggcga atcatcaacc ttgatacatt ggatctctct   1320
ggcaacaatt tttctgggtc tatccctggt tctattggag atttggagca tctcctcaca   1380
ttgaatctga gcagcaatca tcttgatgga caaattcctg tagaatttgg caatctaaaa   1440
agtatacaga ccattgatat gtcaagcaac aagatctctg gtggcatccc aaaagagctg   1500
ggacagctgc agaccatgat aactcttact ttgacaggta actatcttac tggagcaatc   1560
cctgaccaat tgaccaattg tttcagccta actagtttga atatatccta caacaatttt   1620
agtggtgttg ttcctctttc acggaatttc tcgcggtttg cacctgacag cttttttaggg   1680 aacccatttc tttgtggcaa ctggaaaggt tcaatatgtg accccatagc accaaggtct   1740
aacgccttgt tctccagaac agctgttgtt tgcacagcac tgggtttcat tgcactctta   1800
tccatggttg tagtggctgt gtataagtcc aaccaaccac accagttttt gaaggggcct   1860
aagaccaatc aaggctcccc caaacttgtg gttcttcaca tggatatggc catccataca   1920
tatgatgaca ttatgaggat taccgagaac ttcaatgaga aattcataat aggatatggt   1980
gcgtccagca ctgtatataa atgtgatttg aaagattccc gaccaattgc agttaagcga   2040
ctttacaccg cacatccgca cagcttgcga gagtttgaga ctgaactgga gacaattgga   2100
agcattaggc atagaaacct tgttagcttg catggttact ccctttcccc tcatgggaat   2160
ctcctttgtt acgactacat ggagaatggt tcactctggg atctacttca tgggccttcc   2220
aaaaaggtga agcttgactg ggaaacacgt ctgaagattg ctgttggtgc tgctcagggt   2280
cttgcttatc ttcaccacga ttgcaaccca agaataatac acagagatgt aaaatcttca   2340
aacatccttg ttgatgaaaa ttttgaggct catctatctg attttggggt tgcaaaatgc   2400
atccctactg caaaaactca tgcatcaact ttggtgttgg gcaccatagg ttacattgac   2460
cctgagtatg ccaggacttc caggttaact gaaaagtcag acgtctacag ctttggcatt   2520
gttctcctag agcttttgac aggaaagaaa ccggttgata atgacttgaa cctgcatcag   2580
ctgataatgt caaaggcgga tgataacacc gtgatggatg ctgttgatcc tgaggtatct   2640
gttacatgta tggatttaat gcatgttagg aaaacttttc agcttgcgtt gctgtgtgca   2700
aaaagattcc catgtgagag gccaacaatg catgaggttg ctagggtact tgtttccttg   2760
cttcctcccc caccaaccaa accttgttta gacccaccte ccaaatccat tgattataca   2820
aaatttgtga ttggtaaagg actaccgcaa gtccagcagg gtgacaattc ctccgaagct   2880
```

```
cagtggcttg ttagatttca agaagctata tccaaaaact cccttttga              2928

<210> SEQ ID NO 75
<211> LENGTH: 2658
<212> TYPE: DNA
<213> ORGANISM: Lycopersicon esculentum

<400> SEQUENCE: 75
atgtggaaat gtagatactt tgtaagagct tttatgttta ttctgatatt ttcaaaagta    60
tcagggtttg gttcaatgtc ttccattgct atttcctatg gtgaatatgg ttctgttttt   120
tgtgggttga agtcagatgg atctcatttg gtaagctgtt atggctctac atcttctata   180
atatattcaa ctccagctca tttcccttt  attggtctta ctgctggaaa tggctttgta   240
tgtggacttt tgatggattc ttatcagcct tattgctggg ggaaaagtaa ttttgtacaa   300
atgggggtgc ctcagcctat gatcaaaggg tctcagtatt tggaaatatc tgcaggggaa   360
aatcatttgt gtggactaag gcaacccttta atggggaagc ataggaacac ttcacttgtt   420
gattgttggg gttataatat gactacaaat aatgagtttg aaggtcagat ccactctatt   480
tcagctggtt ctgagtttaa ttgtgctttg ttttctgtta ataagagtgt tttatgttgg   540
ggggatgaaa ctagtagtca ggttattacc ctagcaccaa agatttgag  atttattaag   600 attgcagctg ggggatatca tgtttgtggg attctagaag gggtgaattc tcaagtgtat   660
tgctggggta ggagcatgaa tcttgaagaa gaattctctg ttgctcaact taatgttgaa   720
ttggctgccc ctagtgatcc gattatatcg gttgttggtg gtaagtttca tgcttgtggg   780
attaggagct atgaccgtca tgtcgtttgt tggggttata gggttgagaa agcacacca    840 cctcctagtg gagttaggtt ttatgagata gcagctggtg actactttag ttgtggtatc   900
ctggcagaaa tttcactttt gcctgtttgt tgggggtttg gttttccctc atcgctacca   960
ctcgctgttt ctcctggagt ctgcaagcct agaccctgtg cgtctggctt ctatgagttc  1020
aacaatggaa ctacaacttg caagtctcct gattctcgta tttgccttcc ctgcaccaat  1080
ggctgtcctg ctgaaatgta tcaacaggtt gaatgtagct catctaggga cagtcagtgt  1140
acgtataatt gttctagttg tacctctgtt gactgcatta caactgttc  tactgctgtt  1200 tctggaaaga agaacgcaaa attttggtca ctccagttac cagtaattgt tgctgaggtt  1260
gcatttgctg tattcttggt gagtgttgta tctctgactt cgatcgtata tgttcgctac  1320
aaattaagga actgtagatg ttcagggaga agtcctagtc ctaggaagaa cggttctttt  1380
ccaaaggaaa ttgctaaaga tagggctgat ttggatgatc ttaagataag gagagctcag  1440
atgtttacgt atgaagatct tgagagagca actgagggat caaagaaga  atcacaagtt  1500 ggaaagggta gcttttcatg tgtgttcaag ggcgttttga aggacggtac tgtggtcgct  1560
gttaagaggg ctataatgtc atctgacatg aagaagaatt caaggagtt  ccacactgag  1620 ctcgacttgc tgtccaggtt aaatcatgct catttgctca atttgctagg ttattgtgaa  1680
gagggtggag agagactgct agtttatgag tacatggcta atggctcgtt acatgaacat  1740
ctacacggga aaaagaagga gcaattggat tggataagaa gggtaaccat tgcagttcaa  1800
gctgctcggg gaatcgaata tttgcatggt tatgcatgtc cacccgtgat tcacagagac  1860
atcaagtcct caaacatcct tatagatgaa gaacacaatg ctcgagtagc tgattttggg  1920
cttttccttg cttggaccgg ctaatagcagt tccccattag cagagttacc agcaggaaca  1980
cttgggtacc tcgatcccga gtactacaga ctacattatc ttacaaccaa gtctgatgtc  2040
tatagctttg gtgttttgct tttggaaatt ctcagtggtc gtaaagccat tgacatgcaa  2100
```

```
tacgacgaag ggaacatagt ggaatgggca gtcccttaa tcaaagctgg tgatatagaa    2160
gcaatactag atccagtttt gaaaccacct tctgatgctg aagctcttag aagaatcgct    2220
aatatagcca gcaaatgcgt taggatgaga gggaaggaaa ggccgtcaat ggataaagta    2280
acgacagctt tggagagagc acttgctcaa ttgatgggta gtccaagcaa tgatcaacct    2340
atcttaccaa cagaggttgt tctaggaagc agtagaatgc acaagaagtc gtcatcaaat    2400
cgatcaacct cagaaacaac agatgttgca gaaactgagg atcagaggta tgtcgaattc    2460
agagctcctt cgtggattac gttcccaagt gtagcatcat ctcagaggag aaagtcttca    2520
gtatcggacg cagatgttga agcaaagaat ttagaaagta ggaactgtgg aaatggaact    2580
gatggattga gaagtttgga agaagaaatt ggaccagctt ctcctcatga acatttgttc    2640
ttgaaacaca acttctaa                                                  2658
```